(12) United States Patent
Keyt et al.

US010570191B2

(10) Patent No.: US 10,570,191 B2
(45) Date of Patent: Feb. 25, 2020

(54) MULTI-VALENT HUMAN IMMUNODEFICIENCY VIRUS ANTIGEN BINDING MOLECULES AND USES THEREOF

(71) Applicant: IGM Biosciences, Inc., Mountain View, CA (US)

(72) Inventors: Bruce Alan Keyt, Hillsborough, CA (US); Dan T. Stinchcomb, Enumclaw, WA (US); Ole A. Olsen, Everett, WA (US)

(73) Assignee: IGM Biosciences, Inc., Mountain View, CA (US)

( * ) Notice: Subject to any disclaimer, the term of this patent is extended or adjusted under 35 U.S.C. 154(b) by 0 days.

(21) Appl. No.: 15/566,485

(22) PCT Filed: Apr. 15, 2016

(86) PCT No.: PCT/US2016/027979
§ 371 (c)(1),
(2) Date: Oct. 13, 2017

(87) PCT Pub. No.: WO2016/168758
PCT Pub. Date: Oct. 20, 2016

(65) Prior Publication Data
US 2018/0118816 A1 May 3, 2018

Related U.S. Application Data

(60) Provisional application No. 62/149,460, filed on Apr. 17, 2015.

(51) Int. Cl.
*C07K 16/28* (2006.01)
*C07K 16/10* (2006.01)
*C07K 17/00* (2006.01)

(52) U.S. Cl.
CPC ...... *C07K 16/1063* (2013.01); *C07K 16/2809* (2013.01); *C07K 2317/21* (2013.01); *C07K 2317/24* (2013.01); *C07K 2317/31* (2013.01); *C07K 2317/35* (2013.01); *C07K 2317/52* (2013.01); *C07K 2317/522* (2013.01); *C07K 2317/622* (2013.01); *C07K 2317/73* (2013.01); *C07K 2317/734* (2013.01); *C07K 2317/76* (2013.01); *C12N 2740/16011* (2013.01)

(58) Field of Classification Search
CPC .................. C07K 16/1063; C07K 16/2809
See application file for complete search history.

(56) References Cited

U.S. PATENT DOCUMENTS

| 5,834,597 | A | 11/1998 | Tso et al. |
| 8,637,036 | B2 | 1/2014 | Mascola et al. |
| 9,175,070 | B2 * | 11/2015 | Mascola ............ C07K 16/1063 |
| 9,738,703 | B2 * | 8/2017 | Mascola ............ C07K 16/1063 |
| 10,035,845 | B2 * | 7/2018 | Mascola ............ C07K 16/1063 |
| 2006/0104974 | A1 | 5/2006 | Davis et al. |
| 2012/0237523 | A1 | 9/2012 | Mascola et al. |
| 2013/0189247 | A1 | 7/2013 | Bramhill et al. |
| 2016/0222132 | A1 | 8/2016 | Keyt et al. |
| 2016/0326233 | A1 | 11/2016 | Mondelli |
| 2016/0368971 | A1 | 12/2016 | Keyt et al. |
| 2017/0183409 | A1 | 6/2017 | Keyt et al. |
| 2017/0283510 | A1 | 10/2017 | Keyt et al. |
| 2017/0320955 | A1 | 11/2017 | Wang et al. |

FOREIGN PATENT DOCUMENTS

| WO | 2006/044410 A2 | 4/2006 |
| WO | 2006/120230 A2 | 11/2006 |
| WO | 2011/035205 A2 | 3/2011 |
| WO | 2011/038290 A2 | 3/2011 |
| WO | 2012/106578 A1 | 8/2012 |
| WO | 2013/070776 A1 | 5/2013 |
| WO | 2013/086533 A1 | 6/2013 |
| WO | 2013110790 | 8/2013 |
| WO | 2013/142324 A1 | 9/2013 |
| WO | 2015/053887 A1 | 4/2015 |
| WO | 2015/120474 A1 | 8/2015 |
| WO | 2015/153912 A1 | 10/2015 |
| WO | 2016/118641 A1 | 7/2016 |
| WO | 2016/141303 A2 | 9/2016 |
| WO | 2016/154593 A1 | 9/2016 |
| WO | 2017/059380 A1 | 4/2017 |
| WO | 2017/059387 A1 | 4/2017 |

OTHER PUBLICATIONS

Natawitsch et al. AIDS 2005, vol. 19 (17), pp. 1957-1966.*
Barouch et al., "Therapeutic Efficacy of Potent Neutralizing HIV-1-Specific Monoclonal Antibodies in SHIV-Infected Rhesus Monkeys", Nature, Nov. 14, 2013, 10 pages, vol. 503, No. 7475.
Bartlett et al., "Overview of the Effectiveness of Triple Combination Therapy in Antiretroviral-Naive HIV-1 Infected Adults", AIDS, 2001, pp. 1369-1377, vol. 15, No. 11.
Beverley et al., "Distinctive Functional Characteristics of Human "T" Lymphocytes Defined by E Rosetting or a Monoclonal Anti-T Cell Antibody", European Journal of Immunology, 1981, pp. 329-334, vol. 11.
Bonsignori et al, "Analysis of Clonal Lineage of HIV-1 Envelope V2/V3 Conformational Epitope-Specific Broadly Neutralizing Antibodies and Their Inferred Unmutated Common Ancestors", Journal of Virology, Oct. 2011, pp. 9998-10009, vol. 85, No. 19.

(Continued)

*Primary Examiner* — Bao Q Li

(57) ABSTRACT

This disclosure provides a multimeric human immunodeficiency virus (HIV) protein binding molecule, e.g., an dimeric IgA or a pentameric or hexameric IgM binding molecule, comprising at least two bivalent binding units, or variants or fragments thereof, each comprising at least two antibody heavy chain constant regions or fragments thereof, wherein each heavy chain constant region or fragment thereof is associated with an HIV antigen binding domain. Also provided are compositions comprising the multimeric binding molecules, polynucleotides encoding the multimeric binding molecules, and methods to make and use the multimeric binding molecules.

14 Claims, 13 Drawing Sheets

Specification includes a Sequence Listing.

(56) References Cited

OTHER PUBLICATIONS

Brown et al, "Gastrointestinal Tract and the Mucosal Macrophage Reservoir in HIV Infection", Clinical and Vaccine Immunology, Nov. 2014, pp. 1469-1473, vol. 21, No. 11.

Buchacher et al., "Generation of Human Monoclonal Antibodies Against HIV-1 Proteins; Electrofusion and Epstein-Barr Virus Transformation for Peripheral Blood Lymphocyte Immortalization", Aids Research and Human Retroviruses, Nov. 4, 1994, pp. 359-383, vol. 10, No. 4.

Butera et al., "Oscillation of the Human Immunodeficiency Virus Surface Receptor is Regulated by the State of Viral Activation in a CD4 Cell Model of Chronic Infection", Journal of Virology, Sep. 1991. pp. 4645-4653, vol. 65, No. 9.

Deng et al., "Broad CTL Response is Required to Clear Latent HIV-1 Due to Dominance of Escape Mutations", Nature, Jan. 15, 2015. 17 pages, vol. 517.

Denton et al., "Generation of HIV Latency in Humanized BLT Mice", Journal of Virology, Jan. 2012, pp. 630-634, vol. 86, No. 1.

Diskin et al., "Restricting HIV-1 Pathways for Escape Using Rationally Designed Anti-HIV-1 Antibodies", Journal of Experimental Medicine, 2013, pp. 1235-1249, vol. 210, No. 6.

Eroshkin et al.,"bNAber: Database of Broadly Neutralizing HIV Antibodies", Nucleic Acids Research, 2014, pp. 1133-1139, vol. 42.

Finzi et al., "Latent Infection of CD4+ T Cells Provides a Mechanism for Lifelong Persistence of HIV-1, Even in Patients on Effective Combination Therapy", Nature Medicine, May 1999, pp. 512-517, vol. 5, No. 5.

Folks et al., "Tumor Necrosis Factor a Induces Expression of Human Immunodeficiency Virus in a Chronically Infected T-Cell Clone", Proceedings of the National Academy of Science USA, Apr. 1989, pp. 2365-2368, vol. 86.

GenBank Accession No. ABQ52435, dated Jul. 23, 2016, Immunoglobulin heavy chain region, partial.

Go et al.,"Comparative Analysis of the Glycosylation Profiles of Membrane-Anchored HIV-1 Envelope Glycoprotein Trimers of Soluble gp140", Journal of Virology, Aug. 2015, pp. 8245-8257, vol. 89, No. 16.

Hepler et al., "IDEPI: Rapid Prediction of HIV-1 Antibody Epitopes and Other Phenotypic Features From Sequence Data Using a Flexible Machine Learning Platform", PLOS Computational Biology, Sep. 2014, 10 pages, vol. 10, Issue 9, e1003842.

Horwitz et al., "HIV-1 Suppression and Durable Control by Combining Single Broadly Neutralizing Antibodies and Antiretroviral Drugs in Humanized Mice", Proceedings of the National Acedmy of Science, Oct. 8, 2013, pp. 16538-16543, vol. 110, No. 41.

Huang et al., "Broad and Potent HIV-1 Neutralization by a Human Antibody that Binds the gp41-120 Interface", Nature, Nov. 6, 2014, 26 pages, vol. 515, No. 7525.

Huang et al., "Broad and Potent Neutralization of HIV-1 by a GP41-Specific Human Antibody", Nature, Nov. 15, 2012, 22 pages, 22 pages, No. 7424.

Iglesias-Ussel et al.,"HIV Reservoirs: The New Frontier", AIDS Reviews, 2011, pp. 13-29, vol. 13.

Kaetzel et al., "The Polymeric Immunoglobulin Receptor (Secretory Component) Mediates Transport of Immune Complexes Across Epithelial Cells: A Local Defense Function for IgA", Proceedings of the National Academy of Science, USA, Oct. 1991, pp. 8796-8800, vol. 88.

Klein et al., "Antibodies in HIV-1 Vaccine Development and Therapy", Science, Sep. 13, 2013, 17 pages, vol. 341, No. 6151.

Klein et al., "HIV Therapy by a Combination of Broadly Neutralizing Antibodies in Humanized Mice", Nature, Dec. 6, 2012, 14 pages, vol. 492, No. 7427.

Kung et al., "Monoclonal Antibodies Defining Distinctive Human T Cell Surface Antigens", Science, Oct. 19, 1979, pp. 347-349, vol. 206.

Lehman et al.,"Prospective Randomized Comparison of a Combined Ultrasonic and Pneumatic Lithotrite with a Standard Ultrasonic Lithotrite or Percutaneous Nephrolithotomy", Journal of Endourology, Feb. 2008, pp. 285-289, vol. 22, No. 2.

Liao et al., "Co-Evolution of a Broadly Neutralizing HIV-1 Antibody and Founder Virus", Nature, Apr. 25, 2013, 25 pages, vol. 496, No. 7446.

Montero et al.,"The Membrane-Proximal External Region of the Human Immunodeficiency Virus Type 1 Envelope: Dominant Site of Antibody Neutralization and Target for Vaccine Design", Microbiology and Molecular Biology Reviews, Mar. 2008, pp. 54-84, vol. 72, No. 1.

Moore et al., "Antibody Cross-Competition Analysis of the Human Immunodeficiency Virus Type 1 gp120 Exterior Envelope Glycoprotein", Journal of Virology, Mar. 1996, pp. 1863-1872, vol. 70, No. 3.

Mostov, "Transepithelial Transport of Immunoglobulins", Annual Review of Immunology, 1994, pp. 63-84, vol. 12.

Mouquet et al., "Complex-type N-Glycan Recognition by Potent Broadly Neutralizing HIV Antibodies", Proceedings of the National Academy of Science, Oct. 30, 2012, pp. E3268-E3277.

Perez et al., "An HIV-1-Infected T Cell Clone Defective in IL-2 Production and Ca2+ Mobilization After CD3 Stimulation", The Journal of Immunology, Nov. 1, 1991, pp. 3145-3148, vol. 147, No. 9.

Pincus et al., "In Vivo Efficacy of Anti-Glycoprotein 41, But Not Anti-Glycoprotein 120, Immunotoxins in a Mouse Model of HIV Infection", The Journal of Immunology, 2003, pp. 2236-2241, vol. 170.

Richman et al., "Rapid Evolution of the Neutralizing Antibody Response to HIV Type 1 Infection", Proceedings of the National Academy of Science, Apr. 1, 2003, pp. 4144-4149, vol. 100, No. 7.

Scheid et al.,"Sequence and Structural Convergence of Broad and Potent HIV Antibodies that Mimic CD4 Binding", Science, Sep. 16, 2011, 11 pages, vol. 333, No. 6049.

Sok et al., "Recombinant HIV Envelope Trimer Selects for Quatemary-Dependent Antibodies Targeting the Trimer Apex", Proceedings of the National Academy of Science, Dec. 9, 2014, pp. 17624-17629, vol. 111, No. 49.

Walker et al., "Broad Neutralization Coverage of HIV by Multiple Highly Potent Antibodies", Nature, Sep. 22, 2011, 14 pages, vol. 477, No. 7365.

Weiss et al., "Characterization of Stable Chinese Hamster Ovary Cells Expressing Wild-Type, Secreted, and Glycosylphosphatidylinositol-Anchored Human Immunodeficiency Virus Type 1 Envelope Glycoprotein", Journal of Virology, Dec. 1993, pp. 7060-7066, vol. 67, No. 12.

Woof et al.,"Structure and Function Relationships in IgA", Mucosal Immunology, Nov. 2011, pp. 590-597, vol. 1, No. 6.

Wu et al., "Molecular Construction and Optimization of Anti-Human IL-1a/b Dual Variable Domain Immunoglobulin (DVD-Ig™) Molecules", mAbs, 2009, pp. 339-347, vol. 1, Issue 4.

Wu et al.,"Focused Evolution of HIV-1 Neutralizing Antibodies Revealed by Structures and Deep Sequencing", Science, Sep. 16, 2011, 17 pages, vol. 333, No. 6049.

Wu et al.,"Rational Design of Envelope Identifies Broadly Neutralizing Human Monoclonal Antibodies to HIV-1", Science, Aug. 13, 2010, 12 pages, vol. 329, No. 5993.

Wu et al.,"Simultaneous Targeting of Multiple Disease Mediators by a Dual-Variable-Domain Immunoglobulin", Nature Biotechnology, Nov. 2007, pp. 1290-1298, vol. 25, No. 11.

Wyatt et al.,"Involvement of the V1/V2 Variable Loop Structure in the Exposure of Human Immunodeficiency Virus Type 1 gp120 Epitopes Induced by Receptor Binding", Journal of Virology, Sep. 1995, pp. 5723-5733, vol. 69, No. 9.

Zhang et al., "HIV-1 Immunopathogenesis in Humanized Mouse Models", Cellular & Molecular Immunology, 2012, 8 pages, vol. 9.

Zhu et al., "Cross-Reactive HIV-1 Neutralizing Human Monoclonal Antibodies Identified from a Patient with 2F5-Like Antibodies", Journal of Virology, Nov. 2011, pp. 11401-11408, vol. 85, No. 21.

Wolbank, et al., "Characterization of Human Class-Switched Polymeric (Immunoglobulin M [IgM] and IgA) Anti-Human Immunodeficiency Virus Type 1 Antibodies 2F5 and 2G12", Journal of Virology, 2003, pp. 4095-4103, vol. 77, No. 7.

(56) References Cited

OTHER PUBLICATIONS

Liu et al. "Expression and functional activity of isotype and subclass switched human monoclonal antibody reactive with the base of the V3 loop of HIV-1 gp120" AIDS Res. Hum. Retroviruses, 2003, pp. 597-607, vol. 19.
Tudor et al. "Isotype modulates epitope specificity, affinity, and antiviral activities of anti-HIV-1 human broadly neutralizing 2F5 antibody" PNAS, 2012, pp. 12680-12685, vol. 109, No. 31.
International Search Report and Written Opinion dated Aug. 19, 2016 issued in PCT Patent Application No. PCT/US2016/027979.
Muller et al., "High-Resolution Structures of the IgM Fc Domains Reveal Principles of its Hexamer Formation", Proceedings of the National Academy of Sciences, Jun. 18, 2013, pp. 10183-10188, vol. 110, No. 25.

\* cited by examiner

MULTI-VALENT HUMAN IMMUNODEFICIENCY VIRUS ANTIGEN BINDING MOLECULES AND USES THEREOF

CROSS-REFERENCE TO RELATED APPLICATIONS

This application is a U.S. National Stage Entry of PCT Application No. PCT/US2016/027979, filed Apr. 15, 2016, which claims the benefit of U.S. Provisional Application Ser. No. 62/149,460, filed on Apr. 17, 2015, which are hereby incorporated by reference in their entireties.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Oct. 11, 2017, is named 57912-170015_SL.txt and is 196589 bytes in size.

BACKGROUND

Human immunodeficiency virus (HIV) is a retrovirus of the Lentivirus family. HIV is a single stranded, positive sense enveloped RNA virus. HIV causes acquired immunodeficiency syndrome (AIDS) which leads to failure of the immune system due to destruction of T cells, macrophages and dendritic cells. HIV has a very high rate of genetic variability. Two types of HIV have been identified, including HIV-1 and HIV-2, both of which are transmitted by sexual contact or through blood and both cause AIDS. The two viruses differ in that HIV-1 is more prevalent, more virulent, and more easily transmitted than HIV-2. HIV-1 can be further divided into three groups based on sequence differences in the envelope (env) gene, group M, group N group O, and group P. Group M of HIV-1 is further divided into at least nine subtypes (or clades) based on difference in genomic sequence and geographic distribution (subtypes A, B, C, D, F, G, H, J and K). The structure of the HIV RNA genome includes nine genes: gag, pol, env, tat, rev, nef, vif, vpr, and vpu. Some HIV genomes include a tenth gene called tev, a fusion of tat, env, and rev. These genes encode the following proteins:

Viral Structural Proteins gag proteolytically processed to yield matrix protein (p17, MA), capsid protein (p24, CA), nucleocapsid protein (p7, NC), spacer peptide 2 (SP2, p1) and P6 protein
pol proteolytically processed to yield reverse transcriptase (RT), RNase H, integrase (IN) and HIV protease (PR)
env gp160 envelope protein; processed proteolytically to yield gp120

Essential Regulatory Elements tat RNA binding transcriptional activator protein
rev Rev protein, which is a sequence-specific RNA binding regulator protein Accessory Regulatory Proteins vpr Vpr is lentivirus nucleocytoplasmic shuttling/transport regulatory protein
vif Vif is a cell-specific regulatory phosphoprotein
nef Nef is an N-terminal myristoylated membrane-associated regulatory phosphoprotein
vpu Vpu is an HIV-1 specific integral membrane regulatory phosphoprotein
tev tev is a tat/env/rev fusion gene yielding a fusion protein The HIV envelope protein, gp160 is proteolytically cleaved by a host cell protease to yield gp120 and gp41. These two molecules form a cap and stem structure protruding from the viral envelope, also referred to as the spike. The cap is composed of three copies of gp120 and the stem is composed of three copies of gp41. The stem anchors the gp120/gp41 complex to the viral envelope. The envelope glycoprotein gp120 is expressed both on the surface of infected cells and the viral envelope of viral particles. The gp120 portion of the Env protein is responsible for binding to the CD4 receptor on target cells, such as helper T cells, enabling the virus to fuse to the host cell. Structure of the HIV spike glycoprotein is shown in FIG. 1.

The viral protein gp120 has been intensely focused upon in vaccine development research since it is the main point of contact and entry into host cells. However, the mechanism of HIV entry into cells includes masking of gp120 epitopes by covalently attached sugar moieties. It is only when the HIV virion is in close proximity to a host cell that the portion of gp120 that interacts with host cell receptors is unmasked. Likewise, glycoprotein gp41 is non-covalently associated with gp120 and becomes exposed only after gp120 binds to its target and undergoes a conformational change. The conformational change triggered by binding to the host cell allows gp41 to assist in the fusion of the virion to the host cell. Thus, gp41 has also received the attention of clinical research as a potential target for antiviral drugs. While gp120 and gp41 are highly immunogenic, the proteins can vary substantially between HIV types, groups, and/or clades. Moreover, the proteins frequently mutate to form antigenic variants and rapidly evolve to evade the host immune response.

Accordingly, the development of therapeutic monoclonal antibodies that can cross react with antigenic determinants on a large number of HIV types, groups, and clades is currently an area of intense investigation. The broadly neutralizing HIV antibodies, or bnAbs, are described in the literature and have been collected at the web site "Broadly Neutralizing Antibodies Electronic Resource," www.bnaber.org (Eroshkin A M, et al., *Nucleic Acids Res.* 42(1): D1133-9 (2014)).

The epitopes of the bnAbs are found on the heterotrimer HIV envelope spike, composed of gp41 and gp120 and the surrounding glycan layer. A broad range of spike epitopes, both linear and conformational, have been identified, and four epitopes bound by bnAbs have been extensively characterized: the membrane proximal external region (MPER), the CD4 binding site, the variable region 1/variable region 2 (V1/V2) loop and the variable region 3 (V3) loop (Hepler N L. et al. *PLOS Comp. Biol.* 10(9):e1003842 (2014)).

MPER is located on the gp41 protein in the base of the HIV spike (Montero M. et al. *MMBR* 72(1):54-84 (2008)). BnAbs interacting with the CD4 binding site on gp120 can mimic CD4 binding. For example, the binding of bnAb VCR01 to the CD4 binding site causes a conformational shift that is thought to disable the virus receptor thereby neutralizing the HIV virus (Scheid J F. et al., *Science* 333(6049):1633-7 (2011)). The V1/V2 loop on gp120 has been shown to be one of the most frequent epitopes for potent bnAbs (Moore P. L. et al. *J. Virol.* 69(9):5723-33 (2011)). The V3 loop on gp120 has been targeted by neutralizing antibodies in a quaternary-structure specific manner. The glycan shield can also contribute to the conformation of neutralizing HIV antibody epitopes and make direct contacts with bnAbs; conversely the glycans can inhibit antibody binding through steric hindrance.

HIV is thought to remain dormant in reservoir cells in various tissues throughout the body due to the immunoprivileged status of certain tissues, such as the central nervous system, the genitourinary tract, and lymphoid organs. (See, Iglesias-Ussel et al., *AIDS Rev.*, 13:13-29, 2011). It has been postulated that the gastrointestinal tract (GIT) is a primary target for HIV infection, and a major cellular reservoir due to the abundance of macrophages located at mucosal sites in the GIT. (See, Brown et al., *Clin. Vacc. Immunol.*, 21(11): 1469-1473, 2014). However, latently infected memory T cells are the largest and best understood reservoir for HIV. Even when treated with Highly Active Antiretroviral Therapy (HAART), the T cell reservoir alone has a remarkably long half-life (Finzi, D., et al. 1999. *Nature Med* 5:512-7) resulting in rapid rebound and virus reemergence upon cessation of therapy. It is believed that infection of some CD4+ T cells can be followed by transition of the infected T cell into a quiescent state and ultimately formation of a memory CD4+ T cell which contains an integrated genomic copy of the viral genome (proviral DNA) which is not expressed until a later time when transcription is triggered. Others believe that such reservoir cells are not be truly silent, but instead persistently or stochastically produce small amounts of virus. Memory T cells are ideal HIV reservoir cells since they are quiescent and do not undergo cell division, differentiation, or activation and their transcriptional machinery therefor exhibits only minimal activity. However, upon activation, memory T cells can produce large quantities of virus. Targeting of dormant HIV reservoirs is a subject of intensive study and represents the next major hurdle in managing and ultimately eliminating HIV infection. These HIV-infected reservoir cells are most often infected with mutated variants of the originally-infecting HIV virus. (See, Picker et al., *Nature*, 517:381-385, 2015).

Thus, chronically infected individuals, although not harboring detectable levels of expressed HIV nonetheless continue to carry HIV and the potential to succumb to HIV infection, or infect others, without further exposure to HIV. There is presently no publically available treatment known to clear chronic HIV infection. Available therapies merely halt further infection by precluding the virus from replicating. Various monoclonal antibodies and combination therapies have been investigated for the purpose of treating HIV, including chronic HIV infection, but none have been commercialized. Therefore, there remains a continuing need to develop new therapies targeting HIV, e.g., reservoir cells harboring dormant HIV in chronic HIV infection. Thus, there is a strong need for more potent treatments that are readily available and do not present cost barriers to clinical application and availability.

SUMMARY

Disclosed are various embodiments of multimeric binding molecules that possess specificity for binding one or more HIV antigens, e.g., gp120/gp41 antigens.

This disclosure provides a multimeric binding molecule that includes at least two bivalent binding units, or variants or fragments thereof; where each binding unit includes at least two antibody heavy chain constant regions or fragments thereof, where each heavy chain constant region or fragment thereof is associated with an antigen binding domain, where at least one antigen binding domain specifically binds to a human immunodeficiency virus (HIV) antigen expressed on the surface of viral particles, on the surface of HIV-infected cells, or a combination thereof, and where the binding molecule is more potent in preventing, controlling or treating HIV infection than a corresponding reference single binding unit molecule including the HIV antigen binding domain. The corresponding reference single binding unit molecule can be, e.g., an IgG antibody.

In certain aspects, the at least one antigen binding domain specifically binds to the HIV spike protein, e.g., to an epitope on gp120, gp41, or a combination thereof. In certain aspects the epitope is situated in the immunodominant region of gp41, the MPER, the CD4 binding site, the V1/V2 loop, the V3 loop, the carbohydrates associated with these regions, or a combination thereof.

In certain aspects, the provided binding molecule is multispecific, e.g., bispecific, including at least two non-identical antigen binding domains. The two non-identical antigen binding domains can specifically bind, without limitation, to different epitopes of a common HIV antigen, to different HIV antigens, or to an HIV antigen and a heterologous antigen.

In certain aspects, the provided binding molecule is a dimeric binding molecule that includes two bivalent IgA binding units or fragments thereof and a J-chain or fragment thereof or variant thereof. According to these aspects, each binding unit can include two IgA heavy chain constant regions or fragments thereof each associated with an antigen binding domain. In certain aspects a dimeric binding molecule as provided herein can further include an associated secretory component, or fragment or variant thereof. A dimeric binding molecule as provided herein can include the Cα2 domain and/or the Cα3-tp domain if the IgA constant region, and can in some aspects further include the Cα1 domain. In certain aspects the IgA heavy chain constant region is a human IgA heavy chain constant region. An IgA-based dimeric binding molecule as provided herein can include, in some aspects, two IgA heavy chains each including a VH situated amino terminal to the IgA constant region or fragment thereof, and two immunoglobulin light chains each including a VL situated amino terminal to an immunoglobulin light chain constant region.

In certain aspects the provided binding molecule is a pentameric or a hexameric binding molecule including five or six bivalent IgM binding units, respectively, where each binding unit includes two IgA heavy chain constant regions or fragments thereof each associated with an antigen binding domain. In certain aspects the IgM heavy chain constant regions or fragments thereof can each include a Cμ3 domain and a Cμ4-tp domain and can in some aspects, further include a Cμ2 domain, a Cμ1 domain, or any combination thereof. Where the provided binding molecule is pentameric, it can further include a J-chain, or fragment thereof, or variant thereof. In certain aspects, the IgM heavy chain constant region is a human IgM constant region.

In certain aspects, the disclosure provides a bi- or multi-specific dimeric or pentameric binding molecule that includes a J-chain. The J-chain can be a modified J-chain including, e.g., a binding domain. In certain aspects the modified J-chain is derived from a human J-chain, and can include the amino acid sequence 23 to 159 of SEQ ID NO: 2, or a functional fragment thereof. In certain aspects the binding domain is a polypeptide sequence fused in frame with the J-chain or fragment thereof, either with or without a peptide linker. In certain aspects the peptide linker can include at least 5 amino acids, but no more than 25 amino acids. In certain aspects the peptide can consist of SEQ ID NO: 101, SEQ ID NO: 102, SEQ ID NO: 103, or SEQ ID NO: 104. In certain aspects the modified J-chain can include the formula $X[L_n]J$ or $J[L_n]X$, where J includes a mature native J-chain or functional fragment thereof, X includes a heterologous binding domain, and $[L_n]$ is a linker sequence consisting of n amino acids, where n is a positive integer from 1 to 100, 1 to 50, or 1 to 25. In certain aspects N is 5, 10, 15, or 20.

In certain aspects the binding domain is situated at the C-terminus of the J-chain or fragment thereof. In certain aspects the binding domain is situated at the N-terminus of the J-chain or fragment thereof. In certain aspects the binding domain is inserted within the J-chain or fragment thereof. In certain aspects the binding domain of the modified J-chain is an antibody or antigen binding fragment thereof, e.g., an F(ab')$_2$, an F(ab)$_2$, an Fab', an Fab, an Fv, an scFv, or a single domain antibody, e.g., a VHH. In certain aspects, the binding domain of the modified J-chain binds to one or more effector cells, e.g., T-cells, natural killer (NK) cells, macrophages and/or neutrophils. Where the effector cell is a T-cell, the binding domain can bind, e.g., to CD3 or CD8 on the T-cell. Where the effector cell is an NK cells, the binding domain can bind, e.g., to one or more of CD16, CD64, and/or NKG2D on the NK cell. Where the effector cell is a macrophage, the binding domain can bind to, e.g., CD14 on the macrophage. Where the effector cell is a neutrophil, the binding domain can bind to, e.g., CD16b and/or CD177 on the neutrophil. In certain aspects, the heterologous polypeptide includes SEQ ID NO: 105, SEQ ID NO: 106, SEQ ID NO: 107, or a combination thereof. In certain aspects the modified J-chain includes SEQ ID NO: 108, SEQ ID NO: 109, SEQ ID NO: 110, SEQ ID NO: 111, or a combination thereof. In certain aspects the modified J-chain can further include a signal peptide.

In certain aspects, each binding unit of a binding molecule as provided herein can include two heavy chains each including a VH situated amino terminal to the constant region or fragment thereof, and two immunoglobulin light chains each including a VL situated amino terminal to an immunoglobulin light chain constant region. In certain aspects, at least one binding unit includes two antigen binding domains that specifically bind to an HIV antigen expressed on the surface of viral particles, on the surface of HIV-infected cells, or a combination thereof. In some aspects the two heavy chains within the binding unit can be identical. In some aspects the two light chains within the binding unit are identical. The two light chain constant regions can be, e.g., human lambda constant regions or human kappa constant regions.

In certain aspects the binding molecule as provided herein can include at least three, at least four, at least five, at least six, at least seven, at least eight, at least nine, at least ten, at least eleven, or twelve antigen binding domains that specifically bind to an HIV antigen expressed on the surface of viral particles, on the surface of HIV-infected cells, or a combination thereof. In certain aspects at least two, at least three, at least four, at least five, or at least six of the binding units are identical. In certain aspects at least one antigen binding domain of the binding molecule as provided herein can specifically bind to an HIV spike protein expressed or presented on the surface of HIV-infected reservoir cells, e.g., a cell in which HIV antigens are expressed at a low level compared to HIV-infected cells.

In certain aspects at least one antigen binding domain of the binding molecule as provided herein includes an antibody heavy chain variable region (VH) and an antibody light chain variable region (VL), where the VH and VL can include the HCDR1, HCDR2, and HCDR3 regions, or HCDR1, HCDR2, and HCDR3 regions containing one or two single amino acid substitutions, and the LCDR1, LCDR2, and LCDR3 regions, or LCDR1, LCDR2, and LCDR3 containing one or two single amino acid substitutions, of the VH and VL amino acid sequences of SEQ ID NO: 5 and SEQ ID NO: 6, SEQ ID NO: 7 and SEQ ID NO: 8, SEQ ID NO: 9 and SEQ ID NO: 10, SEQ ID NO: 11 and SEQ ID NO: 12, SEQ ID NO: 13 and SEQ ID NO: 14, SEQ ID NO: 15 and SEQ ID NO: 16, SEQ ID NO: 17 and SEQ ID NO: 18, SEQ ID NO: 19 and SEQ ID NO: 20, SEQ ID NO: 21 and SEQ ID NO: 22, SEQ ID NO: 23 and SEQ ID NO: 24, SEQ ID NO: 25 and SEQ ID NO: 26, SEQ ID NO: 27 and SEQ ID NO: 28, SEQ ID NO: 29 and SEQ ID NO: 30, SEQ ID NO: 31 and SEQ ID NO: 32, SEQ ID NO: 33 and SEQ ID NO: 34, SEQ ID NO: 35 and SEQ ID NO: 36, SEQ ID NO: 37 and SEQ ID NO: 38, SEQ ID NO: 39 and SEQ ID NO: 40, SEQ ID NO: 41 and SEQ ID NO: 42, SEQ ID NO: 43 and SEQ ID NO: 44, SEQ ID NO: 45 and SEQ ID NO: 46, SEQ ID NO: 47 and SEQ ID NO: 48, SEQ ID NO: 49 and SEQ ID NO: 50, SEQ ID NO: 51 and SEQ ID NO: 52, SEQ ID NO: 53 and SEQ ID NO: 54, SEQ ID NO: 55 and SEQ ID NO: 56, SEQ ID NO: 57 and SEQ ID NO: 58, SEQ ID NO: 59 and SEQ ID NO: 60, SEQ ID NO: 61 and SEQ ID NO: 62, SEQ ID NO: 63 and SEQ ID NO: 64, SEQ ID NO: 65 and SEQ ID NO: 66, SEQ ID NO: 67 and SEQ ID NO: 68, SEQ ID NO: 69 and SEQ ID NO: 70, SEQ ID NO: 71 and SEQ ID NO: 72, SEQ ID NO: 73 and SEQ ID NO: 74, SEQ ID NO: 75 and SEQ ID NO: 6, SEQ ID NO: 77 and SEQ ID NO: 78, SEQ ID NO: 79 and SEQ ID NO: 80, SEQ ID NO: 81 and SEQ ID NO: 82, SEQ ID NO: 83 and SEQ ID NO: 84, SEQ ID NO: 85 and SEQ ID NO: 86, SEQ ID NO: 87 and SEQ ID NO: 88, SEQ ID NO: 89 and SEQ ID NO: 90, SEQ ID NO: 91 and SEQ ID NO: 92, SEQ ID NO: 93 and SEQ ID NO: 94, SEQ ID NO: 95 and SEQ ID NO: 96, SEQ ID NO: 97 and SEQ ID NO: 98, or SEQ ID NO: 99 and SEQ ID NO: 100, respectively.

In certain aspects, at least one antigen binding domain of the binding molecule as provided herein includes an antibody heavy chain variable region (VH) and an antibody light chain variable region (VL), where the VH and VL include, respectively, amino acid sequences that are at least 80%, at least 85%, at least 90%, at least 95% or 100% identical to amino acid sequences of SEQ ID NO: 5 and SEQ ID NO: 6, SEQ ID NO: 7 and SEQ ID NO: 8, SEQ ID NO: 9 and SEQ ID NO: 10, SEQ ID NO: 11 and SEQ ID NO: 12, SEQ ID NO: 13 and SEQ ID NO: 14, SEQ ID NO: 15 and SEQ ID NO: 16, SEQ ID NO: 17 and SEQ ID NO: 18, SEQ ID NO: 19 and SEQ ID NO: 20, SEQ ID NO: 21 and SEQ ID NO: 22, SEQ ID NO: 23 and SEQ ID NO: 24, SEQ ID NO: 25 and SEQ ID NO: 26, SEQ ID NO: 27 and SEQ ID NO: 28, SEQ ID NO: 29 and SEQ ID NO: 30, SEQ ID NO: 31 and SEQ ID NO: 32, SEQ ID NO: 33 and SEQ ID NO: 34, SEQ ID NO: 35 and SEQ ID NO: 36, SEQ ID NO: 37 and SEQ ID NO: 38, SEQ ID NO: 39 and SEQ ID NO: 40, SEQ ID NO: 41 and SEQ ID NO: 42, SEQ ID NO: 43 and SEQ ID NO: 44, SEQ ID NO: 45 and SEQ ID NO: 46, SEQ ID NO: 47 and SEQ ID NO: 48, SEQ ID NO: 49 and SEQ ID NO: 50, SEQ ID NO: 51 and SEQ ID NO: 52, SEQ ID NO: 53 and SEQ ID NO: 54, SEQ ID NO: 55 and SEQ ID NO: 56, SEQ ID NO: 57 and SEQ ID NO: 58, SEQ ID NO: 59 and SEQ ID NO: 60, SEQ ID NO: 61 and SEQ ID NO: 62, SEQ ID NO: 63 and SEQ ID NO: 64, SEQ ID NO: 65 and SEQ ID NO: 66, SEQ ID NO: 67 and SEQ ID NO: 68, SEQ ID NO: 69 and SEQ ID NO: 70, SEQ ID NO: 71 and SEQ ID NO: 72, SEQ ID NO: 73 and SEQ ID NO: 74, SEQ ID NO: 75 and SEQ ID NO: 6, SEQ ID NO: 77 and SEQ ID NO: 78, SEQ ID NO: 79 and SEQ ID NO: 80, SEQ ID NO: 81 and SEQ ID NO: 82, SEQ ID NO: 83 and SEQ ID NO: 84, SEQ ID NO: 85 and SEQ ID NO: 86, SEQ ID NO: 87 and SEQ ID NO: 88, SEQ ID NO: 89 and SEQ ID NO: 90, SEQ ID NO: 91 and SEQ ID NO: 92, SEQ ID NO: 93 and SEQ ID NO: 94, SEQ ID NO: 95 and SEQ ID NO: 96, SEQ ID NO: 97 and SEQ ID NO: 98, or SEQ ID NO: 99 and SEQ ID NO: 100.

In certain aspects the binding molecule as provided herein is more potent in preventing, controlling or treating HIV infection, enhancing viral clearance, controlling HIV infectivity, and/or controlling HIV growth than a corresponding reference single binding unit molecule including the HIV-binding antigen binding domain. In certain aspects the binding molecule can be more potent in neutralizing HIV, can bind to and neutralize more diverse HIV variants or clades, or a combination thereof, than a corresponding reference single binding unit molecule that includes the HIV-binding antigen binding domain. In certain aspects the binding molecule can effect more potent antibody mediated, complement mediated, or cell mediated, e.g., T-cell mediated, killing of HIV infected cells than a corresponding reference single binding unit molecule that includes the HIV-binding antigen binding domain. In certain aspects the binding molecule can provide equivalent benefit at a lower dosage than a corresponding reference single binding unit molecule that includes the HIV-binding antigen binding domain.

The disclosure further provides an isolated IgM antibody or fragment thereof that includes a J-chain, or functional fragment or variant thereof, and five binding units, each including two heavy chains and two light chains, where each heavy chain or fragment thereof includes a human Mu constant region or fragment thereof, and the heavy chain variable region amino acid sequence SEQ ID NO: 7, and where each light chain includes a human kappa constant region and the light chain variable region amino acid sequence SEQ ID NO: 8; where the antibody or fragment thereof can assemble into a pentameric IgM antibody that can specifically bind to the CD4 binding site of the HIV spike glycoprotein. In certain aspects the IgM antibody or fragment thereof can include the heavy chain amino acid sequence SEQ ID NO: 113 and the light chain amino acid sequence SEQ ID NO: 114. In certain aspects the J-chain can include amino acids 23 to 159 of the amino acid sequence SEQ ID NO: 2 or a functional fragment thereof. In certain aspects the J-chain or fragment thereof can be a modified J-chain that further includes a heterologous polypeptide that can be directly or indirectly fused to the J-chain. In certain aspects the heterologous polypeptide can be fused to the J-chain or fragment thereof via a peptide linker, e.g., a peptide linker that includes at least 5 amino acids, but no more than 25 amino acids, e.g., a peptide linker consisting of SEQ ID NO: 101, SEQ ID NO: 102, SEQ ID NO: 103, or SEQ ID NO: 104. In certain aspects the heterologous polypeptide can be fused to the N-terminus of the J-chain or fragment thereof, the C-terminus of the J-chain or fragment thereof, or to both the N-terminus and C-terminus of the J-chain or fragment thereof. In certain aspects the heterologous polypeptide can include a binding domain, e.g., the heterologous polypeptide can be an antibody or antigen binding fragment thereof, e.g., a scFv fragment, e.g., a scFv fragment that can specifically bind to CD3. In certain aspects the modified J-chain can include a heterologous polypeptide that includes the amino acid sequence SEQ ID NO: 108, SEQ ID NO: 109, SEQ ID NO: 110, or SEQ ID NO: 111. In certain aspects the modified J-chain can further include a signal peptide.

The disclosure further provides a composition that includes the binding molecule or the IgM antibody provided herein.

In addition, the disclosure provides a polynucleotide that includes a nucleic acid sequence encoding a polypeptide subunit of the binding molecule as provided herein, where the polypeptide subunit includes the IgM heavy chain constant region and at least the antibody VH portion of an antibody binding domain that specifically binds to an HIV spike protein antigen expressed on the surface of viral particles, on the surface if HIV-infected cells, or a combination thereof. In certain aspects the polypeptide subunit can include a human IgM constant region or fragment thereof fused to the C-terminal end of a VH domain that includes: the HCDR1, HCDR2, and HCDR3 domains, or the HCDR1, HCDR2, and HCDR3 domains containing one or two single amino acid substitutions in one or more HCDRs, of the VH amino acid sequence SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99; or an amino acid sequence at least 80%, at least 85%, at least 90%, at least 95% or 100% identical to the SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99.

In addition, the disclosure provides a polynucleotide that includes a nucleic acid sequence encoding a polypeptide subunit of the binding molecule as provided herein, where the polypeptide subunit includes the antibody VL portion of an antibody binding domain that specifically binds to an HIV spike protein antigen expressed on the surface of viral particles, on the surface of HIV-infected cells, or a combination thereof. In certain aspects, the polypeptide subunit includes a human antibody light chain constant region or fragment thereof fused to the C-terminal end of a VL that includes: the LCDR1, LCDR2, and LCDR3 domains, or the LCDR1, LCDR2, and LCDR3 domains containing one or two single amino acid substitutions in one or more LCDRs, of the VL amino acid sequence SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 6, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100; or an amino acid sequence at least 80%, at least 85%, at least 90%, at least 95% or 100% identical to SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 6, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100.

The disclosure further provides a composition that includes VH and VL-containing polynucleotide as provided herein. In certain aspects the polynucleotides are situated on the same vector. In certain aspects the polynucleotides are situated on separate vectors. In certain aspects the composition further includes a polynucleotide that includes a nucleic acid sequence encoding a J-chain, a modified J-chain, fragment thereof, or a variant thereof. In certain aspects, the polynucleotides are situated on at least two separate vectors. In certain aspects, the polynucleotides are situated on the same vector. The disclosure further provides the vector or vectors as described, a host cell that includes the provided polynucleotide or the provided polynucleotide composition, or the provided vector or vectors. The disclosure further provides a method of producing the binding molecule provided herein, where the method includes culturing the provided host cell, and recovering the binding molecule.

The disclosure further provides a method of preventing, controlling, or treating HIV infection, or controlling human immunodeficiency virus (HIV) infectivity, where the method includes contacting a mixture of HIV and HIV-susceptible cells with the binding molecule provided herein; where the binding molecule is more potent in preventing, controlling or treating HIV infection, or in controlling HIV infectivity, than a corresponding reference single binding unit molecule including the HIV-binding antigen binding domain. In certain aspects, the binding molecule exhibits increased potency in neutralizing HIV in infected cells, as compared with the single binding unit molecule.

The disclosure further provides a method of treating an human immunodeficiency virus (HIV) infection in a patient, including administering to a patient infected with HIV the binding molecule as provided herein; where the binding molecule is stronger, more potent in preventing, controlling or treating HIV infection or controlling HIV infectivity, or requires a lower binding molecule dose than a corresponding reference single binding unit molecule including the HIV-binding antigen binding domain. According to this method, the binding molecule can exhibit increased potency in (i) reducing the infectivity of an HIV virion, (ii) reducing the number of HIV-infected cells, (iii) preventing HIV infection, (iv) enhancing viral clearance, (v) improving the signs and symptoms of HIV infection, or (vi) any combination thereof, as compared with the corresponding reference single binding unit molecule. In certain aspects, the corresponding reference single binding unit molecule is an IgG antibody.

BRIEF DESCRIPTION OF THE FIGURES

FIG. 3A: 1 µg/ml antigen coating; FIG. 3B: 0.8 µg/ml antigen coating; FIG. 3C: 0.6 µg/ml antigen coating; FIG. 3D: 0.4 µg/ml antigen coating; FIG. 3E: 0.2 µg/ml antigen coating; FIG. 3F: 0.1 µg/ml antigen coating.

FIG. 6: Neutralization of HIV isolates from multiple clades by HIV02 IgM+J.

FIG. 7: Antigen-dependent T-cell activation by HIV02 IgM+V10J.

FIG. 9: Antigen-dependent T-cell activation by SEC-purified HIV02 IgM+V10J.

DETAILED DESCRIPTION

Definitions

Figure 1:
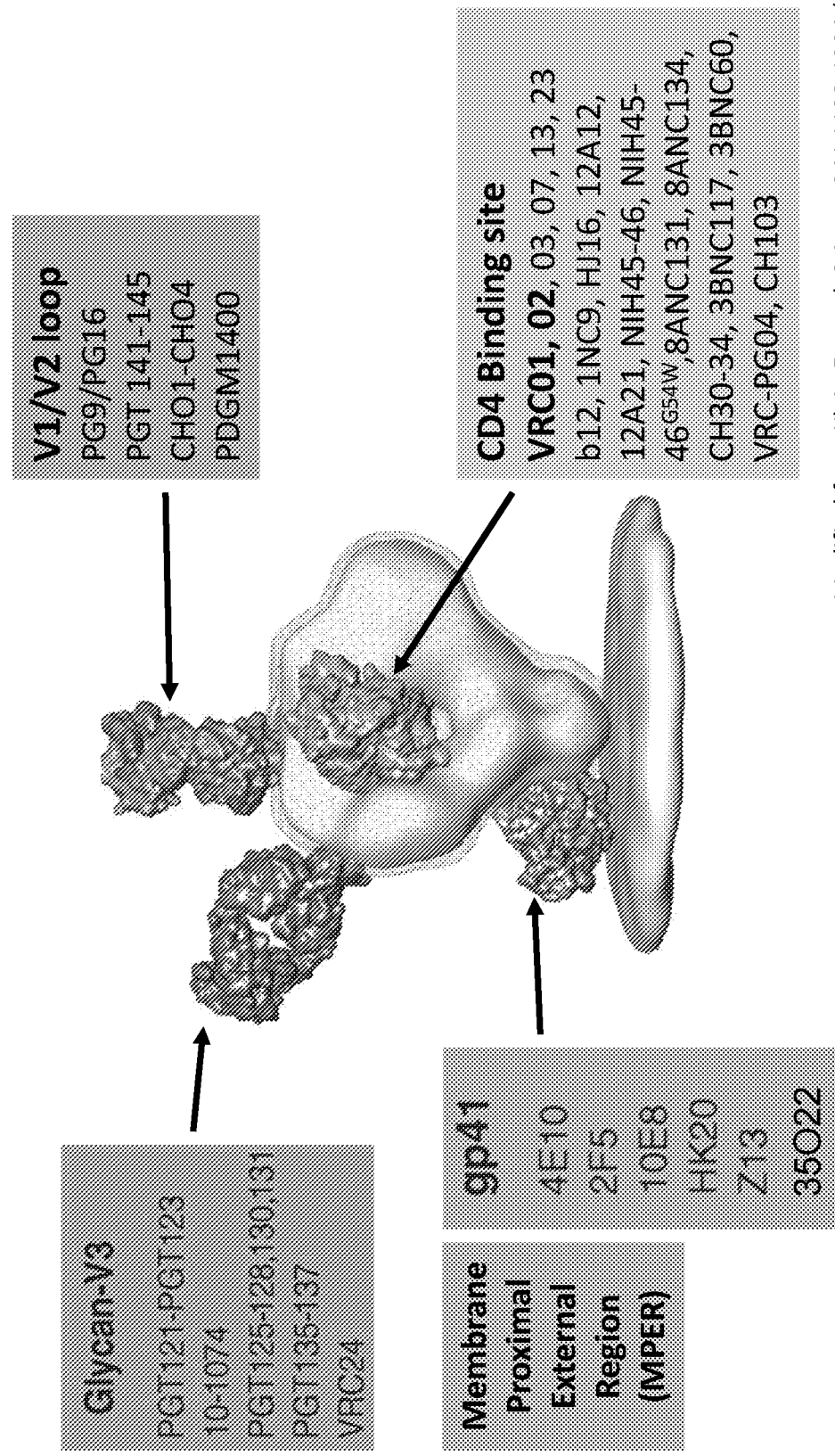
FIG. 1: Illustration of various antibody binding sites on the HIV spike glycoprotein (Modified from Modified from Klein F., et al. *Science* 341:1199-1204 (2013)).

The term "a" or "an" entity refers to one or more of that entity; for example, "a binding molecule," is understood to represent one or more binding molecules. As such, the terms "a" (or "an"), "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are well-understood by persons of ordinary skill in the art as being "naturally-occurring," or that are, or might be at any time, determined or interpreted by a judge or an administrative or judicial body to be, "naturally-occurring."

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, and derivatization by known protecting/blocking groups, proteolytic cleavage, or modification by non-naturally occurring amino acids. A polypeptide can be derived from a biological source or produced by recombinant technology, but is not necessarily translated from a designated nucleic acid sequence. It can be generated in any manner, including by chemical synthesis.

A polypeptide as disclosed herein can be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides can have a defined three-dimensional structure, although they do not necessarily have such structure. Polypeptides with a defined three-dimensional structure are referred to as folded, and polypeptides that do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid, e.g., a serine or an asparagine.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated as disclosed herein, as are native or recombinant polypeptides that have been separated, fractionated, or partially or substantially purified by any suitable technique.

As used herein, the term "non-naturally occurring" polypeptide, or any grammatical variants thereof, is a conditional term that explicitly excludes, but only excludes, those forms of the polypeptide that are well-understood by persons of ordinary skill in the art as being "naturally-occurring," or that are, or might be at any time, determined or interpreted by a judge or an administrative or judicial body to be, "naturally-occurring."

Other polypeptides disclosed herein are fragments, derivatives, analogs, or variants of the foregoing polypeptides, and any combination thereof. The terms "fragment," "variant," "derivative" and "analog" as disclosed herein include any polypeptides that retain at least some of the properties of the corresponding native antibody or polypeptide, for example, specifically binding to an antigen. Fragments of polypeptides include, for example, proteolytic fragments, as well as deletion fragments, in addition to specific antibody fragments discussed elsewhere herein. Variants of, e.g., a polypeptide include fragments as described above, and also polypeptides with altered amino acid sequences due to amino acid substitutions, deletions, or insertions. In certain aspects, variants can be non-naturally occurring. Non-naturally occurring variants can be produced using art-known mutagenesis techniques. Variant polypeptides can comprise conservative or non-conservative amino acid substitutions, deletions or additions. Derivatives are polypeptides that have been altered so as to exhibit additional features not found on the original polypeptide. Examples include fusion proteins. Variant polypeptides can also be referred to herein as "polypeptide analogs." As used herein a "derivative" of a polypeptide can also refer to a subject polypeptide having one or more amino acids chemically derivatized by reaction of a functional side group. Also included as "derivatives" are those peptides that contain one or more derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

A "conservative amino acid substitution" is one in which one amino acid is replaced with another amino acid having a similar side chain. Families of amino acids having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the sequences of the polypeptides and antibodies of the present disclosure do not abrogate the binding of the polypeptide or antibody containing the amino acid sequence, to the antigen to which the binding molecule binds. Methods of identifying nucleotide and amino acid conservative substitutions that do not eliminate antigen binding are well-known in the art (see, e.g., Brummell et al., *Biochem.* 32:1180-1 187 (1993); Kobayashi et al., *Protein Eng.* 12(10):879-884 (1999); and Burks et al., *Proc. Natl. Acad. Sci. USA* 94:.412-417 (1997)).

The term "polynucleotide" is intended to encompass a singular nucleic acid as well as plural nucleic acids, and refers to an isolated nucleic acid molecule or construct, e.g., messenger RNA (mRNA), cDNA, or plasmid DNA (pDNA). A polynucleotide can comprise a conventional phosphodiester bond or a non-conventional bond (e.g., an amide bond, such as found in peptide nucleic acids (PNA)). The terms "nucleic acid" or "nucleic acid sequence" refer to any one or more nucleic acid segments, e.g., DNA or RNA fragments, present in a polynucleotide.

By an "isolated" nucleic acid or polynucleotide is intended any form of the nucleic acid or polynucleotide that is separated from its native environment. For example, gel-purified polynucleotide, or a recombinant polynucleotide encoding a polypeptide contained in a vector would be considered to be "isolated." Also, a polynucleotide segment, e.g., a PCR product, that has been engineered to have restriction sites for cloning is considered to be "isolated." Further examples of an isolated polynucleotide include recombinant polynucleotides maintained in heterologous host cells or purified (partially or substantially) polynucleotides in a non-native solution such as a buffer or saline. Isolated RNA molecules include in vivo or in vitro RNA transcripts of polynucleotides, where the transcript is not one that would be found in nature. Isolated polynucleotides or nucleic acids further include such molecules produced synthetically. In addition, polynucleotide or a nucleic acid can be or can include a regulatory element such as a promoter, ribosome binding site, or a transcription terminator.

As used herein, a "non-naturally occurring" polynucleotide, or any grammatical variants thereof, is a conditional definition that explicitly excludes, but only excludes, those forms of the polynucleotide that are well-understood by persons of ordinary skill in the art as being "naturally-occurring," or that are, or that might be at any time, determined or interpreted by a judge or an administrative or judicial body to be, "naturally-occurring."

As used herein, a "coding region" is a portion of nucleic acid that consists of codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode an immunoglobulin heavy chain variable region and an immunoglobulin light chain variable region. In addition, a vector, polynucleotide, or nucleic acid can include heterologous coding regions, either fused or unfused to another coding region. Heterologous coding regions include without limitation, those encoding specialized elements or motifs, such as a secretory signal peptide or a heterologous functional domain.

In certain embodiments, the polynucleotide or nucleic acid is DNA. In the case of DNA, a polynucleotide comprising a nucleic acid that encodes a polypeptide normally can include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA in predetermined cells. Other transcription control elements, besides a promoter, for example enhancers, operators, repressors, and transcription termination signals, can be operably associated with the polynucleotide to direct cell-specific transcription.

A variety of transcription control regions are known to those skilled in the art. These include, without limitation, transcription control regions that function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide can be RNA, for example, in the form of messenger RNA (mRNA), transfer RNA, or ribosomal RNA.

Polynucleotide and nucleic acid coding regions can be associated with additional coding regions that encode secretory or signal peptides, which direct the secretion of a polypeptide encoded by a polynucleotide as disclosed herein. According to the signal hypothesis, proteins secreted by mammalian cells have a signal peptide or secretory leader sequence that is cleaved from the mature protein once export of the growing protein chain across the rough endoplasmic reticulum has been initiated. Those of ordinary skill in the art are aware that polypeptides secreted by vertebrate cells can have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, can be used. For example, the wild-type leader sequence can be substituted with the leader sequence of human tissue plasminogen activator (TPA) or mouse β-glucuronidase.

Disclosed herein are certain binding molecules, or antigen binding fragments, variants, or derivatives thereof. Unless specifically referring to full-sized antibodies, the term "binding molecule" encompasses full-sized antibodies as well as antigen binding subunits, fragments, variants, analogs, or derivatives of such antibodies, e.g., engineered antibody molecules or fragments that bind antigen in a manner similar to antibody molecules, but which use a different scaffold.

As used herein, the term "binding molecule" refers in its broadest sense to a molecule that specifically binds to a receptor, e.g., an epitope or an antigenic determinant. As described further herein, a binding molecule can comprise one or more "antigen binding domains" described herein. A non-limiting example of a binding molecule is an antibody or fragment thereof that retains antigen-specific binding.

The terms "binding domain" and "antigen binding domain" are used interchangeably herein and refer to a region of a binding molecule that is necessary and sufficient to specifically bind to an epitope. For example, an "Fv," e.g., a variable heavy chain and variable light chain of an antibody, either as two separate polypeptide subunits or as a single chain, is considered to be a "binding domain."

Other antigen binding domains include, without limitation, the variable heavy chain (VHH) of an antibody derived from a camelid species, or six immunoglobulin complementarity determining regions (CDRs) expressed in a fibronectin scaffold. A "binding molecule" as described herein can include one, two, three, four, five, six, seven, eight, nine, ten, eleven, twelve or more "antigen binding domains."

The terms "antibody" and "immunoglobulin" can be used interchangeably herein. An antibody (or a fragment, variant, or derivative thereof as disclosed herein) includes at least the variable region of a heavy chain (for camelid species) or at least the variable regions of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988). Unless otherwise stated, the term "antibody" encompasses anything ranging from a small antigen binding fragment of an antibody to a full sized antibody, e.g., an IgG antibody that includes two complete heavy chains and two complete light chains, an IgA antibody that includes four complete heavy chains and four complete light chains and can include a J-chain and/or a secretory component, or an IgM antibody that includes ten or twelve complete heavy chains and ten or twelve complete light chains and can include a J-chain.

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4 or α1-α2)). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, $IgA_2$, etc. are well characterized and are known to confer functional specialization. Modified versions of each of these classes and isotypes are readily discernible to the skilled artisan in view of the instant disclosure and, accordingly, are within the scope of this disclosure.

Light chains are classified as either kappa or lambda (κ, λ). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. The basic structure of certain antibodies, e.g., IgG antibodies, includes two heavy chain subunits and two light chain subunits covalently connected via disulfide bonds to form a "Y" structure, also referred to herein as an "H2L2" structure, or a "binding unit."

The term "binding unit" is used herein to refer to the portion of a binding molecule, e.g., an antibody or antigen binding fragment thereof that corresponds to a standard immunoglobulin structure, i.e., two heavy chains or fragments thereof and two light chains or fragments thereof, or two heavy chains or fragments thereof derived, e.g., from a camelid or condricthoid antibody. In certain aspects, e.g., where the binding molecule is a bivalent, single binding unit IgG antibody or antigen binding fragment thereof, the terms "binding molecule" and "binding unit" are equivalent. In other aspects, e.g., where the binding molecule is an IgA dimer, an IgM pentamer, or an IgM hexamer, the binding molecule is "multimeric" and comprises two or more "binding units." Two in the case of an IgA dimer, or five or six in the case of an IgM pentamer or hexamer, respectively. A binding unit need not include full-length antibody heavy and light chains, but will typically be bivalent, i.e., will include two "antigen binding domains," as defined below. Certain binding molecules provided in this disclosure are pentameric or hexameric, and include five or six bivalent binding units that include IgM constant regions or fragments thereof.

As used herein, a binding molecule comprising two or more binding units, e.g., two, five, or six binding units, can be referred to as "multimeric." The term "multimeric" means possessing more than one unit. Thus, for example, a "multimeric binding molecule" will possess more than one binding unit. A multimeric binding molecule can possess two, three four, five or even six or more binding units. A "dimeric binding molecule" includes two binding units and is typically a dimeric IgA molecule that further comprises a J-chain. A "pentameric binding molecule" is typically a pentameric IgM binding molecule that further comprises a J-chain. A "hexameric binding molecule" is typically a hexameric IgM binding molecule. In contrast, a "single binding unit molecule" can be, e.g., an IgG antibody.

The terms "wild-type (WT) J-chain," "native sequence J-chain" or "native J-chain" as used herein refer to a J-chain of native sequence IgM or IgA antibodies of any animal species, including mature human J-chain, the amino acid sequence of which is presented as SEQ ID NO: 2.

The term "modified J-chain" is used herein to refer to variants of a native J-chain polypeptide. A modified J-chain can be a full-length mature J-chain polypeptide or a functional fragment thereof, and can include, without limitation, amino acid insertions, deletions, substitutions, non-amino acid modifications such as glycosylation or lipidation. Moreover, a modified J-chain can include a heterologous moiety such as a binding moiety, either introduced into the J-chain amino acid sequence as a fusion protein, or attached or conjugated by other techniques, such as disulfide bonding, or chemical conjugation. A modified J-chain is typically functional, in that the modifications do not interfere with efficient polymerization of IgM or IgA and binding of such polymers to a target. Exemplary modified J-chains are described elsewhere herein and in PCT Publication No. WO 2015/153912, which is incorporated herein by reference in its entirety. The term "modified human J-chain" encompasses, without limitation, a native sequence human J-chain of the amino acid sequence of SEQ ID NO: 2 or functional fragment thereof modified as above, e.g., by the introduction of a heterologous moiety, e.g., a heterologous polypeptide, e.g., an additional desired binding domain.

The terms "valency," "bivalent," "multivalent" and grammatical equivalents, refer to the number of antigen binding domains in given binding molecule or binding unit. For example, the terms "bivalent", "tetravalent", and "hexavalent" in reference to a given binding molecule, e.g., an IgM antibody or fragment thereof, denote the presence of two antigen binding domains, four antigen binding domains, and six antigen binding domains, respectively. In a typical IgM-derived binding molecule, each binding unit is bivalent, whereas the binding molecule itself can have 10 or 12 valencies. A bivalent or multivalent binding molecule can be monospecific, i.e., all of the antigen binding domains are the same, or can be bispecific or multispecific, e.g., where two or more antigen binding domains are different, e.g., bind to different epitopes on the same antigen, or bind to entirely different antigens.

The term "epitope" includes any molecular determinant capable of specific binding to an antibody. In certain aspects, an epitope can include chemically active surface groupings of molecules such as amino acids, sugar side chains, phosphoryl, or sulfonyl, and, in certain aspects, can have three dimensional structural characteristics, and or specific charge characteristics. An epitope is a region of a target that is bound by an antibody.

"Multispecific binding molecules or antibodies" or "bispecific binding molecules or antibodies" refer to binding molecules, antibodies, or antigen binding fragments thereof that have the ability to specifically bind to two or more different epitopes on the same or different target(s). "Monospecific" refers to the ability to bind only one epitope.

The term "target" is used in the broadest sense to include substances that can be bound by a binding molecule. A target can be, e.g., a polypeptide, a nucleic acid, a carbohydrate, a lipid, or other molecule. Moreover, a "target" can, for example, be a cell, an organ, or an organism that comprises an epitope bound that can be bound by a binding molecule.

Both the light and heavy chains are divided into regions of structural and functional homology. The terms "constant" and "variable" are used functionally. In this regard, it will be appreciated that the variable regions (which can be called "variable domains" interchangeably herein) of both the variable light (VL) and variable heavy (VH) chain portions determine antigen recognition and specificity. Conversely, the constant domains of the light chain (CL) and the heavy chain (e.g., CH1, CH2 or CH3) confer biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 (or CH4 in the case of IgM) and CL domains are at the carboxy-terminus of the heavy and light chain, respectively.

A "full length IgM antibody heavy chain" is a polypeptide that includes, in N-terminal to C-terminal direction, an antibody heavy chain variable region (VH), an antibody constant heavy chain constant domain 1 (CM1 or Cµ1), an antibody heavy chain constant domain 2 (CM2 or Cµ2), an antibody heavy chain constant domain 3 (CM3 or Cµ3), and an antibody heavy chain constant domain 4 (CM4 or Cµ4), which can also include a tailpiece.

A "full length IgA antibody heavy chain" is a polypeptide that includes, in N-terminal to C-terminal direction, an antibody heavy chain variable region ($V_H$), an antibody constant heavy chain constant domain 1 (CA1 or Cα1), an antibody heavy chain constant domain 2 (CA2 or Cα2), an antibody heavy chain constant domain 3 (CA3 or Cα3), and a tailpiece and can be either an IgA1 or IgA2. The structure of monomeric, dimeric (J-chain-containing) and secretory IgA is described, e.g., in Woof, J M and Russell, M W, *Mucosal Immunology* 4:590-597 (2011).

Both IgA and IgM possess an 18-amino acid extension in the C terminus called the "tail-piece" (tp). The IgM (µtp) and IgA (αtp) tail-pieces differ at seven amino acid positions. The IgM and IgA tail-piece is highly conserved among various animal species. The conserved penultimate cysteine residue in the IgA and IgM tail-pieces has been demonstrated to be involved in polymerization. Both tail-pieces contain an N-linked carbohydrate addition site, the presence of which is required for dimer formation in IgA and J-chain incorporation and pentamer formation in IgM. However, the structure and composition of the N-linked carbohydrates in the tail-pieces differ, suggesting differences in the accessibility of the glycans to processing by glycosyltransferases.

As indicated above, a variable region, i.e., the "antigen binding domain," allows the binding molecule to selectively recognize and specifically bind epitopes on antigens. That is, the VL domain and VH domain, or subset of the complementarity determining regions (CDRs), of a binding molecule, e.g., an antibody combine to form the variable region that defines a three dimensional antigen binding site. More specifically, the antigen binding site is defined by three CDRs on each of the VH and VL chains. Certain antibodies form larger structures. For example, IgA can form a molecule that includes two H2L2 units and a J-chain, all covalently connected via disulfide bonds, and IgM can form a pentameric or hexameric molecule that includes five or six H2L2 units and, in some embodiments, a J-chain covalently connected via disulfide bonds. In certain embodiments, polymeric IgA and IgM molecules can also contain a secretory component that can also be covalently connected via disulfide bonds. Further, it is known that both IgA and pentameric IgM bind to the polymeric immunoglobulin receptor (pIgR) and are secreted after binding. (See, Mostov K. E., *Ann. Rev. Immunol.*, 12:63-84, 1994, page 65).

The six "complementarity determining regions" or "CDRs" present in an antibody antigen binding domain are short, non-contiguous sequences of amino acids that are specifically positioned to form the antigen binding domain as the antibody assumes its three dimensional configuration in an aqueous environment. The remainder of the amino acids in the antigen binding domain, referred to as "framework" regions, show less inter-molecular variability. The framework regions largely adopt a β-sheet conformation and the CDRs form loops that connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids that make up the CDRs and the framework regions, respectively, can be readily identified for any given heavy or light chain variable region by one of ordinary skill in the art, since they have been defined in various different ways (see, "Sequences of Proteins of Immunological Interest," Kabat, E., et al., U.S. Department of Health and Human Services, (1983); and Chothia and Lesk, *J. Mol. Biol.*, 196:901-917 (1987), which are incorporated herein by reference in their entireties).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. These particular regions have been described, for example, by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference. The Kabat and Chothia definitions include overlapping or subsets of amino acids when compared against each other. Nevertheless, application of either definition (or other definitions known to those of ordinary skill in the art) to refer to a CDR of an antibody or variant thereof is intended to be within the scope of the term as defined and used herein, unless otherwise indicated. The appropriate amino acids that encompass the CDRs as defined by each of the above cited references are set forth below in Table 1 as a comparison. The exact amino acid numbers that encompass a particular CDR will vary depending on the sequence and size of the CDR. Those skilled in the art can routinely determine that amino acids comprise a particular CDR given the variable region amino acid sequence of the antibody.

TABLE 1

CDR Definitions*

|  | Kabat | Chothia |
| --- | --- | --- |
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

*Numbering of all CDR definitions in Table 1 is according to the numbering conventions set forth by Kabat et al. (see below).

Immunoglobulin variable domains can also be analyzed, e.g., using the IMGT information system (www://imgt.cines.fr/) (IMGT®/V-Quest) to identify variable region segments, including CDRs. (See, e.g., Brochet et al., *Nucl. Acids Res.*, 36:W503-508, 2008).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless use of the Kabat numbering system is explicitly noted, however, consecutive numbering is used for all amino acid sequences in this disclosure.

Binding molecules, e.g., antibodies or antigen binding fragments, variants, or derivatives thereof include, but are not limited to, polyclonal, monoclonal, human, humanized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), single domain antibodies such as camelid VHH antibodies, fragments comprising either a VL or VH domain, fragments produced by a Fab expression library. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule. Also contemplated are immunoglobulin new antigen receptor (IgNAR) isotypes that are bivalent and comprise a single chain that includes an IgNAR variable domain (VNAR). (See, Walsh et al., *Virology* 411: 132-141, 2011).

By "specifically binds," it is generally meant that a binding molecule, e.g., an antibody or fragment, variant, or derivative thereof binds to an epitope via its antigen binding domain, and that the binding entails some complementarity between the antigen binding domain and the epitope. According to this definition, a binding molecule is said to "specifically bind" to an epitope when it binds to that epitope, via its antigen binding domain more readily than it would bind to a random, unrelated epitope. The term "specificity" is used herein to qualify the relative affinity by which a certain binding molecule binds to a certain epitope. For example, binding molecule "A" can be deemed to have a higher specificity for a given epitope than binding molecule "B," or binding molecule "A" can be said to bind to epitope "C" with a higher specificity than it has for related epitope "D."

A binding molecule, e.g., an antibody or fragment, variant, or derivative thereof disclosed herein can be said to bind a target antigen with an off rate (k(off)) of less than or equal to $5 \times 10^{-2}$ sec$^{-1}$, $10^{-2}$ sec$^{-1}$, $5 \times 10^{-3}$ sec$^{-1}$, $10^{-3}$ sec$^{-1}$, $5 \times 10^{-4}$ sec$^{-1}$, $10^{-4}$ sec$^{-1}$, $5 \times 10^{-5}$ sec$^{-1}$, or $10^{-5}$ sec$^{-1}$ $5 \times 10^{-6}$ sec$^{-1}$, $10^{-6}$ sec$^{-1}$, $5 \times 10^{-7}$ sec$^{-1}$ or $10^{-7}$ sec$^{-1}$.

A binding molecule, e.g., an antibody or antigen binding fragment, variant, or derivative disclosed herein can be said to bind a target antigen with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^{-1}$, $5 \times 10^4$ M$^{-1}$ sec$^{-1}$, $10^5$ M$^{-1}$ sec$^{-1}$, $5 \times 10^5$ M$^{-1}$ sec$^{-1}$, $10^6$ M$^{-1}$ sec$^{-1}$, or $5 \times 106$M$^{-1}$ sec$^{-1}$ or $10^7$ M$^{-1}$ sec$^{-1}$.

A binding molecule, e.g., an antibody or fragment, variant, or derivative thereof is said to competitively inhibit binding of a reference antibody or antigen binding fragment to a given epitope if it preferentially binds to that epitope to the extent that it blocks, to some degree, binding of the reference antibody or antigen binding fragment to the epitope. Competitive inhibition can be determined by any method known in the art, for example, competition ELISA assays. A binding molecule can be said to competitively inhibit binding of the reference antibody or antigen binding fragment to a given epitope by at least 90%, at least 80%, at least 70%, at least 60%, or at least 50%.

As used herein, the term "affinity" refers to a measure of the strength of the binding of an individual epitope with one or more antigen binding domains, e.g., of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of antigen binding domains and an antigen. See, e.g., Harlow at pages 29-34. Avidity is related to both the affinity of individual antigen binding domains in the population with specific epitopes, and also the valencies of the immunoglobulins and the antigen. For example, the interaction between a bivalent monoclonal antibody and an antigen with a highly repeating epitope structure, such as a polymer, would be one of high avidity. An interaction between a between a bivalent monoclonal antibody with a receptor present at a high density on a cell surface would also be of high avidity.

Binding molecules or antigen binding fragments, variants or derivatives thereof as disclosed herein can also be described or specified in terms of their cross-reactivity. As used herein, the term "cross-reactivity" refers to the ability of a binding molecule, e.g., an antibody or fragment, variant, or derivative thereof, specific for one antigen, to react with a second antigen; a measure of relatedness between two different antigenic substances. Thus, a binding molecule is cross reactive if it binds to an epitope other than the one that induced its formation. The cross reactive epitope generally contains many of the same complementary structural features as the inducing epitope, and in some cases, can actually fit better than the original.

A binding molecule, e.g., an antibody or fragment, variant, or derivative thereof can also be described or specified in terms of its binding affinity to an antigen. For example, a binding molecule can bind to an antigen with a dissociation constant or $K_D$ no greater than $5 \times 10^{-2}$M, $10^{-2}$M, $5 \times 10^{-3}$M, $10^{-3}$M, $5 \times 10^{-4}$M, $10^{-4}$M, $5 \times 10^{-5}$M, $10^{-5}$M, $5 \times 10^{-6}$M, $10^{-6}$M, $5 \times 10^{-7}$M, $10^{-7}$M, $5 \times 10^{-8}$M, $10^{-8}$M, $5 \times 10^{-9}$M, $10^{-9}$M, $5 \times 10^{-10}$M, $10^{-10}$M, $5 \times 10^{-11}$M, $10^{-11}$M, $5 \times 10^{-12}$M, $10^{-12}$M, $5 \times 10^{-13}$M, $10^{-13}$M, $5 \times 10^{-14}$M, $10^{-14}$M, $5 \times 10^{-15}$M, or $10^{-15}$ M.

Antibody fragments including single-chain antibodies or other antigen binding domains can exist alone or in combination with one or more of the following: hinge region, CH1, CH2, CH3, or CH4 domains, J-chain, or secretory component. Also included are antigen binding fragments that can include any combination of variable region(s) with one or more of a hinge region, CH1, CH2, CH3, or CH4 domains, a J-chain, or a secretory component. Binding molecules, e.g., antibodies, or antigen binding fragments thereof can be from any animal origin including birds and mammals. The antibodies can be human, murine, donkey, rabbit, goat, guinea pig, camel, llama, horse, or chicken antibodies. In another embodiment, the variable region can be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and can in some instances express endogenous immunoglobulins and some not, as described infra and, for example in, U.S. Pat. No. 5,939,598 by Kucherlapati et al.

As used herein, the term "heavy chain subunit" or "heavy chain domain" includes amino acid sequences derived from an immunoglobulin heavy chain, a binding molecule, e.g., an antibody comprising a heavy chain subunit can include at least one of: a VH domain, a CH1 domain, a hinge (e.g., upper, middle, and/or lower hinge region) domain, a CH2 domain, a CH3 domain, a CH4 domain, or a variant or fragment thereof. For example, a binding molecule, e.g., an antibody or fragment, variant, or derivative thereof can include, in addition to a VH domain, a CH1 domain; CH1 domain, a hinge, and a CH2 domain; a CH1 domain and a CH3 domain; a CH1 domain, a hinge, and a CH3 domain; or a CH1 domain, a hinge domain, a CH2 domain, and a CH3 domain. In certain aspects a binding molecule, e.g., an antibody or fragment, variant, or derivative thereof can include, in addition to a VH domain, a CH3 domain and a CH4 domain; or a CH3 domain, a CH4 domain, and a J-chain. Further, a binding molecule for use in the disclosure can lack certain constant region portions, e.g., all or part of a CH2 domain. It will be understood by one of ordinary skill in the art that these domains (e.g., the heavy chain subunit) can be modified such that they vary in amino acid sequence from the original immunoglobulin molecule.

The heavy chain subunits of a binding molecule, e.g., an antibody or fragment thereof, can include domains derived from different immunoglobulin molecules. For example, a heavy chain subunit of a polypeptide can include a CH1 domain derived from an IgG1 molecule and a hinge region derived from an IgG3 molecule. In another example, a heavy chain subunit can include a hinge region derived, in part, from an IgG1 molecule and, in part, from an IgG3 molecule. In another example, a heavy chain subunit can comprise a chimeric hinge derived, in part, from an IgG1 molecule and, in part, from an IgG4 molecule.

As used herein, the term "light chain subunit" or "light chain domain" includes amino acid sequences derived from an immunoglobulin light chain. The light chain subunit includes at least one of a VL or CL (e.g., Cκ or Cλ) domain.

Binding molecules, e.g., antibodies or antigen binding fragments, variants, or derivatives thereof can be described or specified in terms of the epitope(s) or portion(s) of an antigen that they recognize or specifically bind. The portion of a target antigen that specifically interacts with the antigen binding domain of an antibody is an "epitope," or an "antigenic determinant." A target antigen can comprise a single epitope or at least two epitopes, and can include any number of epitopes, depending on the size, conformation, and type of antigen.

As previously indicated, the subunit structures and three dimensional configuration of the constant regions of the various immunoglobulin classes are well known. As used herein, the term "VH region" or "VH domain" includes the amino terminal variable domain of an immunoglobulin heavy chain and the term "CH1 domain" includes the first (most amino terminal) constant region domain of an immunoglobulin heavy chain, extending, e.g., from about amino acid 114 to about amino acid 223 of an IgG antibody using conventional numbering schemes (amino acids 114 to 223, Kabat numbering system; and amino acids 118-215, EU numbering system; see Kabat E A et al., op. cit). The CH1 domain is adjacent to the VH domain and is amino terminal to the hinge region of a typical IgG heavy chain molecule.

As used herein the term "CH2 domain" includes the portion of a heavy chain molecule that extends, e.g., from about amino acid 244 to amino acid 360 of an IgG antibody using conventional numbering schemes (amino acids 244 to 360, Kabat numbering system; and amino acids 231-340, EU numbering system; see Kabat E A et al., op. cit). The CH3 domain extends from the CH2 domain to the C-terminal of the IgG molecule and comprises approximately 108 amino acids. Certain immunoglobulin classes, e.g., IgM, further include a CH4 region.

As used herein, the term "hinge region" includes the portion of a heavy chain molecule that joins the CH1 domain to the CH2 domain in IgG, IgA, and IgD heavy chains. This hinge region comprises approximately 25 amino acids and is flexible, thus allowing the two N-terminal antigen binding regions to move independently.

As used herein the term "disulfide bond" includes the covalent bond formed between two sulfur atoms. The amino acid cysteine comprises a thiol group that can form a disulfide bond or bridge with a second thiol group. In certain IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" refers to an antibody in which the immunoreactive region or site is obtained or derived from a first species and the constant region (which can be intact, partial or modified) is obtained from a second species. In some embodiments the target binding region or site will be from a non-human source (e.g. mouse or primate) and the constant region is human.

The terms "multispecific antibody, or "bispecific antibody" refer to an antibody that has antigen binding domains that are specific for two or more different epitopes within a single antibody molecule (or "binding unit"). Other binding molecules in addition to the canonical antibody structure can be constructed with two different binding specificities. Epitope binding by bispecific or multispecific antibodies can be simultaneous or sequential. Triomas and hybrid hybridomas are two examples of cell lines that can secrete bispecific antibodies. Bispecific antibodies can also be constructed by recombinant means. (Strohlein and Heiss, *Future Oncol.* 6:1387-94 (2010); Mabry and Snavely, *IDrugs.* 13:543-9 (2010)). A bispecific antibody can also be a diabody. Thus, a bispecific binding molecule that is multimeric could potentially possess several different antigen binding domains, each with a different specificity. For instance, an IgM binding molecule would be considered multimeric, containing five or six binding units, and each binding unit possessing possibly two antigen binding domains. Such an IgM binding molecule could therefore have as many as two, three, four, five, six, seven, eight, nine, ten, eleven, or even twelve different specificities, since each antigen binding domain can bind a different, distinguishable epitope. In certain aspects each binding unit is a monospecific H2L2 structure. Bispecific and multi-specific IgM and IgA binding molecules, including antibodies, are described, for example, in PCT Publication No. WO 2015/053887 and PCT Publication No. WO 2015/120474, the entire contents of which are hereby expressly incorporated by reference. In certain aspects a heterologous binding domain can be associated with a J-chain, as described in PCT Publication No. WO 2015/153912, and elsewhere herein.

As used herein, the term "engineered antibody" refers to an antibody in which the variable domain in either the heavy and light chain or both is altered by at least partial replacement of one or more amino acids in either the CDR or framework regions. In certain aspects entire CDRs from an antibody of known specificity can be grafted into the framework regions of a heterologous antibody. Although alternate CDRs can be derived from an antibody of the same class or even subclass as the antibody from which the framework regions are derived, CDRs can also be derived from an antibody of different class, e.g., from an antibody from a different species. An engineered antibody in which one or more "donor" CDRs from a non-human antibody of known specificity are grafted into a human heavy or light chain framework region is referred to herein as a "humanized antibody." In certain aspects not all of the CDRs are replaced with the complete CDRs from the donor variable region and yet the antigen binding capacity of the donor can still be transferred to the recipient variable domains. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

As used herein, the terms "linked," "fused" or "fusion" or other grammatical equivalents can be used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the translational reading frame of the original ORFs. Thus, a recombinant fusion protein is a single protein containing two or more segments that correspond to polypeptides encoded by the original ORFs (which segments are not normally so joined in nature.) Although the reading frame is thus made continuous throughout the fused segments, the segments can be physically or spatially separated by, for example, in-frame linker sequence. For example, polynucleotides encoding the CDRs of an immunoglobulin variable region can be fused, in-frame, but be separated by a polynucleotide encoding at least one immunoglobulin framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which amino acids that neighbor each other in the sequence are contiguous in the primary structure of the polypeptide.

A portion of a polypeptide that is "amino-terminal" or "N-terminal" to another portion of a polypeptide is that portion that comes earlier in the sequential polypeptide chain. Similarly a portion of a polypeptide that is "carboxy-terminal" or "C-terminal" to another portion of a polypeptide is that portion that comes later in the sequential polypeptide chain. For example in a typical antibody, the variable domain is "N-terminal" to the constant region, and the constant region is "C-terminal" to the variable domain.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide that is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

Terms such as "treating" or "treatment" or "to treat" or "alleviating" or "to alleviate" refer to therapeutic measures that cure, slow down, lessen symptoms of, and/or halt or slow the progression of an existing diagnosed pathologic condition or disorder. Terms such as "prevent," "prevention," "avoid," "deterrence" and the like refer to prophylactic or preventative measures that prevent the development of an undiagnosed targeted pathologic condition or disorder. Thus, "those in need of treatment" can include those already with the disorder; those prone to have the disorder; and those in whom the disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, swine, cows, bears, and so on.

As used herein, phrases such as "a subject that would benefit from therapy" and "an animal in need of treatment" includes subjects, such as mammalian subjects, that would benefit from administration of a binding molecule such as an antibody, comprising one or more antigen binding domains. Such binding molecules, e.g., antibodies, can be used, e.g., for a diagnostic procedures and/or for treatment or prevention of a disease.

Multimeric Binding Molecules

This disclosure provides a multimeric HIV binding molecule, i.e., a binding molecule possessing at least two, e.g., two, five, or six "binding units" as defined herein, where at least one antigen binding domain of the multimeric binding molecule can specifically bind to an HIV antigen, e.g., an HIV protein, e.g., gp120 and/or gp41. Exemplary epitopes on gp120 and/or gp41 that can be bound by a multimeric HIV binding molecule provided herein, include, without limitation, the immunodominant region of gp41, the membrane proximal external region (MPER), the CD4 binding site, the variable region 1/variable Region 2 (V1/V2) loop, the glycan-variable region 3 (V3) loop, and/or any carbohydrates associated with these regions. Exemplary multimeric binding molecules include, but are not limited to, an IgM binding molecule with five or six binding units (a pentameric or hexameric binding molecule), or an IgA binding molecule with two binding units.

A multimeric binding molecule as provided herein can have improved binding characteristics or biological activity as compared to a binding molecule composed of a single binding unit, e.g., a bivalent IgG antibody. In some embodiments, a multimeric binding molecule as provided herein can more potently neutralize HIV, bind and neutralize more diverse HIV variants or clades, enhance viral clearance, improve tissue distribution (e.g., to mucosal surfaces), and/or be more potent in preventing, controlling or treating HIV infection than a corresponding reference single binding unit molecule comprising only two HIV antigen binding domains. In certain embodiments a multimeric binding molecule as provided herein can be more potent in controlling HIV infectivity and growth as compared with a corresponding reference single binding unit molecule comprising only two HIV antigen binding domains. In certain embodiments a multimeric binding molecule as provided herein can be used to treat chronic infection, e.g., by binding to and/or effecting antibody and/or cell-mediated killing of HIV infected cells, e.g., reservoir cells that express extremely low levels of HIV antigens on their surface. In certain embodiments, the multimeric binding molecule can be more effective at activating and killing such HIV-infected cells or killing such cells after activation with an independent activating agent such as an effector cell. In certain embodiments, a multimeric binding molecule as provided herein can provide equivalent benefit at a lower dosage than that of a corresponding reference single binding unit molecule comprising only two HIV antigen binding domains. In certain embodiments administration of a multimeric binding molecule as provided herein can allow for reduced or modified dosages of other retroviral therapies, e.g., ART. See, e.g., Example 7 below. The term "corresponding reference single binding unit molecule" refers to a binding molecule composed of a single binding unit, which has one or two HIV antigen binding domains similar or identical to one or more HIV antigen binding domains of a dimeric, pentameric, or hexameric HIV binding molecule, e.g., an IgM antibody provided herein.

In certain aspects, a "corresponding reference single binding unit molecule" is an IgG antibody comprising two identical antigen binding domains, where those antigen binding domains are identical to those contained in at least one binding unit, or at least two, three, four, five, or six binding units, of a dimeric, pentameric, or hexameric HIV binding molecule, e.g., an IgM antibody provided herein.

The term "improved binding characteristics" is a non-limiting term that can apply to any characteristic of the multimeric binding molecule that is improved or distinctive relative to a monomeric binding molecule. A multimeric binding molecule can, e.g., neutralize HIV in infected cells, e.g., cells in a human infected with HIV, and when administered to an individual in need thereof, can exhibit an activity that is empirically determined to be stronger, more potent, or require less binding molecule by mass or molar equivalents, such as, but not limited to (i) reducing the infectivity of an HIV virion, (ii) neutralizing more diverse HIV variants or clades, (iii) reducing the number of HIV-infected cells (including reservoir cells), (iv) preventing HIV infection, (v) enhancing viral clearance, and/or (vi) improving the signs and symptoms of HIV infection, as compared with a corresponding reference single binding unit molecule (e.g., an IgG molecule) that possesses antigen binding domains similar or identical in sequence to those of a dimeric, pentameric, or hexameric HIV binding molecule, e.g., an IgM antibody provided herein.

A corresponding reference single binding unit molecule as referred to above can be an IgG binding molecule. The reference IgG binding molecule can be of any isotype, such as IgG1, IgG2, IgG3, or IgG4, etc. The reference binding molecule is typically from the same animal. Thus if the multimeric binding molecule is human, the corresponding reference single binding unit molecule would typically also be human. Conversely, if the multimeric binding molecule is a rabbit binding molecule, the corresponding reference single binding unit molecule would also be a rabbit binding molecule.

IgM Binding Molecules

IgM is the first immunoglobulin produced by B cells in response to stimulation by antigen, and is present at around 1.5 mg/ml in serum with a half-life of 5 days. IgM is typically multimeric, e.g., a pentameric or hexameric molecule. Thus, IgM molecules are "multimeric" binding molecules. Each of the five, or six, IgM binding units includes two light and two heavy chains. While IgG contains three heavy chain constant domains (CH1, CH2 and CH3), as explained above, the heavy (µ) chain of IgM additionally contains a fourth constant domain (CH4), that includes a C-terminal "tailpiece." The human IgM constant region typically comprises the amino acid sequence SEQ ID NO: 1. The human Cμ1 region ranges from about amino acid 5 to about amino acid 102 of SEQ ID NO: 1; the human Cμ2 region ranges from about amino acid 114 to about amino acid 205 of SEQ ID NO: 1, the human Cμ3 region ranges from about amino acid 224 to about amino acid 319 of SEQ ID NO: 1, the Cμ 4 region ranges from about amino acid 329 to about amino acid 430 of SEQ ID NO: 1, and the tailpiece ranges from about amino acid 431 to about amino acid 453 of SEQ ID NO: 1. The amino acid sequence of the human IgM constant region (SEQ ID NO: 1) is provided below:

GSASAPTLFPLVSCENSPSDTSSVAVGCLAQDFLPDSITLSWKYKNN

SDISSTRGFPSVLRGGKYAATSQVLLPSKDVMQGTDEHVVCKVQHPN

GNKEKNVPLPVIAELPPKVSVFVPPRDGFFGNPRKSKLICQATGFSP

RQIQVSWLREGKQVGSGVTTDQVQAEAKESGPTTYKVTSTLTIKESD

WLGQSMFTCRVDHRGLTFQQNASSMCVPDQDTAIRVFAIPPSFASIF

LTKSTKLTCLVTDLTTYDSVTISWTRQNGEAVKTHTNISESHPNATF

SAVGEASICEDDWNSGERFTCTVTHTDLPSPLKQTISRPKGVALHRP

DVYLLPPAREQLNLRESATITCLVTGFSPADVFVQWMQRGQPLSPEK

YVTSAPMPEPQAPGRYFAHSILTVSEEEWNTGETYTCVAHEALPNRV

TERTVDKSTGKPTLYNVSLVMSDTAGTCY

An IgM binding molecule can comprise five binding units (each an "IgM binding unit") that can form a complex with an additional small polypeptide chain (the J-chain) to form a pentameric IgM binding molecule. The human J-chain comprises the amino acid sequence SEQ ID NO: 2. As described elsewhere herein the J-chain can be a variant J-chain comprising, e.g., a binding moiety such as an ScFv or a camelid antibody. Without the J-chain, IgM binding units typically assemble into a hexameric IgM binding molecule. While not wishing to be bound by theory, the assembly of IgM binding units into a hexameric or pentameric binding molecule is thought to involve the Cμ3 and Cμ4 domains. Accordingly, a hexameric or pentameric IgM binding molecule provided in this disclosure typically includes IgM constant regions that include at least the Cμ3 and Cμ4 domains. The amino acid sequence of the human J-chain (SEQ ID NO: 2) is provided below:

MKNHLLFWGVLAVFIKAVHVKAQEDERIVLVDNKCKCARITSRIIRS

SEDPNEDIVERNIRIIVPLNNRENISDPTSPLRTRFVYHLSDLCKKC

DPTEVELDNQIVTATQSNICDEDSATETCYTYDRNKCYTAVVPLVYG

GETKMVETALTPDACYPD

The signal peptide (amino acids 1 to 22 of SEQ ID NO: 2) is double underlined, the mature J-chain sequence is amino acids 23 to 159 of SEQ ID NO: 2.

An IgM heavy chain constant region can additionally include a Cμ2 domain or a fragment thereof, a Cμ1 domain or a fragment thereof, and/or other IgM heavy chain domains. In certain aspects, a binding molecule as provided herein can include a complete IgM heavy (μ) chain constant domain, e.g., SEQ ID NO: 1, or a variant, derivative, or analog thereof.

Pentameric or Hexameric HIV Binding Molecules

This disclosure provides a pentameric or hexameric HIV binding molecule, a binding molecule that has five or six IgM-derived "binding units" as defined herein, which can specifically bind to an HIV antigen, e.g., an HIV protein, e.g., the HIV spike protein. In certain aspects, each binding unit includes two IgM heavy chain constant regions or fragments thereof. In certain aspects, the two IgM heavy chain constant regions are human heavy chain constant regions. In certain aspects, the antigen binding domains in the IgM binding molecule are human in origin, or humanized, or a combination thereof. A pentameric or hexameric IgM binding molecule as provided herein can have improved binding characteristics or biological activity as compared to a binding molecule composed of a single binding unit, e.g., a bivalent IgG-derived antibody. In some embodiments, a pentameric or hexameric binding molecule provided herein can, e.g., through increased avidity or affinity, or enhanced effector functions, be more potent in targeting chronic infections, e.g., by binding to and/or effecting complement-mediated killing of HIV reservoir cells, as compared with a corresponding reference single binding unit molecule containing only two HIV-specific antigen binding domains.

A pentameric or hexameric HIV binding molecule as provided herein can likewise possess distinctive characteristics as compared to univalent or multivalent binding molecules composed of synthetic or chimeric structures. For example, use of human IgM constant regions can afford reduced immunogenicity and thus increased safety relative to a binding molecule containing chimeric constant regions or synthetic structures. Moreover, an IgM-based binding molecule can consistently form hexameric or pentameric oligomers resulting in a more homogeneous expression product. Superior complement fixation can also be an advantageous effector function of IgM-based binding molecules.

The reference single binding unit referred to above can be an IgG binding unit. The reference IgG binding unit can be of any isotype, such as IgG1, IgG2, IgG3, or IgG4, etc. The reference binding unit is typically from the same animal. Thus if the multimeric binding molecule is human, the reference single binding unit would also be human, but not necessarily human. That is, the reference single binding unit can be a humanized antibody of the IgG type. Conversely, if the multimeric binding molecule is a rabbit binding molecule, the reference single binding unit would also be a rabbit binding unit. Further, if the multimeric binding molecule is comprised of one or more binding unit fragments, then the reference single binding unit would also be an equivalent single binding unit fragment. In other words, the reference single binding unit is otherwise identical in sequence and structure to the binding units contained in the multimeric binding molecule except that the reference single binding unit is an equivalent single binding unit.

In certain aspects, the disclosure provides a pentameric or hexameric binding molecule comprising five or six binding units, respectively, where each binding unit includes two IgM heavy chain constant regions or fragments thereof. In certain aspects, the two IgM heavy chain constant regions are human heavy chain constant regions. In some embodiments, the antigen binding domains in the IgM binding molecule are human in origin, or humanized, or a combination thereof.

Where the multimeric binding molecule provided herein is pentameric, the binding molecule can further comprise a J-chain, or functional fragment thereof, or variant thereof. Where the pentameric IgM binding molecule contains a J-chain, the J-chain can be of the same species as the IgM binding molecule. That is, if the pentameric IgM binding molecule is human, the J-chain can also be human. In certain aspects, the J-chain can be a modified J-chain comprising a heterologous moiety or one or more heterologous moieties, e.g., a heterologous polypeptide sequence, e.g., an additional desired binding domain introduced into the native sequence. In certain aspects the additional binding domain specifically binds to CD3, e.g., CD3 c, or CD16.

In certain aspects each of the two IgM heavy chain constant regions in a binding unit is associated with an antigen binding domain, for example an Fv portion of an antibody, e.g., a VH and a VL of a human or murine antibody. In certain aspects, at least one antigen binding domain of a binding molecule as provided herein is a cross-reactive HIV antigen binding domain, e.g., an antigen binding domain that can bind to an HIV antigen from two or more HIV types, Groups, or clades. In certain aspects, the antigen binding domain can bind to the HIV antigen from both HIV types (types 1 and 2). In certain aspects, the binding molecule can bind to the HIV antigen from two or more Groups (M, N and O) of HIV-2. In certain aspects, the antigen binding domain can specifically bind to the HIV antigen from two, three, four, or more HIV groups or clades. In certain aspects, the binding molecule can bind to the HIV spike protein, e.g., gp120 and/or gp41, of two or more HIV types, groups, or clades. Exemplary epitopes on gp120 and/or gp41 epitopes include, without limitation, gp41, e.g., the immunodominant region of gp41, the MPER, the CD4 binding site, the V1/V2 loop, the V3 loop, and/or any carbohydrates associated with these regions In other embodiments, each antigen binding domain of a pentameric or hexameric HIV binding molecule as provided herein can independently bind a different antigen or different epitope on the same antigen. Thus, a pentameric IgM binding molecule can bind as many as two, three, four, five, six, seven, eight, nine or even ten different antigens or epitopes, across different HIV groups, subtypes or clades. Likewise, a hexameric IgM binding molecule can bind as many as two, three, four, five, six, seven, eight, nine, ten, eleven, or twelve different antigens or epitopes, across different HIV groups, subtypes or clades.

In certain aspects, a pentameric or hexameric HIV binding molecule as provided herein comprises at least one antigen binding domain that binds to an epitope on the HIV spike protein, e.g., gp120 and/or gp41, of two or more HIV types, groups, or clades. In other aspects, two or more antigen binding domains of a pentameric or hexameric HIV binding molecule provided herein, e.g., two, three, four, five, six, seven, eight, nine, ten, eleven, or twelve antigen binding domains, can bind to two or more distinct HIV spike protein epitopes, e.g., the immunodominant region of gp41, the MPER, the CD4 binding site, the V1/V2 loop, the V3 loop, and/or any carbohydrates associated with these regions. In some aspects, a pentameric or hexameric HIV binding molecule as provided herein can comprise at least one antigen binding domain that specifically binds the HIV spike protein, and can comprise other antigen binding domains that specifically bind to other HIV proteins, e.g., gag, pol, tat, rev, nef, vpr, vif, and/or vpu. Alternatively, all of the antigen binding domains can possess the same specificity, e.g., for a specific epitope on the HIV spike protein. In one aspect, all binding units of the pentameric or hexameric HIV binding molecule specifically bind to the HIV spike protein, for example, a pentameric or hexameric HIV binding molecule can comprise ten or twelve antigen binding domains that bind to the same spike protein epitope. In certain aspects the ten or twelve antigen binding domains can be identical.

In certain aspects, a pentameric or hexameric HIV binding molecule as provided herein can bind to an HIV virion particle, and/or can bind to the surface of an HIV-infected cell. In certain aspects, at least two, at least three, at least four, at least five, at least six, at least seven, at least eight, at least nine, at least ten, at least eleven, or at least twelve antigen binding domains of the pentameric or hexameric HIV binding molecule can specifically bind to an HIV virion particle, and/or can bind to the surface of an HIV-infected cell.

An HIV antigen or epitope bound by a pentameric or hexameric HIV binding molecule provided herein can be any one or more of the HIV proteins, including the HIV spike protein, e.g., gp120 and/or gp41, e.g., the immunodominant region of gp41, the MPER, the CD4 binding site, the V1/V2 loop, the V3 loop, and/or any carbohydrates associated with these regions. Moreover, a pentameric or hexameric HIV binding molecule as provided herein can be multispecific, including antigen binding domains that specifically bind to two or more antigens, e.g., one or more HIV antigens or epitopes and one or more heterologous antigens or epitopes, or two or more HIV antigens or epitopes. For example in certain aspects a multispecific hexameric or pentameric HIV binding molecule provided herein can include five or six binding units each comprising two antigen binding domains, where at least two individual binding domains bind to different antigens or epitopes. In certain non-limiting aspects one or more binding domains can bind to, e.g., an epitope within the CD4 binding site of the spike protein, while one or more of the remaining binding domains can bind to, e.g., the immunodominant region of gp41, another epitope within the CD4 binding site, an epitope within the MPER region, the V1/V2 loop, the V3 loop, and/or any carbohydrates associated with these regions, or any other region of the spike protein (exemplary binding domains are provided in Table 3), or an epitope of another HIV protein. In another aspect, a multispecific IgM binding molecule can comprise binding domains that are specific for different subsets of or individual HIV groups or clades, thereby providing a binding molecule with activity over a broader range of HIV viruses. Methods of making bispecific and multi-specific IgM and IgA binding molecules, including antibodies, are described, for example, in PCT Publication No. WO 2015/053887 and PCT Publication No. WO 2015/120474, the entire contents of which are hereby expressly incorporated by reference. In certain aspects a heterologous binding domain can be associated with a J-chain, as described in PCT Publication No. WO 2015/153912, and elsewhere herein.

IgA Binding Molecules

IgA plays a critical role in mucosal immunity, and comprises about 15% of total immunoglobulin produced. IgA is a monomeric or dimeric molecule. Dimeric IgA molecules are relatively smaller in size than IgM molecules, but can also possess improved binding characteristics relative to a corresponding reference single binding unit molecule. Moreover, a dimeric IgA binding molecule can reach mucosal sites providing greater tissue distribution for the binding molecules provided herein. Likewise, a dimeric IgA-derived binding molecule as provided herein can possess binding characteristics or biological activity that can be distinguished from a binding molecule comprising five or six binding units, e.g., a hexameric or pentameric IgM-derived binding molecule as described elsewhere herein. For example, a dimeric binding molecule would be smaller, and could, for example, achieve better tissue penetration. Dimeric IgA binding molecules can be manufactured by expression in vitro to include two IgA monomers and a J-chain. The dimeric J-chain-containing IgA molecules can then be administered to an individual where the IgA molecules that migrate to mucous membranes or mucosal tissue can bind to, and form a complex with, a membrane-bound secretory component (mSC, also referred to as the polymeric Ig receptor (pIgR)) produced by epithelial cells. The complex is translocated across epithelial cells and the mSC is cleaved, delivering sIgA to the mucosal surfaces. (See, Kaetzel et al., *Proc. Natl. Acad. Sci. USA* 88(19):8796-8800, 1991). Therefore, delivery of IgA to the blood stream can provide targeting of mucosal tissues.

An IgA binding unit includes two light and two IgA heavy chains. IgA contains three heavy chain constant domains (Cα1, Cα2 and Cα3), and includes a C-terminal "tailpiece." Human IgA has two subtypes, IgA1 and IgA2. The mature human IgA1 constant region typically comprises the amino acid sequence SEQ ID NO: 3, provided below:

ASPTSPKVFPLSLCSTQPDGNVVIACLVQGFFPQEPLSVTWSESGQG

VTARNFPPSQDASGDLYTTSSQLTLPATQCLAGKSVTCHVKHYTNPS

QDVTVPCPVPSTPPTPSPSTPPTPSPSCCHPRLSLHRPALEDLLLGS

EANLTCTLTGLRDASGVTFTWTPSSGKSAVQGPPERDLCGCYSVSSV

LPGCAEPWNHGKTFTCTAAYPESKTPLTATLSKSGNTFRPEVHLLPP

PSEELALNELVTLTCLARGFSPKDVLVRWLQGSQELPREKYLTWASR

QEPSQGTTTFAVTSILRVAAEDWKKGDTFSCMVGHEALPLAFTQKTI

DRLAGKPTHVNVSVVMAEVDGTCY

The human Cα1 region ranges from about amino acid 6 to about amino acid 98 of SEQ ID NO: 3; the human Cα2 region ranges from about amino acid 125 to about amino acid 220 of SEQ ID NO: 3 the human Cα3 region ranges from about amino acid 228 to about amino acid 330 of SEQ ID NO: 3, and the tailpiece ranges from about amino acid 331 to about amino acid 352 of SEQ ID NO: 3.

The mature human IgA2 constant region typically comprises the amino acid sequence SEQ ID NO: 4, provided below:

ASPTSPKVFPLSLDSTPQDGNVVVACLVQGFFPQEPLSVTWSESGQN

VTARNFPPSQDASGDLYTTSSQLTLPATQCPDGKSVTCHVKHYTNPS

QDVTVPCPVPPPPCCHPRLSLHRPALEDLLLGSEANLTCTLTGLRD

ASGATFTWTPSSGKSAVQGPPERDLCGCYSVSSVLPGCAQPWNHGET

FTCTAAHPELKTPLTANITKSGNTFRPEVHLLPPPSEELALNELVTL

TCLARGFSPKDVLVRWLQGSQELPREKYLTWASRQEPSQGTTTFAVT

SILRVAAEDWKKGDTFSCMVGHEALPLAFTQKTIDRMAGKPTHVNVS

VVMAEVDGTCY

The human Cα1 region ranges from about amino acid 6 to about amino acid 98 of SEQ ID NO: 4; the human Cα2 region ranges from about amino acid 112 to about amino acid 207 of SEQ ID NO: 4, the human Cα3 region ranges from about amino acid 215 to about amino acid 317 of SEQ ID NO: 4, and the tailpiece ranges from about amino acid 318 to about amino acid 340 of SEQ ID NO: 4.

Two IgA binding units can form a complex with two additional polypeptide chains, the J-chain (SEQ ID NO: 2) and the secretory component (SEQ ID NO: 76) to form a secretory IgA (sIgA) antibody. The amino acid sequence of the mature secretory component (SEQ ID NO: 76) is provided below:

KSPIFGPEEVNSVEGNSVSITCYYPPTSVNRHTRKYWCRQGARGGCI

TLISSEGYVSSKYAGRANLTNFPENGTFVVNIAQLSQDDSGRYKCGL

GINSRGLSFDVSLEVSQGPGLLNDTKVYTVDLGRTVTINCPFKTENA

QKRKSLYKQIGLYPVLVIDSSGYVNPNYTGRIRLDIQGTGQLLFSVV

INQLRLSDAGQYLCQAGDDSNSNKKNADLQVLKPEPELVYEDLRGSV

TFHCALGPEVANVAKFLCRQSSGENCDVVVNTLGKRAPAFEGRILLN

PQDKDGSFSVVITGLRKEDAGRYLCGAHSDGQLQEGSPIQAWQLFVN

EESTIPRSPTVVKGVAGGSVAVLCPYNRKESKSIKYWCLWEGAQNGR

CPLLVDSEGWVKAQYEGRLSLLEEPGNGTFTVILNQLTSRDAGFYWC

LTNGDTLWRTTVEIKIIEGEPNLKVPGNVTAVLGETLKVPCHFPCKF

SSYEKYWCKWNNTGCQALPSQDEGPSKAFVNCDENSRLVSLTLNLVT

RADEGWYWCGVKQGHFYGETAAVYVAVEERKAAGSRDVSLAKADAAP

DEKVLDSGFREIENKAIQDPR

While not wishing to be bound by theory, the assembly of IgA binding units into a dimeric sIgA binding molecule is thought to involve the Cα3 and tailpiece domains. Accordingly, a dimeric sIgA binding molecule provided in this disclosure typically includes IgA constant regions that include at least the Cα3 and tailpiece domains. An IgA heavy chain constant region can additionally include a Cα2 domain or a fragment thereof, a Cα1 domain or a fragment thereof, and/or other IgA heavy chain domains. In certain aspects, a binding molecule as provided herein can include a complete IgA heavy (α) chain constant domain, e.g., SEQ ID NO: 3 or SEQ ID NO: 4, or a variant, derivative, or analog thereof.

Dimeric HIV Binding Molecules

This disclosure provides a dimeric binding molecule comprising two or more IgA binding units as defined herein, where the dimeric HIV binding molecule comprises at least one antigen binding domain that can specifically bind to an HIV antigen, e.g., an HIV protein, e.g., the HIV spike protein. As explained above in the context of a pentameric or hexameric HIV binding molecule, a dimeric HIV binding molecule as provided herein can possess improved binding characteristics or biological activity as compared to a binding molecule composed of corresponding reference single binding unit molecule, e.g., a bivalent IgG antibody. For example, a dimeric HIV binding molecule can effect improved tissue penetration or tissue distribution, especially to mucosal surfaces. Thus, a dimeric IgA binding molecule processed for transport and secretion could target HIV-reservoir cells in the GIT.

The reference single binding unit referred to above can be an IgG binding unit. The reference IgG binding unit can be of any isotype, such as IgG1, IgG2, IgG3, or IgG4, etc. The reference binding unit is typically from the same animal. Thus if the multimeric binding molecule is human, the reference single binding unit would also be human, but not necessarily human. That is, the reference single binding unit can be a humanized antibody of the IgG type. Conversely, if the multimeric binding molecule is a rabbit binding molecule, the reference single binding unit would also be a rabbit binding unit. Further, if the multimeric binding molecule is comprised of one or more binding unit fragments, then the reference single binding unit would also be an equivalent single binding unit fragment. In other words, the reference single binding unit is otherwise identical in sequence and structure to the binding units contained in the multimeric binding molecule except that the reference single binding unit is an equivalent single binding unit.

In certain aspects, the disclosure provides a dimeric HIV binding molecule comprising two binding units, where each binding unit includes two IgA heavy chain constant regions or fragments thereof. In certain aspects, the two IgA heavy chain constant regions are human heavy chain constant regions. The anti-HIV binding domain(s) can be, e.g., human or humanized.

A dimeric HIV binding molecule as provided herein can further comprise a J-chain, or fragment thereof, or variant thereof. A dimeric HIV binding molecule as provided herein can further comprise a secretory component, or fragment thereof, or variant thereof.

An IgA heavy chain constant region can include one or more of a Cα1 domain, a Cα2 domain, and/or a Cα3 domain, provided that the constant region can serve a desired function in the binding molecule, e.g., associate with second IgA constant region to form an antigen binding domain, or associate with another IgA binding unit to form a dimeric binding molecule. In certain aspects the two IgA heavy chain constant regions or fragments thereof within an individual binding unit each comprise a Cα3 domain or fragment thereof, a tailpiece (TP) or fragment thereof, or any combination of a Cα3 domain, a TP, or fragment thereof. In certain aspects the two IgA heavy chain constant regions or fragments thereof within an individual binding unit each further comprise a Cα2 domain or fragment thereof, a Cα1 domain or fragment thereof, or a Cα1 domain or fragment thereof and a Cα2 domain or fragment thereof.

In certain aspects each of the two IgA heavy chain constant regions in a given binding unit is associated with an antigen binding domain, for example an Fv portion of an antibody, e.g., a VH and a VL of a human or murine antibody. In certain aspects, at least one antigen binding domain of a binding molecule as provided herein is a cross-reactive HIV antigen binding domain, e.g., an antigen binding domain that can specifically bind to two, three, four, or more HIV types, subtypes or clades. In certain aspects, the antigen binding domain can specifically bind to the HIV antigen from two, three, four, or more HIV groups or clades. In certain aspects, the binding molecule can bind to the HIV spike protein, e.g., gp120 and/or gp41, of two or more HIV types, groups, or clades. Exemplary epitopes on gp120 and/or gp41 epitopes include, without limitation, the immunodominant region of gp41, the MPER, the CD4 binding site, the V1/V2 loop, the V3 loop, and/or any carbohydrates associated with these regions.

In other embodiments, a dimeric HIV binding molecule of the present disclosure can comprise binding units wherein each binding unit can possess two antigen binding domains, each with a different and distinguishable specificity. Thus, a dimeric HIV binding molecule could possess as many as four different specificities.

In certain aspects, the antigen binding domain can bind to the HIV antigen from both HIV types (types 1 and 2). In certain aspects, the dimeric binding molecule can bind to the HIV antigen from two or more Groups (M, N, and O) of HIV-2. In certain aspects, the antigen binding domain can specifically bind to the HIV antigen from two, three, four, or more HIV groups or clades.

In other embodiments, each antigen binding domain of a dimeric HIV binding molecule as provided herein can independently bind a different antigen or different epitope on the same antigen. Thus, a dimeric HIV binding molecule can bind as many as two, three, or four different antigens or epitopes, across different HIV groups, subtypes or clades.

In certain aspects, a dimeric HIV binding molecule as provided herein comprises at least one antigen binding domain that binds to an epitope on the HIV spike protein, e.g., gp120 and/or gp41, of two or more HIV types, groups, or clades. In other aspects, two or more antigen binding domains of a dimeric HIV binding molecule provided herein, e.g., two, three, or four antigen binding domains, can bind to two or more distinct HIV spike protein epitopes, e.g., the immunodominant region of gp41, the MPER, the CD4 binding site, the V1/V2 loop, the V3 loop, and/or any carbohydrates associated with these regions. In some aspects, a dimeric HIV binding molecule as provided herein can comprise at least one antigen binding domain that specifically binds to the HIV spike protein, and can comprise other antigen binding domains that specifically bind other HIV proteins, e.g., gag, pol, tat, rev, nef, vpr, vif, and/or vpu. Alternatively, all of the antigen binding domains can possess the same specificity, e.g., for a specific epitope on the HIV spike protein. In one aspect, all binding units of the dimeric HIV binding molecule specifically bind to the HIV spike protein; for example, a dimeric HIV binding molecule can comprise four antigen binding domains that bind to the same spike protein epitope. In certain aspects the four antigen binding domains can be identical.

In certain aspects, a dimeric HIV binding molecule as provided herein can bind to an HIV virion particle, and/or can bind to the surface of an HIV-infected cell. In certain aspects, at least two, at least three, or at least four antigen binding domains of the pentameric or hexameric HIV binding molecule can specifically bind to an HIV virion particle, and/or can bind to the surface of an HIV-infected cell.

An HIV antigen or epitope bound by a dimeric HIV binding molecule provided herein can be any one or more of the HIV proteins, including the HIV spike protein, e.g., gp120 and/or gp41, e.g., the immunodominant region of gp41, the MPER, the CD4 binding site, the V1N2 loop, the V3 loop, and/or any carbohydrates associated with these regions. Moreover, a dimeric HIV binding molecule as provided herein can be multispecific, including antigen binding domains that specifically bind to two or more antigens, e.g., one or more HIV antigens or epitopes and one or more heterologous antigens or epitopes, or two or more HIV antigens or epitopes. For example in certain aspects a multispecific dimeric HIV binding molecule provided herein can include two binding units each comprising two antigen binding domains, where at least two individual binding domains bind to different antigens or epitopes. In certain aspects one or more binding domains can bind to, e.g., an epitope within the CD4 binding site of the spike protein, while one or more of the remaining binding domains can bind to, e.g., another epitope within the CD4 binding site, an epitope within the MPER region, any other region of the spike protein (exemplary binding domains are provided in Table 3), or an epitope of another HIV protein. In another aspect, a multispecific IgA binding molecule can comprise binding domains that are specific for different subsets of or individual HIV groups or clades, thereby providing a binding molecule with activity over a broader range of HIV viruses. Methods of making bispecific and multi-specific IgM and IgA binding molecules, including antibodies, are described, for example, in PCT Publication No. WO 2015/

053887 and PCT Publication No. WO 2015/120474, the entire contents of which are hereby expressly incorporated by reference. In certain aspects a heterologous binding domain can be associated with a J-chain, as described in PCT Publication No. WO 2015/153912, and elsewhere herein.

Multispecific Dimeric, Pentameric, or Hexameric HIV Binding Molecules

A multi-specific, e.g., bispecific dimeric HIV binding molecule as provided herein can be based on the dimeric form of an IgA antibody or a hexameric or pentameric form of an IgM antibody, in which two, five, or six pairs of heavy chain sequences can be present with or without associated light chain sequences. For example, a bispecific dimeric HIV binding molecule as provided herein can be composed of two IgA (IgA1 or IgA2) binding units, or five or six IgM binding units, and can include a J-chain, e.g., a modified J-chain as provided elsewhere herein.

A multi-specific, e.g., bispecific dimeric HIV binding molecule as provided herein can include mono- and/or bispecific binding units as long as the molecule as a whole has at least two binding specificities, e.g., at least two non-identical antigen binding domains, e.g., different regions of the gp120/41 spike protein, spike protein epitopes and epitopes from other HIV antigens, or HIV antigens and heterologous antigens. In certain aspects, one or more heterologous antigens can be situated on effector cells, e.g., CD3 on T-cells or CD16 on NK cells. In certain aspects the non-identical antigen binding domain can be part of a modified J-chain.

Thus, in one embodiment, a multi-specific, e.g., bispecific dimeric binding molecule as provided herein can include two monospecific binding units (AA, BB), each having bivalent binding specificity to a different binding target. In another embodiment, a multi-specific, e.g., bispecific dimeric binding molecule as provided herein can include two bispecific binding units, each binding unit binding to the same two binding targets (AB, AB) to form a bispecific dimeric binding molecule. In a further embodiment, one binding unit present in a multi-specific dimeric binding molecule as provided herein is monospecific (AA) while the other binding units are bispecific (BC), resulting in a multispecific binding molecule with three (A, B, C) binding specificities. In a further embodiment, each binding unit is bispecific, but one specificity is overlapping (e.g. AB, AC), resulting in a multispecific binding molecule with three (A, B, C) binding specificities. As discussed above for multispecific dimeric binding molecules, each of the five or six binding units can independently be monospecific or bispecific (e.g., AA, BB, CC, etc.) or one or more binding units can be bispecific (e.g., AB, AB, AC, CD, etc.). Thus, a multi-specific, e.g., bispecific pentameric or hexameric binding molecule as provided herein can include at least two independent antigen binding domains, and up to twelve different, independent antigen binding domains. Other combinations, e.g., with four non-identical antigen binding domains (A, B, C, and D) can be readily made based on this disclosure. In another embodiment all of the IgM or IgA binding units can be monospecific (e.g., AA) and the non-identical antigen binding domain can be part of a modified J-chain.

Modified J-Chains

In certain aspects, HIV binding molecules provided herein can be multispecific, e.g., bispecific, incorporating a modified J-chain. As provided herein and in PCT Publication No. WO 2015/153912, a modified J-chain can comprise a heterologous moiety, e.g., a heterologous polypeptide, e.g., an additional desired binding domain, which can include, for example, a polypeptide binding domain capable of specifically binding to a target. The binding domain can be, for example, an antibody or antigen binding fragment thereof, an antibody-drug conjugate or antigen binding fragment thereof, or an antibody-like molecule. A polypeptide binding domain can be introduced into a J-chain by appropriately selecting the location and type of addition (e.g. direct or indirect fusion, chemical tethering, etc.).

In some embodiments, a modified J-chain can comprise a binding domain that can include without limitation a polypeptide capable of specifically binding to a target antigen. In certain aspects, a binding domain associated with a modified J-chain can be an antibody or an antigen binding fragment thereof, including monospecific, bispecific, and multi-specific antibodies and antibody fragments. The antibody fragment can be, without limitation, a Fab fragment, a Fab' fragment, a F(ab')$_2$ fragment, an scFv, (scFv)$_2$ fragment, single-chain antibody molecules, single domain antibodies, e.g., camelid VHH antibodies, minibodies, or multispecific antibodies formed from antibody fragments. In certain aspects, the antibody fragment is a scFv.

In other aspects, the binding domain can be an antibody-like molecule, for example, a human domain antibody (dAb), Dual-Affinity Re-Targeting (DART) molecule, a diabody, a di-diabody, dual-variable domain antibody, a Stacked Variable Domain antibody, a Small Modular Immuno Pharmaceutical (SMIP), a Surrobody, a strand-exchange engineered domain (SEED)-body, or TandAb.

The binding domain can be introduced into the native J-chain sequence at any location that allows the binding of the binding domain to its binding target without interfering with the binding of the recipient IgM or IgA molecule to its binding target or binding targets or the ability of the J-chain to effectively incorporate into an IgA dimer or an IgM pentamer. In certain aspects the binding domain can be inserted at or near the C-terminus, at or near the mature N-terminus (i.e., amino acid number 23 of SEQ ID NO: 2 following cleavage of the signal peptide) or at an internal location that, based on the three-dimensional structure of the J-chain is accessible. In certain aspects, the binding domain can be introduced into the native sequence J-chain without about 10 residues from the C-terminus or without about 10 amino acid residues from the mature N-terminus, of the human J-chain of SEQ ID NO: 2. In another aspect, the binding domain can be introduced into the native sequence human J-chain of SEQ ID NO: 2 in between cysteine residues 114 and 123 of SEQ ID NO: 2, or at an equivalent location of another native sequence J-chain. In a further aspect, the binding domain can be introduced into a native sequence J-chain, such as a J-chain of SEQ ID NO: 2, at or near a glycosylation site. In certain aspects, the binding domain can be introduced into the native sequence human J-chain of SEQ ID NO: 2 within about 10 amino acid residues from the C-terminus.

Introduction can be accomplished by direct or indirect fusion, i.e. by the combination of the J-chain and binding domain in one polypeptide chain by in-frame combination of their coding nucleotide sequences, with or without a peptide linker. The peptide linker (indirect fusion), if used, can be about 1 to 50, or about 1 to 40, or about 1 to 30, or about 1 to 20, or about 1 to 10, or about 1 to 5, or about 10 to 20 amino acids in length, and can be present at one or both ends of the binding domain to be introduced into the J-chain sequence. In certain aspects, the peptide linker can be about 1 to 100 amino acids long. In certain aspects the peptide linker is 5, 10, 15, or 20 amino acids long.

In certain aspects the modified J-chain comprises the formula X[L$_n$]J or J[L$_n$]X, where J is a native J-chain or functional fragment thereof, e.g., a native human J-chain (amino acids 23 to 159 of SEQ ID NO: 2), X is a binding domain, and [L$_n$] is a linker sequence consisting of n amino acids, where n is a positive integer, e.g., from 1 to 100, 1 to 50, or 1 to 25. In certain aspects n=5, 10, 15, or 20. In certain aspects L$_n$ can consist of GGGGS (L$_5$, SEQ ID NO: 101), GGGGSGGGGS (L$_{10}$ SEQ ID NO: 102), GGGGSGGGGSGGGGS (L$_{15}$, SEQ ID NO: 103), or GGGGSGGGGSGGGGSGGGGS (L$_{20}$, SEQ ID NO: 104). In certain aspects, X can comprise an anti-CD3 binding domain, e.g., an anti-CD3 ScFv. In certain aspects X comprises or consists of SEQ ID NO: 105, SEQ ID NO: 106, or SEQ ID NO: 107.

It is also possible to introduce more than one heterologous polypeptide, e.g., more than one binding domain, into a J-chain.

The modified J-chain can be produced by well-known techniques of recombinant DNA technology, by expressing a nucleic acid encoding the modified J-chain in a suitable prokaryotic or eukaryotic host organism.

The modified J-chain can be co-expressed with the heavy and light chains of the recipient IgM or IgA binding molecules as described elsewhere herein. The recipient binding molecule, prior to the modified J-chain incorporation can be monospecific, bispecific or multi-specific, e.g., a monospecific, bispecific, or multispecific IgA or IgM antibody. Bispecific and multi-specific IgM and IgA binding molecules, including antibodies, are described, for example, in PCT Publication No. WO 2015/053887 and PCT Publication No. WO 2015/120474, the entire contents of which are hereby expressly incorporated by reference.

In certain aspects, an anti-HIV IgM or IgA binding molecule as described herein can include a modified J-chain with binding specificity for an immune effector cell, such as a T-cell, NK-cell, a macrophage, or a neutrophil. In certain aspects the effector cell is a T-cell and the binding target is CD3 (discussed below), or CD8. By activating and redirecting effector cells, e.g. effector T-cells (T-cell dependent killing or TDCC), or NK cells to infected cells expressing HIV antigens, e.g., the HIV spike glycoprotein, on their surface, including reservoir cells, a bispecific anti-HIV IgM or IgA binding molecule comprising an effector cell-directed modified J-chain as provided herein can produce an enhanced immune response against the target, the response comprising, e.g., complement-mediated cytotoxicity, antibody dependent cellular cytotoxicity (ADCC), TDCC, and/or NK-cell mediated killing, thereby further increasing potency and efficacy. In certain aspects, a bispecific anti-HIV IgM or IgA binding molecule as provided herein comprising a modified J-chain can be used for the treatment of a disease or condition caused by, or exacerbated by infection with HIV, and/or can direct HIV neutralization, and/or clearance or killing of an HIV-infected cells, such as reservoir cells.

In the case of T-cells, cluster of differentiation 3 (CD3) is a multimeric protein complex, known historically as the T3 complex, and is composed of four distinct polypeptide chains (ε, γ, δ, ζ) that assemble and function as three pairs of dimers (εγ, εδ, ζζ) The CD3 complex serves as a T-cell co-receptor that associates non-covalently with the T-cell receptor (TCR). Components of this CD3 complex, especially CD3ε, can be targets for a modified J-chain of a bispecific IgM or IgA binding molecule provided herein.

In certain aspects, a bispecific anti-HIV x anti-CD3 IgM or IgA binding molecule binds to HIV-infected cells or HIV virus particles via the antibody binding domains, while the J-chain is modified to bind to CD3, e.g., CD3ε.

In certain aspects the anti-CD3 binding domain of a modified J-chain provided herein is a scFv. The anti CD3 scFv can be fused at or near the N-terminus of the J-chain, or at or near the C-terminus of the J-chain either directly or indirectly via a synthetic linker introduced in between the scFv and the J-chain sequences, e.g., GGGGS (L$_5$, SEQ ID NO: 101), GGGGSGGGGS (L$_{10}$, SEQ ID NO: 102), GGGGSGGGGSGGGGS (L$_{15}$, SEQ ID NO: 103), or GGGGSGGGGSGGGGSGGGGS (L$_{20}$, SEQ ID NO: 104). Suitable anti-CD3 binding domains for inclusion in a modified J-chain as provided herein include, but are not limited to, ScFv antigen binding domains comprising the amino acid sequences SEQ ID NO: 105, SEQ ID NO: 106, SEQ ID NO: 107, as shown in Table 2.

TABLE 2

Exemplary CD3 Heterologous Binding Domains

| SEQ ID NO | Source | Binds to | Sequence |
|---|---|---|---|
| 105 | Kung, P. C., et al. (1979) Science, 206, 347-349 | CD3ε | QVQLQQSGAELARPGASVKMSCKASGYTFTRYTMHWVKQ RPGQGLEWIGYINPSRGYTNYNQKFKDKATLTTDKSSSTAY MQLSSLTSEDSAVYYCARYYDDHYSLDYWGQGTTLTVSSG GGGSGGGGSGGGGSQIVLTQSPAIMSASPGEKVTMTCSASSS VSYMNWYQQKSGTSPKRWIYDTSKLASGVPAHFRGSGSGT SYSLTISGMEAEDAATYYCQQWSSNPFFTFGSGTKLEIK |
| 106 | U.S. Pat. No. 5,834,597 | CD3ε | QVQLVQSGAEVKKPGASVKVSCKASGYTFISYTMHWVRQA PGQGLEWMGYINPRSGYTHYNQKLKDKATLTADKSASTAY MELSSLRSEDTAVYYCARSAYYDYDGFAYWGQGTLVTVSS GGGGSGGGGSGGGGSDIQMTQSPSSLSASVGDRVTITCSASS SVSYMNWYQQKPGKAPKRLIYDTSKLASGVPSRFSGSGSGT DFTLTISSLQPEDFATYYCQQWSSNPPTFGGGTKLEIK |
| 107 | Beverley, P. C. & Callard, R E. (1981) Eur. J. Immunol. 11, 329-334 | CD3ε | EVQLVESGGGLVQPGGSLRLSCAASGYSFTGYTMNWVRQA PGKGLEWVALINPYKGVTTYADSVKGRFTISVDKSKNTAYL QMNSLRAEDTAVYYCARSGYYGDSDWYFDVWGQGTLVTV SSGGGGSGGGGSGGGGSDIQMTQSPSSLSASVGDRVTITCRA SQDIRNYLNWYQQKPGKAPKLLIYYTSRLESGVPSRFSGSGS GTDYTLTISSLQPEDFATYYCQQGNTLPWTFGQGTKVEIK |

TABLE 2-continued

Exemplary CD3 Heterologous Binding Domains

| SEQ ID NO | Source | Binds to | Sequence |
|---|---|---|---|
| 112 | GenBank: ABQ52435.1 | CD16 | EVQLVESGGELVQAGGSLRLSCAASGLTFSSYNMGWFRRAP GKEREFVASITWSGRDTFYADSVKGRFTISRDNAKNTVYLQ MSSLKPEDTAVYYCAANPWPVAAPRSGTYWGQGTQVTVSS |

In certain aspects the modified J-chain comprises the mature scFv amino acid sequence of SEQ ID NO: 105 fused to the N-terminus of the human J-chain through a linker, e.g., GGGGS ($L_5$, SEQ ID NO: 101), GGGGSGGGGS ($L_{10}$, SEQ ID NO: 102), GGGGSGGGGSGGGGS ($L_{15}$, SEQ ID NO: 103), or GGGGSGGGGSGGGGSGGGGS ($L_{20}$, SEQ ID NO: 104), a modified J-chain referred to herein as $OL_nJ$, where n=5, 10, 15, or 20. $OL_nJ$ can further include a signal peptide to facilitate transport and assembly into an IgM or IgA binding molecules. In certain aspects the mature modified J-chain comprises a scFv of SEQ ID NO: 105 fused to the C-terminus of the human J-chain through an amino acid linker, e.g., GGGGS ($L_5$, SEQ ID NO: 101), GGGGSGGGGS ($L_{10}$, SEQ ID NO: 102), GGGGSGGGGSGGGGS ($L_{15}$, SEQ ID NO: 103), or GGGGSGGGGSGGGGSGGGGS ($L_{20}$, SEQ ID NO: 104), a modified J-chain referred to herein as $JL_nO$, where n=5, 10, 15, or 20. $JL_nO$ can further include a signal peptide, e.g., amino acids 1 to 22 of SEQ ID NO: 2, to facilitate transport and assembly into an IgM or IgA binding molecules. In certain aspects, other signal peptides can be used. Selection and inclusion of suitable signal peptides to facilitate expression, secretion, and incorporation of a modified J-chain into an anti-HIV IgM or IgA binding molecule as provided herein is well within the capabilities of a person of ordinary skill in the art.

In certain aspects the modified J-chain comprises the mature scFv amino acid sequence SEQ ID NO: 106 fused to the N-terminus of the human J-chain through a linker, e.g., GGGGS ($L_5$, SEQ ID NO: 101), GGGGSGGGGS ($L_{10}$ SEQ ID NO: 102), GGGGSGGGGSGGGGS ($L_{15}$, SEQ ID NO: 103), or GGGGSGGGGSGGGGSGGGGS ($L_{20}$, SEQ ID NO: 104), a modified J-chain referred to herein as $VL_nJ$, where n=5, 10, 15, or 20. $VL_nJ$ can further include a signal peptide to facilitate transport and assembly into an IgM or IgA binding molecules. In certain aspects the mature modified J-chain comprises a scFv of SEQ ID NO: 106 fused to the C-terminus of the human J-chain through an amino acid linker, e.g., GGGGS ($L_5$, SEQ ID NO: 101), GGGGSGGGGS ($L_{10}$, SEQ ID NO: 102), GGGGSGGGGSGGGGS ($L_{15}$, SEQ ID NO: 103), or GGGGSGGGGSGGGGSGGGGS ($L_{20}$, SEQ ID NO: 104), a modified J-chain referred to herein as $JL_nV$, where n=5, 10, 15, or 20. $JL_nV$ can further include a signal peptide, e.g., amino acids 1 to 22 of SEQ ID NO: 2, to facilitate transport and assembly into an IgM or IgA binding molecules. In certain aspects, other signal peptides can be used. Selection and inclusion of suitable signal peptides to facilitate expression, secretion, and incorporation of a modified J-chain into an anti-HIV IgM or IgA binding molecule as provided herein is well within the capabilities of a person of ordinary skill in the art. Exemplary modified J chains include, without limitation V5J (SEQ ID NO: 108), V10J (SEQ ID NO: 109), V15J (SEQ ID NO: 110), or V20J (SEQ ID NO: 111). For each sequence, the mature anti-CD3 ScFv sequence is single underlined, and the mature human J-chain sequence is shown in italics. In certain aspects, the mature modified J chain can SEQ ID NO: 108, SEQ ID NO: 109, SEQ ID NO: 110, SEQ ID NO: 111, or a combination thereof.

V5J
(SEQ ID NO: 108)
<u>QVQLVQSGAEVKKPGASVKVSCKASGYTFISYTMHWVRQAPGQGLEW</u>

<u>MGYINPRSGYTHYNQKLKDKATLTADKSASTAYMELSSLRSEDTAVY</u>

<u>YCARSAYYDYDGFAYWGQGTLVTVSS</u>GGGGSGGGGSGGGGSDIQMTQ

SPSSLSASVGDRVTITCSASSSVSYMNWYQQKPGKAPKRLIYDTSKL

ASGVPSRFSGSGSGTDFTLTISSLQPEDFATYYCQQWSSNPPTFGGG

TKLEIKGGGGS*QEDERIVLVDNKCKCARITSRIIRSSEDPNEDIVER*

*NIRIIVPLNNRENISDPTSPLRTRFVYHLSDLCKKCDPTEVELDNQI*

*VTATQSNICDEDSATETCYTYDRNKCYTAVVPLVYGGETKMVETALT*

*PDACYPD.*

V10J
(SEQ ID NO: 109)
<u>QVQLVQSGAEVKKPGASVKVSCKASGYTFISYTMHWVRQAPGQGLEW</u>

<u>MGYINPRSGYTHYNQKLKDKATLTADKSASTAYMELSSLRSEDTAVY</u>

<u>YCARSAYYDYDGFAYWGQGTLVTVSS</u>GGGGSGGGGSGGGGSDIQMTQ

SPSSLSASVGDRVTITCSASSSVSYMNWYQQKPGKAPKRLIYDTSKL

ASGVPSRFSGSGSGTDFTLTISSLQPEDFATYYCQQWSSNPPTFGGG

TKLEIKGGGGSGGGGS*QEDERIVLVDNKCKCARITSRIIRSSEDPNE*

*DIVERNIRIIVPLNNRENISDPTSPLRTRFVYHLSDLCKKCDPTEVE*

*LDNQIVTATQSNICDEDSATETCYTYDRNKCYTAVVPLVYGGETKMV*

*ETALTPDACYPD.*

J-chain sequence for V15J
(SEQ ID NO: 110)
<u>QVQLVQSGAEVKKPGASVKVSCKASGYTFISYTMHWVRQAPGQGLEW</u>

<u>MGYINPRSGYTHYNQKLKDKATLTADKSASTAYMELSSLRSEDTAVY</u>

<u>YCARSAYYDYDGFAYWGQGTLVTVSS</u>GGGGSGGGGSGGGGSDIQMTQ

SPSSLSASVGDRVTITCSASSSVSYMNWYQQKPGKAPKRLIYDTSKL

ASGVPSRFSGSGSGTDFTLTISSLQPEDFATYYCQQWSSNPPTFGGG

TKLEIKGGGGSGGGGSGGGGS*QEDERIVLVDNKCKCARITSRIIRSS*

*EDPNEDIVERNTRIIVPLNNRENTSDPTSPLRTRFVYHLSDLCKKCD*

*PTEVELDNQIVTATQSNICDEDSATETCYTYDRNKCYTAVVPLVYGG*

*ETKMVETALTPDACYPD.*

-continued

J-chain sequence for V20J (SEQ ID NO: 111)

QVQLVQSGAEVKKPGASVKVSCKASGYTFISYTMHWVRQAPGQGLEW

MGYINPRSGYTHYNQKLKDKATLTADKSASTAYMELSSLRSEDTAVY

YCARSAYYDYDGFAYWGQGTLVTVSSGGGGSGGGGSGGGGSDIQMTQ

SPSSLSASVGDRVTITCSASSSVSYMNWYQQKPGKAPKRLIYDTSKL

ASGVPSRFSGSGSGTDFTLTISSLQPEDFATYYCQQWSSNPPTFGGG

TKLEIKGGGGSGGGGSGGGGSGGGGSQEDERIVLVDNKCKCARITSR

IIRSSEDPNEDIVERNIRIIVPLNNRENISDPTSPLRTRFVYHLSDL

CKKCDPTEVELDNQIVTATQSNICDEDSATETCYTYDRNKCYTAVVP

LVYGGETKMVETALTPDACYPD.

In certain aspects the modified J-chain comprises the mature scFv amino acid sequence SEQ ID NO: 107 fused to the N-terminus of the human J-chain through a linker, e.g., GGGGS ($L_5$, SEQ ID NO: 101), GGGGSGGGGS ($L_{10}$ SEQ ID NO: 102), GGGGSGGGGSGGGGS ($L_{15}$, SEQ ID NO: 103), or GGGGSGGGGSGGGGSGGGGS ($L_{20}$, SEQ ID NO: 104), a modified J-chain referred to herein as $UL_nJ$, where n=5, 10, 15, or 20. $UL_nJ$ can further include a signal peptide to facilitate transport and assembly into an IgM or IgA binding molecules. In certain aspects the mature modified J-chain comprises a scFv of a SEQ ID NO: 107 fused to the C-terminus of the human J-chain through an amino acid linker, e.g., GGGGS ($L_5$, SEQ ID NO: 101), GGGGSGGGGS ($L_{10}$, SEQ ID NO: 102), GGGGSGGGGSGGGGS ($L_{15}$, SEQ ID NO: 103), or GGGGSGGGGSGGGGSGGGGS ($L_{20}$, SEQ ID NO: 104), a modified J-chain referred to herein as $JL_nU$, where n=5, 10, 15, or 20. $JL_nU$ can further include a signal peptide, e.g., amino acids 1 to 22 of SEQ ID NO: 2, to facilitate transport and assembly into an IgM or IgA binding molecules. In certain aspects, other signal peptides can be used. Selection and inclusion of suitable signal peptides to facilitate expression, secretion, and incorporation of a modified J-chain into an anti-HIV IgM or IgA binding molecule as provided herein is well within the capabilities of a person of ordinary skill in the art.

A person of ordinary skill in the art would readily be able to make additional modified J-chains according to the description provided herein.

In certain aspects such as those noted above, a modified J-chain associated with a dimeric or pentameric HIV binding molecule as provided herein can comprise an antigen binding domain that binds to an effector cell, e.g. a T cell, an NK cell, or a macrophage. In certain aspects the effector cell is a T cell, e.g., a cytotoxic T cell, expressing CD3, CD8, or a combination thereof. According to this aspect, the J-chain can be modified by covalent attachment of a CD3 (CD3ε) binding domain or a CD8 binding domain. In this configuration, a dimeric or pentameric binding molecule as provided herein provides binding specificity to a target HIV antigen, e.g., an HIV spike protein, while the T-cell tethering of the J-chain through CD3 binding or CD8 binding delivers cytotoxic potency. The CD3 binding domain or CD8 binding domain covalently attached to a J-chain, or a variant thereof, can, for example be a single-chain Fv (scFv) of an anti-CD3 antibody, or a naturally occurring heavy chain only antibody, e.g. a camelid (camels, llamas, alpacas) or single-chain antibody of cartilaginous fish (sharks, rays), a scaffold, e.g. fibronectin (e.g. fibronectin III) with CD3 binding specificity.

In another aspect, the effector cell is a Natural killer (NK) cell. NK cells are important components of the innate immunity and play a key role in host defense by virtue of their ability to release cytokines and to mediate cytolytic activity against tumor cells and virus-infected cells. NK cell antigens include, without limitation, CD16, CD32a, CD56, CD57, CD64, CD117 (or c-kit), adhesion molecules including lymphocyte-associated molecule-2 (LFA-2 or CD2), LFA-3 (CD58), and LFA-1 (CD11a/CD18). According to this aspect, the J-chain can be modified, e.g., by covalent attachment of a CD16 binding domain. In this configuration, a dimeric or pentameric binding molecule as provided herein provides binding specificity to a target HIV antigen, e.g., an HIV spike protein, while the NK-cell tethering of the J-chain delivers cytotoxic potency. The CD16 binding domain covalently attached to a J-chain, or a variant thereof can, for example be a single-chain Fv (scFv) of an anti-CD16 antibody, or a naturally occurring heavy chain only antibody (VHH), e.g. a camelid (camels, llamas, alpacas) or single-chain antibody of cartilaginous fish (sharks, rays), a scaffold, e.g. fibronectin (e.g. fibronectin III) with CD16 binding specificity.

In certain aspects the modified J-chain comprises the mature VHH amino acid sequence SEQ ID NO: 112 (Table 2) fused to the N-terminus of the human J-chain through a linker, e.g., GGGGS ($L_5$, SEQ ID NO: 101), GGGGSGGGGS ($L_{10}$, SEQ ID NO: 102), GGGGSGGGGSGGGGS ($L_{15}$, SEQ ID NO: 103), or GGGGSGGGGSGGGGSGGGGS ($L_{20}$, SEQ ID NO: 104), a modified J-chain referred to herein as $CD16L_nJ$, where n=5, 10, 15, or 20. $CD16L_nJ$ can further include a signal peptide to facilitate transport and assembly into an IgM or IgA binding molecules. An exemplary modified J-chain according to this aspect can comprise the amino acid sequence SEQ ID NO: 125, described in Example 1. In certain aspects the mature modified J-chain comprises a VHH of SEQ ID NO: 112 fused to the C-terminus of the human J-chain through an amino acid linker, e.g., GGGGS ($L_5$, SEQ ID NO: 101), GGGGSGGGGS ($L_{10}$, SEQ ID NO: 102), GGGGSGGGGSGGGGS ($L_{15}$, SEQ ID NO: 103), or GGGGSGGGGSGGGGSGGGGS ($L_{20}$, SEQ ID NO: 104), a modified J-chain referred to herein as $JL_nCD16$, where n=5, 10, 15, or 20. $JL_nCD16$ can further include a signal peptide, e.g., amino acids 1 to 22 of SEQ ID NO: 2, to facilitate transport and assembly into an IgM or IgA binding molecules. In certain aspects, other signal peptides can be used. Selection and inclusion of suitable signal peptides to facilitate expression, secretion, and incorporation of a modified J-chain into an anti-HIV IgM or IgA binding molecule as provided herein is well within the capabilities of a person of ordinary skill in the art.

In another aspect, the effector cell is a macrophage. According to this aspect, the J-chain can be modified, e.g., by covalent attachment of a CD14 binding domain. In this configuration, a dimeric or pentameric binding molecule as provided herein provides binding specificity to a target HIV antigen, e.g., an HIV spike protein, while the macrophage tethering of the J-chain delivers cytotoxic potency. The CD14 binding domain covalently attached to a J-chain, or a variant thereof can, for example be a single-chain Fv (scFv) of an anti-CD14 antibody, or a naturally occurring heavy chain only antibody, e.g. a camelid (camels, llamas, alpacas) or single-chain antibody of cartilaginous fish (sharks, rays), a scaffold, e.g. fibronectin (e.g. fibronectin III) with CD14 binding specificity.

In another aspect, the effector cell is a neutrophil. According to this aspect, the J-chain can be modified, e.g., by covalent attachment of a CD16b or CD177 binding domain. In this configuration, a dimeric or pentameric binding molecule as provided herein provides binding specificity to a target HIV antigen, e.g., an HIV spike protein, while the neutrophil tethering of the J-chain delivers cytotoxic potency. The CD16b or CD177 binding domain covalently attached to a J-chain, or a variant thereof can, for example be a single-chain Fv (scFv) of an anti-CD16b or CD177 antibody, or a naturally occurring heavy chain only antibody, e.g. a camelid (camels, llamas, alpacas) or single-chain antibody of cartilaginous fish (sharks, rays), a scaffold, e.g. fibronectin (e.g. fibronectin III) with CD16b or CD177 binding specificity.

Engineered HIV Antigen Binding Domains

In certain aspects an HIV antigen binding domain as provided herein can include as many as six immunoglobulin complementarity determining regions HCDR1, HCDR2, HCDR3, LCDR1, LCDR2, and LCDR3, wherein at least one, at least two, at least three, at least four, at least five, or at least six CDRs are related to, or in some embodiments identical, or identical except for one, two, three, four, five, six, seven, eight, nine, or ten single amino acid substitutions, to the corresponding CDRs of the HIV mAbs set forth in Table 3, below.

Methods for genetically engineering cloned variable regions into immunoglobulin domains, and expressing and purifying such constructs are published and within the capability of one of skill in the art. (See, for instance, Wu et al., *MAbs,* 1(4):339-47, 2009, and Wu et al., *Nat. Biotechnol.,* 25:1290-7, 2007).

Exemplary peptide sequences encoding mature VH and VL domains that combine to form antibodies specific for HIV epitopes are set forth in Table 3. These sequences, or variants, fragments, or derivatives thereof, can then be engineered into a standard pentameric or hexameric IgM structure, as explained above, or an IgA structure.

TABLE 3

Exemplary Monoclonal Antibodies that Bind to HIV

| Reference | Binding Site | VH SEQ ID NO | VH Sequence | VL SEQ ID NO | VL Sequence |
|---|---|---|---|---|---|
| Wu et al., Science, 329(5993): 856-861, 2010; WO 2011/038290; | CD4bs | 5 | QVQLVQSGGQMKKPGESMRISCRASGYEFIDCTLNWIRLAPGKRPEWMGWLKPRGGAVNYARPLQGRVTMTRDVYSDTAFLELRSLTVDDTAVYFCTRGKNCDYNWDFEHWGRGTPVIVSS | 6 | EIVLTQSPGTLSLSPGETAIISCRTSQYGSLAWYQQRPGQAPRLVIYSGSTRAAGIPDRFSGSRWGPDYNLTISNLESGDFGVYYCQQYEFFGQGTKVQVDIKR |
| U.S. Pat. No. 8,637,036 | CD4bs | 7 | QVQLVQSGGQMKKPGESMRISCQASGYEFIDCTLNWVRLAPGRRPEWMGWLKPRGGAVNYARPLQGRVTMTRDVYSDTAFLELRSLTADDTAVYYCTRGKNCDYNWDFEHWGRGTPVTVSS | 8 | EIVLTQSPGTLSLSPGETAIISCRTSQYGSLAWYQQRPGQAPRLVIYSGSTRAAGIPDRFSGSRWGPDYNLTIRNLESGDFGLYYCQQYEFFGQGTKVQVDIKR |
| | CD4bs | 9 | QVQLVQSGAVIKTPGSSVKISCRASGYNFRDYSIHWVRLIPDKGFEWIGWIKPLWGAVSYARQLQGRVSMTRQLSQDPDDPDWGVAYMEFSGLTPADTAEYFCVRRGSCDYCGDFPWQYWGQGTVVVVSS | 10 | EIVLTQSPGILSLSPGETATLFCKASQGGNAMTWYQKRRGQVPRLLIYDTSRRASGVPDRFVGSGSGTDFFLTINKLDREDFAVYYCQQFEFFGLGSELEVHR |
| Wu et al., Science, 333(6049): 1593-1602, 2011 | CD4bs | 11 | QVQLVQSGSGVKKPGASVRVSCWTSEDIFERTELIHWVRQAPGQGLEWIGWVKTVTGAVNFGSPDFRQRVSLTRDRDLFTAHMDIRGLTQGDTATYFCARQKFYTGGQGWYFDLWGRGTLIVVSS | 12 | EIVLTQSPGTLSLSPGETASLSCTAASYGHMTWYQKKPGQPPKLLIFATSKRASGIPDRFSGSQFGKQYTLTITRMEPEDFARYYCQQLEFFGQGTRLEIRR |
| | CD4bs | 13 | QVQLVQSGSGVKKPGASVRVSCWTSEDIFERTELIHWVRQAPGQGLEWIGWVKTVTGAVNFGSPNFRHRVSLTRDRDLFTAHMDIRGLTQGDTATYFCARQKFERGGQGWYFDLWGRGTLIVVSS | 14 | EIVLTQSPGTLSLSPGETASLSCTAASYGHMTWYQKKPGQPPKLLIFATSKRASGIPDRFSGSQFGKQYTLTITRMEPEDFAGYYCQQVEFFGQGTRLEIR |
| | CD4bs | 15 | QVQLVQSGAAVRKPGASVTVSCKFAEDDDYSPYWVNPAPEHFIHFLRQAPGQQLEWLAWMNPTNGAVNYAWYLNGRVTATRDRSMTTAFLEVKSLRSDDTAVYYCARAQKRGRSEWAYAHWGQGTPVVVSS | 16 | DIQMTQSPSSLSASLGDRVTITCQASRGIGKDLNWYQQKAGKAPKLLVSDASTLEGGVPSRFSGSGFHQNFSLTISSLQAEDVATYFCQQYETFGQGTKVDIK |
| | CD4bs | 17 | QVQLVQSGAAVRKPGASVTVSCKFAEDDDYSPHWVNPAPEHYIHFLRQAPGQQLEWLAWMNPTNGAVNYAWQLHGRLTATRDGSMTTAFLEVRSLRSDDTAVYYCARAQKRGRSEWAYAHWGQGTPVAVSS | 18 | DIQMTQSPSSLSASLGDRVTITCQASRGIGKDLNWYQQKPGKAPKLLVSDASILEGGVPSRFSGSGFHQNFSLTISSLQPEDVATYFCQQYETFGQGTKVDIK |
| | CD4bs | 19 | QVQLVQSGAAVRKPGASVTVSCKFAEDDDFSPHWVNPAPEHYIHFLRQAPGQQLEWLAWMKPTNGAVNYAWQLQGRVTVTRDRSQTTAFLEVKNLRSDDTAVYYCARAQKRGRSEWAYAHWGQGTPVVISA | 20 | DIQMTQSPSSLSASLGDRVTITCQASRGIGKDLNWYQQKPGRAPKLLVSDASILEGGVPTRFSGSGFHQNFSLTISSLQAEDVATYFCQQYETFGQGTKVDIK |
| | CD4bs | 21 | QVQLVQSGAAVRKPGASISVSCKFADADDYSPHWMNPAPEHYIHFLRQAPGQQLEWLAWMNPTNGAVNYAWYLNGRVTATRDRSMTTAFLEVRSLRSDDTAVYYCARAQKRARSEWAYAHWGQGTPVVVSS | 22 | DIQMTQSPSSLSASLGDRVTITCQASRGIGKDLNWYQQKRGRAPRLLVSDASVLEGGVPSRFSGSGFHQNFSLTISTLQPEDVATYFCQQYETFGQGTKVDIK |

TABLE 3-continued Exemplary Monoclonal Antibodies that Bind to HIV

| Reference | Binding Site | VH SEQ ID NO | VH Sequence | VL SEQ ID NO | VL Sequence |
|---|---|---|---|---|---|
| | CD4bs | 23 | QVQLVQSGAAVRKPGASVTVSCKFAEDDDWSPHWVNPAPEHYIHFLRQAPGQQLEWLAWMNPTNGAVNYAWQLNGRLTATRDTSMTTAFLEVKSLRSDDTAVYYCARAQKRGRSEWAYAHWGQGTPVVVSS | 24 | DIQMTQSPSSLSASLGDRVTITCQASRGIGKDLNWYQQKAGKAPKLLVSDASILEGGVPSRFSGSGFHQNFSLTISSLQPEDVATYFCQQYETFGQGTKVDIK |
| Lehman et al., Science, 326(5950): 285-289, 2009 | V1/V2 | 25 | QRLVESGGGVVQPGSSLRLSCAASGFDFSRQGMHWVRQAPGQGLEWVAFIKYDGSEKYHADSVWGRLSISRDNSKDTLYLQMNSLRVEDTATYFCVREAGGPDYRNGYNYYDFYDGYYNYHYMDVWGKGTTVTVSS | 26 | QSALTQPASVSGSPGQSITISCNGTSNDVGGYESVSWYQQHPGKAPKVVIYDVSKRPSGVSNRFSGSKSGNTASLTISGLQAEDEGDYYCKSLTSTRRRVFGTGTKLTVL |
| | V1/V2 | 27 | QEQLVESGGGVVQPGGSLRLSCLASGFTFHKYGMHWVRQAPGKGLEWVALISDDGMRKYHSDSMWGRVTISRDNSKNTLYLQFSSLKVEDTAMFFCAREAGGPIWHDDVKYYDFNDGYNYHMDVWGKGTTVTVSS | 28 | QSALTQPASVSGSPGQTITISCNGTSSDVGGFDSVSWYQQSPGKAPKVMVFDVSHRPSGISNRFSGSKSGNTASLTISGLHIEDEGDYFCSSLTDRSHRIFGGGTKVTVL |
| Scheid et al., Science, 333(6049): 1633-1637, 2011 | CD4bs | 29 | QVQLLQSGAAVTKPGASVRVSCEASGYNIRDYFIHWWRQAPGQGLQWVGWINPKTGQPNNPRQFQGRVSLTRHASWDFDTFSFYMDLKALRSDDTAVYFCARQRSDYWDFDVWGSGTQVTVSSASTKGP | 30 | DIQMTQSPSSLSASVGDTVTITCQANGYLNWYQQRRGKAPKLLIYDGSKLERGVPSRFSGRRWGQEYNLTINNLQPEDIATYFCQVYEFVVPGTRLDLKRTVAAP |
| | CD4bs | 31 | QVRLSQSGGQMKKPGESMRLSCRASGYEFLNCPINWIRLAPGRRPEWMGWLKPRGGAVNYARKFQGRVTMTRDVYSDTAFLELRSLTSDDTAVYFCTRGKYCTARDYYNWDFEHWGRGAPVTVSSASTKGPSV | 32 | EIVLTQSPATLSLSPGETAIISCRTSQSGSLAWYQQRPGQAPRLVIYSGSTRAAGIPDRFSGSRWGADYNLSISNLESGDFGVYYCQQYEFFGQGTKVQVDIKRTVAAP |
| | Other | 33 | QIHLVQSGTEVKKPGSSVTVSCKAYGVNTFGLYAVNWVRQAPGQSLEYIGQIWRWKSSASHHFRGRVLISAVDLTGSSPPISSLEIKNLTSDDTAVYFCTTTSTYDKWSGLFIHDGVMAFSSWGQGTLISVSAASTKGPSVF | 34 | DIQMTQSPSTLSASIGDTVRISCRASQSITGNWVAWYQQRPGKAPRLLIYRGAALLGGVPSRFSGSAAGTDFTLTIGNLQAEDFGTFYCQQYDTYPGTFGQGTKVEVKRTVAAPSVFIFPPPSDEQLKSGT |
| | CD4bs | 35 | QVHLSQSGAAVTKPGASVRVSCEASGYKISDHFIHWWRQAPGQGLQWVGWINPKTGQPNNPRQFQGRVSLTRQASWDFDTYSFYMDLKAVRSDDTAIYFCARQRSDFWDFDVWGSGTQVTVSSASTKGPSX | 36 | DIQMTQSPSSLSARVGDTVTITCQANGYLNWYQQRRGKAPKLLIYDGSKLERGVPARFSGRRWGQEYNLTINNLQPEDVATYFCQVYEFIVPGTRLDLKRTVAA |
| | CD4bs | 37 | SQHLVQSGTQVKKPGASVRVSCQASGYTFTNYILHWWRQAPGQGLEWMGLIKPVFGAVNYARQFQGRIQLTRDIYREIAFLDLSGLRSDDTAVYYCARDESGDDLKWHLHPWGQGTQVIVSPASTKGP | 38 | DIQMTQSPSSLSASVGDRVTINCQAGQGIGSSLNWYQKKPGRAPKLLVHGASNLQRGVPSRFSGSGFHTTFTLTISSLQPDDVATYFCAVFQWFGPGTKVDIKRT |
| Walker et al., Nature, 477(7365): 466-70, 2011 | V3glycan | 39 | QMQLQESGPGLVKPSETLSLTCSVSGASISDSYWSWIRRSPGKGLEWIGYVHKSGDTNYSPSLKSRVNLSLDTSKNQVSLSLVAATAADSGKYYCARTLHGRRIYGIVAFNEWFTYFYMDVWGNGTQVTVSS | 40 | SDISVAPGETARISCGEKSLGSRAVQWYQHRAGQAPSLIIYNNQDRPSGIPERFSGSPDSPFGTTATLTITSVEAGDEADYYCHIWDSRVPTKWVFGGGTTLTVL |
| | V3glycan | 41 | QVHLQESGPGLVKPSETLSLTCNVSGTLVRDNYWSWIRQPLGKQPEWIGYVPIDSGDTNYNPSLKSRVHLSLDKSKNLVSLRLTGVTAADSAIYYCATTKHGRRIYGVVAFKEWFTYFYMDVWGKGTSVTVSS | 42 | TFVSVAPGQTARITCGEESLGSRSVIWYQQRPGQAPSLIIYNNNDRPSGIPDRFSGSPGSTFGTTATLTITSVEAGDEADYCHIWDSRRVINWVFGEGTTLIVL |
| | V3glycan | 43 | QLHLQESGPGLVKPPETLSLTCSVSGASINDAYWSWIRQSPGKRPEWVGYVHHSGDTNYNPSLKRRVTFSLDTAKNEVSLKLVDLTAADSATYFCARALHGKRIYGIVALGELFTYFYMDVWGKGTAVTVSS | 44 | SSMSVSPGETAKISCGKESIGSRAVQWYQQKPGQPPSLIIYNNQDRPAGVPERFSASPDFRPGTTATLTITNVDAEDEADYYCHIYDARGGTNWVFDRGTTLTVL |
| | V3glycan | 45 | QSQLQESGPRLVEASETLSLTCNVSGESTGACTYFWGWVRQAPGKGLEWIGSLSHCQSFWGSGWTFHNPSLKSRLTISLDTPKNQVFLKLTSLTAADTATYYCARFDGEVLVYNHWPKPAWVDLWGRGIPVTVTVSS | 46 | QSALTQPPSASGSPGQSITISCNGTATNFVSWYQQFPDKAPKLIIFGVDKRPPGVPDRFSGSRSGTTASLTVSRLQTDDEAVYYCGSLVGNWDVIFGGGTTLTVL |

TABLE 3-continued

Exemplary Monoclonal Antibodies that Bind to HIV

| Reference | Binding Site | VH SEQ ID NO | VH Sequence | VL SEQ ID NO | VL Sequence |
|---|---|---|---|---|---|
| | V3glycan | 47 | QPQLQESGPGLVEASETLSLTCTVSGDSTAACDYFWGWVRQPPGKGLEWIGGLSHCAGYYNTGWTYHNPSLKSRLTISLDTPKNQVFLKLNSVTAADTAIYYCARFDGEVLVYHDWPKPAWVDLWGRGTLVTVTVSS | 48 | QSALTQPPSASGSPGQSISISCTGTSNRFVSWYQQHPGKAPKLVIYGVNKRPSGVPDRFSGSKSGNTASLTVSGLQTDDEAVYYCSSLVGNWDVIFGGGTKLTVL |
| | V3glycan | 49 | QPQLQESGPGLVEASETLSLTCTVSGDSTGRCNYFWGWVRQPPGKGLEWIGSLSHCRSYYNTDWTYHNPSLKSRLTISLDTPKNQVFLRLTSVTAADTATYYCARFGGEVLVYRDWPKPAWVDLWGRGTLVTVSS | 50 | QSALTQPPSASGSPGQSITISCTGTSNNFVSWYQQYPGKAPKLVIYEVNKRPSGVPDRFSGSKSGSTASLTVSGLQADDEGVYYCSSLVGNWDVIFGGGTKLTVL |
| | V3glycan | 51 | QPQLQESGPTLVEASETLSLTCAVSGDSTAACNSFWGWVRQPPGKGLEWVGSLSHCASYWNRGWTYHNPSLKSRLTLALDTPKNLVFLKLNSVTAADTATYYCARFGGEVLRYTDWPKPAWVDLWGRGTLVTVSS | 52 | QSALTQPPSASGSPGQSITISCTGTSNNFVSWYQQHAGKAPKLVIYDVNKRPSGVPDRFSGSKSGNTASLTVSGLQTDDEAVYYCGSLVGNWDVIFGGGTKLTVL |
| | V3glycan | 53 | QVQLQESGPGLVKPAETLSLTCSVSGESINTGHYYWGWVRQVPGKGLEWIGHIHYTTAVLHNPSLKSRLTIKIYTLRNQITLRLSNVTAADTAVYHCVRSGGDILYYYEWQKPHWFSPWGPGIHVTVSS | 54 | QSALTQPPSASGSLGQSVTISCNGTSSDIGGWNFVSWYQQFPGRAPRLIIFEVNKRPSGVPGRFSGSKSGNSASLTVSGLQSDDEGQYFCSSLFGRWDVVFGGGTKLTVL |
| | V3glycan | 55 | QVQLQESGPGLVKPSETLSLTCTVSGDSINTGHHYWGWVRQVPGKGPEWIAHIHYNTAVLHNPALKSRVTISIFTLKNLITLSLSNVTAADTAVYFCVRSGGDILYYIEWQKPHWFYPWGPGILVTVSS | 56 | QSALTQPPSASGSLGQSLTISCSGTGSDIGWNFVSWYQQFPGRAPNLIIFEVNRRSGVPDRFSGSKSGNTASLTVSGLRSEDEAEYFCSSLSGRWDIVFGGGTKVTVL |
| | V3glycan | 57 | QLQMQESGPGLVKPSETLSLSCTVSGDSIRGGEWGDKDYHWGWVRHSAGKGLEWIGSIHWRGTTHYKESLRRRVSMSIDTSRNWFSLRLASVTAADTAVYFCARHRHHDVFMLVPIAGWFDVWGPGVQVTVSS | 58 | EIVMTQSPDTLSVSPGETVTLSCRASQNINKNLAWYQYKPGQSPRLVIFETYSKIAAFPARFVASGSGTEFTLTINNMQSEDVAVYYCQQYEEWPRTFGQGTKVDIK |
| | V1/V2 | 59 | QVQLVQSGPEVKKPGSSVKVSCKASGNTFSKYDVHWVRQATGQGLEWVGWMSHEGDKTESAQRFKGRVTFTRDTSASTAYMELRGLTSDDTAIYYCTRGSKHRLRDYVLYDDYGLINYQEWNDYLEFLDVWGHGTAVTVSS | 60 | DTVVTQSPLSLPVTPGEAASMSCSSTQSLRHSNGANYLAWYQHKPGQSPRLLIRLGSQRASGVPDRFSGSGSGTHFTLKISRVEAEDAAIYYCMQGLNRPWTFGKGTKLEIK |
| | V1/V2 | 61 | QVQLEQSGAEVKKPGSSVKVSCKASGNTFSKYDVHWVRQATGQGLEWVGWMSHEGDKTESAQRFKGRVTFTRDTSASTAYMELRGLTSDDTAIYYCTRGSKHRLRDYVLYDDYGLINYQEWNDYLEFLDVWGHGTAVTVSS | 62 | DTVVTQSPLSLPVTPGEAASMSCTSTQSLRHSNGANYLAWYQHKPGQSPRLLIRLGSQRASGVPDRFSGSGSGTHFTLKISRVEPEDAAIYYCMQGLNRPWTFGKGTKLEIK |
| | V1/V2 | 63 | QVQLVQSGAEVKKPGSSVKVSCKASGNTFRKYDVHWVRQATGQGLEWVGWMSHEGDKTESAQRFKGRVSFTRDNSASTAYIELRGLTSDDTAIYYCTGGSKHRLRDYVLYDDYGLINQQEWNDYLEFLDVWGHGTAVTVSS | 64 | DTVVTQSPLSLSVTPGEAASMSCTSTQSLRHSNGANYLAWYQHKPGQSPRLLIRLGSQRASGVPDRFSGSGSGTHFTLKISRVEADDAIYYCMQGLNRPWTFGKGTKLEIK |
| | V1/V2 | 65 | QVQLVQSGAEVKKPGSSVKVSCKASGNSFSNHDVHWVRQATGQGLEWMGWMSHEGDKTGLAQKFQGRVTITRDSGASTVYMELRGLTADDTAIYYCLTGSKHRLRDYFLYNEYGPNYEEWGDYLATLDVWGHGTAVTVSS | 66 | EVVITQSPLFLPVTPGEAASLSCKCSHSLQHSTGANYLAWYLQRPGQTPRLLIHLATHRASGVPDRFSGSGSGTDFTLKISRVESDDVGTYYCMQGLHSPWTFGQGTKVEIK |
| | V1/V2 | 67 | QVQLVQSGPEVKKPGSSVKVSCKASGNTFSKYDVHWVRQATGQGLEWVGWISHERDKTESAQRFKGRVTFTRDTSATTAYMELRGLTSDDTAIYYCTRGSKHRLRDYVLYDDYGLINYQEWNDYLEFLDVWGHGTAVTVSS | 68 | DTVVTQSPLSLPVTPGEAASMSCSSTQSLRHSNGANYLAWYQHKPGQSPRLLIRLGSQRASGVPDRFSGSGSGTHFTLKISRVEAEDAAIYYCMQGLNRPWTFGKGTKLEIK |
| Zhu et al., J. Virol., 85(21): 11401-11408, 2011 | MPER | 69 | QVQLVQSGAEVKKPGESLKISCKVSGYNFASEWIGWVRQMPGKGLEWMGIIYPGDSDTKYSPSFQGQVIISADKSINTAYLQWSSLKASDTAIYYCARQNHYGSGSYFYRTAYYYAMDVWGQGTTVTVSS | 70 | DIQLTQSPSSLSASLGDKVTITCRASQHIKKYLNWYQQKPGKAPKLLIYGALNLQSGVPSRFGRGSGTDFTLTISSLQPEDFATYYCQQYSTPFTFGPGTKVDIKR |

TABLE 3-continued

Exemplary Monoclonal Antibodies that Bind to HIV

| Reference | Binding Site | VH SEQ ID NO | VH Sequence | VL SEQ ID NO | VL Sequence |
|---|---|---|---|---|---|
| Liao et al., Nature, 496(7446): 469-476, 2013 | CD4bs | 71 | SETLSLTCTVSGGSMGGTYWSWLRLS PGKGLEWIGYIFHTGETNYSPSLKGRV SISVDTSEDQFSLRLRSVTAADTAVYF CASLPRGQLVNAYFRNWGRGSLVSV TA | 72 | SYELTQPPSVSVSPGQTATITCSG ASTNVCWYQVKPGQSPEVVIFEN YKRPSGIPDRFSGSKSGSTATLTIR GTQAIDEADYYCQVWDSFSTFVF GSGTQVTVL |
| Huang et al., Nature, 491(7424): 406-412, 2012; WO 2013/070776 | MPER | 73 | EVQLVESGGGLVKPGGSLRLSCSASG FDFDNAWMTWVRQPPGKGLEWVGRI TGPGEGWSVDYAAPVEGRFTISRLNSI NFLYLEMNNLRMEDSGLYFCARTGK YYDFWSGYPPGEEYFQDWGRGTLVT VSS | 74 | SYELTQETGVSVALGRTVTITCRG DSLRSHYASWYQKKPGQAPILLF YGKNNRPSGVPDRFSGSASGNRA SLTISGAQAEDDAEYYCSSRDKS GSRLSVFGGGTKLTVLX |
| WO 2013/086533 | CD4bs | 75 | QVRLSQSGGQMKKPGDSMRISCRASG YEFINCPINWIRLAPGKRPEWMGWM KPRGGAVSYARQLQGRVTMTRDMYS ETAFLELRSLTDDDTAVYFCTRGKYC TARDYYNWDFEHWGQGTPVTVSS | 6 | EIVLTQSPGTLSLSPGETAIISCRTS QYGSLAWYQQRPGQAPRLVIYSG STRAAGIPDRFSGSRWGPDYNLTI SNLESGDFGVYYCQQYEFFGQGT KVQVDIKR |
| WO 2013/142324 | CD4bs/b19 | 77 | QVQLVQPGTAMKSLGSSLTITCRVSG DDLGSFHFGTYFMIWVRQAPGQGLE YMGGILPSTKTPTYAHKFRGRVSISAP GVPPVLSLALTNLTYDDTATYFCARE RGRHFEPKNRDNLEGKFFDLWGRGTF VRVSP | 78 | QSALTQPASVSGSPGQSINISCAG RSDRVSWYQQRPNGVPKLLMFD VYRRPSGVSDRFSGSHSGDTAFL TISGLQTEDEADYYCTSHPYAFG AGTKVNVL |
| Diskin et al., J Exp. Med., 210(6): 1235-1249, 2013 | CD4bs | 79 | XVRLSQSGGQMKKPGESMRLSCRAS GYEFLNCPINWIRLAPGRRPEWMGWL KPRWGAVNYARKFQGRVTMTRDVY SDTAFLELRSLTSDDTAVYFCTRGKY CTARDYYNWDFEHWGRGAPVTVSS | 80 | EIVLTQSPATLSLSPGETAIISCRTS QYGSLAWYQQRPGQAPRLVIYSG STRAAGIPDRFSGSRWGADYNLSI SNLESGDFGVYYCQQYEFFGQGT KVQVDIKR |
| Mouquet et al., PNAS USA, 109: E3268-E3277, 2012 | V3 glycan | 81 | QVQLQESGPGLVKPSETLSVTCSVSG DSMYYWTWIRQSPGKGLEWIGYIS DRESATYNPSLNSRVVISRDTSKNQLS LKLNSVTPADTAVYYCATARRGQRIY GVVSFGEFFYYYSMDVWGKGTTVTV SS | 82 | SYVRPLSVALGETARISCGRQAL GSRAVQWYQHRPGQAPILLIYNN QDRPSGIPERFSGTPDINFGTRATL TISGVEAGDEADYYCHMWDSRS GFSWSFGGATRLTVLG |
| Huang, J. et al. Nature 515, 138-142 (2014) | face of contiguous areas of gp41 and gp120 | 83 | QGQLVQSGAELKKPGASVKISCKTSG YRFNFYHINWIRQTAGRGPEMGWIS PYSGDKNLAPAFQDRVIMTTDTEVPV TSFTSTGAAYMEIRNLKFDDTGTYFC AKGLLRDGSSTWLPYLWGQGTLLTV SS | 84 | QSVLTQSASVSGSLGQSVTISCTG PNSVCCSHKSISWYQWPPGRAPT LIIYEDNERAPGISPRFSGYKSYW SAYLTISDLRPEDETTYYCCSYTH NSGCVFGTGTKVSVL |
| Bonsignori M, et al., J Virol. 85(19): 9998-10009 2011. | V1/V2 | 85 | EVQLVESGANVRPGGSLRLSCKASG FIFENFGFSWVRQAPGKGLQWVAGL NWNGGDTRYADSVKGRFRMSRDNSN NFVYLDMDKVGDDTAFYYCARGT DYTIDDAGIHYQGSGTFWYFDLWGR GTLVSVSS | 86 | EIVLAQSPGTLSLSPGERATLSCR ASHNVHPKYFAWYQQKPGQSPR LLIYGGSTRAAGIPGKFSGSGSGT DFTLTISRVDPEDFAVYYCQQYG GSPYTFGQGTKVEIK |
| | V1/V2 | 87 | EVQLVESGGSVVRPGGSLRLSCRASG FIFENYGLTWVRQVPGKGLHWVSGM NWNGGDTRYADSVRGRFSMSRDNSN NIAYLQMNNLRVEDTALYYCARGTD YTIDDQGRFYQGSGTFWYFDFWGRG TLVTVSS | 88 | EIVLTQSPATLSVSPGERATLSCR ASQNVHPRYFAWYQQKRGQSPR LLIHSGSTRAAGIADRFSGGGSGM HFTLTITRVEPEDFAVYFCQQYG GSPYTFGQGTRVELR |
| | V1/V2 | 89 | EVQLVESGGGVVRPGGSLRLSCAASG FIFENYGLTWVRQVPGKGLHWVSGM NWNGGDTRYADSVRGRFSMSRDNSN NIAYLQMKNLRVDDTALYYCARGTD YTIDDQGIFYKGSGTFWYFDLWGRGT LVTVSS | 90 | EIVLTQSPATLSLSPGERATLSCR ASQSVHPKYFAWYQQKPGQSPR LLIYSGSTRAAGIADRFSGGGSGI HFTLTITRVEPEDFAVYFCQQYG GSPYTFGQGTKVELR |
| | V1/V2 | 91 | EVQLVESGGGLIRPGGSLRLSCKGSGF IPENFGFGWVRQGPGKGLEWVSGTN WNGGDSRYGDSVKGRFTISRDNSNNF VYLQMNSLRPEDTAIYYCARGTDYTI DDQGIRYQGSGTFWYFDVWGRGTLV TVSS | 92 | EIVLTQSPDTLSLSPGERATLSCR ASQSVRSRYFAWYQHKPGQPPRL LIYGGSTRATGIPNRFSAGGSGTQ FTLTVNRLEAEDFAVYYCQQYGR SPYTFGQGTKVEIR |
| Sok, D. et al., Proc. Natl. Acad. Sci. USA 111: 17624- | | 93 | QVHLTQSGPEVRKPGTSVKVSCKAPG NTLKTYDLHWVRSVPGQGLQWMGW ISHEGDKKVIVERFKAKVTIDWDRST NTAYLQLSGLTSGDTAVYYCAKGSK | 94 | DFVLTQSPHSLSVTPGESASISCKS SHSLIHGDRNNYLAWYVQKPGRS PQLLIYLASSRASGVPDRFSGSGS DKDFTLKISRVETEDVGTYYCMQ |

TABLE 3-continued

Exemplary Monoclonal Antibodies that Bind to HIV

| Reference | Binding Site | VH SEQ ID NO | VH Sequence | VL SEQ ID NO | VL Sequence |
|---|---|---|---|---|---|
| 17629 (2014) | | | HRLRDYALYDDDGALNWAVDVDYL SNLEFWGQGTAVTVSS | | GRESPWTFGQGTKVDIK |
| Buchacher, A., et al., AIDS Res. Hum. Retroviruses 10: 359-369 (1994); WO 2011/035205 | V3/glycan | 95 | EVQLVESGGGLVKAGGSLILSCGVSN FRISAHTMNWVRRVPGGGLEWVASIS TSSTYRDYADAVKGRFTVSRDDLEDF VYLQMHKMRVEDTAIYYCARKGSDR LSDNDPFDAWGPGTVVTVSP | 96 | DIQMTQSPSTLSASVGDTITITCRA SQSIETWLAWYQQKPGKAPKLLI YKASTLKTGVPSRFSGSGSGTEFT LTISGLQFDDFATYHCQHYAGYS ATFGQGTRVEIK |
| Pincus SH, et al. J Immunol 170: 2236-2241(2003) | The immuno-dominant region of gp41 | 97 | QVQLVQSGGGVFKPGGSLRLSCEASG FTFTEYYMTWVRQAPGKGLEWLAYI SKNGEYSKYSPSSNGRFTISRDNAKNS VFLQLDRLSADDTAVYYCARADGLT YFSELLQYIFDLWGQGARVTVSS | 98 | DIVMTQSPDSLAVSPGERATIHCK SSQTLLYSSNNRHSIAWYQQRPG QPPKLLLYWASMRLSGVPDRFSG SGSGTDFTLTINNLQAEDVAIYYC HQYSSHPPTFGHGTRVEIK |
| Moore, J. P., and J. Sodroski J. Virol 70: 1863-1872 (1996); WO 2006/044410 | CD4bs | 99 | QVQLQESGPGLVKPSQTLSLSCTVSG GSSSSGAHYWSWIRQYPGKGLEWIGY IHYSGNTYYNPSLKSRITISQHTSENQF SLKLNSVTVADTAVYYCARGTRLRTL RNAFDIWGQGTMVTVSS | 100 | QSVLTQPPSASGSPGQSVTISCTG TSSDVGGYNYVSWYQHHPGKAP KLIISEVNNRPSGVPDRFSGSKSG NTASLTVSGLQAEDEAEYYCSSY TDIHNFVFGGGTKLTVLR |

In certain aspects the HIV antigen binding domain of a dimeric, hexameric, or pentameric binding molecule as provided herein comprises an antibody heavy chain variable region (VH) and an antibody light chain variable region (VL), wherein the VH region, the VL region, or both the VH and VL regions are related to the corresponding VH and VL of HIV monoclonal antibodies disclosed in the references set forth in Table 3, above. In certain aspects, the binding molecules provided herein exhibit greater potency than an IgG antibody comprising the VH and VL of antibodies listed in Table 3.

In certain aspects the VH can comprise an amino acid sequence at least 60%, at least 65%, at least 70%, at least 75%, at least 80%, at least 85%, at least 90%, at least 95% or 100% identical to any one or more of the amino acid sequences of SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99.

In certain aspects the VL can comprise an amino acid sequence at least at least 60%, at least 65%, at least 70%, at least 75%, at least 80%, at least 85%, at least 90%, at least 95% or 100% identical to any one or more of SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 6, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100.

In certain aspects the VH and VL amino acid sequences can comprise amino acid sequences at least at least 60%, at least 65%, at least 70%, at least 75%, at least 80%, at least 85%, at least 90%, at least 95% or 100% identical to SEQ ID NO: 5 and SEQ ID NO: 6, SEQ ID NO: 7 and SEQ ID NO: 8, SEQ ID NO: 9 and SEQ ID NO: 10, SEQ ID NO: 11 and SEQ ID NO: 12, SEQ ID NO: 13 and SEQ ID NO: 14, SEQ ID NO: 15 and SEQ ID NO: 16, SEQ ID NO: 17 and SEQ ID NO: 18, SEQ ID NO: 19 and SEQ ID NO: 20, SEQ ID NO: 21 and SEQ ID NO: 22, SEQ ID NO: 23 and SEQ ID NO: 24, SEQ ID NO: 25 and SEQ ID NO: 26, SEQ ID NO: 27 and SEQ ID NO: 28, SEQ ID NO: 29 and SEQ ID NO: 30, SEQ ID NO: 31 and SEQ ID NO: 32, SEQ ID NO: 33 and SEQ ID NO: 34, SEQ ID NO: 35 and SEQ ID NO: 36, SEQ ID NO: 37 and SEQ ID NO: 38, SEQ ID NO: 39 and SEQ ID NO: 40, SEQ ID NO: 41 and SEQ ID NO: 42, SEQ ID NO: 43 and SEQ ID NO: 44, SEQ ID NO: 45 and SEQ ID NO: 46, SEQ ID NO: 47 and SEQ ID NO: 48, SEQ ID NO: 49 and SEQ ID NO: 50, SEQ ID NO: 51 and SEQ ID NO: 52, SEQ ID NO: 53 and SEQ ID NO: 54, SEQ ID NO: 55 and SEQ ID NO: 56, SEQ ID NO: 57 and SEQ ID NO: 58, SEQ ID NO: 59 and SEQ ID NO: 60, SEQ ID NO: 61 and SEQ ID NO: 62, SEQ ID NO: 63 and SEQ ID NO: 64, SEQ ID NO: 65 and SEQ ID NO: 66, SEQ ID NO: 67 and SEQ ID NO: 68, SEQ ID NO: 69 and SEQ ID NO: 70, SEQ ID NO: 71 and SEQ ID NO: 72, SEQ ID NO: 73 and SEQ ID NO: 74, SEQ ID NO: 75 and SEQ ID NO: 6, SEQ ID NO: 77 and SEQ ID NO: 78, SEQ ID NO: 79 and SEQ ID NO: 80, SEQ ID NO: 81 and SEQ ID NO: 82, SEQ ID NO: 83 and SEQ ID NO: 84, SEQ ID NO: 85 and SEQ ID NO: 86, SEQ ID NO: 87 and SEQ ID NO: 88, SEQ ID NO: 89 and SEQ ID NO: 90, SEQ ID NO: 91 and SEQ ID NO: 92, SEQ ID NO: 93 and SEQ ID NO: 94, SEQ ID NO: 95 and SEQ ID NO: 96, SEQ ID NO: 97 and SEQ ID NO: 98, or SEQ ID NO: 99 and SEQ ID NO: 100, respectively.

In certain aspects the HIV antigen binding domain of a dimeric, hexameric, or pentameric binding molecule as provided herein comprises the HCDR1, HCDR2, and HCDR3 regions, or HCDR1, HCDR2, and HCDR3 regions containing one or two single amino acid substitutions, and the LCDR1, LCDR2, and LCDR3 regions, or LCDR1, LCDR2, and LCDR3 containing one or two single amino acid substitutions, of the VH and VL amino acid sequences of SEQ ID NO: 5 and SEQ ID NO: 6, SEQ ID NO: 7 and SEQ ID NO: 8, SEQ ID NO: 9 and SEQ ID NO: 10, SEQ ID NO: 11 and SEQ ID NO: 12, SEQ ID NO: 13 and SEQ ID NO: 14, SEQ ID NO: 15 and SEQ ID NO: 16, SEQ ID NO: 17 and SEQ ID NO: 18, SEQ ID NO: 19 and SEQ ID NO: 20, SEQ ID NO: 21 and SEQ ID NO: 22, SEQ ID NO: 23 and SEQ ID NO: 24, SEQ ID NO: 25 and SEQ ID NO: 26, SEQ ID NO: 27 and SEQ ID NO: 28, SEQ ID NO: 29 and SEQ ID NO: 30, SEQ ID NO: 31 and SEQ ID NO: 32, SEQ ID NO: 33 and SEQ ID NO: 34, SEQ ID NO: 35 and SEQ ID NO: 36, SEQ ID NO: 37 and SEQ ID NO: 38, SEQ ID NO: 39 and SEQ ID NO: 40, SEQ ID NO: 41 and SEQ ID NO: 42, SEQ ID NO: 43 and SEQ ID NO: 44, SEQ ID NO: 45 and SEQ ID NO: 46, SEQ ID NO: 47 and SEQ ID NO: 48, SEQ ID NO: 49 and SEQ ID NO: 50, SEQ ID NO: 51 and SEQ ID NO: 52, SEQ ID NO: 53 and SEQ ID NO: 54, SEQ ID NO: 55 and SEQ ID NO: 56, SEQ ID NO: 57 and SEQ ID NO: 58, SEQ ID NO: 59 and SEQ ID NO: 60, SEQ ID NO: 61 and SEQ ID NO: 62, SEQ ID NO: 63 and SEQ ID NO: 64, SEQ ID NO: 65 and SEQ ID NO: 66, SEQ ID NO: 67 and SEQ ID NO: 68, SEQ ID NO: 69 and SEQ ID NO: 70, SEQ ID NO: 71 and SEQ ID NO: 72, SEQ ID NO: 73 and SEQ ID NO: 74, SEQ ID NO: 75 and SEQ ID NO: 6, SEQ ID NO: 77 and SEQ ID NO: 78, SEQ ID NO: 79 and SEQ ID NO: 80, SEQ ID NO: 81 and SEQ ID NO: 82, SEQ ID NO: 83 and SEQ ID NO: 84, SEQ ID NO: 85 and SEQ ID NO: 86, SEQ ID NO: 87 and SEQ ID NO: 88, SEQ ID NO: 89 and SEQ ID NO: 90, SEQ ID NO: 91 and SEQ ID NO: 92, SEQ ID NO: 93 and SEQ ID NO: 94, SEQ ID NO: 95 and SEQ ID NO: 96, SEQ ID NO: 97 and SEQ ID NO: 98, or SEQ ID NO: 99 and SEQ ID NO: 100.

In certain aspects a hexameric or pentameric IgM antibody designated herein as HIV02M is provided comprising an IgM heavy chain comprising the amino acid sequence SEQ ID NO: 114 and a kappa light chain comprising the amino acid sequence SEQ ID NO: 115. In certain aspects a hexameric or pentameric IgM antibody designated herein as HIV12M is provided comprising an IgM heavy chain comprising the amino acid sequence SEQ ID NO: 117 and a kappa light chain comprising the amino acid sequence SEQ ID NO: 118. In certain aspects a hexameric or pentameric IgM antibody designated herein as HIV32M is provided comprising an IgM heavy chain comprising the amino acid sequence SEQ ID NO: 120 and a kappa light chain comprising the amino acid sequence SEQ ID NO: 121. In certain aspects a hexameric or pentameric IgM antibody designated herein as HIV72M is provided comprising an IgM heavy chain comprising the amino acid sequence SEQ ID NO: 123 and a kappa light chain comprising the amino acid sequence SEQ ID NO: 124. Where the IgM antibody HIV02M, HIV12M, HIV32M, or HIV72M is pentameric, it can further include a J-chain or functional fragment thereof, e.g., a wild-type human J-chain comprising amino acids 23 to 159 of SEQ ID NO: 2, or a modified J-chain as provided elsewhere herein, e.g., a J-chain comprising the formula X[$L_n$]J or J[$L_n$]X, where J is a native J-chain or functional fragment thereof, e.g., a native human J-chain (amino acids 23 to 159 of SEQ ID NO: 2), X is a binding domain, e.g., SEQ ID NO: 105, SEQ ID NO: 106, SEQ ID NO: 107, or SEQ ID NO: 112, and [$L_n$] is a linker sequence consisting of n amino acids, where n is a positive integer, e.g., from 1 to 100, 1 to 50, or 1 to 25. In certain aspects n=5, 10, 15, or 20, e.g., SEQ ID NO: 101, SEQ ID NO: 102, SEQ ID NO: 103, or SEQ ID NO: 104. In certain aspects the modified J-chain can comprise or consist of V5J (SEQ ID NO: 108), V10J (SEQ ID NO: 109), V15J (SEQ ID NO: 110), V20J (SEQ ID NO: 111), C15J (SEQ ID NO: 125), or any combination thereof.

In certain aspects an IgM antibody as provided herein, e.g., an IgM antibody comprising HIV02M, HIV12M, HIV32M, or HIV72M, either without a J-chain or further comprising a wild-type or modified J-chain as provided herein can exhibit greater potency than a single binding unit antibody, e.g., an IgG antibody comprising the corresponding VH and VL of an antibody listed in Table 3. For example, an IgM antibody as provided herein, e.g., an IgM antibody comprising HIV02M, HIV12M, HIV32M, or HIV72M can more potently neutralize HIV, bind and neutralize more diverse HIV variants or clades, enhance viral clearance, and/or be more potent in preventing, controlling or treating HIV infection than a corresponding reference single binding unit molecule comprising only two HIV antigen binding domains. Moreover, an IgM antibody as provided herein, e.g., an IgM antibody comprising HIV02M, HIV12M, HIV32M, or HIV72M can be more potent in controlling HIV infectivity and growth as compared with a corresponding reference single binding unit molecule comprising only two HIV antigen binding domains. In addition, an IgM antibody as provided herein, e.g., an IgM antibody comprising HIV02M, HIV12M, HIV32M, or HIV72M can be used to treat chronic infection, e.g., by binding to and/or effecting antibody and/or cell-mediated killing of HIV infected cells, e.g., reservoir cells that express extremely low levels of HIV antigens on their surface. In a further example, an IgM antibody as provided herein, e.g., an IgM antibody comprising HIV02M, HIV12M, HIV32M, or HIV72M can be more effective at activating and killing such HIV-infected cells or killing such cells after activation with an independent activating agent such as an effector cell, e.g., a T-cell. In a further example, an IgM antibody as provided herein, e.g., an IgM antibody comprising HIV02M, HIV12M, HIV32M, or HIV72M can provide equivalent benefit at a lower dosage than that of a corresponding reference single binding unit molecule comprising only two HIV antigen binding domains. In certain aspects, administration of an IgM antibody as provided herein, e.g., an IgM antibody comprising HIV02M, HIV12M, HIV32M, or HIV72M can allow for reduced or modified dosages of other anti-retroviral therapies, such as ART (see, e.g., Example 7 below).

While a variety of different dimeric, hexameric, and pentameric binding molecules can be contemplated by a person of ordinary skill in the art based on this disclosure, and as such are included in this disclosure, in certain aspects, a binding molecule as described above is provided in which each binding unit comprises two IgM heavy chains each comprising a VH situated amino terminal to the IgM constant region or fragment thereof, and two immunoglobulin light chains each comprising a VL situated amino terminal to an immunoglobulin light chain constant region. In certain aspects, a binding molecule as described above is provided in which each binding unit comprises two IgA heavy chains each comprising a VH situated amino terminal to the IgA constant region or fragment thereof, and two immunoglobulin light chains each comprising a VL situated amino terminal to an immunoglobulin light chain constant region.

Moreover in certain aspects, at least one binding unit of the binding molecule, or two, three, four, five, or six binding units of the binding molecule, each comprise two of the HIV antigen binding domains as described above. In certain aspects the two HIV antigen binding domains in the one binding unit of the binding molecule, or two, three, four, five, or six binding units of the binding molecule, can be different from each other, or they can be similar or identical.

In certain aspects, the two IgA heavy chains within one binding unit of the binding molecule, or two binding units of the binding molecule, are identical. In certain aspects, the two IgM heavy chains within one binding unit of the binding molecule, or two, three, four, five, or six binding units of the binding molecule, are identical.

In certain aspects, the two light chains within one binding unit of the binding molecule, or two, three, four, five, or six binding units of the binding molecule, are identical. In certain aspects, two identical light chains within at least one binding unit, or within two, three, four, five, or six binding units of the binding molecule are kappa light chains, e.g., human kappa light chains, or lambda light chains, e.g., human lambda light chains.

In certain aspects at least one, two, three, four, five, or six binding units of a dimeric, pentameric, or hexameric HIV binding molecule, e.g., an IgM antibody provided by this disclosure comprises or each comprise two identical IgA or IgM heavy chains, and two identical light chains. According to this aspect, the HIV antigen binding domains in the one binding unit of the binding molecule, or two, three, four, five, or six binding units of the binding molecule, can be identical. Further according to this aspect, a dimeric, pentameric, or hexameric HIV binding molecule, e.g., an IgM antibody as provided herein can comprise at least one, two, three, four, five, six, seven, eight, nine, ten, eleven, or twelve copies of an HIV antigen binding domain as described above. In certain aspects at least two, at least three, at least four, at least five, or at least six of the binding units can be identical and, in certain aspects the binding units can comprise identical antigen binding domains, e.g., at least two, at least three, at least four, at least five, at least six, at least seven, at least eight, at least nine, at least ten, at least eleven, or at least twelve HIV antigen binding domains can be identical.

In certain aspects, a dimeric, pentameric, or hexameric HIV binding molecule as provided herein can possess advantageous structural and/or functional properties, or "improved binding characteristics," as compared to other binding molecules, such as a corresponding reference single binding unit molecule comprising the same antigen binding domain. For example, the dimeric, pentameric, or hexameric HIV binding molecule can possess improved activity or potency in a biological assay, either in vitro or in vivo, relative to a corresponding reference single binding unit molecule, e.g., an IgG1 binding molecule comprising the same VH and VL region sequences as are present in the multimeric binding molecule, as described above. Biological assays include, but are not limited to, Antibody-Dependent Cell-mediated Cytotoxicity (ADCC) assays, T-cell dependent Cellular Cytotoxicity (TDCC) assays, Complement-Dependent Cytotoxicity (CDC) assays, Cell-To-Cell Spread (CTCS) assays, viral transcytosis assays, complement-dependent virolysis assays, virus neutralization assays, cell attachment assays, viral egress assays, immunohistochemical assays, direct cytotoxicity assays, complement-mediated cytotoxicity assays, etc. Suitable HIV glycoprotein-expressing cells for performing such assays include, but are not limited to .g., CHO-gp120, CHO-gp140, Jurkat-522 F/Y cells, or mammalian cells expressing membrane anchored trimeric forms of gp140, e.g., strain JR-FL (Go et al. 2015 *J Virol* 89:8245-8257). In certain aspects a dimeric, pentameric, or hexameric HIV binding molecule, e.g., an IgM antibody as provided herein can direct HIV neutralization, and/or clearance or killing of an HIV-infected cells, such as reservoir cells, at higher potency than an equivalent amount of a monospecific, bivalent IgG1 antibody or fragment thereof that specifically binds to the same HIV epitope as the HIV antigen binding domain.

By "potency" or "binding characteristics" refers to the ability of a binding molecule to achieve a given biological result. For example, potency can be referred to as the amount of a given binding molecule necessary to achieve a given biological result (EC100 or IC100) or the amount of a given binding molecule necessary to achieve 50% of a desired biological result (EC50 or IC50). Biological results can include, for example, binding to recombinant gp120 or gp41, binding to gp120/41 expressing cells, binding to chronically and/or latently infected cell lines, neutralization of HIV viruses or HIV pseudo-typed viruses, neutralization of more diverse HIV viruses or HIV pseudo-typed viruses, killing of latent HIV-infected cells, reduction of HIV virus or HIV infected cells in therapeutic animal models, or prolonged absence of HIV virus after cessation of ART.

Polynucleotides, Vectors, and Host Cells

The disclosure further provides a polynucleotide, e.g., an isolated, recombinant, and/or non-naturally-occurring polynucleotide, comprising a nucleic acid sequence that encodes a polypeptide subunit of the dimeric, hexameric, or pentameric binding molecule as described above. By "polypeptide subunit" is meant a portion of a binding molecule, binding unit, or antigen binding domain that can be independently translated. Examples include, without limitation, an antibody variable domain, e.g., a VH or a VL, a J-chain, a secretory component, a single chain Fv, an antibody heavy chain, an antibody light chain, an antibody heavy chain constant region, an antibody light chain constant region, and/or any fragment, variant, or derivative thereof.

In certain aspects, the polypeptide subunit can comprise an IgM or an IgA heavy chain constant region or fragment thereof, and VH portion of an HIV antigen binding domain. In certain aspects the polynucleotide can encode a polypeptide subunit comprising a human IgM or IgA constant region or fragment thereof fused to the C-terminal end of a VH, where the VH comprises the HCDR1, HCDR2, and HCDR3 regions, or the HCDR1, HCDR2, and HCDR3 regions containing one or two single amino acid substitutions of a VH comprising the amino acid sequence SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99.

In certain aspects, the polypeptide subunit can comprise an antibody VL portion of an HIV antigen binding domain as described above. In certain aspects the polypeptide subunit can comprise a human antibody light chain constant region or fragment thereof fused to the C-terminal end of a VL, where the VL comprises LCDR1, LCDR2, and LCDR3 regions, or the LCDR1, LCDR2, and LCDR3 regions containing one or two single amino acid substitutions of a VL comprising the amino acid sequence SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 6, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100.

In certain aspects the polynucleotide can encode a polypeptide subunit comprising a human IgM or IgA constant region or fragment thereof fused to the C-terminal end of a VH, where the VH comprises an amino acid sequence at least 60%, at least 65%, at least 70%, at least 75%, at least 80%, at least 85%, at least 90%, at least 95% or 100% identical to any one or more of the amino acid sequences of SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99.

In certain aspects the polynucleotide can encode a polypeptide subunit comprising a human light chain constant region or fragment thereof fused to the C-terminal end of a VL, where the VL comprises an amino acid sequence at least at least 60%, at least 65%, at least 70%, at least 75%, at least 80%, at least 85%, at least 90%, at least 95% or 100% identical to any one or more of SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 6, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100.

Thus, to form the antigen binding domains, the variable regions of antibodies that specifically bind to an HIV antigen, e.g., that specifically bind to an epitope on the HIV spike protein, can be inserted into expression vector templates for IgM and/or IgA structures, thereby creating multimeric binding molecules having at least two bivalent binding units. In brief, nucleic acid sequences encoding the heavy and light chain variable domain sequences can be synthesized or amplified from existing molecules, and inserted into vectors in the proper orientation and in frame such that upon expression, the vector will yield a full length heavy or light chain. Vectors useful for these purposes are known in the art. Such vectors can also comprise enhancer and other sequences needed to achieve expression of the desired chains. Multiple vectors or single vectors can be used. These vectors are transfected into host cells and then the chains are expressed and purified. Upon expression the chains form fully functional multimeric binding molecules, as has been reported in the literature. The fully assembled multimeric binding molecules can then be purified by standard methods. The expression and purification processes can be performed at commercial scale, if needed.

The disclosure further provides a composition comprising two or more polynucleotides, where the two or more polynucleotides collectively can encode a dimeric, hexameric, or pentameric binding molecule as described above. In certain aspects the composition can include a polynucleotide encoding an IgM and/or IgA heavy chain or fragment thereof, e.g., a human IgM heavy chain as described above where the IgM and/or IgA heavy chain comprises at least the VH of an HIV antigen binding domain, and a polynucleotide encoding a light chain or fragment thereof, e.g., a human kappa or lambda light chain that comprises at least the VL of an HIV antigen binding domain. A polynucleotide composition as provided can further include a polynucleotide encoding a J-chain, e.g., a human J-chain, or a fragment, variant, or derivative thereof. In certain aspects the polynucleotides making up a composition as provided herein can be situated on two, three, or more separate vectors, e.g., expression vectors. Such vectors are provided by the disclosure. In certain aspects two or more of the polynucleotides making up a composition as provided herein can be situated on a single vector, e.g., an expression vector. Such a vector is provided by the disclosure.

The disclosure further provides a host cell, e.g., a prokaryotic or eukaryotic host cell, comprising a polynucleotide or two or more polynucleotides encoding a dimeric, pentameric, or hexameric HIV binding molecule as provided herein, or any subunit thereof, a polynucleotide composition as provided herein, or a vector or two, three, or more vectors that collectively encode a dimeric, pentameric, or hexameric HIV binding molecule as provided herein, or any subunit thereof. In certain aspects a host cell provided by the disclosure can express a dimeric, pentameric, or hexameric HIV binding molecule as provided by this disclosure, or a subunit thereof.

In a related aspect, the disclosure provides a method of producing a dimeric, pentameric, or hexameric HIV binding molecule as provided by this disclosure, where the method comprises culturing a host cell as described above, and recovering the binding molecule.

Methods of Use

This disclosure provides improved methods for preventing, controlling, or treating HIV infection, and/or methods for neutralizing HIV infectivity, e.g., across two or more types, groups, or clades, using a dimeric IgA-based HIV binding molecule, or pentameric or hexameric IgM-based HIV binding molecule. The methods described below can utilize multimeric binding molecules comprising HIV antigen binding domains including without limitation, the antibodies and corresponding VH and VL sequences disclosed in the references set forth in Table 3, or variants, derivatives, or analogs thereof, where the dimeric, pentameric, or hexameric HIV binding molecule can provide improved virus neutralization and/or clearance potency as compared to a corresponding reference single binding unit molecule, fragment, variant, derivative, or analog, as disclosed and explained above. Exemplary corresponding single binding unit molecules are described in the references presented in Table 3. Based on this disclosure, construction of a dimeric IgA binding molecule, or pentameric or hexameric IgM binding molecule comprising any HIV-specific antigen binding domain of interest is well within the capabilities of a person of ordinary skill in the art. The improved binding characteristics of such compositions can, for example, allow a reduced dose to be used, or can result in more effective neutralization of viruses resistant to neutralization by the original antibody, as explained above. By "resistant" is meant any degree of reduced activity of an HIV antibody, on HIV infectivity, replication, release, etc.

In certain aspects, this disclosure provides a method for directing improved neutralization of HIV, or killing of HIV infected cells, where the method includes contacting an HIV, or an HIV-infected cell with a dimeric, pentameric, or hexameric HIV binding molecule, e.g., an IgM antibody as described herein, where the binding molecule can direct virus neutralization, or killing of HIV reservoir cells, at a higher potency than an equivalent amount of a corresponding reference single binding unit molecule, e.g., a monospecific, bivalent IgG antibody or fragment thereof. In certain aspects a dimeric, pentameric, or hexameric HIV binding molecule, e.g., an IgM antibody as provided herein can direct virus neutralization of two or more HIV types, subtypes or clades at higher potency than an equivalent amount of a corresponding reference single binding unit molecule, where the corresponding reference single binding unit molecule is, or comprises similar or identical VH and VL regions as at least one binding unit of a dimeric, pentameric, or hexameric HIV binding molecule, e.g., an IgM antibody as provided herein.

In certain aspects, this disclosure provides a method for testing the ability of a given binding molecule to bind to and effect killing of HIV reservoir cells. The method includes providing cells, e.g., cells from chronically infected HIV patients, or a series of recombinant cell lines that express an HIV antigen, e.g., an HIV protein, e.g., to an epitope on the HIV spike protein, e.g., gp120 and/or gp41 at a series of predetermined levels from high copy number down to low, or even a single copy number. The cells can then be contacted with a dimeric, pentameric, or hexameric HIV binding molecule, e.g., an IgM antibody as provided herein under conditions that would allow antibody-dependent, T-cell dependent, or complement-dependent killing of the cells, and recovering those binding molecules that can effect killing of the cells expressing the lowest copy numbers of the HIV antigen. In certain aspects the dimeric, pentameric, or hexameric HIV binding molecule can direct killing of cells expressing a lower copy number of the HIV antigen than cells killed by an equivalent amount of a corresponding reference single binding unit molecule, e.g., a monospecific, bivalent IgG antibody or fragment thereof.

For instance, methods include screening of various binding molecules whose affinities and/or avidities for enveloped HIV viral particles of a different type, group, or clade, have not been determined. The present methods can be employed to identify more broadly neutralizing binding molecules that bind to the surface of HIV viral particles, on the surface if HIV-infected cells, such as reservoir cells, or a combination thereof. In this manner, additional binding molecules useful in the methods of the present disclosure can be identified and utilized, as disclosed herein.

This screening method can be accomplished by contacting a test binding molecule known to specifically bind to an HIV or HIV-infected cell of a first type, group, or clade with an HIV or HIV-infected cell of a second type, group, or clade, and measuring the affinity and/or avidity of the test binding molecule for binding to the second HIV or infected cell. The dimeric, pentameric, or hexameric HIV binding molecule can thus be tested for cross-reactivity that might not have been evident for a single binding unit molecule having the same antigen binding domains.

The cells in such methods can be any cell capable of being infected by HIV, such as a human cell.

In certain aspects, this disclosure provides a method for directing more broadly cross-reacting neutralization of HIV, or killing of HIV reservoir cells, where the method includes contacting an HIV virion, or an HIV-infected cell with a dimeric, pentameric, or hexameric HIV binding molecule, e.g., an IgM antibody as described herein, where the virus is of a different type, group, or clade than that typically bound by the one or more antigen binding domains of the binding molecule, where the binding molecule can direct virus neutralization, or killing of HIV reservoir cells of the different type, group, or clade, at a higher potency than an equivalent amount of a corresponding reference single binding unit molecule, e.g., a monospecific, bivalent IgG antibody or fragment thereof. In certain aspects a dimeric, pentameric, or hexameric HIV binding molecule, e.g., an IgM antibody as provided herein can direct virus neutralization of more HIV types, subtypes or clades than an equivalent amount of a corresponding reference single binding unit molecule, where the corresponding reference single binding unit molecule is, or comprises similar or identical VH and VL regions as at least one binding unit of a dimeric, pentameric, or hexameric HIV binding molecule, e.g., an IgM antibody as provided herein.

For instance, methods include screening of various binding molecules whose affinities and/or avidities for enveloped HIV viral particles of a different type, group, or clade, have not been determined. The present methods can be employed to identify more broadly neutralizing binding molecules that bind to the surface of HIV viral particles, on the surface if HIV-infected cells, such as reservoir cells, or a combination thereof. In this manner, additional binding molecules useful in the methods of the present disclosure can be identified and utilized, as disclosed herein.

This screening method can be accomplished by contacting a test binding molecule known to specifically bind to an HIV or HIV-infected cell of a first type, group, or clade with an HIV or HIV-infected cell of a second type, group, or clade, and measuring the affinity and/or avidity of the test binding molecule for binding to the second HIV or infected cell. The dimeric, pentameric, or hexameric HIV binding molecule can thus be tested for cross-reactivity that might not have been evident for a single binding unit molecule having the same antigen binding domains.

The cells in such methods can be any cell capable of being infected by HIV, such as a human cell.

Dimeric, pentameric, or hexameric HIV binding molecules for use in the methods provided herein can possess advantageous structural or functional properties compared to other binding molecules. For example, a dimeric, pentameric, or hexameric HIV binding molecule, e.g., an IgM antibody for use in the methods provided herein can possess improved binding characteristics in a biological assay, as described above, either in vitro or in vivo, than a corresponding reference single binding unit molecule, e.g., IgG or a variant, analog, or derivative thereof, as also described above. Biological assays include, but are not limited to, T-cell Dependent Cell-mediated Cytotoxicity assays (TDCC), Antibody-Dependent Cell-mediated Cytotoxicity (ADCC) assays, Complement-Dependent Cytotoxicity (CDC) assays, Cell-To-Cell Spread (CTCS) assays, complement-dependent virolysis assays, virus neutralization assays, cell attachment assays, viral egress assays, immunohistochemical assays, or direct cytotoxicity assays.

Pharmaceutical Compositions and Administration Methods

Methods of preparing and administering a multimeric, e.g., a dimeric, pentameric, or hexameric HIV binding molecule, e.g., an IgM antibody as provided herein to a subject in need thereof are well known to or are readily determined by those skilled in the art in view of this disclosure. The route of administration of a multimeric binding molecule can be, for example, oral, parenteral, by inhalation or topical. The term parenteral as used herein includes, e.g., intravenous, intraarterial, intraperitoneal, intramuscular, subcutaneous, rectal, or vaginal administration. While these forms of administration are contemplated as suitable forms, another example of a form for administration would be a solution for injection, in particular for intravenous or intraarterial injection or drip. A suitable pharmaceutical composition can comprise a buffer (e.g. acetate, phosphate or citrate buffer), a surfactant (e.g. polysorbate), and in some embodiments a stabilizer agent (e.g. human albumin).

A dimeric, pentameric, or hexameric HIV binding molecule as provided herein can be administered in a pharmaceutically effective amount for the in vivo treatment of diseases or disorders in which it is desirable to clear, remove or otherwise eliminate an HIV infection in a subject infected with HIV. In this regard, it will be appreciated that the disclosed multimeric binding molecules can be formulated so as to facilitate administration and promote stability of the active agent. Pharmaceutical compositions accordingly can comprise a pharmaceutically acceptable, non-toxic, sterile carrier such as physiological saline, non-toxic buffers, preservatives and the like. A pharmaceutically effective amount of a dimeric, pentameric, or hexameric HIV binding molecule as provided herein means an amount sufficient to achieve effective binding to a target and to achieve a therapeutic benefit. Suitable formulations are described in Remington's Pharmaceutical Sciences (Mack Publishing Co.) 16th ed. (1980).

Certain pharmaceutical compositions provided herein can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of a dimeric, pentameric, or hexameric HIV binding molecule that can be combined with carrier materials to produce a single dosage form will vary depending, e.g., upon the subject treated and the particular mode of administration. The composition can be administered as a single dose, multiple doses or over an established period of time in an infusion. Dosage regimens also can be adjusted to provide the optimum desired response (e.g., a therapeutic or prophylactic response).

In keeping with the scope of the present disclosure, a dimeric, pentameric, or hexameric HIV binding molecule as provided herein can be administered to a subject in need of therapy in an amount sufficient to produce a therapeutic effect. A multimeric binding molecule as provided herein can be administered to the subject in a conventional dosage form prepared by combining the antibody or antigen binding fragment, variant, or derivative thereof of the disclosure with a conventional pharmaceutically acceptable carrier or diluent according to known techniques. The form and character of the pharmaceutically acceptable carrier or diluent can be dictated by the amount of active ingredient with which it is to be combined, the route of administration and other well-known variables.

By "therapeutically effective dose or amount" or "effective amount" is intended an amount of a dimeric, pentameric, or hexameric HIV binding molecule, that when administered brings about a positive therapeutic response with respect to treatment of a patient with a disease or condition to be treated.

Therapeutically effective doses of the compositions disclosed herein, for treatment of HIV infection is desired, can vary depending upon many different factors, including means of administration, target site, physiological state of the patient, whether the patient is human or an animal, other medications administered, and whether treatment is prophylactic or therapeutic. In certain aspects, the subject or patient is a human, but non-human mammals including transgenic mammals can also be treated. Treatment dosages can be titrated using routine methods known to those of skill in the art to optimize safety and efficacy.

The amount of a dimeric, pentameric, or hexameric HIV binding molecule, e.g., an IgM antibody to be administered is readily determined by one of ordinary skill in the art without undue experimentation given this disclosure. Factors influencing the mode of administration and the respective amount of a multimeric binding molecule include, but are not limited to, the severity of the disease, the history of the disease, and the age, height, weight, health, and physical condition of the individual undergoing therapy. Similarly, the amount of a dimeric, pentameric, or hexameric HIV binding molecule to be administered will be dependent upon the mode of administration and whether the subject will undergo a single dose or multiple doses of this agent.

This disclosure also provides for the use of a dimeric, pentameric, or hexameric HIV binding molecule in the manufacture of a medicament for treating, preventing, or managing a disease or disorder caused by HIV infection.

This disclosure employs, unless otherwise indicated, conventional techniques of cell biology, cell culture, molecular biology, transgenic biology, microbiology, recombinant DNA, and immunology, which are within the skill of the art. Such techniques are explained fully in the literature. (See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described can be followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevier, Amsterdam); Goldsby et al., eds. (2000) Kuby Immunology (4th ed.; H. Freeman & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlag); Sambrook and Russell (2001) Molecular Cloning: A Laboratory Manual (Cold Spring Harbor Press); Lewin (2003) Genes VIII (Prentice Hall, 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties. The following examples are offered by way of illustration and not by way of limitation.

EXAMPLES

Example 1

Construction and Assembly of Engineered Anti-HIV Binding Molecules

VH and VL regions of various HIV antibodies provided herein can be cloned into IgG and IgM backgrounds by standard methods through a commercial contractor. The mature proteins presented below can be expressed with a signal peptide to promote secretion.

HIV02: The VH and VL of a human antibody specific for the CD4 binding site on gp120 provided in U.S. Pat. No. 8,637,036, presented herein as SEQ ID NO: 7 and SEQ ID NO: 8, respectively, were cloned into appropriate vectors to encode the human IgG and IgM heavy chains comprising the amino acid sequences SEQ ID NO: 113 and SEQ ID NO: 114, respectively, and the kappa light chain comprising SEQ ID NO: 115. The vectors were transfected in to HEK293 cells (with, where appropriate, a vector encoding a human wild-type or modified J-chain as described below) and expression was permitted, producing the IgG molecule HIV02 IgG (HIV02G), the IgM molecule HIV02 IgM (HIV02M), the IgM+J (HIV02M+J), or the IgM+J containing a modified J-chain.

SEQ ID NO: 113: HIV02 Gamma 1 heavy chain
QVQLVQSGGQMKKPGESMRISCQASGYEFIDCTLNWVRLAPGRRPEWMG

WLKPRGGAVNYARPLQGRVTMTRDVYSDTAFLELRSLTADDTAVYYCTR

GKNCDYNWDFEHWGRGTPVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYT

QKSLSLSPG

SEQ ID NO: 114: HIV02 Mu heavy chain
QVQLVQSGGQMKKPGESMRISCQASGYEFIDCTLNWVRLAPGRRPEWMG

WLKPRGGAVNYARPLQGRVTMTRDVYSDTAFLELRSLTADDTAVYYCTR

GKNCDYNWDFEHWGRGTPVTVSSGSASAPTLFPLVSCENSPSDTSSVAV

GCLAQDFLPDSITFSWKYKNNSDISSTRGFPSVLRGGKYAATSQVLLPS

KDVMQGTDEHVVCKVQHPNGNKEKNVPLPVIAELPPKVSVFVPPRDGFF

GNPRKSKLICQATGFSPRQIQVSWLREGKQVGSGVTTDQVQAEAKESGP

TTYKVTSTLTIKESDWLSQSMFTCRVDHRGLTFQQNASSMCVPDQDTAI

RVFAIPPSFASIFLTKSTKLTCLVTDLTTYDSVTISWTRQNGEAVKTHT

NISESHPNATFSAVGEASICEDDWNSGERFTCTVTHTDLPSPLKQTISR

PKGVALHRPDVYLLPPAREQLNLRESATITCLVTGFSPADVFVQWMQRG

QPLSPEKYVTSAPMPEPQAPGRYFAHSILTVSEEEWNTGETYTCVVAHE

ALPNRVTERTVDKSTGKPTLYNVSLVMSDTAGTCY

SEQ ID NO: 115 HIV02 Kappa light chain
EIVLTQSPGTLSLSPGETAIISCRTSQYGSLAWYQQRPGQAPRLVIYSG

STRAAGIPDRFSGSRWGPDYNLTIRNLESGDFGLYYCQQYEFFGQGTKV

QVDIKRTVAAPSVFIFPPSDEQLKSGTASVVCLLNNFYPREAKVQWKVD

NALQSGNSQESVTEQDSKDSTYSLSSTLTLSKADYEKHKVYACEVTHQG

LSSPVTKSFNRGEC

HIV12: The VH and VL of a human antibody specific for the V3/glycan region on gp120 provided in Buchacher, A., I., AIDS Res. Hum. Retroviruses 10:359-369 (1994) and in WO 2011/035205, presented herein as SEQ ID NO: 95 and SEQ ID NO: 96, respectively, were cloned into appropriate vectors to encode the human IgG and IgM heavy chains comprising the amino acid sequences SEQ ID NO: 116 and SEQ ID NO: 117, respectively, and the kappa light chain comprising SEQ ID NO: 118. The vectors were transfected in to HEK293 cells (with, where appropriate, a vector encoding a human wild-type or modified J-chain as described below) and expression was permitted, producing the IgG molecule HIV12 IgG (HIV12G), the IgM molecule HIV12 IgM (HIV12M), the IgM+J (HIV12M+J), or the IgM+J containing a modified J-chain.

```
SEQ ID NO: 116: HIV12 Gamma 1 heavy chain
EVQLVESGGGLVKAGGSLILSCGVSNFRISAHTMNWVRRVPGGGLEWVA

SISTSSTYRDYADAVKGRFTVSRDDLEDFVYLQMHKMRVEDTAIYYCAR

KGSDRLSDNDPFDAWGPGTVVTVSPASTKGPSVFPLAPSSKSTSGGTAA

LGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTIS

KAKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHNH

YTQKSLSLSPG

SEQ ID NO: 117: HIV12 Mu heavy chain
EVQLVESGGGLVKAGGSLILSCGVSNFRISAHTMNWVRRVPGGGLEWVA

SISTSSTYRDYADAVKGRFTVSRDDLEDFVYLQMHKMRVEDTAIYYCAR

KGSDRLSDNDPFDAWGPGTVVTVSPASTKGPSVFPLAPSSKSTSGGTAA

LGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTIS

KAKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHNH

YTQKSLSLSPG

SEQ ID NO: 118: HIV12 Light chain
DIQMTQSPSTLSASVGDTITITCRASQSIETWLAWYQQKPGKAPKLLIY

KASTLKTGVPSRFSGSGSGTEFTLTISGLQFDDFATYHCQHYAGYSATF

GQGTRVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC
```

HIV32: The VH and VL of a human antibody specific for the CD4 binding site on gp120 provided in Moore, J. P., and J. Sodroski J. Virol 70:1863-1872 (1996) and in WO 2006/044410, presented herein as SEQ ID NO: 99 and SEQ ID NO: 100, respectively, were cloned into appropriate vectors to encode the human IgG and IgM heavy chains comprising the amino acid sequences SEQ ID NO: 119 and SEQ ID NO: 120, respectively, and the kappa light chain comprising SEQ ID NO: 121. The vectors were transfected in to HEK293 cells (with, where appropriate, a vector encoding a human wild-type or modified J-chain as described below) and expression was permitted, producing the IgG molecule HIV32 IgG (HIV32G), the IgM molecule HIV32 IgM (HIV32M), the IgM+J (HIV32M+J), or the IgM+J containing a modified J-chain.

```
SEQ ID NO: 119: HIV32 Gamma 1 heavy chain
QVQLQESGPGLVKPSQTLSLSCTVSGGSSSSGAHYWSWIRQYPGKGLEW

IGYIHYSGNTYYNPSLKSRITISQHTSENQFSLKLNSVTVADTAVYYCA

RGTRLRTLRNAFDIWGQGTMVTVSSASTKGPSVFPLAPSSKSTSGGTAA

LGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTIS

KAKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHNH

YTQKSLSLSPG

SEQ ID NO: 120: HIV32 Mu heavy chain
QVQLQESGPGLVKPSQTLSLSCTVSGGSSSSGAHYWSWIRQYPGKGLEW

IGYIHYSGNTYYNPSLKSRITISQHTSENQFSLKLNSVTVADTAVYYCA

RGTRLRTLRNAFDIWGQGTMVTVSSGSASAPTLFPLVSCENSPSDTSSV

AVGCLAQDFLPDSITFSWKYKNNSDISSTRGFPSVLRGGKYAATSQVLL

PSKDVMQGTDEHVVCKVQHPNGNKEKNVPLPVIAELPPKVSVFVPPRDG

FFGNPRKSKLICQATGFSPRQIQVSWLREGKQVGSGVTTDQVQAEAKES

GPTTYKVTSTLTIKESDWLSQSMFTCRVDHRGLTFQQNASSMCVPDQDT

AIRVFAIPPSFASIFLTKSTKLTCLVTDLTTYDSVTISWTRQNGEAVKT

HTNISESHPNATFSAVGEASICEDDWNSGERFTCTVTHTDLPSPLKQTI

SRPKGVALHRPDVYLLPPAREQLNLRESATITCLVTGFSPADVFVQWMQ

RGQPLSPEKYVTSAPMPEPQAPGRYFAHSILTVSEEEWNTGETYTCVVA

HEALPNRVTERTVDKSTGKPTLYNVSLVMSDTAGTCY

SEQ ID NO: 121: HIV32 Kappa light chain
QSVLTQPPSASGSPGQSVTISCTGTSSDVGGYNYVSWYQHHPGKAPKLI

ISEVNNRPSGVPDRFSGSKSGNTASLTVSGLQAEDEAEYYCSSYTDIHN

FVFGGGTKLTVLRTVAAPSVFIFPPSDEQLKSGTASVVCLLNNFYPREA

KVQWKVDNALQSGNSQESVTEQDSKDSTYSLSSTLTLSKADYEKHKVYA

CEVTHQGLSSPVTKSFNRGEC
```

HIV72: The VH and VL of a human antibody specific for the immunodominant region of gp41, provided in Pincus S H, et al., *J Immunol* 170: 2236-2241(2003), presented herein as SEQ ID NO: 97 and SEQ ID NO: 98, respectively, were cloned into appropriate vectors to encode the human IgG and IgM heavy chains comprising the amino acid sequences SEQ ID NO: 122 and SEQ ID NO: 123, respectively, and the kappa light chain comprising SEQ ID NO: 124. The vectors were transfected in to HEK293 cells (with, where appropriate, a vector encoding a human wild-type or modified J-chain as described below) and expression was permitted, producing the IgG molecule HIV72 IgG (HIV72G), the IgM molecule HIV72 IgM (HIV72M), the IgM+J (HIV72M+J), or the IgM+J containing a modified J-chain.

```
SEQ ID NO: 122: HIV72 Gamma-1 heavy chain
QVQLVQSGGGVFKPGGSLRLSCEASGFTFTEYYMTWVRQAPGKGLEWLA

YISKNGEYSKYSPSSNGRFTISRDNAKNSVFLQLDRLSADDTAVYYCAR
```

-continued

ADGLTYFSELLQYIFDLWGQGARVTVSSASTKGPSVFPLAPSSKSTSGG

TAALGCLVKDYFPEPVTVSWNSGALTSGVHTFPAVLQSSGLYSLSSVVT

VPSSSLGTQTYICNVNHKPSNTKVDKKVEPKSCDKTHTCPPCPAPELLG

GPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEK

TISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEAL

HNHYTQKSLSLSPG

SEQ ID NO: 123: HIV72 Mu heavy chain
QVQLVQSGGGVFKPGGSLRLSCEASGFTFTEYYMTWVRQAPGKGLEWLA

YISKNGEYSKYSPSSNGRFTISRDNAKNSVFLQLDRLSADDTAVYYCAR

ADGLTYFSELLQYIFDLWGQGARVTVSSGSASAPTLFPLVSCENSPSDT

SSVAVGCLAQDFLPDSITFSWKYKNNSDISSTRGFPSVLRGGKYAATSQ

VLLPSKDVMQGTDEHVVCKVQHPNGNKEKNVPLPVIAELPPKVSVFVPP

RDGFFGNPRKSKLICQATGFSPRQIQVSWLREGKQVGSGVTTDQVQAEA

KESGPTTYKVTSTLTIKESDWLSQSMFTCRVDHRGLTFQQNASSMCVPD

QDTAIRVFAIPPSFASIFLTKSTKLTCLVTDLTTYDSVTISWTRQNGEA

VKTHTNISESHPNATFSAVGEASICEDDWNSGERFTCTVTHTDLPSPLK

QTISRPKGVALHRPDVYLLPPAREQLNLRESATITCLVTGFSPADVFVQ

WMQRGQPLSPEKYVTSAPMPEPQAPGRYFAHSILTVSEEEWNTGETYTC

VVAHEALPNRVTERTVDKSTGKPTLYNVSLVMSDTAGTCY

SEQ ID NO: 124 HIV72 Kappa Light chain
DIVMTQSPDSLAVSPGERATIHCKSSQTLLYSSNNRHSIAWYQQRPGQP

PKLLLYWASMRLSGVPDRFSGSGSGTDFTLTINNLQAEDVAIYYCHQYS

SHPPTFGHGTRVEIKRTVAAPSVFIFPPSDEQLKSGTASVVCLLNNFYP

REAKVQWKVDNALQSGNSQESVTEQDSKDSTYSLSSTLTLSKADYEKHK

VYACEVTHQGLSSPVTKSFNRGEC

Wild type and modified J-Chains: Modified J-chains, V5J (SEQ ID NO: 108) and V10J (SEQ ID NO: 109), comprising an anti-CD3 ScFv corresponding to visilizumab fused to the N-terminus of the mature human J-chain via a 5-amino acid linker (GGGGS, SEQ ID NO: 101) or a 10-amino acid linker (GGGGSGGGGS, SEQ ID NO: 102), respectively were constructed by standard methods. See, e.g., PCT Publication No. WO 2015/153912.

The mature expressed construct has a molecular weight of about 45 kD and can bind to soluble epsilon chain of CD3 (Sino Biological), or T-cells (data not shown).

The DNA constructs corresponding to the various anti-HIV heavy and light chains as well as those corresponding to either the wild-type (wt) J-chain or a modified J-chain (e.g., V5J or V10J) sequences were co-transfected into HEK293 cells, and proteins were expressed and purified according to standard methods. HEK293 cells transfected with IgG or IgM+J versions of HIV02, HIV12, HIV32 and HIV72 antibodies produced sufficient protein to allow purification by standard methods.

Non-Reducing SDS-Native-PAGE. Protein samples were loaded into a NativePAGE 3-12% Bis-Tris gel (Novex). Tris-Acetate SDS Running Buffer (Novex) was added and the gel was run at 40V for 15 min and then at 90V for 2 hours. The gel was then fixed in 40% methanol, 10% acetic acid for 10 minutes, stained using a Colloidal Blue Staining Kit (Novex) for at least 3 hours and subsequently de-stained in water.

Western Blot Detection. After was complete, the gel was removed from the XCell SureLock Mini-Cell and transferred to a PVDF membrane at 30 volts for 1 hour (refer to Life Technologies' manual). The PVDF membrane was then blocked with 20 ml 3% BSA in PBST at 25° C. for 1 hour.

For anti-J-chain Western blots, anti-human J chain antibody (SP105, Thermo Fisher) was added at a 1:500 dilution in 3% bovine serum albumin (BSA) in phosphate-buffered saline, 0.05% TWEEN™ 20 (PBST) overnight at 4° C. After washing with PBST four times at room temperature, horseradish peroxidase (HRP)-conjugated goat anti rabbit IgG (Jackson Immunology) was added at 1:5,000 dilution in 3% BSA in PBST and was incubated for 1 hour at room temperature. The membrane was washed with PBST 4 times at room temperature and was developed by addition of 10 ml of HRP chemiluminescent substrate (Thermo Fisher) for 10 minutes before exposing the blot to film. Anti-J-chain antibody only reacts with IgM which is co-expressed with either unmodified J-chain or modified J-chain.

Antibody expression and assembly: Antibodies present in cell supernatants were recovered by affinity chromatography using CaptureSelectM (BAC, ThermoFisher catalog 2890.05) for IgM antibodies or Protein A for IgG antibodies per the manufacturer's instructions. The purified proteins were evaluated as outlined below.

Figure 2A:
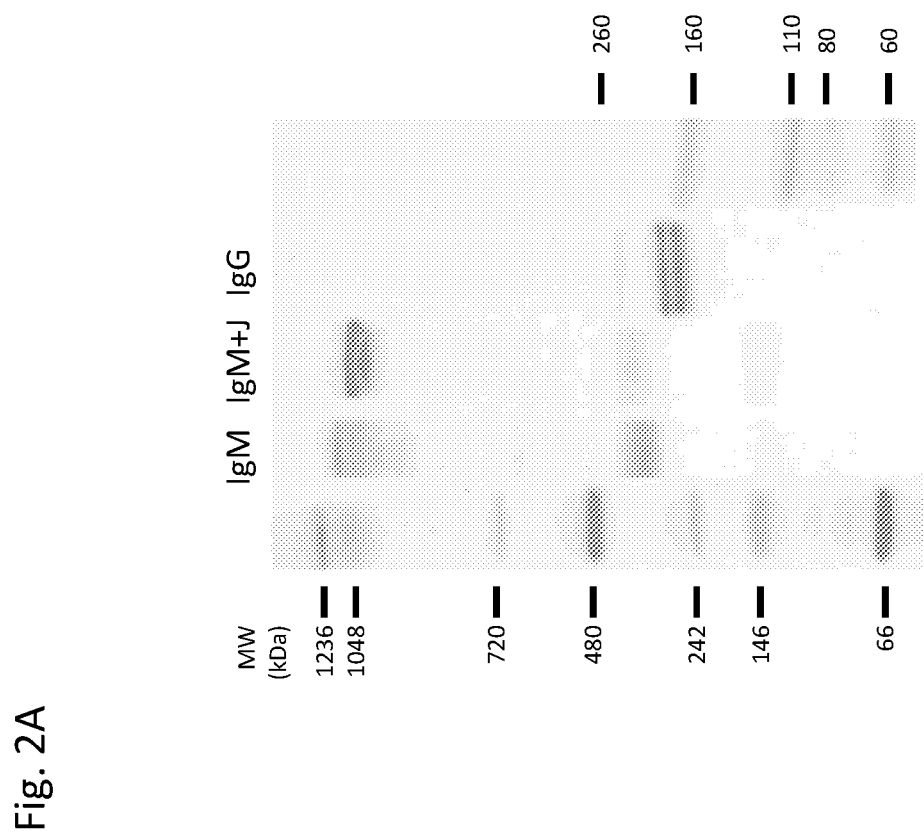
FIG. 2A: Expression and assembly of the HIV02 antibodies, as measured by non-reducing SDS native-PAGE.

Expression and assembly of the HIV02 antibodies, as assessed by non-reducing SDS native-PAGE is shown in FIG. 2A. HIV02G expressed well and efficiently assembled into an IgG antibody. HIV02M expressed without a J-chain produced a mixture of assembled high molecular weight IgM and lower molecular weight antibody forms. When HIV02M was expressed with a wild-type J-chain (HIV02M+J), most of the material produced ran as a fully assembled IgM antibody. HIV02M also properly assembled into a high molecular weight bispecific IgM antibody when expressed with a modified J-chain targeting CD3 (e.g., HIV02M+V10J; see FIG. 9).

Figure 2B:
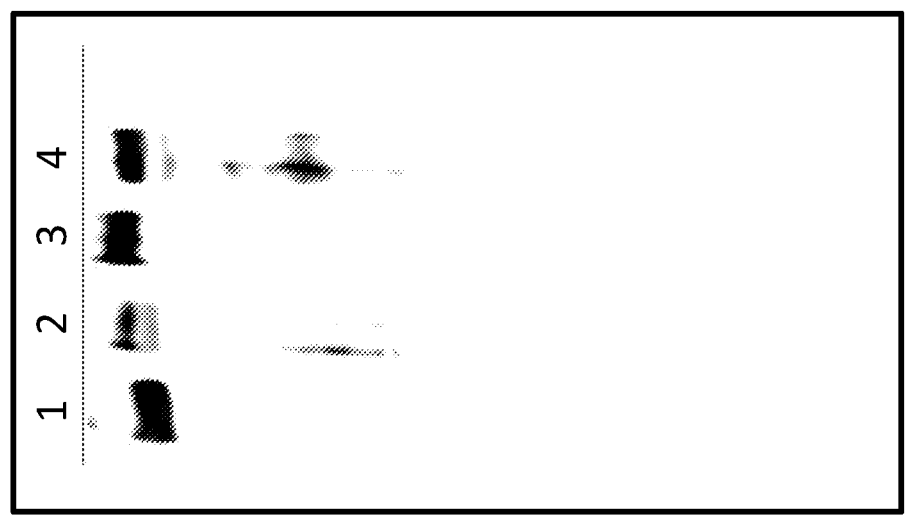
FIG. 2B: Assembly of HIV12, HIV32 and HIV72 IgM+J proteins. Proteins were electrophoresed in non-reducing SDS native-PAGE, transferred to membrane and probed with anti-J antibody. Lane 1, reference IgM+J; lane 2, HIV02; lane 3, HIV32; lane 4, HIV72.

Expression and assembly of HIV12M+J, HIV32M+J, and HIV72M+J is shown in FIG. 2B. All three IgM+J anti-HIV proteins properly assembled into high molecular weight IgM antibodies, as evidenced by Western analysis demonstrating the presence of J-chain in each of the proteins.

Figure 2C:
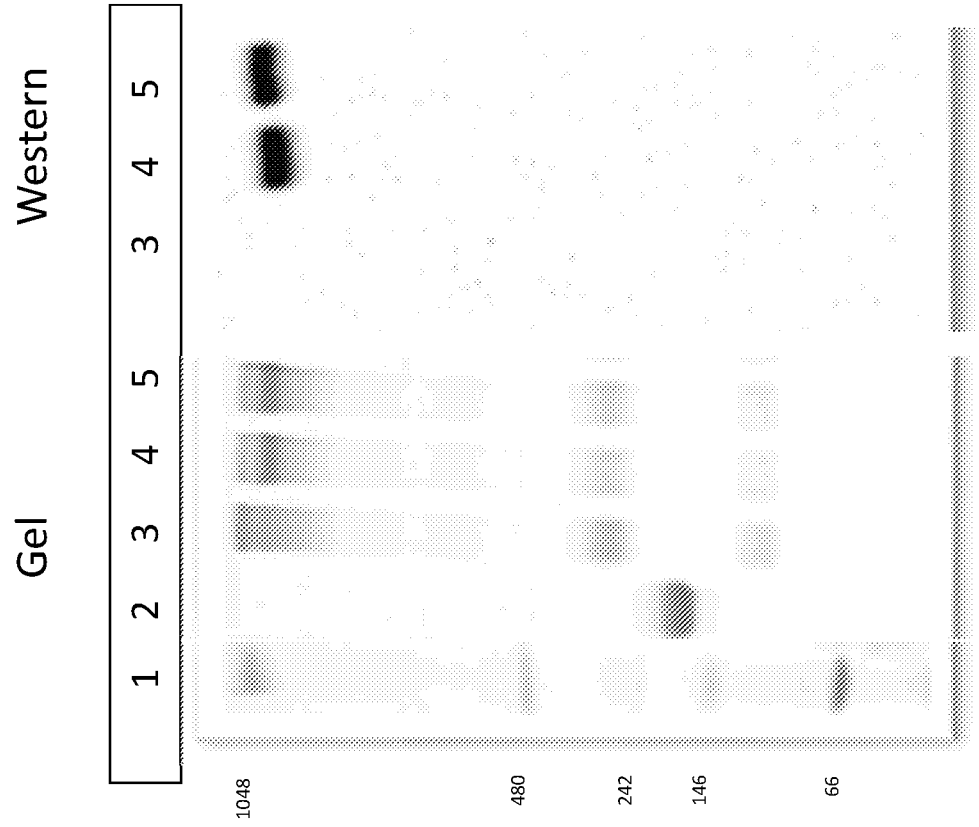
FIG. 2C: Assembly of HIV72 IgG, IgM+J and the IgM+V5J bispecific. Lane 1, Native markers, lane 2, HIV72 IgG; lane 3, HIV72 IgM; lane 4, HIV72 IgM+J; lane 5 HIV72 IgM+V5J. The left side of the figure shows Coomassie staining of the gel, and the right side shows an anti-J chain western blot.
Figure 3B:
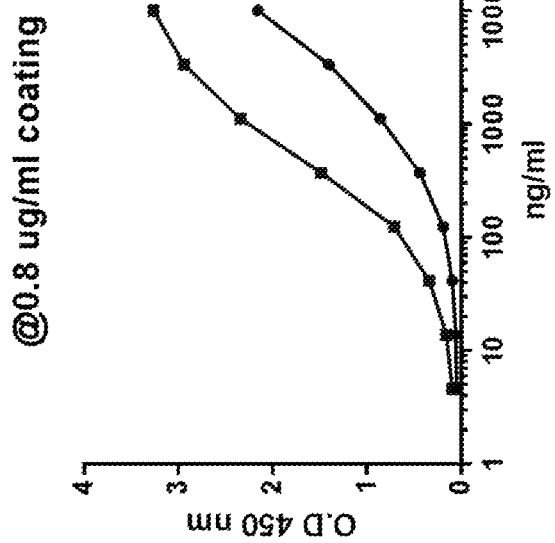
FIG. 3A-F: Effect of antigen coating concentration on the binding of HIV02 IgG and HIV02 IgM+J to gp120 by ELISA.
Figure 3A:
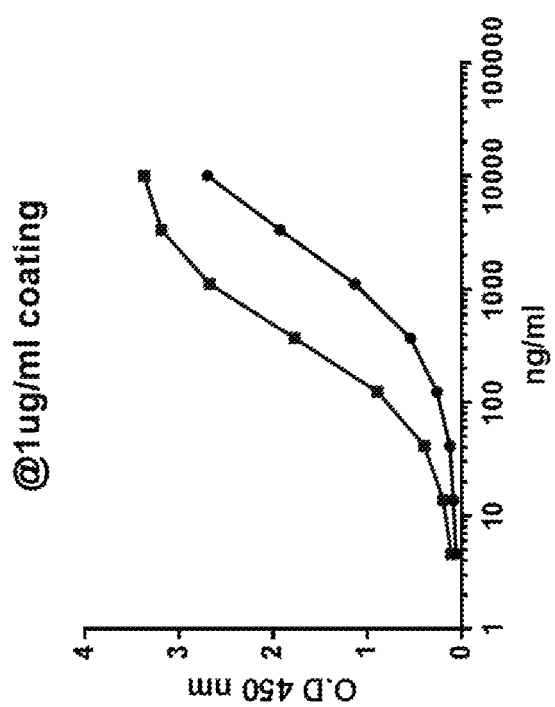
Figures 3C, 3D:
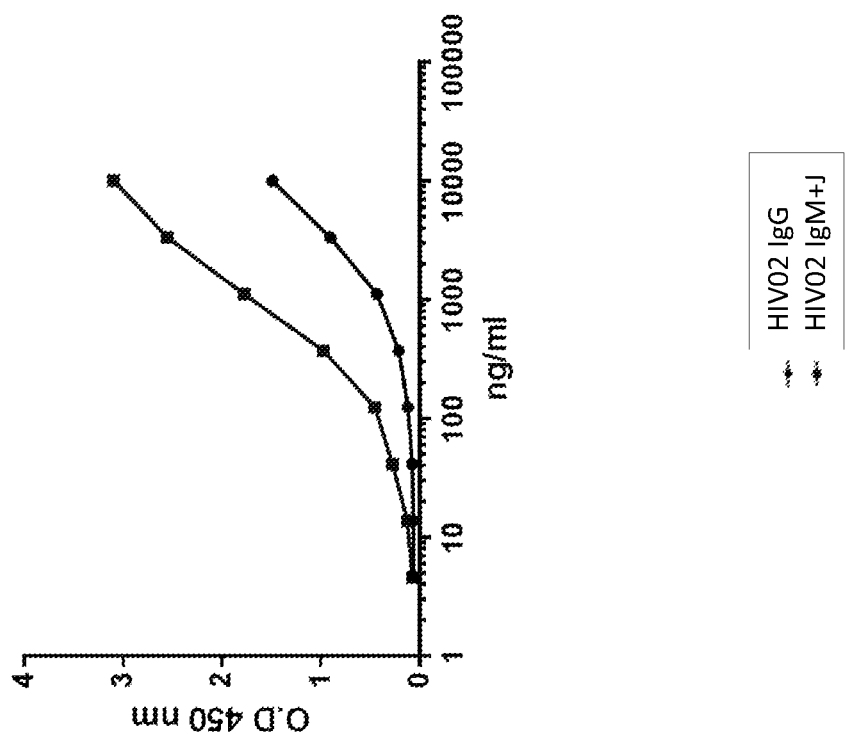
Figures 3E, 3F:
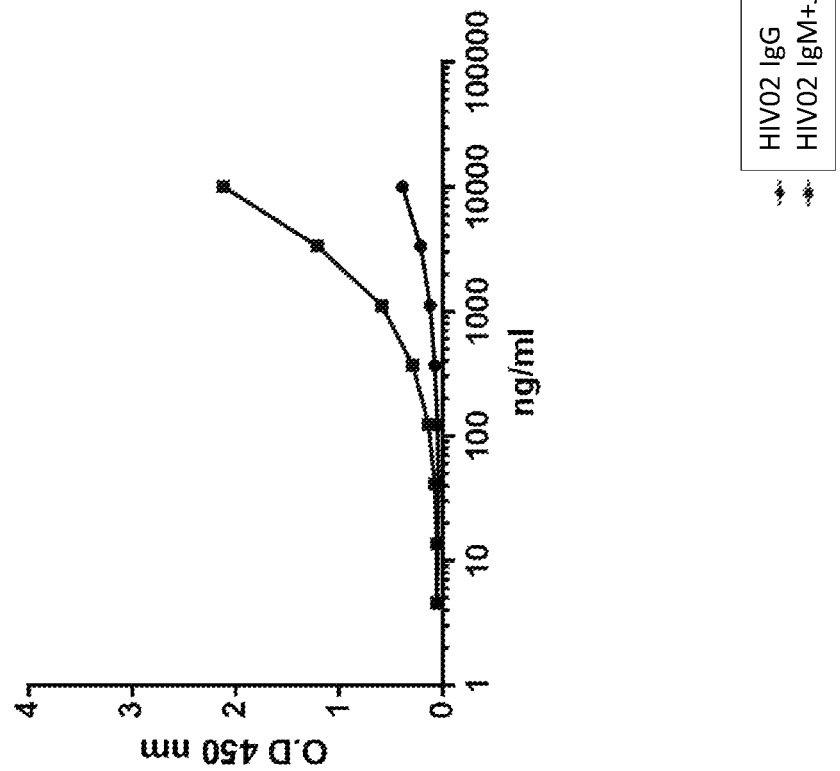
Figure 4:
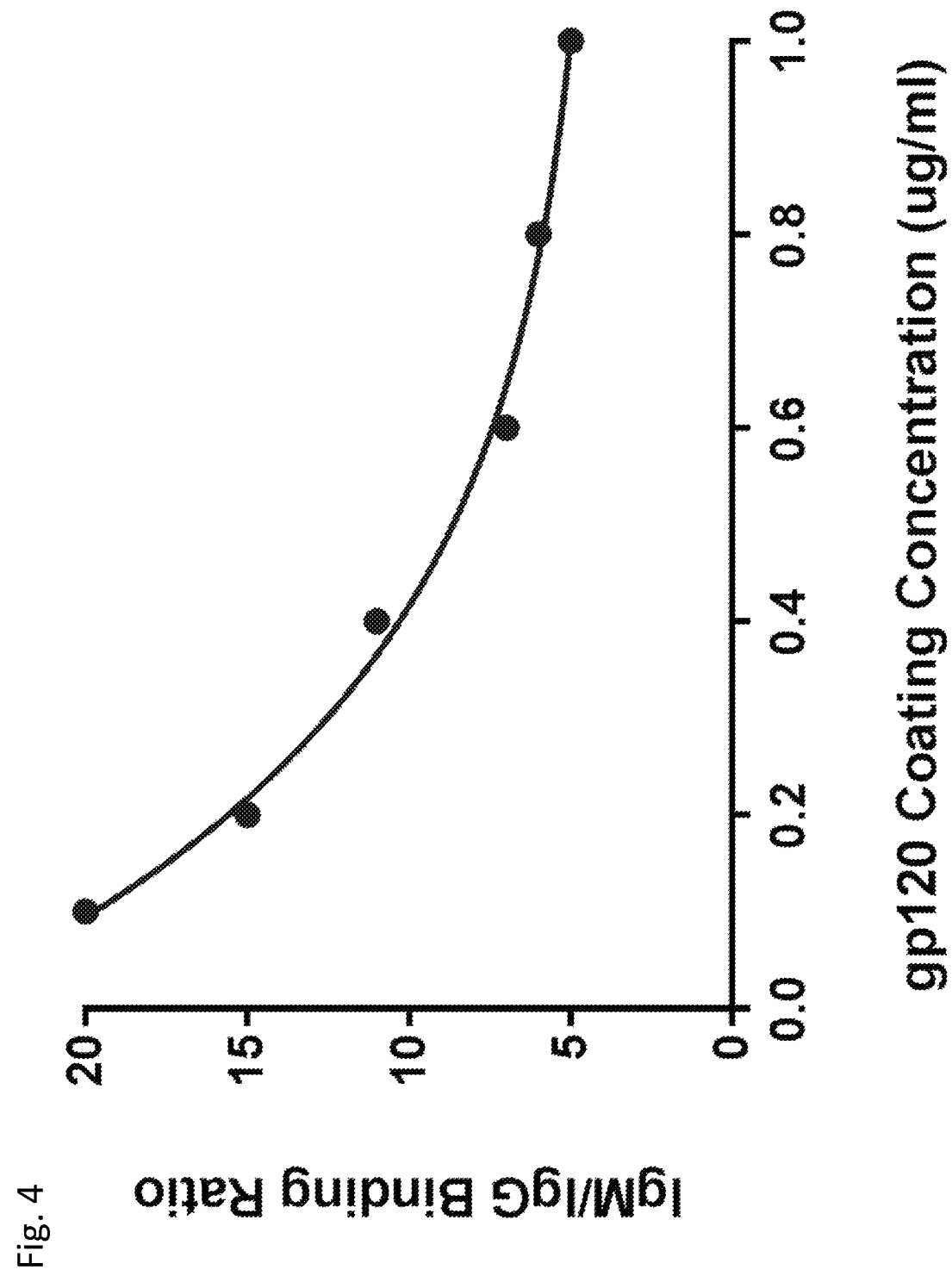
FIG. 4: Comparison of HIV02 IgG and HIV02 IgM+J binding to gp120 by ELISA. The IgM+J molecule is 20x better than the IgG molecule at low antigen densities.
Figure 5A:
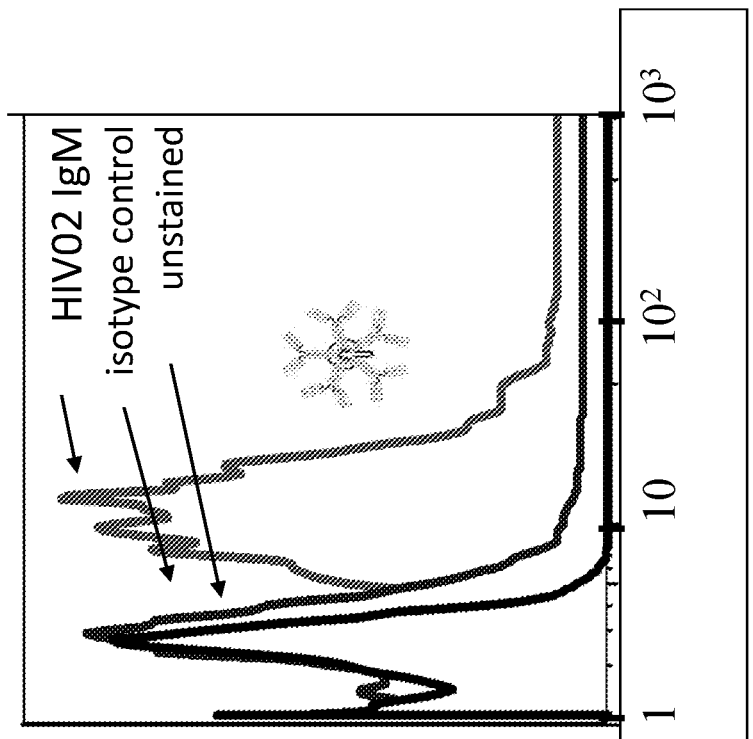
FIG. 5A-B: HIV02 IgG (FIG. 5A) and IgM+J (FIG. 5B) binding to gp140-expressing CHO-PI cells.
Figure 5B:
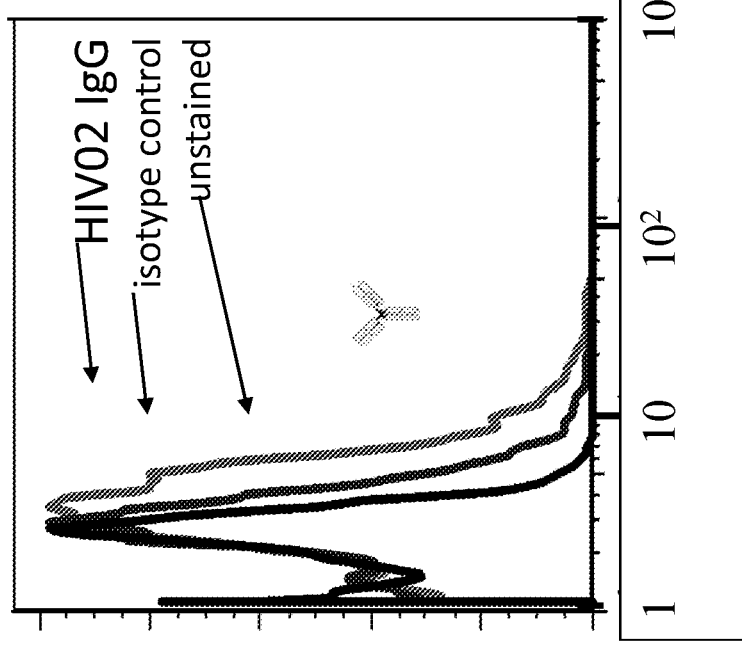

Expression and assembly of HIV72G, HIV72M, HIV72M+J and HIV72M+V5J is shown in FIG. 2C. The heavy and light chains of HIV72G expressed well and properly assembled into and IgG antibody (lane 2). The mu and light chains of HIV72M, expressed without a J-chain, were also produced well and mostly assembled into a high molecular weight IgM antibody (lane 3). Co-expression of the HIV72 mu and light chains with wild type J-chain or a modified J-chain targeting CD3 (V5J) resulted in efficient assembly of monospecific (HIV72M+J; lane 4) or bispecific (HIV72M+V5J; lane 5) IgM antibodies, respectively, as evidenced by Coomassie staining of the gel (left) or by an anti-J-chain Western of the electrophoresed proteins.

Other modified J-chains: Alternatively, modified J-chains can be constructed that allow binding to the CD16 antigen on natural killer cells (NK cells). For example, a modified J-chain can be constructed that expresses a camelid VHH binding domain specific for CD16 (e.g., SEQ ID NO: 112). The binding domain is linked to a J-chain using a flexible amino acid linker (e.g., 15 amino acids) to produce anti- CD16 camelid domain linked to the J chain (C15J). The bispecific IgM is expressed and purified as described above and assembly is confirmed by analyzing on non-reducing SDS-Native-PAGE gels. Further, incorporation of the modified J-chain (C15J, SEQ ID NO: 125) into the pentameric IgM is confirmed using the Western blot method.

SEQ ID NO: 125
EVQLVESGGELVQAGGSLRLSCAASGLTFSSYNMGWFRRAPGKEREFVA

SITWSGRDTFYADSVKGRFTISRDNAKNTVYLQMSSLKPEDTAVYYCAA

NPWPVAAPRSGTYWGQGTQVTVSSGGGGSGGGGSGGGGSQEDERIVLVD

NKCKCARITSRIIRSSEDPNEDIVERNIRIIVPLNNRENISDPTSPLRT

RFVYHLSDLCKKCDPTEVELDNQIVTATQSNICDEDSATETCYTYDRNK

CYTAVVPLVYGGETKMVETALTPDACYPD

As described above, an expression vector containing DNA corresponding to this sequence is synthesized and transfected into HEK293 cells along with the heavy and light chains for an anti-HIV gp120/41 IgM (SEQ ID NOs 114 and 115) to produce protein which is then purified using the camelid antibody affinity matrix specific for IgM. J-chains fused to the new anti-CD16 binding domain with the 15 amino acid linker are able to incorporate into the IgM and the pentameric form of bi-specific IgM with the corresponding J-chain is distinguishable from the hexameric form without a J-chain.

Example 2

Binding of HIV Specific IgM Binding Molecules to HIV Antigens and Antigen-Expressing Cells HIV02G and HIV02M+J were evaluated for binding to HIV gp120 by an ELISA assay. The assays were carried out by the following method. Wells of 96-well microtiter plates (polystyrene, MaxiSorp ELISA plates, Nunc) were coated with gp120 antigen (strain HXB2, Immune Tech, cat #IT-001-0022p-PBS) at 1.0 μg/mL (high-density antigen) or dilutions down to 0.1 μg/mL (low density antigen) in 100 μL coating buffer (100 mM bicarbonate, pH 9.5) overnight at 4° C. The plates were then washed with 0.05% PBS-Tween and blocked with 2% BSA-PBS. After blocking, 100 μL of the serial diluted samples (purified protein or cell culture supernatant) were added to the wells and incubated at room temperature for 1 hour. The plates were then washed and incubated with HRP conjugated mouse anti-human kappa antibody (Southern Biotech, 9230-05. 1:6000 diluted in 2% BSA-PBS) for 1 hour. After 5 final washes using 0.05% PBS-Tween, 100 μL TMB substrate (BD Biosciences, 555214) was added to each well and incubated in the dark for 15 min. The reaction was then stopped by adding 50 μL of 2N H2SO4 or 2N HCl per well. A450 data was then collected on a microplate reader and analyzed with Prism software (GraphPad) using a 4-parameter logistic model.

The results for binding to gp120 HBX2 are shown in FIG. 3A-F. At a typical high-antigen coating of 1 μg/mL (FIG. 3A), HIV02M+J exhibited more effective binding than the IgG version (HIV02G), exhibiting an EC50 of 2,300 ng/mL vs 320 ng/mL, respectively, a 7-fold difference by weight. On a molar basis, HIV02M+J bound gp120 42-fold better than HIV02G at this coating concentration.

When the gp120 coating concentration was successively decreased from 1.0 μg/mL to 0.8, 0.6, 0.4, 0.2 and 0.1 μg/mL (FIG. 3B to FIG. 3F), thereby reducing the antigen density on the plate, HIV02M+J continued to show strong binding whereas HIV02G binding decreased rapidly. At the lowest antigen density (FIG. 3F, 0.1 μg/mL coat), HIV02G binding was barely detectable.

Since binding of HIV02G to gp120 fell off rapidly as the coating concentration was decreased, EC10 values were interpolated from the binding curves to allow a binding comparison of antigen binding at all coating concentrations. The results of this analysis are shown in FIG. 4. As the gp120 coating concentration in the ELISA decreased from 1.0 μg/mL to 0.1 μg/mL, the binding of IgM+J relative to that of the IgG increased 5-fold to 20-fold on a weight basis. On a molar basis, the IgM+J bound gp120 120-fold better than the IgG when the antigen was coated at the lowest concentration tested (0.1 μg/mL).

HIV02G and HIV02M+J were further evaluated for binding to cells transfected to express gp120 on their cell surface, by the following method.

CHO cells engineered to express HBX2 gp140 (gp120+ the extracellular portion of gp41; CHO-gp140) or gp160 (full-length protein; CHO-gp160) on their surface (Weiss et al., 1993 *J Virol* 67:7060-7066) were obtained from the NIH AIDS Reagent Program (catalog #2284 & 2239) and cultured per their instructions. Cells were passaged in T75 flask at 3×10^6 cells per flask in 20 ml of media—cells were replenished with fresh media containing 10 mM of Sodium Butyrate (Sigma, cat#B5887) 15 to 18 hrs prior to use. On the day of staining, the cells were dislodged with 10 mL of cell dissociation buffer (Gibco, cat#131510). After aspirating off the media the cells were rinsed with PBS without Calcium & Magnesium. Ten mL of cell dissociation buffer was added to all the flasks and incubated for 20~30 min at 37° C. The cells were then dislodged by tapping the flask to create a single cell suspension. An equal volume of the media was added to the flask to neutralize the cell dissociation buffer and live cell counts were determined using trypan blue exclusion on a cell counter (BioRad TC20). Cells at 1.5×10^4/well in 60 μL of FACS 2% FBS buffer (BD Pharmingen, cat#554656) were added to "V" bottom 96 well plates. Antibodies and isotype controls were diluted in FACS 2% FBS buffer and 50 μL were added to the respective wells such that the final concentration was 30 μg/mL. The plates were then incubated for 30 min at 4° C. After washing the cells with 150 μL of FACS 2% FBS buffer, the plates were centrifuged (Sorvall Legend XIR centrifuge) at 1200 rpm for 5 min and supernatants were gently aspirated without disturbing the cell pellets. Antibody binding was detected by incubating the treated cells with AlexaFluor 647-labeled anti human kappa light chain (BioLegend, cat#316514) at 4° C. for 30 min. The wash step was repeated as above and the cells were resuspended in 60 μL of FACS 2% FBS containing 1:100 7_AAD (BD Pharm, cat#68981E). At least 1,000 events were acquired for each sample on a FACSCALIBUR™ (Becton Dickinson) and data analysis was done in FLOWJO™ (FlowJo LLC).

The binding of HIV02 antibodies to CHO-gp140 cells is shown in FIG. 5A and FIG. 5B. HIV02G binding to CHO-gp140 cells was relatively low when analyzed by FACS (FIG. 5A). However, binding of the IgM version HIV02M+J was readily detected and much stronger (FIG. 5B).

Similarly, the binding of anti-HIV antibodies to cells chronically or latently infected with HIV can be examined. Chronically infected cell lines such as CEM cells (CEM-IIIb) (Popovic, M., et al., 1984. *Science* 224:497-500) constitutively express HIV gp120/41 envelope glycoprotein on the cell surface whereas the latently infected cell lines ACH2

(Folks T M, et al., *Proc Natl Acad Sci USA* 86:2365-2368, 1989.), J1.1 (Perez V L, et al., *J Immunol* 147:3145-3148, 1991) and OM10 (Butera et al., 1991 *J Virol.* 65(9):4645-4653) cell lines are activated with the cytokine tumor necrosis alpha to express HIV gp-120/41 envelope glycoprotein on the cell surface. Serial dilutions of the monoclonal or bispecific IgM antibodies as described above as well as appropriate controls, e.g., IgG antibodies carrying equivalent anti-HIV binding domains, are incubated with the respective cell lines, washed to remove unbound antibody, then mixed with a fluorochrome-labeled secondary antibody which is specific for the isotype of antibody to be detected e.g., IgG, IgM, or the kappa or lambda light chain of an antibody. After incubation the binding of monoclonal or bispecific antibodies is analyzed by flow cytometry on a FACSCALIBUR™ (Becton Dickson).

Example 3

HIV Virus Neutralization by HIV Specific IgM Binding Molecules

In vitro HIV virus neutralization assays can be conducted using a variety of standard techniques, such as those described by Richman et al., *PNAS USA*, 100(7): 4144-4149, 2003.

In this assay, anti-HIV antibodies were examined for activity and potency by using HIV pseudo-virus capable of a single round of replication. One or more HIV pseudo-viruses are produced by co-transfection of HEK293 cells with a sub-genomic plasmid, pHIV-1lucΔu3, that incorporates a firefly luciferase indicator gene and a second plasmid, pCXAS that expresses the HIV-1 envelope proteins of interest. Following transfection, pseudo-viruses were harvested and incubated for 1 hour at 37° C. with serial dilutions of the antibodies to be tested. U87 cells that express CD4 plus the CCR5 and CXCR4 co-receptors were then inoculated with the virus-antibody dilutions in the absence of added cations. Virus infectivity was determined 72 hour post-inoculation by measuring the amount of luciferase activity expressed in infected cells. Neutralizing activity is described as the percent inhibition of viral replication (luciferase activity) at each antibody dilution compared with an antibody-negative control: % inhibition={1−[luciferase+Ab/luciferase−Ab]}×100.

Figure 6:
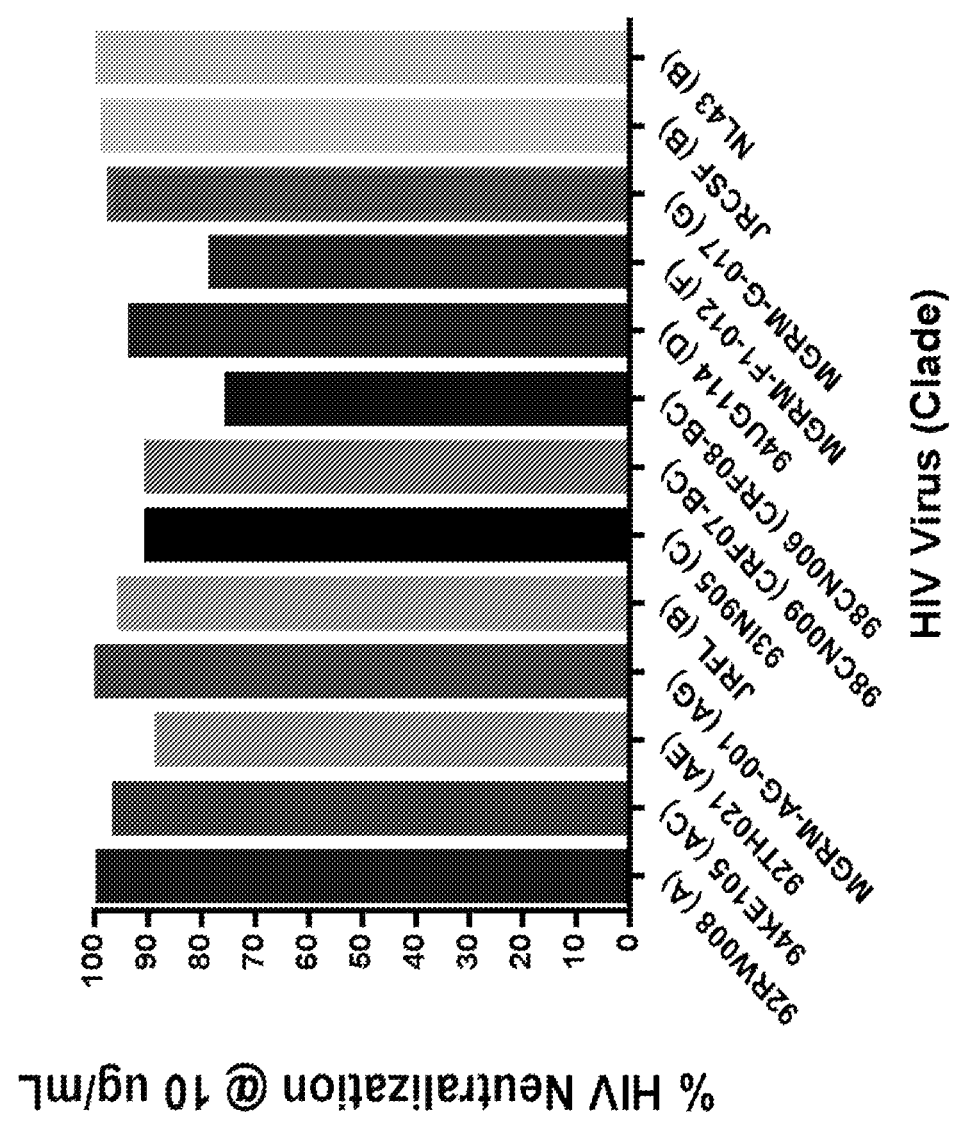

The results of a virus neutralization assay are shown in FIG. 6. HIV02M+J was tested against a panel of viruses that included clades A, B, C, D, F, G, AE, AG, CRF07-BC and CRF08-BC. HIV02M+J successfully neutralized all the viruses tested, exhibiting 75% to 100% neutralization at 10 μg/mL, indicating that HIV02M+J binds to all the different gp120 proteins expressed by these clinically relevant HIV clades. Irrelevant isotype control IgM+J antibodies did not neutralized any of the pseudo-viruses tested (data not shown).

Example 4

T-Cell Activation by HIV Specific IgM Binding Molecules

To demonstrate whether a bispecific HIVxCD3 antibody can activate T cells upon binding to antigen-positive target cells, the following assay was performed. Engineered Jurkat T cells (Promega CS176403) and CHO-gp140 cells expressing gp120/gp41 were cultured in RPMI (Invitrogen) supplemented with 10% Fetal Bovine Serum (Invitrogen). Serial dilutions of HIV02M, HIV02M+J, and HIV02M+V10J were incubated with the antigen-expressing cells in 20 μL in a white 384 well assay plate for 2 h at 37° C. with 5% $CO_2$. The engineered Jurkat cells (25000) were then added to the mixture to a final volume of 40 μL. The mixture was incubated for 5 h at 37° C. with 5% $CO_2$. The cell mixtures were then mixed with 20 μL lysis buffer containing luciferin (Promega, Cell Titer Glo) to allow measurement of luciferase reporter activity. Light output was measured by EnVision plate reader.

Figure 7:
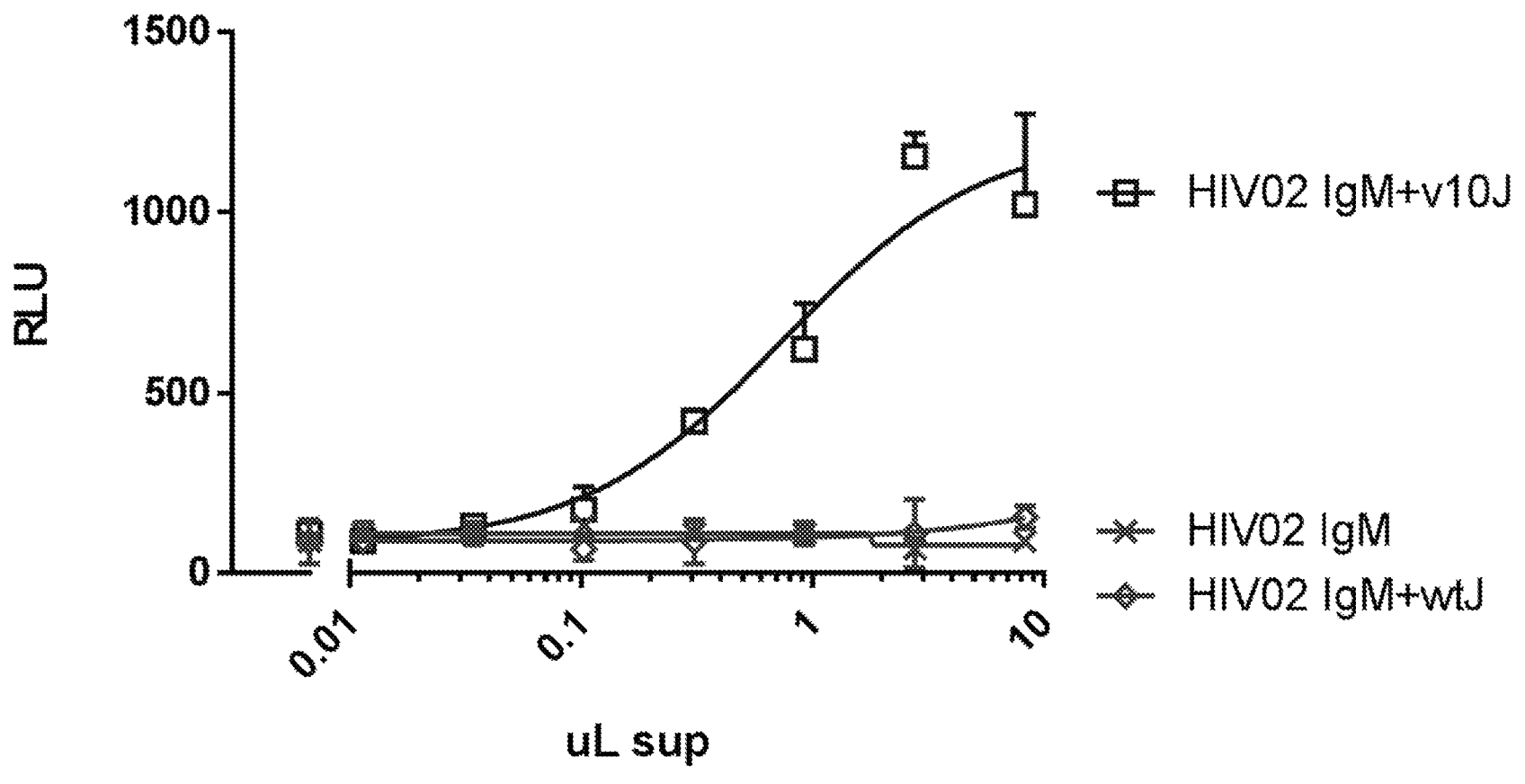

The results of an experiment examining the gp120-specific HIV02M, HIV02M+J, and HIV02M+V10J antibodies is shown in FIG. 7. Whereas the monospecific HIV02M and HIV02M+J antibodies were without activity, the gp120xCD3 bispecific HIV02M+V10J antibody caused T-cell activation in a dose-dependent fashion.

Figure 8:
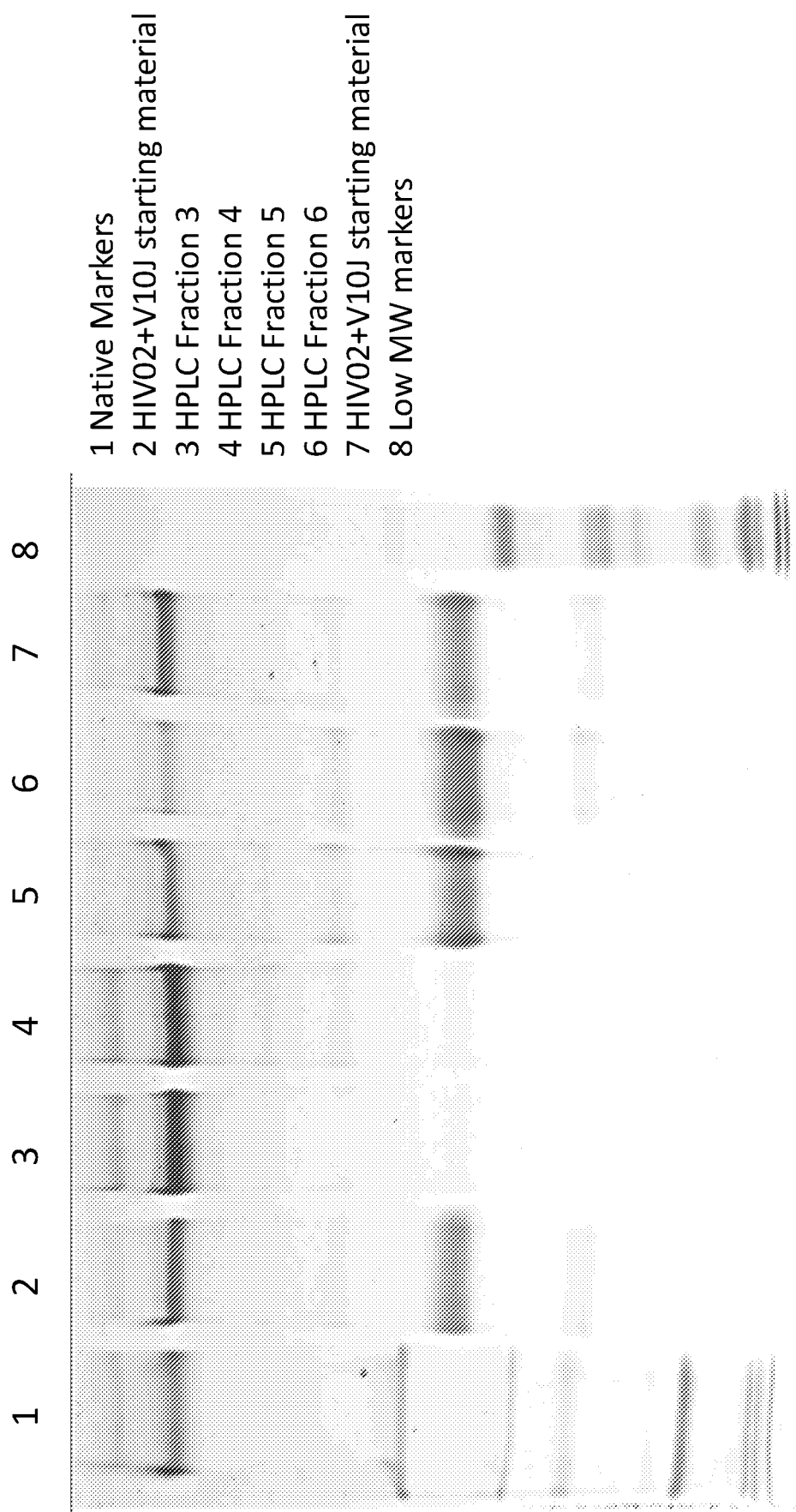
FIG. 8: PAGE analysis of HIV02+V10J HPLC-SEC column fractions.

PAGE analysis indicated that this preparation of HIV02M+V10J contained a mixture of unassembled and fully assembled IgM proteins (FIG. 8, lanes 2 & 8). The preparation was subsequently further purified by size-exclusion chromatography utilizing a Waters 2695 HPLC system equipped with a TOSOH G4000 SWXL chromatography column. The column was equilibrated with degassed mobile phase (0.1 M Sodium Phosphate, 0.1 M Sodium Sulfate pH 6.7) for 45 minutes at a flow rate of 1 ml/min and a temperature of 25° C. Samples were filtered and 100 μl was injected at a flow rate of 1 ml/min for a run time of 15 minutes. The absorbance was monitored at 280 nm using Waters EMPOWER™ software suite, which was also used to generate and analyze the chromatograms. One mL fractions were collected using a Waters Fraction Collector II. Collected fractions were subsequently concentrated and buffer exchanged into 20 mM citric acid, 150 mM sodium chloride, pH 6.0 using Spin X UF-6 Concentrators (Corning, Ref#431486).

Analysis of the HIV02M+V10J antibody is shown in FIG. 8. Based on non-reduced SDS-Native-PAGE, size-exclusion HPLC separated the preparation into purified high molecular weight properly assembled IgM HIV02M+V10J bispecific (fractions 3 and 4) and unassembled, lower molecular weight material (fractions 5 and 6).

Figure 9:
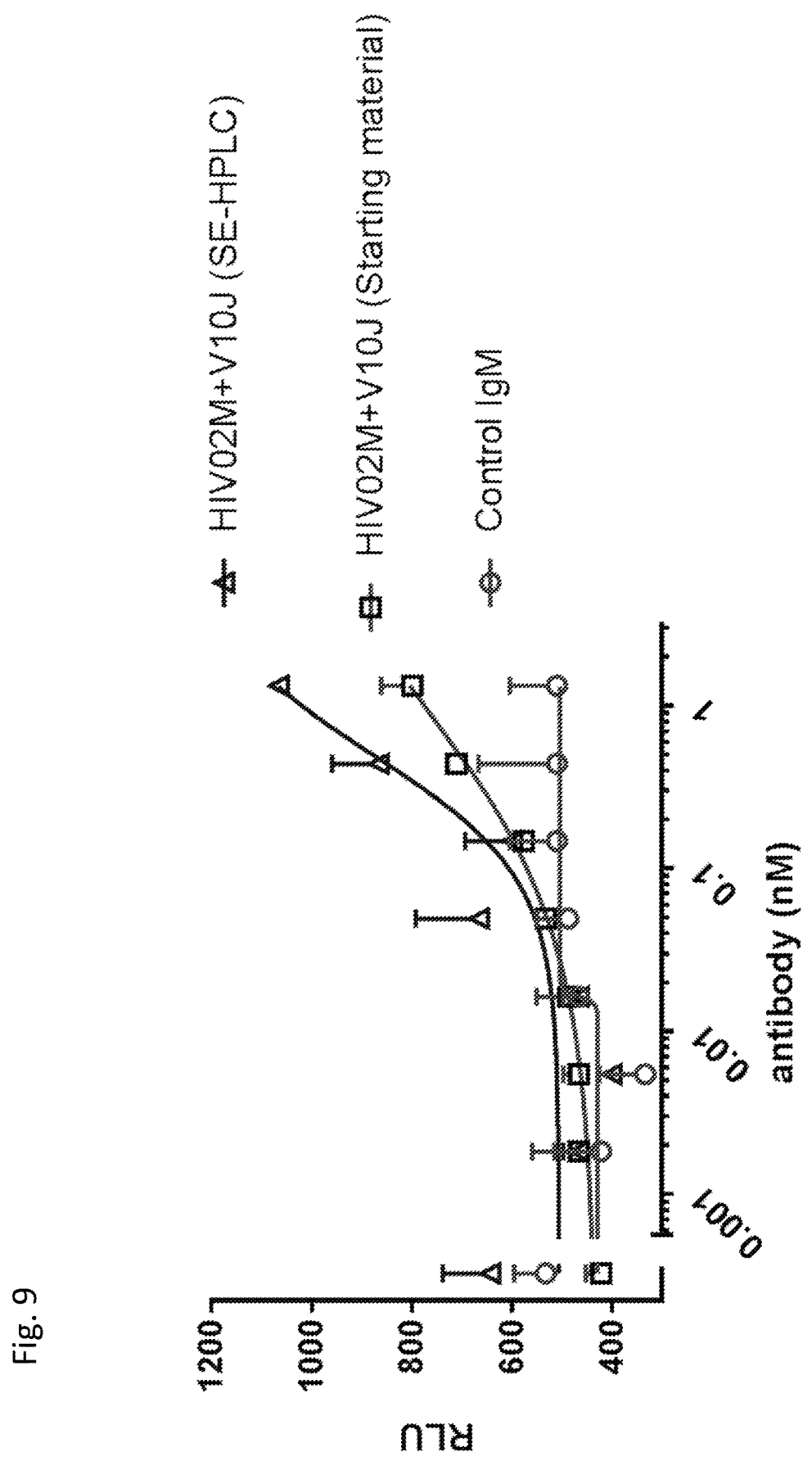

The antigen-dependent T-cell activation induced by the highly purified HIV02M+V10J is shown in FIG. 9. In this assay, the purified HIV02M+V10J antibody was more potent than the HIV02M+V10J starting material as evidenced by the higher activation signal.

Example 5

Complement-Dependent Cytotoxicity of HIV Specific IgM Binding Molecules

Antibodies of the IgM phenotype are particularly well-suited to use the efficient engagement of complement protein C1q to affect complement dependent cytotoxicity (CDC) activity on target cells. To measure CDC, recombinant cells expressing gp120 on their surface are used (e.g., CHO-gp120, CHO-gp140, Jurkat-522 F/Y cells, or mammalian cells expressing membrane anchored trimeric forms of gp140, e.g., strain JR-FL (Go et al. 2015 *J Virol* 89:8245-8257)). The target cells are washed and resuspended in CDC assay medium (RPMI 1640, 10% heat-inactivated FBS) at a density of $1.0 \times 10^6$ cells/mL and 10 μL/well is added to a Nunc 384-well tissue culture-treated white polystyrene plate. Serial 3-fold dilutions of test antibodies including, e.g., a pentameric or hexameric HIV binding molecule, e.g., an IgM antibody such as HIV02M, HIV02M+J, or HIV02M+V10J and appropriate controls, are prepared in assay medium, 10 µL/well is added to the assay plate, and the plate is incubated for 2 hr at 37° C. in a 5% $CO_2$ incubator to allow opsonization to occur. Normal human serum complement (Quidel) is diluted to 30% in assay medium, and 10 µL/well is added to the assay plate. The plate is incubated for 4 hr at 37° C. in a 5% $CO_2$ incubator. Cell Titer-Glo reagent (Promega) is thawed for use and 15 µL/well is added to the assay plate. The plate is gently mixed for 2 min on a plate shaker to lyse the cells and then for another 10 min at room temperature before measuring luminescence on an EnVision plate reader (Perkin-Elmer). After subtracting background signal, percent viability is plotted against antibody concentration and EC50 values are determined using GraphPad Prism.

Alternatively, chronically HIV-infected cell lines (e.g., CEM-IIIb) or latently infected cell lines (e.g., ACH2, J1.1, OM10) can be used. The CEM-IIIb cells constitutively express the gp120/41 HIV envelope glycoprotein on their cell surface, whereas the latent cell lines are activated to express the gp120/41 HIV envelope glycoprotein that is indicative of HIV latency. Cells are seeded at 50,000 cells per well in a 96-well plate, serially diluted monoclonal or bispecific antibodies such as those described herein are added, and then human serum complement (Quidel cat. #A113) is added to a final concentration of 10 percent of normal serum. The reaction mixture is incubated at 37° C. for 4 hours. Cell Titer Glo reagent (Promega cat. #G7572) is added at a volume equal to the volume of culture medium present in each well. The plate is shaken for 2 minutes, incubated for 10 minutes at room temperature, and luminescence is then measured on a luminometer.

Example 6

T-Cell Directed Killing of HIV Antigen-Expressing Cells by HIV Specific IgM Binding Molecules Bispecific HIVxCD3 antibodies such as, but not limited to HIV02M+V10J, are tested for the induction of T-cell dependent cell cytotoxicity (TDCC) using HIV+ cells as targets. The target HIV+ cells used are cells recombinantly expressing gp120/gp41 on their surface (e.g., CHO-gp140, CHO-gp160, Jurkat-522 F/Y, or mammalian cells expressing membrane anchored trimeric forms of gp140, e.g., strain JR-FL (Go et al. 2015 *J Virol* 89:8245-8257)), chronically infected CEM cells (e.g., CEM-IIIb) or latently infected cell lines (e.g., ACH2, J1.1, OM10). Bispecific HIVxCD3 antibodies are serially diluted and mixed with the target cells and PBMCs or purified/enriched CD8+ T cells from normal donors as effector cells at various target:effector cell ratios. After 24-72 hours the amount of cell lysis or killing is analyzed by the addition of Cell titer glo (Promega) and luminescence is then measured on a luminometer.

Alternately, TDCC co-culture experiments can be conducted using CD8+ T-cell acute lymphoblastic leukemia (TALL) cells. gp120/pg41-expressing cells (about $6 \times 10^3$ cells), e.g., CHO-gp140, CHO-gp160, Jurkat-522 F/Y, or mammalian cells expressing membrane anchored trimeric forms of gp140, e.g., strain JR-FL (Go et al. 2015 *J Virol* 89:8245-8257)), chronically infected CEM cells (e.g., CEM-IIIb) or latently infected cell lines (e.g., ACH2, J1.1, OM10), are co-cultured with $3 \times 10^4$ TALL cells (ATCC CRL-11386) in the presence of different concentrations of test compounds, e.g., HIVxCD3 bispecific antibodies, in 45 µL total volume of RPMI 1640 media supplemented with 10% heat-inactivated FBS per well on a 384-well black tissue culture plate. After 24 hours of incubation at 37° C. in a 5% $CO_2$ incubator, 15 µL of CytoTox-ONE substrate reagent (Promega, G7891) is added to each well to measure the level of LDH released from dead cells. The plates are shaken briefly to mix the reagents, and then incubated at room temperature for 90 min before measuring fluorescence signal (485 nm for excitation and 615 nm for emission) on an EnVision plate reader (Perkin-Elmer). The data is then analyzed with Prism software (GraphPad) to determine the EC50.

Example 7

Treatment of HIV-Infected Animals with HIV IgM Binding Molecules

Effective control of HIV-1 infection in humans is achieved using combinations of antiretroviral therapy (ART) drugs (Bartlett et al., *AIDS* 15(11): 1369-1377). However, when ART is stopped HIV virus re-appears or "rebounds" after a short period of time indicating a small number of latently infected cells still remain in the ART-treated individual. This latent "reservoir" is the single biggest obstacle to HIV-infected individuals being cured of their infection. Therefore, since ART effectively reduces HIV infection to below detectable levels there is considerable interest in targeting and killing the reservoir of latently infected cells which can result in the HIV-infected individual being cured of their infection.

A model of HIV latency has been described in humanized BLT mice (Denton et al., *J Virol.* 2012 January; 86(1):630-4 (2012)) which has been used by Horowitz et al., (*Proc. Natl. Acad. Sci. USA.* 2013 110(40:16538-43 and Klein et al., *Nature* 492(7427): 118-122 (2012)) to analyze the combination of ART plus immunotherapy to determine the possibility of suppressing or eliminating the rebound of virus after ART is stopped as a promising approach toward developing a cure for HIV infection. Humanized mice are screened at 8 weeks of age for reconstitution of human lymphocytes as described by Klein et al. *Nature* 492(7427): 118-122 (2012. Mice with measurable human lymphocytes are injected intra-peritoneally with infectious HIV-1 YU2 virus and screened for viremia at 2 to 3 weeks post-infection by quantitative reverse-transcriptase PCR. Individual tablets of tenofovir disproxil-fumarate (TDF; Gilead Sciences), emtricitabine (FTC; Gilead Sciences), raltegravir (RAL; Merck), and efavirenz (EFV; Bristol-Myers Squibb) are crushed into a fine powder form using a mortar and pestle and suspended in PBS. ART preparations are aliquotted into 200-µL doses in sterile Eppendorf tubes and are administered daily by oral gavage at 2.5, 1.5, 1.2, and 2.5 mg per mouse for TDF, FTC, RAL, and EFV, respectively, based on effective doses reported by Denton et al. (2012). Four (4) groups of humanized YU2-infected mice will begin receiving ART by oral lavage daily on day 0 for 5 days and then groups 2, 3, and 4 will begin receiving HIV02G, HIV02M, and HIV02M+V10J, respectively, at 20 mg/kg on day 5. Groups 2, 3, and 4 continue to receive antibody therapy twice a week from day 5 to day 42. On day 21, ART is terminated in all groups. HIV plasma viral load, cell-associated HIV DNA and RNA are determined at various time points through the duration of the study to day 63 to determine the kinetics of virus rebound from latency. Similarly, other humanized mouse models can be used (see Xhang & Su 2012 *Cell. & Mol. Immunol.* 9,237-244).

Alternately, in vivo efficacy studies can be conducted in non-human primates. In one such model of chronic infection (Barouch et al. 2013 *Nature* 503, 224-228), specific pathogen-free rhesus monkeys (*Macaca mulatta*) that do not express the class I alleles Mamu-A*01, Mamu-B*08, and Mamu-B*17 associated with spontaneous virologic control are used. Groups are balanced for susceptible and resistant TRIM5α alleles. Groups of 4 to 5 monkeys are randomly allocated to balance baseline viral loads. Animals are infected by the intrarectal route with rhesus-derived SHIV-SF162P3 challenge stock for 9 months prior to antibody administration. Dimeric, pentameric, or hexameric HIV binding molecules, e.g., IgM antibodies such as HIV02M, HIV02M+J, or HIV02M+V10J, and appropriate controls, are administered to monkeys once or twice by the intravenous route at doses up to 10 mg/kg, and the monkeys are bled up to three times per week for assessment of viral loads. Alternatively, infected monkeys are treated with or without anti-retroviral therapy (e.g., ART) in addition to the dimeric, pentameric, or hexameric HIV binding molecules. Once the anti-retroviral therapy has stopped, viral rebound is quantified. Similarly, infected monkeys can be treated with anti-retroviral therapy and, once stopped, then treated with the dimeric, pentameric, or hexameric HIV binding molecules and viral rebound is quantified.

The breadth and scope of the present disclosure should not be limited by any of the above-described exemplary embodiments, but should be defined only in accordance with the following claims and their equivalents.

What is claimed is:

1. A multimeric binding molecule comprising two or five bivalent binding units and a modified J-chain; wherein each binding unit comprises two antibody heavy chain constant regions or fragments thereof, each associated with an antigen binding domain, wherein at least one antigen binding domain specifically binds to a human immunodeficiency virus (HIV) antigen expressed on the surface of HIV viral particles, on the surface of HIV-infected cells, or a combination thereof, wherein the modified J-chain comprises a J-chain or functional fragment or variant thereof and a heterologous polypeptide directly or indirectly fused to the J-chain or variant or fragment thereof, wherein the heterologous polypeptide comprises an antigen binding scFv antibody fragment that binds to an effector cell wherein the scFv antibody fragment specifically binds to CD3 or CD8 on a T-cell, CD16, CD64, or NKG2D on an NK cell, CD14 on a macrophage, or CD16b or CD177 on a neutrophil, wherein the binding molecule is more potent than a reference single binding unit molecule comprising the at least one antigen binding domain that specifically binds to an HIV antigen, and wherein the reference single binding unit molecule is an IgG antibody.

2. The binding molecule of claim 1, which is a dimeric binding molecule comprising two bivalent IgA binding units, wherein each binding unit comprises two IgA heavy chain constant regions or fragments thereof each associated with an antigen binding domain, and wherein the IgA heavy chain constant regions each comprise a Cα3-tp domain.

3. The binding molecule of claim 1, which is a pentameric binding molecule comprising five bivalent IgM binding units, wherein each binding unit comprises two human IgM heavy chain constant regions each associated with an antigen binding domain, and wherein the IgM heavy chain constant regions each comprise a Cμ4-tp domain.

4. The binding molecule of claim 1, wherein the heterologous polypeptide of the modified J-chain is fused to the N-terminus of the J-chain or fragment or variant thereof, the C-terminus of the J-chain or fragment or variant thereof, or to both the N-terminus and C-terminus of the J-chain or fragment or variant thereof.

5. The binding molecule of claim 1, wherein the scFv can specifically bind to the T-cell antigen CD3, or the NK cell antigen CD16.

6. The binding molecule of claim 1, wherein each binding unit comprises two heavy chains each comprising a VH situated amino terminal to the constant region or fragment thereof, and two immunoglobulin light chains each comprising a VL situated amino terminal to an immunoglobulin light chain constant region.

7. The binding molecule of claim 6, wherein the at least one antigen binding domain specifically binds to the HIV spike protein.

8. The binding molecule of claim 7, wherein at least one binding unit comprises two antigen binding domains that specifically bind to an HIV antigen expressed on the surface of viral particles, on the surface of HIV-infected cells, or a combination thereof, and wherein the two heavy chains within the at least one binding unit are identical, and wherein the two light chains within the at least one binding unit are identical.

9. The binding molecule of claim 7, comprising at least three, at least four, at least five, at least six, at least seven, at least eight, at least nine, at least ten, at least eleven, or at least twelve antigen binding domains that specifically bind to an HIV antigen expressed on the surface of viral particles, on the surface of HIV-infected cells, or a combination thereof.

10. The binding molecule of claim 7, wherein the at least one antigen binding domain comprises an antibody heavy chain variable region (VH) and an antibody light chain variable region (VL), wherein the VH and VL comprise the HCDR1, HCDR2, and HCDR3 regions and the LCDR1, LCDR2, and LCDR3 regions of the VH and VL amino acid sequences of SEQ ID NO: 5 and SEQ ID NO: 6, SEQ ID NO: 7 and SEQ ID NO: 8, SEQ ID NO: 9 and SEQ ID NO: 10, SEQ ID NO: 11 and SEQ ID NO: 12, SEQ ID NO: 13 and SEQ ID NO: 14, SEQ ID NO: 15 and SEQ ID NO: 16, SEQ ID NO: 17 and SEQ ID NO: 18, SEQ ID NO: 19 and SEQ ID NO: 20, SEQ ID NO: 21 and SEQ ID NO: 22, SEQ ID NO: 23 and SEQ ID NO: 24, SEQ ID NO: 25 and SEQ ID NO: 26, SEQ ID NO: 27 and SEQ ID NO: 28, SEQ ID NO: 29 and SEQ ID NO: 30, SEQ ID NO: 31 and SEQ ID NO: 32, SEQ ID NO: 33 and SEQ ID NO: 34, SEQ ID NO: 35 and SEQ ID NO: 36, SEQ ID NO: 37 and SEQ ID NO: 38, SEQ ID NO: 39 and SEQ ID NO: 40, SEQ ID NO: 41 and SEQ ID NO: 42, SEQ ID NO: 43 and SEQ ID NO: 44, SEQ ID NO: 45 and SEQ ID NO: 46, SEQ ID NO: 47 and SEQ ID NO: 48, SEQ ID NO: 49 and SEQ ID NO: 50, SEQ ID NO: 51 and SEQ ID NO: 52, SEQ ID NO: 53 and SEQ ID NO: 54, SEQ ID NO: 55 and SEQ ID NO: 56, SEQ ID NO: 57 and SEQ ID NO: 58, SEQ ID NO: 59 and SEQ ID NO: 60, SEQ ID NO: 61 and SEQ ID NO: 62, SEQ ID NO: 63 and SEQ ID NO: 64, SEQ ID NO: 65 and SEQ ID NO: 66, SEQ ID NO: 67 and SEQ ID NO: 68, SEQ ID NO: 69 and SEQ ID NO: 70, SEQ ID NO: 71 and SEQ ID NO: 72, SEQ ID NO: 73 and SEQ ID NO: 74, SEQ ID NO: 75 and SEQ ID NO: 6, SEQ ID NO: 77 and SEQ ID NO: 78, SEQ ID NO: 79 and SEQ ID NO: 80, SEQ ID NO: 81 and SEQ ID NO: 82, SEQ ID NO: 83 and SEQ ID NO: 84, SEQ ID NO: 85 and SEQ ID NO: 86, SEQ ID NO: 87 and SEQ ID NO: 88, SEQ ID NO: 89 and SEQ ID NO: 90, SEQ ID NO: 91 and SEQ ID NO: 92, SEQ ID NO: 93 and SEQ ID NO: 94, SEQ ID NO: 95 and SEQ ID NO: 96, SEQ ID NO: 97 and SEQ ID NO: 98, or SEQ ID NO: 99 and SEQ ID NO: 100, respectively; or wherein the at least one antigen binding domain comprises an antibody heavy chain variable region (VH) and an antibody light chain variable region (VL), wherein the VH and VL comprise, respectively, amino acid sequences that are at least 95% or 100% identical to amino acid sequences of SEQ ID NO: 5 and SEQ ID NO: 6, SEQ ID NO: 7 and SEQ ID NO: 8, SEQ ID NO: 9 and SEQ ID NO: 10, SEQ ID NO: 11 and SEQ ID NO: 12, SEQ ID NO: 13 and SEQ ID NO: 14, SEQ ID NO: 15 and SEQ ID NO: 16, SEQ ID NO: 17 and SEQ ID NO: 18, SEQ ID NO: 19 and SEQ ID NO: 20, SEQ ID NO: 21 and SEQ ID NO: 22, SEQ ID NO: 23 and SEQ ID NO: 24, SEQ ID NO: 25 and SEQ ID NO: 26, SEQ ID NO: 27 and SEQ ID NO: 28, SEQ ID NO: 29 and SEQ ID NO: 30, SEQ ID NO: 31 and SEQ ID NO: 32, SEQ ID NO: 33 and SEQ ID NO: 34, SEQ ID NO: 35 and SEQ ID NO: 36, SEQ ID NO: 37 and SEQ ID NO: 38, SEQ ID NO: 39 and SEQ ID NO: 40, SEQ ID NO: 41 and SEQ ID NO: 42, SEQ ID NO: 43 and SEQ ID NO: 44, SEQ ID NO: 45 and SEQ ID NO: 46, SEQ ID NO: 47 and SEQ ID NO: 48, SEQ ID NO: 49 and SEQ ID NO: 50, SEQ ID NO: 51 and SEQ ID NO: 52, SEQ ID NO: 53 and SEQ ID NO: 54, SEQ ID NO: 55 and SEQ ID NO: 56, SEQ ID NO: 57 and SEQ ID NO: 58, SEQ ID NO: 59 and SEQ ID NO: 60, SEQ ID NO: 61 and SEQ ID NO: 62, SEQ ID NO: 63 and SEQ ID NO: 64, SEQ ID NO: 65 and SEQ ID NO: 66, SEQ ID NO: 67 and SEQ ID NO: 68, SEQ ID NO: 69 and SEQ ID NO: 70, SEQ ID NO: 71 and SEQ ID NO: 72, SEQ ID NO: 73 and SEQ ID NO: 74, SEQ ID NO: 75 and SEQ ID NO: 6, SEQ ID NO: 77 and SEQ ID NO: 78, SEQ ID NO: 79 and SEQ ID NO: 80, SEQ ID NO: 81 and SEQ ID NO: 82, SEQ ID NO: 83 and SEQ ID NO: 84, SEQ ID NO: 85 and SEQ ID NO: 86, SEQ ID NO: 87 and SEQ ID NO: 88, SEQ ID NO: 89 and SEQ ID NO: 90, SEQ ID NO: 91 and SEQ ID NO: 92, SEQ ID NO: 93 and SEQ ID NO: 94, SEQ ID NO: 95 and SEQ ID NO: 96, SEQ ID NO: 97 and SEQ ID NO: 98, or SEQ ID NO: 99 and SEQ ID NO: 100.

11. An isolated IgM antibody comprising a modified J-chain and five binding units, each comprising two heavy chains and two light chains, wherein each heavy chain or fragment thereof comprises a human Mu constant region or fragment thereof, and the heavy chain variable region amino acid sequence SEQ ID NO: 7, and wherein each light chain comprises a human kappa constant region and the light chain variable region amino acid sequence SEQ ID NO: 8; wherein the antibody or fragment thereof can assemble into a pentameric IgM antibody that can specifically bind to the CD4 binding site of the HIV spike glycoprotein, and wherein the modified J-chain comprises a J-chain or functional fragment or variant thereof and an antigen binding scFv antibody fragment that binds to CD3 directly or indirectly fused to the J-chain or variant or fragment thereof.

12. The IgM antibody or fragment thereof of claim 11 wherein the modified J-chain comprises SEQ ID NO: 108, SEQ ID NO: 109, SEQ ID NO: 110, or SEQ ID NO: 111.

13. A composition comprising:
a polynucleotide comprising a nucleic acid sequence that encodes a human IgM constant region or fragment thereof fused to the C-terminal end of a VH domain comprising:
(a) the HCDR1, HCDR2, and HCDR3 domains of the VH amino acid sequence SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99; or
(b) an amino acid sequence at least 95% or 100% identical to the SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99;
a polynucleotide comprising a nucleic acid sequence encoding a human antibody light chain constant region or fragment thereof fused to the C-terminal end of a VL comprising:
(c) the LCDR1, LCDR2, and LCDR3 domains of the VL amino acid sequence SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 6, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100; or
(d) an amino acid sequence at least 95% or 100% identical to SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 6, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100; and a polynucleotide comprising a nucleic acid sequence encoding a modified J-chain comprising the amino acid sequence SEQ ID NO: 108, SEQ ID NO: 109, SEQ ID NO: 110, or SEQ ID NO: 111.

14. A method of, controlling or treating human immunodeficiency virus (HIV) infection, or controlling HIV infectivity, comprising contacting HIV virions, HIV-infected cells, or a mixture thereof with the multimeric binding molecule of claim 1;
  wherein the binding molecule is more potent in controlling or treating HIV infection, or in controlling HIV infectivity, than a corresponding IgG antibody comprising an identical HIV-binding antigen binding domain.

* * * * *

SEQUENCE LISTING

<160> NUMBER OF SEQ ID NOS: 125

<210> SEQ ID NO 1
<211> LENGTH: 452
<212> TYPE: PRT
<213> ORGANISM: Homo sapiens

<400> SEQUENCE: 1

```
Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
                20                  25                  30

Phe Leu Pro Asp Ser Ile Thr Leu Ser Trp Lys Tyr Lys Asn Asn Ser
            35                  40                  45

Asp Ile Ser Ser Thr Arg Gly Phe Pro Ser Val Leu Arg Gly Gly Lys
        50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270
```

```
Ile Ser Glu Ser His Pro Asn Ala Thr Phe Ser Ala Val Gly Glu Ala
            275                 280                 285

Ser Ile Cys Glu Asp Asp Trp Asn Ser Gly Glu Arg Phe Thr Cys Thr
    290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
            355                 360                 365

Gly Gln Pro Leu Ser Pro Glu Lys Tyr Val Thr Ser Ala Pro Met Pro
370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Ala His
                405                 410                 415

Glu Ala Leu Pro Asn Arg Val Thr Glu Arg Thr Val Asp Lys Ser Thr
            420                 425                 430

Gly Lys Pro Thr Leu Tyr Asn Val Ser Leu Val Met Ser Asp Thr Ala
            435                 440                 445

Gly Thr Cys Tyr
    450

<210> SEQ ID NO 2
<211> LENGTH: 159
<212> TYPE: PRT
<213> ORGANISM: Homo sapiens

<400> SEQUENCE: 2

Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
            20                  25                  30

Asn Lys Cys Lys Cys Ala Arg Ile Thr Ser Arg Ile Ile Arg Ser Ser
        35                  40                  45

Glu Asp Pro Asn Glu Asp Ile Val Glu Arg Asn Ile Arg Ile Ile Val
    50                  55                  60

Pro Leu Asn Asn Arg Glu Asn Ile Ser Asp Pro Thr Ser Pro Leu Arg
65                  70                  75                  80

Thr Arg Phe Val Tyr His Leu Ser Asp Leu Cys Lys Lys Cys Asp Pro
                85                  90                  95

Thr Glu Val Glu Leu Asp Asn Gln Ile Val Thr Ala Thr Gln Ser Asn
            100                 105                 110

Ile Cys Asp Glu Asp Ser Ala Thr Glu Thr Cys Tyr Thr Tyr Asp Arg
        115                 120                 125

Asn Lys Cys Tyr Thr Ala Val Val Pro Leu Val Tyr Gly Gly Glu Thr
    130                 135                 140

Lys Met Val Glu Thr Ala Leu Thr Pro Asp Ala Cys Tyr Pro Asp
145                 150                 155

<210> SEQ ID NO 3
<211> LENGTH: 353
<212> TYPE: PRT
<213> ORGANISM: Homo sapiens
```

<400> SEQUENCE: 3

| | | | | | | | | | | | | | | |
|---|---|---|---|---|---|---|---|---|---|---|---|---|---|---|
| Ala | Ser | Pro | Thr | Ser | Pro | Lys | Val | Phe | Pro | Leu | Ser | Leu | Cys | Ser | Thr |
| 1 | | | | 5 | | | | | 10 | | | | | 15 | |
| Gln | Pro | Asp | Gly | Asn | Val | Val | Ile | Ala | Cys | Leu | Val | Gln | Gly | Phe | Phe |
| | | | 20 | | | | | 25 | | | | | 30 | | |
| Pro | Gln | Glu | Pro | Leu | Ser | Val | Thr | Trp | Ser | Glu | Ser | Gly | Gln | Gly | Val |
| | | 35 | | | | | 40 | | | | | 45 | | | |
| Thr | Ala | Arg | Asn | Phe | Pro | Pro | Ser | Gln | Asp | Ala | Ser | Gly | Asp | Leu | Tyr |
| | 50 | | | | | 55 | | | | | 60 | | | | |
| Thr | Thr | Ser | Ser | Gln | Leu | Thr | Leu | Pro | Ala | Thr | Gln | Cys | Leu | Ala | Gly |
| 65 | | | | | 70 | | | | | 75 | | | | | 80 |
| Lys | Ser | Val | Thr | Cys | His | Val | Lys | His | Tyr | Thr | Asn | Pro | Ser | Gln | Asp |
| | | | | 85 | | | | | 90 | | | | | 95 | |
| Val | Thr | Val | Pro | Cys | Pro | Val | Pro | Ser | Thr | Pro | Pro | Thr | Pro | Ser | Pro |
| | | | 100 | | | | | 105 | | | | | 110 | | |
| Ser | Thr | Pro | Pro | Thr | Pro | Ser | Pro | Ser | Cys | Cys | His | Pro | Arg | Leu | Ser |
| | | 115 | | | | | 120 | | | | | 125 | | | |
| Leu | His | Arg | Pro | Ala | Leu | Glu | Asp | Leu | Leu | Leu | Gly | Ser | Glu | Ala | Asn |
| | 130 | | | | | 135 | | | | | 140 | | | | |
| Leu | Thr | Cys | Thr | Leu | Thr | Gly | Leu | Arg | Asp | Ala | Ser | Gly | Val | Thr | Phe |
| 145 | | | | | 150 | | | | | 155 | | | | | 160 |
| Thr | Trp | Thr | Pro | Ser | Ser | Gly | Lys | Ser | Ala | Val | Gln | Gly | Pro | Pro | Glu |
| | | | | 165 | | | | | 170 | | | | | 175 | |
| Arg | Asp | Leu | Cys | Gly | Cys | Tyr | Ser | Val | Ser | Ser | Val | Leu | Pro | Gly | Cys |
| | | | 180 | | | | | 185 | | | | | 190 | | |
| Ala | Glu | Pro | Trp | Asn | His | Gly | Lys | Thr | Phe | Thr | Cys | Thr | Ala | Ala | Tyr |
| | | 195 | | | | | 200 | | | | | 205 | | | |
| Pro | Glu | Ser | Lys | Thr | Pro | Leu | Thr | Ala | Thr | Leu | Ser | Lys | Ser | Gly | Asn |
| | 210 | | | | | 215 | | | | | 220 | | | | |
| Thr | Phe | Arg | Pro | Glu | Val | His | Leu | Leu | Pro | Pro | Pro | Ser | Glu | Glu | Leu |
| 225 | | | | | 230 | | | | | 235 | | | | | 240 |
| Ala | Leu | Asn | Glu | Leu | Val | Thr | Leu | Thr | Cys | Leu | Ala | Arg | Gly | Phe | Ser |
| | | | | 245 | | | | | 250 | | | | | 255 | |
| Pro | Lys | Asp | Val | Leu | Val | Arg | Trp | Leu | Gln | Gly | Ser | Gln | Glu | Leu | Pro |
| | | | 260 | | | | | 265 | | | | | 270 | | |
| Arg | Glu | Lys | Tyr | Leu | Thr | Trp | Ala | Ser | Arg | Gln | Glu | Pro | Ser | Gln | Gly |
| | | 275 | | | | | 280 | | | | | 285 | | | |
| Thr | Thr | Thr | Phe | Ala | Val | Thr | Ser | Ile | Leu | Arg | Val | Ala | Ala | Glu | Asp |
| | 290 | | | | | 295 | | | | | 300 | | | | |
| Trp | Lys | Lys | Gly | Asp | Thr | Phe | Ser | Cys | Met | Val | Gly | His | Glu | Ala | Leu |
| 305 | | | | | 310 | | | | | 315 | | | | | 320 |
| Pro | Leu | Ala | Phe | Thr | Gln | Lys | Thr | Ile | Asp | Arg | Leu | Ala | Gly | Lys | Pro |
| | | | | 325 | | | | | 330 | | | | | 335 | |
| Thr | His | Val | Asn | Val | Ser | Val | Val | Met | Ala | Glu | Val | Asp | Gly | Thr | Cys |
| | | | 340 | | | | | 345 | | | | | 350 | | |
| Tyr | | | | | | | | | | | | | | | |

<210> SEQ ID NO 4
<211> LENGTH: 340
<212> TYPE: PRT
<213> ORGANISM: Homo sapiens

<400> SEQUENCE: 4

```
Ala Ser Pro Thr Ser Pro Lys Val Phe Pro Leu Ser Leu Asp Ser Thr
1               5                   10                  15

Pro Gln Asp Gly Asn Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Cys Cys His Pro
            100                 105                 110

Arg Leu Ser Leu His Arg Pro Ala Leu Glu Asp Leu Leu Leu Gly Ser
            115                 120                 125

Glu Ala Asn Leu Thr Cys Thr Leu Thr Gly Leu Arg Asp Ala Ser Gly
        130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
            165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
            195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
            245                 250                 255

Glu Leu Pro Arg Glu Lys Tyr Leu Thr Trp Ala Ser Arg Gln Glu Pro
        260                 265                 270

Ser Gln Gly Thr Thr Thr Phe Ala Val Thr Ser Ile Leu Arg Val Ala
    275                 280                 285

Ala Glu Asp Trp Lys Lys Gly Asp Thr Phe Ser Cys Met Val Gly His
    290                 295                 300

Glu Ala Leu Pro Leu Ala Phe Thr Gln Lys Thr Ile Asp Arg Met Ala
305                 310                 315                 320

Gly Lys Pro Thr His Val Asn Val Ser Val Val Met Ala Glu Val Asp
                325                 330                 335

Gly Thr Cys Tyr
            340

<210> SEQ ID NO 5
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Val Gln Ser Gly Gly Gln Met Lys Lys Pro Gly Glu
1               5                   10                  15
```

-continued

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                85                  90                  95

Thr Arg Gly Lys Asn Cys Asp Tyr Asn Trp Asp Phe Glu His Trp Gly
            100                 105                 110

Arg Gly Thr Pro Val Ile Val Ser Ser
        115                 120

<210> SEQ ID NO 6
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp Ile Lys Arg
            100

<210> SEQ ID NO 7
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Gln Ser Gly Gly Gln Met Lys Lys Pro Gly Glu
1               5                   10                  15

Ser Met Arg Ile Ser Cys Gln Ala Ser Gly Tyr Glu Phe Ile Asp Cys
            20                  25                  30

Thr Leu Asn Trp Val Arg Leu Ala Pro Gly Arg Arg Pro Glu Trp Met
        35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

```
Leu Glu Leu Arg Ser Leu Thr Ala Asp Asp Thr Ala Val Tyr Tyr Cys
                85                  90                  95

Thr Arg Gly Lys Asn Cys Asp Tyr Asn Trp Asp Phe Glu His Trp Gly
            100                 105                 110

Arg Gly Thr Pro Val Thr Val Ser Ser
        115                 120

<210> SEQ ID NO 8
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Arg Asn Leu Glu Ser Gly Asp
65                  70                  75                  80

Phe Gly Leu Tyr Tyr Cys Gln Gln Tyr Glu Phe Phe Gly Gln Gly Thr
                85                  90                  95

Lys Val Gln Val Asp Ile Lys Arg
            100

<210> SEQ ID NO 9
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Gln Ser Gly Ala Val Ile Lys Thr Pro Gly Ser
1               5                   10                  15

Ser Val Lys Ile Ser Cys Arg Ala Ser Gly Tyr Asn Phe Arg Asp Tyr
            20                  25                  30

Ser Ile His Trp Val Arg Leu Ile Pro Asp Lys Gly Phe Glu Trp Ile
        35                  40                  45

Gly Trp Ile Lys Pro Leu Trp Gly Ala Val Ser Tyr Ala Arg Gln Leu
    50                  55                  60

Gln Gly Arg Val Ser Met Thr Arg Gln Leu Ser Gln Asp Pro Asp Asp
65                  70                  75                  80

Pro Asp Trp Gly Val Ala Tyr Met Glu Phe Ser Gly Leu Thr Pro Ala
                85                  90                  95

Asp Thr Ala Glu Tyr Phe Cys Val Arg Arg Gly Ser Cys Asp Tyr Cys
            100                 105                 110

Gly Asp Phe Pro Trp Gln Tyr Trp Gly Gln Gly Thr Val Val Val Val
        115                 120                 125

Ser Ser
    130
```

<210> SEQ ID NO 10
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Ile Val Leu Thr Gln Ser Pro Gly Ile Leu Ser Leu Ser Pro Gly
1               5                   10                  15

Glu Thr Ala Thr Leu Phe Cys Lys Ala Ser Gln Gly Gly Asn Ala Met
            20                  25                  30

Thr Trp Tyr Gln Lys Arg Arg Gly Gln Val Pro Arg Leu Leu Ile Tyr
        35                  40                  45

Asp Thr Ser Arg Arg Ala Ser Gly Val Pro Asp Arg Phe Val Gly Ser
    50                  55                  60

Gly Ser Gly Thr Asp Phe Phe Leu Thr Ile Asn Lys Leu Asp Arg Glu
65                  70                  75                  80

Asp Phe Ala Val Tyr Tyr Cys Gln Gln Phe Glu Phe Phe Gly Leu Gly
                85                  90                  95

Ser Glu Leu Glu Val His Arg
            100

<210> SEQ ID NO 11
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Val Gln Ser Gly Ser Gly Val Lys Lys Pro Gly Ala
1               5                   10                  15

Ser Val Arg Val Ser Cys Trp Thr Ser Glu Asp Ile Phe Glu Arg Thr
            20                  25                  30

Glu Leu Ile His Trp Val Arg Gln Ala Pro Gly Gln Gly Leu Glu Trp
        35                  40                  45

Ile Gly Trp Val Lys Thr Val Thr Gly Ala Val Asn Phe Gly Ser Pro
    50                  55                  60

Asp Phe Arg Gln Arg Val Ser Leu Thr Arg Asp Arg Asp Leu Phe Thr
65                  70                  75                  80

Ala His Met Asp Ile Arg Gly Leu Thr Gln Gly Asp Thr Ala Thr Tyr
                85                  90                  95

Phe Cys Ala Arg Gln Lys Phe Tyr Thr Gly Gly Gln Gly Trp Tyr Phe
                100                 105                 110

Asp Leu Trp Gly Arg Gly Thr Leu Ile Val Val Ser Ser
        115                 120                 125

<210> SEQ ID NO 12
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Ile Val Leu Thr Gln Ser Pro Gly Thr Leu Ser Leu Ser Pro Gly
1               5                   10                  15

Glu Thr Ala Ser Leu Ser Cys Thr Ala Ala Ser Tyr Gly His Met Thr
            20                  25                  30

Trp Tyr Gln Lys Lys Pro Gly Gln Pro Pro Lys Leu Leu Ile Phe Ala
        35                  40                  45

Thr Ser Lys Arg Ala Ser Gly Ile Pro Asp Arg Phe Ser Gly Ser Gln
50                  55                  60

Phe Gly Lys Gln Tyr Thr Leu Thr Ile Thr Arg Met Glu Pro Glu Asp
65                  70                  75                  80

Phe Ala Arg Tyr Tyr Cys Gln Gln Leu Glu Phe Phe Gly Gln Gly Thr
                85                  90                  95

Arg Leu Glu Ile Arg Arg
            100

<210> SEQ ID NO 13
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ser Gly Val Lys Lys Pro Gly Ala
1               5                   10                  15

Ser Val Arg Val Ser Cys Trp Thr Ser Glu Asp Ile Phe Glu Arg Thr
            20                  25                  30

Glu Leu Ile His Trp Val Arg Gln Ala Pro Gly Gln Gly Leu Glu Trp
        35                  40                  45

Ile Gly Trp Val Lys Thr Val Thr Gly Ala Val Asn Phe Gly Ser Pro
50                  55                  60

Asn Phe Arg His Arg Val Ser Leu Thr Arg Asp Arg Asp Leu Phe Thr
65                  70                  75                  80

Ala His Met Asp Ile Arg Gly Leu Thr Gln Gly Asp Thr Ala Thr Tyr
                85                  90                  95

Phe Cys Ala Arg Gln Lys Phe Glu Arg Gly Gly Gln Gly Trp Tyr Phe
            100                 105                 110

Asp Leu Trp Gly Arg Gly Thr Leu Ile Val Val Ser Ser
        115                 120                 125

<210> SEQ ID NO 14
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Ile Val Leu Thr Gln Ser Pro Gly Thr Leu Ser Leu Ser Pro Gly
1               5                   10                  15

Glu Thr Ala Ser Leu Ser Cys Thr Ala Ala Ser Tyr Gly His Met Thr
            20                  25                  30

Trp Tyr Gln Lys Lys Pro Gly Gln Pro Pro Lys Leu Leu Ile Phe Ala
        35                  40                  45

Thr Ser Lys Arg Ala Ser Gly Ile Pro Asp Arg Phe Ser Gly Ser Gln
50                  55                  60

Phe Gly Lys Gln Tyr Thr Leu Thr Ile Thr Arg Met Glu Pro Glu Asp
65                  70                  75                  80

Phe Ala Gly Tyr Tyr Cys Gln Gln Val Glu Phe Phe Gly Gln Gly Thr
                85                  90                  95

Arg Leu Glu Ile Arg
            100

<210> SEQ ID NO 15
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Gln Ser Gly Ala Ala Val Arg Lys Pro Gly Ala
1               5                   10                  15

Ser Val Thr Val Ser Cys Lys Phe Ala Glu Asp Asp Tyr Ser Pro
            20                  25                  30

Tyr Trp Val Asn Pro Ala Pro Glu His Phe Ile His Phe Leu Arg Gln
            35                  40                  45

Ala Pro Gly Gln Gln Leu Glu Trp Leu Ala Trp Met Asn Pro Thr Asn
50                  55                  60

Gly Ala Val Asn Tyr Ala Trp Tyr Leu Asn Gly Arg Val Thr Ala Thr
65                  70                  75                  80

Arg Asp Arg Ser Met Thr Thr Ala Phe Leu Glu Val Lys Ser Leu Arg
                85                  90                  95

Ser Asp Asp Thr Ala Val Tyr Tyr Cys Ala Arg Ala Gln Lys Arg Gly
            100                 105                 110

Arg Ser Glu Trp Ala Tyr Ala His Trp Gly Gln Gly Thr Pro Val Val
            115                 120                 125

Val Ser Ser
        130

<210> SEQ ID NO 16
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Gln Met Thr Gln Ser Pro Ser Ser Leu Ser Ala Ser Leu Gly
1               5                   10                  15

Asp Arg Val Thr Ile Thr Cys Gln Ala Ser Arg Gly Ile Gly Lys Asp
            20                  25                  30

Leu Asn Trp Tyr Gln Gln Lys Ala Gly Lys Ala Pro Lys Leu Leu Val
            35                  40                  45

Ser Asp Ala Ser Thr Leu Glu Gly Gly Val Pro Ser Arg Phe Ser Gly
50                  55                  60

Ser Gly Phe His Gln Asn Phe Ser Leu Thr Ile Ser Ser Leu Gln Ala
65                  70                  75                  80

Glu Asp Val Ala Thr Tyr Phe Cys Gln Gln Tyr Glu Thr Phe Gly Gln
                85                  90                  95

Gly Thr Lys Val Asp Ile Lys
            100

<210> SEQ ID NO 17
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Gln Ser Gly Ala Ala Val Arg Lys Pro Gly Ala
1               5                   10                  15

Ser Val Thr Val Ser Cys Lys Phe Ala Glu Asp Asp Tyr Ser Pro
            20                  25                  30

His Trp Val Asn Pro Ala Pro Glu His Tyr Ile His Phe Leu Arg Gln
        35                  40                  45

Ala Pro Gly Gln Gln Leu Glu Trp Leu Ala Trp Met Asn Pro Thr Asn
    50                  55                  60

Gly Ala Val Asn Tyr Ala Trp Gln Leu His Gly Arg Leu Thr Ala Thr
65                  70                  75                  80

Arg Asp Gly Ser Met Thr Thr Ala Phe Leu Glu Val Arg Ser Leu Arg
                85                  90                  95

Ser Asp Asp Thr Ala Val Tyr Tyr Cys Ala Arg Ala Gln Lys Arg Gly
            100                 105                 110

Arg Ser Glu Trp Ala Tyr Ala His Trp Gly Gln Gly Thr Pro Val Ala
        115                 120                 125

Val Ser Ser
    130

<210> SEQ ID NO 18
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Gln Met Thr Gln Ser Pro Ser Ser Leu Ser Ala Ser Leu Gly
1               5                   10                  15

Asp Arg Val Thr Ile Thr Cys Gln Ala Ser Arg Gly Ile Gly Lys Asp
            20                  25                  30

Leu Asn Trp Tyr Gln Gln Lys Pro Gly Lys Ala Pro Lys Leu Leu Val
        35                  40                  45

Ser Asp Ala Ser Ile Leu Glu Gly Gly Val Pro Ser Arg Phe Ser Gly
    50                  55                  60

Ser Gly Phe His Gln Asn Phe Ser Leu Thr Ile Ser Ser Leu Gln Pro
65                  70                  75                  80

Glu Asp Val Ala Thr Tyr Phe Cys Gln Gln Tyr Glu Thr Phe Gly Gln
                85                  90                  95

Gly Thr Lys Val Asp Ile Lys
            100

<210> SEQ ID NO 19
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 19

Gln Val Gln Leu Val Gln Ser Gly Ala Ala Val Arg Lys Pro Gly Ala
1               5                   10                  15

Ser Val Thr Val Ser Cys Lys Phe Ala Glu Asp Asp Phe Ser Pro
                20                  25                  30

His Trp Val Asn Pro Ala Pro Glu His Tyr Ile His Phe Leu Arg Gln
            35                  40                  45

Ala Pro Gly Gln Gln Leu Glu Trp Leu Ala Trp Met Lys Pro Thr Asn
50                  55                  60

Gly Ala Val Asn Tyr Ala Trp Gln Leu Gln Gly Arg Val Thr Val Thr
65                  70                  75                  80

Arg Asp Arg Ser Gln Thr Thr Ala Phe Leu Glu Val Lys Asn Leu Arg
                85                  90                  95

Ser Asp Asp Thr Ala Val Tyr Tyr Cys Ala Arg Ala Gln Lys Arg Gly
            100                 105                 110

Arg Ser Glu Trp Ala Tyr Ala His Trp Gly Gln Gly Thr Pro Val Val
        115                 120                 125

Ile Ser Ala
    130

<210> SEQ ID NO 20
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Gln Met Thr Gln Ser Pro Ser Ser Leu Ser Ala Ser Leu Gly
1               5                   10                  15

Asp Arg Val Thr Ile Thr Cys Gln Ala Ser Arg Gly Ile Gly Lys Asp
                20                  25                  30

Leu Asn Trp Tyr Gln Gln Lys Pro Gly Arg Ala Pro Lys Leu Leu Val
            35                  40                  45

Ser Asp Ala Ser Ile Leu Glu Gly Gly Val Pro Thr Arg Phe Ser Gly
50                  55                  60

Ser Gly Phe His Gln Asn Phe Ser Leu Thr Ile Ser Ser Leu Gln Ala
65                  70                  75                  80

Glu Asp Val Ala Thr Tyr Phe Cys Gln Gln Tyr Glu Thr Phe Gly Gln
                85                  90                  95

Gly Thr Lys Val Asp Ile Lys
            100

<210> SEQ ID NO 21
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Gln Ser Gly Ala Ala Val Arg Lys Pro Gly Ala
1               5                   10                  15

Ser Ile Ser Val Ser Cys Lys Phe Ala Asp Ala Asp Tyr Ser Pro
                20                  25                  30

His Trp Met Asn Pro Ala Pro Glu His Tyr Ile His Phe Leu Arg Gln
```

-continued

```
                35                  40                  45
Ala Pro Gly Gln Gln Leu Glu Trp Leu Ala Trp Met Asn Pro Thr Asn
 50                  55                  60

Gly Ala Val Asn Tyr Ala Trp Tyr Leu Asn Gly Arg Val Thr Ala Thr
 65                  70                  75                  80

Arg Asp Arg Ser Met Thr Thr Ala Phe Leu Glu Val Arg Ser Leu Arg
                 85                  90                  95

Ser Asp Asp Thr Ala Val Tyr Tyr Cys Ala Arg Ala Gln Lys Arg Ala
                100                 105                 110

Arg Ser Glu Trp Ala Tyr Ala His Trp Gly Gln Gly Thr Pro Val Val
            115                 120                 125

Val Ser Ser
130

<210> SEQ ID NO 22
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Gln Met Thr Gln Ser Pro Ser Ser Leu Ser Ala Ser Leu Gly
 1               5                  10                  15

Asp Arg Val Thr Ile Thr Cys Gln Ala Ser Arg Gly Ile Gly Lys Asp
                20                  25                  30

Leu Asn Trp Tyr Gln Gln Lys Arg Gly Arg Ala Pro Arg Leu Leu Val
            35                  40                  45

Ser Asp Ala Ser Val Leu Glu Gly Gly Val Pro Ser Arg Phe Ser Gly
 50                  55                  60

Ser Gly Phe His Gln Asn Phe Ser Leu Thr Ile Ser Thr Leu Gln Pro
 65                  70                  75                  80

Glu Asp Val Ala Thr Tyr Phe Cys Gln Gln Tyr Glu Thr Phe Gly Gln
                 85                  90                  95

Gly Thr Lys Val Asp Ile Lys
            100

<210> SEQ ID NO 23
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Val Gln Ser Gly Ala Ala Val Arg Lys Pro Gly Ala
 1               5                  10                  15

Ser Val Thr Val Ser Cys Lys Phe Ala Glu Asp Asp Trp Ser Pro
                20                  25                  30

His Trp Val Asn Pro Ala Pro Glu His Tyr Ile His Phe Leu Arg Gln
            35                  40                  45

Ala Pro Gly Gln Gln Leu Glu Trp Leu Ala Trp Met Asn Pro Thr Asn
 50                  55                  60

Gly Ala Val Asn Tyr Ala Trp Gln Leu Asn Gly Arg Leu Thr Ala Thr
 65                  70                  75                  80

Arg Asp Thr Ser Met Thr Thr Ala Phe Leu Glu Val Lys Ser Leu Arg
```

```
            85                  90                  95
Ser Asp Asp Thr Ala Val Tyr Tyr Cys Ala Arg Ala Gln Lys Arg Gly
            100                 105                 110

Arg Ser Glu Trp Ala Tyr Ala His Trp Gly Gln Gly Thr Pro Val Val
        115                 120                 125

Val Ser Ser
        130

<210> SEQ ID NO 24
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Gln Met Thr Gln Ser Pro Ser Ser Leu Ser Ala Ser Leu Gly
1               5                   10                  15

Asp Arg Val Thr Ile Thr Cys Gln Ala Ser Arg Gly Ile Gly Lys Asp
            20                  25                  30

Leu Asn Trp Tyr Gln Gln Lys Ala Gly Lys Ala Pro Lys Leu Leu Val
        35                  40                  45

Ser Asp Ala Ser Ile Leu Glu Gly Gly Val Pro Ser Arg Phe Ser Gly
    50                  55                  60

Ser Gly Phe His Gln Asn Phe Ser Leu Thr Ile Ser Ser Leu Gln Pro
65                  70                  75                  80

Glu Asp Val Ala Thr Tyr Phe Cys Gln Gln Tyr Glu Thr Phe Gly Gln
                85                  90                  95

Gly Thr Lys Val Asp Ile Lys
            100

<210> SEQ ID NO 25
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Arg Leu Val Glu Ser Gly Gly Gly Val Gln Pro Gly Ser Ser
1               5                   10                  15

Leu Arg Leu Ser Cys Ala Ala Ser Gly Phe Asp Phe Ser Arg Gln Gly
            20                  25                  30

Met His Trp Val Arg Gln Ala Pro Gly Gln Gly Leu Glu Trp Val Ala
        35                  40                  45

Phe Ile Lys Tyr Asp Gly Ser Glu Lys Tyr His Ala Asp Ser Val Trp
    50                  55                  60

Gly Arg Leu Ser Ile Ser Arg Asp Asn Ser Lys Asp Thr Leu Tyr Leu
65                  70                  75                  80

Gln Met Asn Ser Leu Arg Val Glu Asp Thr Ala Thr Tyr Phe Cys Val
                85                  90                  95

Arg Glu Ala Gly Gly Pro Asp Tyr Arg Asn Gly Tyr Asn Tyr Tyr Asp
            100                 105                 110

Phe Tyr Asp Gly Tyr Tyr Asn Tyr His Tyr Met Asp Val Trp Gly Lys
        115                 120                 125

Gly Thr Thr Val Thr Val Ser Ser
```

```
                   130                 135

<210> SEQ ID NO 26
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Ser Ala Leu Thr Gln Pro Ala Ser Val Ser Gly Ser Pro Gly Gln
1               5                   10                  15

Ser Ile Thr Ile Ser Cys Asn Gly Thr Ser Asn Asp Val Gly Gly Tyr
                20                  25                  30

Glu Ser Val Ser Trp Tyr Gln Gln His Pro Gly Lys Ala Pro Lys Val
            35                  40                  45

Val Ile Tyr Asp Val Ser Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Gly Asp Tyr Tyr Cys Lys Ser Leu Thr Ser Thr
                85                  90                  95

Arg Arg Arg Val Phe Gly Thr Gly Thr Lys Leu Thr Val Leu
            100                 105                 110

<210> SEQ ID NO 27
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Glu Gln Leu Val Glu Ser Gly Gly Gly Val Val Gln Pro Gly Gly
1               5                   10                  15

Ser Leu Arg Leu Ser Cys Leu Ala Ser Gly Phe Thr Phe His Lys Tyr
                20                  25                  30

Gly Met His Trp Val Arg Gln Ala Pro Gly Lys Gly Leu Glu Trp Val
            35                  40                  45

Ala Leu Ile Ser Asp Asp Gly Met Arg Lys Tyr His Ser Asp Ser Met
        50                  55                  60

Trp Gly Arg Val Thr Ile Ser Arg Asp Asn Ser Lys Asn Thr Leu Tyr
65                  70                  75                  80

Leu Gln Phe Ser Ser Leu Lys Val Glu Asp Thr Ala Met Phe Phe Cys
                85                  90                  95

Ala Arg Glu Ala Gly Gly Pro Ile Trp His Asp Asp Val Lys Tyr Tyr
            100                 105                 110

Asp Phe Asn Asp Gly Tyr Tyr Asn Tyr His Tyr Met Asp Val Trp Gly
        115                 120                 125

Lys Gly Thr Thr Val Thr Val Ser Ser
130                 135

<210> SEQ ID NO 28
<211> LENGTH: 110
<212> TYPE: PRT
<213> ORGANISM: Artificial Sequence
<220> FEATURE:
<223> OTHER INFORMATION: Description of Artificial Sequence: Synthetic
```

```
                        polypeptide

<400> SEQUENCE: 28

Gln Ser Ala Leu Thr Gln Pro Ala Ser Val Ser Gly Ser Pro Gly Gln
1               5                   10                  15

Thr Ile Thr Ile Ser Cys Asn Gly Thr Ser Ser Asp Val Gly Gly Phe
            20                  25                  30

Asp Ser Val Ser Trp Tyr Gln Gln Ser Pro Gly Lys Ala Pro Lys Val
        35                  40                  45

Met Val Phe Asp Val Ser His Arg Pro Ser Gly Ile Ser Asn Arg Phe
    50                  55                  60

Ser Gly Ser Lys Ser Gly Asn Thr Ala Ser Leu Thr Ile Ser Gly Leu
65                  70                  75                  80

His Ile Glu Asp Glu Gly Asp Tyr Phe Cys Ser Ser Leu Thr Asp Arg
                85                  90                  95

Ser His Arg Ile Phe Gly Gly Gly Thr Lys Val Thr Val Leu
            100                 105                 110

<210> SEQ ID NO 29
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Leu Gln Ser Gly Ala Ala Val Thr Lys Pro Gly Ala
1               5                   10                  15

Ser Val Arg Val Ser Cys Glu Ala Ser Gly Tyr Asn Ile Arg Asp Tyr
            20                  25                  30

Phe Ile His Trp Trp Arg Gln Ala Pro Gly Gln Gly Leu Gln Trp Val
        35                  40                  45

Gly Trp Ile Asn Pro Lys Thr Gly Gln Pro Asn Pro Arg Gln Phe
    50                  55                  60

Gln Gly Arg Val Ser Leu Thr Arg His Ala Ser Trp Asp Phe Asp Thr
65                  70                  75                  80

Phe Ser Phe Tyr Met Asp Leu Lys Ala Leu Arg Ser Asp Asp Thr Ala
                85                  90                  95

Val Tyr Phe Cys Ala Arg Gln Arg Ser Asp Tyr Trp Asp Phe Asp Val
            100                 105                 110

Trp Gly Ser Gly Thr Gln Val Thr Val Ser Ser Ala Ser Thr Lys Gly
        115                 120                 125

Pro

<210> SEQ ID NO 30
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Gln Met Thr Gln Ser Pro Ser Ser Leu Ser Ala Ser Val Gly
1               5                   10                  15

Asp Thr Val Thr Ile Thr Cys Gln Ala Asn Gly Tyr Leu Asn Trp Tyr
            20                  25                  30
```

```
Gln Gln Arg Arg Gly Lys Ala Pro Lys Leu Leu Ile Tyr Asp Gly Ser
            35                  40                  45

Lys Leu Glu Arg Gly Val Pro Ser Arg Phe Ser Gly Arg Arg Trp Gly
 50                  55                  60

Gln Glu Tyr Asn Leu Thr Ile Asn Asn Leu Gln Pro Glu Asp Ile Ala
 65                  70                  75                  80

Thr Tyr Phe Cys Gln Val Tyr Glu Phe Val Val Pro Gly Thr Arg Leu
                 85                  90                  95

Asp Leu Lys Arg Thr Val Ala Ala Pro
            100                 105

<210> SEQ ID NO 31
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Arg Leu Ser Gln Ser Gly Gly Gln Met Lys Lys Pro Gly Glu
1               5                   10                  15

Ser Met Arg Leu Ser Cys Arg Ala Ser Gly Tyr Glu Phe Leu Asn Cys
            20                  25                  30

Pro Ile Asn Trp Ile Arg Leu Ala Pro Gly Arg Arg Pro Glu Trp Met
            35                  40                  45

Gly Trp Leu Lys Pro Arg Gly Gly Ala Val Asn Tyr Ala Arg Lys Phe
 50                 55                  60

Gln Gly Arg Val Thr Met Thr Arg Asp Val Tyr Ser Asp Thr Ala Phe
 65                 70                  75                  80

Leu Glu Leu Arg Ser Leu Thr Ser Asp Asp Thr Ala Val Tyr Phe Cys
                85                  90                  95

Thr Arg Gly Lys Tyr Cys Thr Ala Arg Asp Tyr Tyr Asn Trp Asp Phe
            100                 105                 110

Glu His Trp Gly Arg Gly Ala Pro Val Thr Val Ser Ser Ala Ser Thr
            115                 120                 125

Lys Gly Pro Ser Val
            130

<210> SEQ ID NO 32
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Ile Val Leu Thr Gln Ser Pro Ala Thr Leu Ser Leu Ser Pro Gly
1               5                   10                  15

Glu Thr Ala Ile Ile Ser Cys Arg Thr Ser Gln Ser Gly Ser Leu Ala
            20                  25                  30

Trp Tyr Gln Gln Arg Pro Gly Gln Ala Pro Arg Leu Val Ile Tyr Ser
            35                  40                  45

Gly Ser Thr Arg Ala Ala Gly Ile Pro Asp Arg Phe Ser Gly Ser Arg
 50                 55                  60

Trp Gly Ala Asp Tyr Asn Leu Ser Ile Ser Asn Leu Glu Ser Gly Asp
 65                 70                  75                  80
```

Phe Gly Val Tyr Tyr Cys Gln Gln Tyr Glu Phe Phe Gly Gln Gly Thr
                85                  90                  95

Lys Val Gln Val Asp Ile Lys Arg Thr Val Ala Ala Pro
            100                 105

<210> SEQ ID NO 33
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Ile His Leu Val Gln Ser Gly Thr Glu Val Lys Pro Gly Ser
1               5                   10                  15

Ser Val Thr Val Ser Cys Lys Ala Tyr Gly Val Asn Thr Phe Gly Leu
            20                  25                  30

Tyr Ala Val Asn Trp Val Arg Gln Ala Pro Gly Gln Ser Leu Glu Tyr
        35                  40                  45

Ile Gly Gln Ile Trp Arg Trp Lys Ser Ser Ala Ser His His Phe Arg
    50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Leu Thr Ser Asp Asp Thr Ala Val
                85                  90                  95

Tyr Phe Cys Thr Thr Thr Ser Thr Tyr Asp Lys Trp Ser Gly Leu His
            100                 105                 110

His Asp Gly Val Met Ala Phe Ser Ser Trp Gly Gln Gly Thr Leu Ile
        115                 120                 125

Ser Val Ser Ala Ala Ser Thr Lys Gly Pro Ser Val Phe
    130                 135                 140

<210> SEQ ID NO 34
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Gln Met Thr Gln Ser Pro Ser Thr Leu Ser Ala Ser Ile Gly
1               5                   10                  15

Asp Thr Val Arg Ile Ser Cys Arg Ala Ser Gln Ser Ile Thr Gly Asn
            20                  25                  30

Trp Val Ala Trp Tyr Gln Gln Arg Pro Gly Lys Ala Pro Arg Leu Leu
        35                  40                  45

Ile Tyr Arg Gly Ala Ala Leu Leu Gly Gly Val Pro Ser Arg Phe Ser
    50                  55                  60

Gly Ser Ala Ala Gly Thr Asp Phe Thr Leu Thr Ile Gly Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe Gly Gln Gly Thr Lys Val Glu Val Lys Arg Thr Val Ala
            100                 105                 110

Ala Pro Ser Val Phe Ile Phe Pro Pro Ser Asp Glu Gln Leu Lys Ser
        115                 120                 125

```
Gly Thr
    130

<210> SEQ ID NO 35
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (131)..(131)
<223> OTHER INFORMATION: Any amino acid

<400> SEQUENCE: 35

Gln Val His Leu Ser Gln Ser Gly Ala Ala Val Thr Lys Pro Gly Ala
1               5                   10                  15

Ser Val Arg Val Ser Cys Glu Ala Ser Gly Tyr Lys Ile Ser Asp His
                20                  25                  30

Phe Ile His Trp Trp Arg Gln Ala Pro Gly Gln Gly Leu Gln Trp Val
            35                  40                  45

Gly Trp Ile Asn Pro Lys Thr Gly Gln Pro Asn Asn Pro Arg Gln Phe
        50                  55                  60

Gln Gly Arg Val Ser Leu Thr Arg Gln Ala Ser Trp Asp Phe Asp Thr
65                  70                  75                  80

Tyr Ser Phe Tyr Met Asp Leu Lys Ala Val Arg Ser Asp Asp Thr Ala
                85                  90                  95

Ile Tyr Phe Cys Ala Arg Gln Arg Ser Asp Phe Trp Asp Phe Asp Val
            100                 105                 110

Trp Gly Ser Gly Thr Gln Val Thr Val Ser Ser Ala Ser Thr Lys Gly
        115                 120                 125

Pro Ser Xaa
    130

<210> SEQ ID NO 36
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Gln Met Thr Gln Ser Pro Ser Ser Leu Ser Ala Arg Val Gly
1               5                   10                  15

Asp Thr Val Thr Ile Thr Cys Gln Ala Asn Gly Tyr Leu Asn Trp Tyr
                20                  25                  30

Gln Gln Arg Arg Gly Lys Ala Pro Lys Leu Leu Ile Tyr Asp Gly Ser
            35                  40                  45

Lys Leu Glu Arg Gly Val Pro Ala Arg Phe Ser Gly Arg Arg Trp Gly
        50                  55                  60

Gln Glu Tyr Asn Leu Thr Ile Asn Asn Leu Gln Pro Glu Asp Val Ala
65                  70                  75                  80

Thr Tyr Phe Cys Gln Val Tyr Glu Phe Ile Val Pro Gly Thr Arg Leu
                85                  90                  95

Asp Leu Lys Arg Thr Val Ala Ala
            100

<210> SEQ ID NO 37
```

<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ser Gln His Leu Val Gln Ser Gly Thr Gln Val Lys Lys Pro Gly Ala
1               5                   10                  15

Ser Val Arg Val Ser Cys Gln Ala Ser Gly Tyr Thr Phe Thr Asn Tyr
            20                  25                  30

Ile Leu His Trp Trp Arg Gln Ala Pro Gly Gln Gly Leu Glu Trp Met
        35                  40                  45

Gly Leu Ile Lys Pro Val Phe Gly Ala Val Asn Tyr Ala Arg Gln Phe
    50                  55                  60

Gln Gly Arg Ile Gln Leu Thr Arg Asp Ile Tyr Arg Glu Ile Ala Phe
65                  70                  75                  80

Leu Asp Leu Ser Gly Leu Arg Ser Asp Thr Ala Val Tyr Tyr Cys
                85                  90                  95

Ala Arg Asp Glu Ser Gly Asp Asp Leu Lys Trp His Leu His Pro Trp
            100                 105                 110

Gly Gln Gly Thr Gln Val Ile Val Ser Pro Ala Ser Thr Lys Gly Pro
        115                 120                 125

<210> SEQ ID NO 38
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Gln Met Thr Gln Ser Pro Ser Ser Leu Ser Ala Ser Val Gly
1               5                   10                  15

Asp Arg Val Thr Ile Asn Cys Gln Ala Gly Gln Gly Ile Gly Ser Ser
            20                  25                  30

Leu Asn Trp Tyr Gln Lys Lys Pro Gly Arg Ala Pro Lys Leu Leu Val
        35                  40                  45

His Gly Ala Ser Asn Leu Gln Arg Gly Val Pro Ser Arg Phe Ser Gly
    50                  55                  60

Ser Gly Phe His Thr Thr Phe Thr Leu Thr Ile Ser Ser Leu Gln Pro
65                  70                  75                  80

Asp Asp Val Ala Thr Tyr Phe Cys Ala Val Phe Gln Trp Phe Gly Pro
                85                  90                  95

Gly Thr Lys Val Asp Ile Lys Arg Thr
            100                 105

<210> SEQ ID NO 39
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Met Gln Leu Gln Glu Ser Gly Pro Gly Leu Val Lys Pro Ser Glu
1               5                   10                  15

```
Thr Leu Ser Leu Thr Cys Ser Val Ser Gly Ala Ser Ile Ser Asp Ser
            20                  25                  30

Tyr Trp Ser Trp Ile Arg Arg Ser Pro Gly Lys Gly Leu Glu Trp Ile
        35                  40                  45

Gly Tyr Val His Lys Ser Gly Asp Thr Asn Tyr Ser Pro Ser Leu Lys
    50                  55                  60

Ser Arg Val Asn Leu Ser Leu Asp Thr Ser Lys Asn Gln Val Ser Leu
65                  70                  75                  80

Ser Leu Val Ala Ala Thr Ala Ala Asp Ser Gly Lys Tyr Tyr Cys Ala
                85                  90                  95

Arg Thr Leu His Gly Arg Arg Ile Tyr Gly Ile Val Ala Phe Asn Glu
            100                 105                 110

Trp Phe Thr Tyr Phe Tyr Met Asp Val Trp Gly Asn Gly Thr Gln Val
        115                 120                 125

Thr Val Ser Ser
    130
```

<210> SEQ ID NO 40
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Ser Asp Ile Ser Val Ala Pro Gly Glu Thr Ala Arg Ile Ser Cys Gly
1               5                   10                  15

Glu Lys Ser Leu Gly Ser Arg Ala Val Gln Trp Tyr Gln His Arg Ala
            20                  25                  30

Gly Gln Ala Pro Ser Leu Ile Ile Tyr Asn Asn Gln Asp Arg Pro Ser
        35                  40                  45

Gly Ile Pro Glu Arg Phe Ser Gly Ser Pro Asp Ser Pro Phe Gly Thr
    50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Val Pro Thr Lys Trp Val Phe
                85                  90                  95

Gly Gly Gly Thr Thr Leu Thr Val Leu
            100                 105
```

<210> SEQ ID NO 41
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Gln Val His Leu Gln Glu Ser Gly Pro Gly Leu Val Lys Pro Ser Glu
1               5                   10                  15

Thr Leu Ser Leu Thr Cys Asn Val Ser Gly Thr Leu Val Arg Asp Asn
            20                  25                  30

Tyr Trp Ser Trp Ile Arg Gln Pro Leu Gly Lys Gln Pro Glu Trp Ile
        35                  40                  45

Gly Tyr Val His Asp Ser Gly Asp Thr Asn Tyr Asn Pro Ser Leu Lys
    50                  55                  60
```

```
Ser Arg Val His Leu Ser Leu Asp Lys Ser Lys Asn Leu Val Ser Leu
 65                  70                  75                  80

Arg Leu Thr Gly Val Thr Ala Ala Asp Ser Ala Ile Tyr Tyr Cys Ala
                 85                  90                  95

Thr Thr Lys His Gly Arg Arg Ile Tyr Gly Val Val Ala Phe Lys Glu
            100                 105                 110

Trp Phe Thr Tyr Phe Tyr Met Asp Val Trp Gly Lys Gly Thr Ser Val
        115                 120                 125

Thr Val Ser Ser
        130

<210> SEQ ID NO 42
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Thr Phe Val Ser Val Ala Pro Gly Gln Thr Ala Arg Ile Thr Cys Gly
  1               5                  10                  15

Glu Glu Ser Leu Gly Ser Arg Ser Val Ile Trp Tyr Gln Gln Arg Pro
                 20                  25                  30

Gly Gln Ala Pro Ser Leu Ile Ile Tyr Asn Asn Asn Asp Arg Pro Ser
             35                  40                  45

Gly Ile Pro Asp Arg Phe Ser Gly Ser Pro Gly Ser Thr Phe Gly Thr
         50                  55                  60

Thr Ala Thr Leu Thr Ile Thr Ser Val Glu Ala Gly Asp Glu Ala Asp
 65                  70                  75                  80

Tyr Tyr Cys His Ile Trp Asp Ser Arg Arg Pro Thr Asn Trp Val Phe
                 85                  90                  95

Gly Glu Gly Thr Thr Leu Ile Val Leu
            100                 105

<210> SEQ ID NO 43
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Leu His Leu Gln Glu Ser Gly Pro Gly Leu Val Lys Pro Pro Glu
  1               5                  10                  15

Thr Leu Ser Leu Thr Cys Ser Val Ser Gly Ala Ser Ile Asn Asp Ala
                 20                  25                  30

Tyr Trp Ser Trp Ile Arg Gln Ser Pro Gly Lys Arg Pro Glu Trp Val
             35                  40                  45

Gly Tyr Val His His Ser Gly Asp Thr Asn Tyr Asn Pro Ser Leu Lys
         50                  55                  60

Arg Arg Val Thr Phe Ser Leu Asp Thr Ala Lys Asn Glu Val Ser Leu
 65                  70                  75                  80

Lys Leu Val Asp Leu Thr Ala Ala Asp Ser Ala Thr Tyr Phe Cys Ala
                 85                  90                  95

Arg Ala Leu His Gly Lys Arg Ile Tyr Gly Ile Val Ala Leu Gly Glu
            100                 105                 110
```

```
Leu Phe Thr Tyr Phe Tyr Met Asp Val Trp Gly Lys Gly Thr Ala Val
            115                 120                 125

Thr Val Ser Ser
        130

<210> SEQ ID NO 44
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ser Ser Met Ser Val Ser Pro Gly Glu Thr Ala Lys Ile Ser Cys Gly
1               5                  10                  15

Lys Glu Ser Ile Gly Ser Arg Ala Val Gln Trp Tyr Gln Gln Lys Pro
            20                  25                  30

Gly Gln Pro Pro Ser Leu Ile Ile Tyr Asn Asn Gln Asp Arg Pro Ala
        35                  40                  45

Gly Val Pro Glu Arg Phe Ser Ala Ser Pro Asp Phe Arg Pro Gly Thr
    50                  55                  60

Thr Ala Thr Leu Thr Ile Thr Asn Val Asp Ala Glu Asp Glu Ala Asp
65                  70                  75                  80

Tyr Tyr Cys His Ile Tyr Asp Ala Arg Gly Gly Thr Asn Trp Val Phe
                85                  90                  95

Asp Arg Gly Thr Thr Leu Thr Val Leu
            100                 105

<210> SEQ ID NO 45
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Ser Gln Leu Gln Glu Ser Gly Pro Arg Leu Val Glu Ala Ser Glu
1               5                   10                  15

Thr Leu Ser Leu Thr Cys Asn Val Ser Gly Glu Ser Thr Gly Ala Cys
            20                  25                  30

Thr Tyr Phe Trp Gly Trp Val Arg Gln Ala Pro Gly Lys Gly Leu Glu
        35                  40                  45

Trp Ile Gly Ser Leu Ser His Cys Gln Ser Phe Trp Gly Ser Gly Trp
    50                  55                  60

Thr Phe His Asn Pro Ser Leu Lys Ser Arg Leu Thr Ile Ser Leu Asp
65                  70                  75                  80

Thr Pro Lys Asn Gln Val Phe Leu Lys Leu Thr Ser Leu Thr Ala Ala
                85                  90                  95

Asp Thr Ala Thr Tyr Tyr Cys Ala Arg Phe Asp Gly Glu Val Leu Val
            100                 105                 110

Tyr Asn His Trp Pro Lys Pro Ala Trp Val Asp Leu Trp Gly Arg Gly
        115                 120                 125

Ile Pro Val Thr Val Thr Val Ser Ser
    130                 135

<210> SEQ ID NO 46
<211> LENGTH: 105
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Ser Ala Leu Thr Gln Pro Pro Ser Ala Ser Gly Ser Pro Gly Gln
1               5                   10                  15

Ser Ile Thr Ile Ser Cys Asn Gly Thr Ala Thr Asn Phe Val Ser Trp
            20                  25                  30

Tyr Gln Gln Phe Pro Asp Lys Ala Pro Lys Leu Ile Ile Phe Gly Val
        35                  40                  45

Asp Lys Arg Pro Pro Gly Val Pro Asp Arg Phe Ser Gly Ser Arg Ser
    50                  55                  60

Gly Thr Thr Ala Ser Leu Thr Val Ser Arg Leu Gln Thr Asp Asp Glu
65                  70                  75                  80

Ala Val Tyr Tyr Cys Gly Ser Leu Val Gly Asn Trp Asp Val Ile Phe
                85                  90                  95

Gly Gly Gly Thr Thr Leu Thr Val Leu
            100                 105

<210> SEQ ID NO 47
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Pro Gln Leu Gln Glu Ser Gly Pro Gly Leu Val Glu Ala Ser Glu
1               5                   10                  15

Thr Leu Ser Leu Thr Cys Thr Val Ser Gly Asp Ser Thr Ala Ala Cys
            20                  25                  30

Asp Tyr Phe Trp Gly Trp Val Arg Gln Pro Pro Gly Lys Gly Leu Glu
        35                  40                  45

Trp Ile Gly Gly Leu Ser His Cys Ala Gly Tyr Tyr Asn Thr Gly Trp
    50                  55                  60

Thr Tyr His Asn Pro Ser Leu Lys Ser Arg Leu Thr Ile Ser Leu Asp
65                  70                  75                  80

Thr Pro Lys Asn Gln Val Phe Leu Lys Leu Asn Ser Val Thr Ala Ala
                85                  90                  95

Asp Thr Ala Ile Tyr Tyr Cys Ala Arg Phe Asp Gly Glu Val Leu Val
            100                 105                 110

Tyr His Asp Trp Pro Lys Pro Ala Trp Val Asp Leu Trp Gly Arg Gly
        115                 120                 125

Thr Leu Val Thr Val Thr Val Ser Ser
    130                 135

<210> SEQ ID NO 48
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Ser Ala Leu Thr Gln Pro Pro Ser Ala Ser Gly Ser Pro Gly Gln

Ser Ile Ser Ile Ser Cys Thr Gly Thr Ser Asn Arg Phe Val Ser Trp
1               5                   10                  15

Tyr Gln Gln His Pro Gly Lys Ala Pro Lys Leu Val Ile Tyr Gly Val
            20                  25                  30

Asn Lys Arg Pro Ser Gly Val Pro Asp Arg Phe Ser Gly Ser Lys Ser
        35                  40                  45

Gly Asn Thr Ala Ser Leu Thr Val Ser Gly Leu Gln Thr Asp Asp Glu
65                  70                  75                  80

Ala Val Tyr Tyr Cys Ser Ser Leu Val Gly Asn Trp Asp Val Ile Phe
                85                  90                  95

Gly Gly Gly Thr Lys Leu Thr Val Leu
            100                 105

<210> SEQ ID NO 49
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Pro Gln Leu Gln Glu Ser Gly Pro Gly Leu Val Glu Ala Ser Glu
1               5                   10                  15

Thr Leu Ser Leu Thr Cys Thr Val Ser Gly Asp Ser Thr Gly Arg Cys
            20                  25                  30

Asn Tyr Phe Trp Gly Trp Val Arg Gln Pro Pro Gly Lys Gly Leu Glu
        35                  40                  45

Trp Ile Gly Ser Leu Ser His Cys Arg Ser Tyr Tyr Asn Thr Asp Trp
    50                  55                  60

Thr Tyr His Asn Pro Ser Leu Lys Ser Arg Leu Thr Ile Ser Leu Asp
65                  70                  75                  80

Thr Pro Lys Asn Gln Val Phe Leu Arg Leu Thr Ser Val Thr Ala Ala
                85                  90                  95

Asp Thr Ala Thr Tyr Tyr Cys Ala Arg Phe Gly Gly Glu Val Leu Val
            100                 105                 110

Tyr Arg Asp Trp Pro Lys Pro Ala Trp Val Asp Leu Trp Gly Arg Gly
        115                 120                 125

Thr Leu Val Thr Val Ser Ser
    130                 135

<210> SEQ ID NO 50
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Ser Ala Leu Thr Gln Pro Pro Ser Ala Ser Gly Ser Pro Gly Gln
1               5                   10                  15

Ser Ile Thr Ile Ser Cys Thr Gly Thr Ser Asn Asn Phe Val Ser Trp
            20                  25                  30

Tyr Gln Gln Tyr Pro Gly Lys Ala Pro Lys Leu Val Ile Tyr Glu Val
            35                  40                  45

Asn Lys Arg Pro Ser Gly Val Pro Asp Arg Phe Ser Gly Ser Lys Ser

```
                50                  55                  60
Gly Ser Thr Ala Ser Leu Thr Val Ser Gly Leu Gln Ala Asp Asp Glu
 65                  70                  75                  80

Gly Val Tyr Tyr Cys Ser Ser Leu Val Gly Asn Trp Asp Val Ile Phe
                 85                  90                  95

Gly Gly Gly Thr Lys Leu Thr Val Leu
            100                 105

<210> SEQ ID NO 51
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Pro Gln Leu Gln Glu Ser Gly Pro Thr Leu Val Glu Ala Ser Glu
 1               5                  10                  15

Thr Leu Ser Leu Thr Cys Ala Val Ser Gly Asp Ser Thr Ala Ala Cys
                 20                  25                  30

Asn Ser Phe Trp Gly Trp Val Arg Gln Pro Pro Gly Lys Gly Leu Glu
             35                  40                  45

Trp Val Gly Ser Leu Ser His Cys Ala Ser Tyr Trp Asn Arg Gly Trp
 50                  55                  60

Thr Tyr His Asn Pro Ser Leu Lys Ser Arg Leu Thr Leu Ala Leu Asp
 65                  70                  75                  80

Thr Pro Lys Asn Leu Val Phe Leu Lys Leu Asn Ser Val Thr Ala Ala
                 85                  90                  95

Asp Thr Ala Thr Tyr Tyr Cys Ala Arg Phe Gly Gly Glu Val Leu Arg
                100                 105                 110

Tyr Thr Asp Trp Pro Lys Pro Ala Trp Val Asp Leu Trp Gly Arg Gly
            115                 120                 125

Thr Leu Val Thr Val Ser Ser
        130                 135

<210> SEQ ID NO 52
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Ser Ala Leu Thr Gln Pro Pro Ser Ala Ser Gly Ser Pro Gly Gln
 1               5                  10                  15

Ser Ile Thr Ile Ser Cys Thr Gly Thr Ser Asn Asn Phe Val Ser Trp
                 20                  25                  30

Tyr Gln Gln His Ala Gly Lys Ala Pro Lys Leu Val Ile Tyr Asp Val
             35                  40                  45

Asn Lys Arg Pro Ser Gly Val Pro Asp Arg Phe Ser Gly Ser Lys Ser
 50                  55                  60

Gly Asn Thr Ala Ser Leu Thr Val Ser Gly Leu Gln Thr Asp Asp Glu
 65                  70                  75                  80

Ala Val Tyr Tyr Cys Gly Ser Leu Val Gly Asn Trp Asp Val Ile Phe
                 85                  90                  95

Gly Gly Gly Thr Lys Leu Thr Val Leu
```

<210> SEQ ID NO 53
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Gln Glu Ser Gly Pro Gly Leu Val Lys Pro Ala Glu
1               5                   10                  15

Thr Leu Ser Leu Thr Cys Ser Val Ser Gly Glu Ser Ile Asn Thr Gly
            20                  25                  30

His Tyr Tyr Trp Gly Trp Val Arg Gln Val Pro Gly Lys Gly Leu Glu
        35                  40                  45

Trp Ile Gly His Ile His Tyr Thr Thr Ala Val Leu His Asn Pro Ser
    50                  55                  60

Leu Lys Ser Arg Leu Thr Ile Lys Ile Tyr Thr Arg Asn Gln Ile
65                  70                  75                  80

Thr Leu Arg Leu Ser Asn Val Thr Ala Ala Asp Thr Ala Val Tyr His
                85                  90                  95

Cys Val Arg Ser Gly Gly Asp Ile Leu Tyr Tyr Tyr Glu Trp Gln Lys
            100                 105                 110

Pro His Trp Phe Ser Pro Trp Gly Pro Gly Ile His Val Thr Val Ser
        115                 120                 125

Ser

<210> SEQ ID NO 54
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Ser Ala Leu Thr Gln Pro Pro Ser Ala Ser Gly Ser Leu Gly Gln
1               5                   10                  15

Ser Val Thr Ile Ser Cys Asn Gly Thr Ser Ser Asp Ile Gly Gly Trp
            20                  25                  30

Asn Phe Val Ser Trp Tyr Gln Gln Phe Pro Gly Arg Ala Pro Arg Leu
        35                  40                  45

Ile Ile Phe Glu Val Asn Lys Arg Pro Ser Gly Val Pro Gly Arg Phe
    50                  55                  60

Ser Gly Ser Lys Ser Gly Asn Ser Ala Ser Leu Thr Val Ser Gly Leu
65                  70                  75                  80

Gln Ser Asp Asp Glu Gly Gln Tyr Phe Cys Ser Ser Leu Phe Gly Arg
                85                  90                  95

Trp Asp Val Val Phe Gly Gly Gly Thr Lys Leu Thr Val Leu
            100                 105                 110

<210> SEQ ID NO 55
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Asn Thr Gly
            20                  25                  30

His His Tyr Trp Gly Trp Val Arg Gln Val Pro Gly Lys Gly Pro Glu
        35                  40                  45

Trp Ile Ala His Ile His Tyr Asn Thr Ala Val Leu His Asn Pro Ala
    50                  55                  60

Leu Lys Ser Arg Val Thr Ile Ser Ile Phe Thr Leu Lys Asn Leu Ile
65                  70                  75                  80

Thr Leu Ser Leu Ser Asn Val Thr Ala Ala Asp Thr Ala Val Tyr Phe
                85                  90                  95

Cys Val Arg Ser Gly Gly Asp Ile Leu Tyr Tyr Ile Glu Trp Gln Lys
            100                 105                 110

Pro His Trp Phe Tyr Pro Trp Gly Pro Gly Ile Leu Val Thr Val Ser
        115                 120                 125

Ser

<210> SEQ ID NO 56
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Ser Ala Leu Thr Gln Pro Pro Ser Ala Ser Gly Ser Leu Gly Gln
1               5                   10                  15

Ser Leu Thr Ile Ser Cys Ser Gly Thr Gly Ser Asp Ile Gly Ser Trp
            20                  25                  30

Asn Phe Val Ser Trp Tyr Gln Gln Phe Pro Gly Arg Ala Pro Asn Leu
        35                  40                  45

Ile Ile Phe Glu Val Asn Arg Arg Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Arg Ser Glu Asp Glu Ala Glu Tyr Phe Cys Ser Ser Leu Ser Gly Arg
                85                  90                  95

Trp Asp Ile Val Phe Gly Gly Thr Lys Val Thr Val Leu
            100                 105                 110

<210> SEQ ID NO 57
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Leu Gln Met Gln Glu Ser Gly Pro Gly Leu Val Lys Pro Ser Glu
1               5                   10                  15

Thr Leu Ser Leu Ser Cys Thr Val Ser Gly Asp Ser Ile Arg Gly Gly
            20                  25                  30

Glu Trp Gly Asp Lys Asp Tyr His Trp Gly Trp Val Arg His Ser Ala

```
                35                  40                  45
Gly Lys Gly Leu Glu Trp Ile Gly Ser Ile His Trp Arg Gly Thr Thr
 50                  55                  60
His Tyr Lys Glu Ser Leu Arg Arg Val Ser Met Ser Ile Asp Thr
 65                  70                  75                  80
Ser Arg Asn Trp Phe Ser Leu Arg Leu Ala Ser Val Thr Ala Ala Asp
                    85                  90                  95
Thr Ala Val Tyr Phe Cys Ala Arg His Arg His Asp Val Phe Met
                100                 105                 110
Leu Val Pro Ile Ala Gly Trp Phe Asp Val Trp Gly Pro Gly Val Gln
                115                 120                 125
Val Thr Val Ser Ser
130
```

<210> SEQ ID NO 58
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Glu Ile Val Met Thr Gln Ser Pro Asp Thr Leu Ser Val Ser Pro Gly
 1                   5                  10                  15
Glu Thr Val Thr Leu Ser Cys Arg Ala Ser Gln Asn Ile Asn Lys Asn
                    20                  25                  30
Leu Ala Trp Tyr Gln Tyr Lys Pro Gly Gln Ser Pro Arg Leu Val Ile
                35                  40                  45
Phe Glu Thr Tyr Ser Lys Ile Ala Ala Phe Pro Ala Arg Phe Val Ala
 50                  55                  60
Ser Gly Ser Gly Thr Glu Phe Thr Leu Thr Ile Asn Asn Met Gln Ser
 65                  70                  75                  80
Glu Asp Val Ala Val Tyr Tyr Cys Gln Gln Tyr Glu Trp Pro Arg
                    85                  90                  95
Thr Phe Gly Gln Gly Thr Lys Val Asp Ile Lys
                100                 105
```

<210> SEQ ID NO 59
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Gln Val Gln Leu Val Gln Ser Gly Pro Glu Val Lys Lys Pro Gly Ser
 1                   5                  10                  15
Ser Val Lys Val Ser Cys Lys Ala Ser Gly Asn Thr Phe Ser Lys Tyr
                    20                  25                  30
Asp Val His Trp Val Arg Gln Ala Thr Gly Gln Gly Leu Glu Trp Val
                35                  40                  45
Gly Trp Met Ser His Glu Gly Asp Lys Thr Glu Ser Ala Gln Arg Phe
 50                  55                  60
Lys Gly Arg Val Thr Phe Thr Arg Asp Thr Ser Ala Ser Thr Ala Tyr
 65                  70                  75                  80
Met Glu Leu Arg Gly Leu Thr Ser Asp Asp Thr Ala Ile Tyr Tyr Cys
```

```
                    85                  90                  95
Thr Arg Gly Ser Lys His Arg Leu Arg Asp Tyr Val Leu Tyr Asp Asp
                100                 105                 110

Tyr Gly Leu Ile Asn Tyr Gln Glu Trp Asn Asp Tyr Leu Glu Phe Leu
            115                 120                 125

Asp Val Trp Gly His Gly Thr Ala Val Thr Val Ser Ser
        130                 135                 140
```

<210> SEQ ID NO 60
<211> LENGTH: 112
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 60

```
Asp Thr Val Val Thr Gln Ser Pro Leu Ser Leu Pro Val Thr Pro Gly
1               5                   10                  15

Glu Ala Ala Ser Met Ser Cys Ser Ser Thr Gln Ser Leu Arg His Ser
            20                  25                  30

Asn Gly Ala Asn Tyr Leu Ala Trp Tyr Gln His Lys Pro Gly Gln Ser
        35                  40                  45

Pro Arg Leu Leu Ile Arg Leu Gly Ser Gln Arg Ala Ser Gly Val Pro
    50                  55                  60

Asp Arg Phe Ser Gly Ser Gly Ser Gly Thr His Phe Thr Leu Lys Ile
65                  70                  75                  80

Ser Arg Val Glu Ala Glu Asp Ala Ala Ile Tyr Tyr Cys Met Gln Gly
                85                  90                  95

Leu Asn Arg Pro Trp Thr Phe Gly Lys Gly Thr Lys Leu Glu Ile Lys
                100                 105                 110
```

<210> SEQ ID NO 61
<211> LENGTH: 141
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 61

```
Gln Val Gln Leu Glu Gln Ser Gly Ala Glu Val Lys Lys Pro Gly Ser
1               5                   10                  15

Ser Val Lys Val Ser Cys Lys Ala Ser Gly Asn Thr Phe Ser Lys Tyr
            20                  25                  30

Asp Val His Trp Val Arg Gln Ala Thr Gly Gln Gly Leu Glu Trp Val
        35                  40                  45

Gly Trp Met Ser His Glu Gly Asp Lys Thr Glu Ser Ala Gln Arg Phe
    50                  55                  60

Lys Gly Arg Val Thr Phe Thr Arg Asp Thr Ser Ala Ser Thr Ala Tyr
65                  70                  75                  80

Met Glu Leu Arg Gly Leu Thr Ser Asp Asp Thr Ala Ile Tyr Tyr Cys
                85                  90                  95

Thr Arg Gly Ser Lys His Arg Leu Arg Asp Tyr Val Leu Tyr Asp Asp
                100                 105                 110

Tyr Gly Leu Ile Asn Tyr Gln Glu Trp Asn Asp Tyr Leu Glu Phe Leu
            115                 120                 125

Asp Val Trp Gly His Gly Thr Ala Val Thr Val Ser Ser
```

<210> SEQ ID NO 62
<211> LENGTH: 112
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 62

```
Asp Thr Val Val Thr Gln Ser Pro Leu Ser Leu Pro Val Thr Pro Gly
1               5                   10                  15

Glu Ala Ala Ser Met Ser Cys Thr Ser Thr Gln Ser Leu Arg His Ser
            20                  25                  30

Asn Gly Ala Asn Tyr Leu Ala Trp Tyr Gln His Lys Pro Gly Gln Ser
        35                  40                  45

Pro Arg Leu Leu Ile Arg Leu Gly Ser Gln Arg Ala Ser Gly Val Pro
    50                  55                  60

Asp Arg Phe Ser Gly Ser Gly Ser Gly Thr His Phe Thr Leu Lys Ile
65                  70                  75                  80

Ser Arg Val Glu Pro Glu Asp Ala Ala Ile Tyr Tyr Cys Met Gln Gly
                85                  90                  95

Leu Asn Arg Pro Trp Thr Phe Gly Lys Gly Thr Lys Leu Glu Ile Lys
            100                 105                 110
```

<210> SEQ ID NO 63
<211> LENGTH: 141
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 63

```
Gln Val Gln Leu Val Gln Ser Gly Ala Glu Val Lys Lys Pro Gly Ser
1               5                   10                  15

Ser Val Lys Val Ser Cys Lys Ala Ser Gly Asn Thr Phe Arg Lys Tyr
            20                  25                  30

Asp Val His Trp Val Arg Gln Ala Thr Gly Gln Gly Leu Glu Trp Val
        35                  40                  45

Gly Trp Met Ser His Glu Gly Asp Lys Thr Glu Ser Ala Gln Arg Phe
    50                  55                  60

Lys Gly Arg Val Ser Phe Thr Arg Asp Asn Ser Ala Ser Thr Ala Tyr
65                  70                  75                  80

Ile Glu Leu Arg Gly Leu Thr Ser Asp Thr Ala Ile Tyr Tyr Cys
                85                  90                  95

Thr Gly Gly Ser Lys His Arg Leu Arg Asp Tyr Val Leu Tyr Asp Asp
            100                 105                 110

Tyr Gly Leu Ile Asn Gln Gln Glu Trp Asn Asp Tyr Leu Glu Phe Leu
        115                 120                 125

Asp Val Trp Gly His Gly Thr Ala Val Thr Val Ser Ser
    130                 135                 140
```

<210> SEQ ID NO 64
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 64

Asp Thr Val Val Thr Gln Ser Pro Leu Ser Leu Ser Val Thr Pro Gly
1               5                   10                  15

Glu Ala Ala Ser Met Ser Cys Thr Ser Thr Gln Ser Leu Arg His Ser
            20                  25                  30

Asn Gly Ala Asn Tyr Leu Ala Trp Tyr Gln His Lys Pro Gly Gln Ser
        35                  40                  45

Pro Arg Leu Leu Ile Arg Leu Gly Ser Gln Arg Ala Ser Gly Val Pro
    50                  55                  60

Asp Arg Phe Ser Gly Ser Gly Ser Gly Thr His Phe Thr Leu Lys Ile
65                  70                  75                  80

Ser Arg Val Glu Ala Asp Asp Ala Ala Ile Tyr Tyr Cys Met Gln Gly
                85                  90                  95

Leu Asn Arg Pro Trp Thr Phe Gly Lys Gly Thr Lys Leu Glu Ile Lys
            100                 105                 110

<210> SEQ ID NO 65
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Val Gln Ser Gly Ala Glu Val Lys Lys Pro Gly Ser
1               5                   10                  15

Ser Val Lys Val Ser Cys Lys Ala Ser Gly Asn Ser Phe Ser Asn His
            20                  25                  30

Asp Val His Trp Val Arg Gln Ala Thr Gly Gln Gly Leu Glu Trp Met
        35                  40                  45

Gly Trp Met Ser His Glu Gly Asp Lys Thr Gly Leu Ala Gln Lys Phe
    50                  55                  60

Gln Gly Arg Val Thr Ile Thr Arg Asp Ser Gly Ala Ser Thr Val Tyr
65                  70                  75                  80

Met Glu Leu Arg Gly Leu Thr Ala Asp Asp Thr Ala Ile Tyr Tyr Cys
                85                  90                  95

Leu Thr Gly Ser Lys His Arg Leu Arg Asp Tyr Phe Leu Tyr Asn Glu
            100                 105                 110

Tyr Gly Pro Asn Tyr Glu Glu Trp Gly Asp Tyr Leu Ala Thr Leu Asp
        115                 120                 125

Val Trp Gly His Gly Thr Ala Val Thr Val Ser Ser
    130                 135                 140

<210> SEQ ID NO 66
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Glu Val Val Ile Thr Gln Ser Pro Leu Phe Leu Pro Val Thr Pro Gly
1               5                   10                  15

Glu Ala Ala Ser Leu Ser Cys Lys Cys Ser His Ser Leu Gln His Ser
            20                  25                  30

```
Thr Gly Ala Asn Tyr Leu Ala Trp Tyr Leu Gln Arg Pro Gly Gln Thr
        35                  40                  45

Pro Arg Leu Leu Ile His Leu Ala Thr His Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ser Asp Asp Val Gly Thr Tyr Tyr Cys Met Gln Gly
                 85                  90                  95

Leu His Ser Pro Trp Thr Phe Gly Gln Gly Thr Lys Val Glu Ile Lys
            100                 105                 110

<210> SEQ ID NO 67
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Val Gln Leu Val Gln Ser Gly Pro Glu Val Lys Lys Pro Gly Ser
 1               5                  10                  15

Ser Val Lys Val Ser Cys Lys Ala Ser Gly Asn Thr Phe Ser Lys Tyr
                 20                  25                  30

Asp Val His Trp Val Arg Gln Ala Thr Gly Gln Gly Leu Glu Trp Val
            35                  40                  45

Gly Trp Ile Ser His Glu Arg Asp Lys Thr Glu Ser Ala Gln Arg Phe
 50                  55                  60

Lys Gly Arg Val Thr Phe Thr Arg Asp Thr Ser Ala Thr Thr Ala Tyr
 65                  70                  75                  80

Met Glu Leu Arg Gly Leu Thr Ser Asp Asp Thr Ala Ile Tyr Tyr Cys
                 85                  90                  95

Thr Arg Gly Ser Lys His Arg Leu Arg Asp Tyr Val Leu Tyr Asp Asp
            100                 105                 110

Tyr Gly Leu Ile Asn Tyr Gln Glu Trp Asn Asp Tyr Leu Glu Phe Leu
        115                 120                 125

Asp Val Trp Gly His Gly Thr Ala Val Thr Val Ser Ser
        130                 135                 140

<210> SEQ ID NO 68
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Asp Thr Val Val Thr Gln Ser Pro Leu Ser Leu Pro Val Thr Pro Gly
 1               5                  10                  15

Glu Ala Ala Ser Met Ser Cys Ser Ser Thr Gln Ser Leu Arg His Ser
                 20                  25                  30

Asn Gly Ala Asn Tyr Leu Ala Trp Tyr Gln His Lys Pro Gly Gln Ser
            35                  40                  45

Pro Arg Leu Leu Ile Arg Leu Gly Ser Gln Arg Ala Ser Gly Val Pro
 50                  55                  60

Asp Arg Phe Ser Gly Ser Gly Ser Gly Thr His Phe Thr Leu Lys Ile
 65                  70                  75                  80
```

```
Ser Arg Val Glu Ala Glu Asp Ala Ala Ile Tyr Tyr Cys Met Gln Gly
                85                  90                  95

Leu Asn Arg Pro Trp Thr Phe Gly Lys Gly Thr Lys Leu Glu Ile Lys
            100                 105                 110

<210> SEQ ID NO 69
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Val Gln Leu Val Gln Ser Gly Ala Glu Val Lys Lys Pro Gly Glu
1               5                   10                  15

Ser Leu Lys Ile Ser Cys Lys Val Ser Gly Tyr Asn Phe Ala Ser Glu
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Lys Tyr Ser Pro Ser Phe
    50                  55                  60

Gln Gly Gln Val Ile Ile Ser Ala Asp Lys Ser Ile Asn Thr Ala Tyr
65                  70                  75                  80

Leu Gln Trp Ser Ser Leu Lys Ala Ser Asp Thr Ala Ile Tyr Tyr Cys
                85                  90                  95

Ala Arg Gln Asn His Tyr Gly Ser Gly Ser Tyr Phe Tyr Arg Thr Ala
            100                 105                 110

Tyr Tyr Tyr Ala Met Asp Val Trp Gly Gln Gly Thr Thr Val Thr Val
        115                 120                 125

Ser Ser
    130

<210> SEQ ID NO 70
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Asp Ile Gln Leu Thr Gln Ser Pro Ser Ser Leu Ser Ala Ser Leu Gly
1               5                   10                  15

Asp Lys Val Thr Ile Thr Cys Arg Ala Ser Gln His Ile Lys Lys Tyr
            20                  25                  30

Leu Asn Trp Tyr Gln Gln Lys Pro Gly Lys Ala Pro Lys Leu Leu Ile
        35                  40                  45

Tyr Gly Ala Leu Asn Leu Gln Ser Gly Val Pro Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys Arg
            100                 105

<210> SEQ ID NO 71
```

<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Ser Glu Thr Leu Ser Leu Thr Cys Thr Val Ser Gly Gly Ser Met Gly
1               5                   10                  15

Gly Thr Tyr Trp Ser Trp Leu Arg Leu Ser Pro Gly Lys Gly Leu Glu
            20                  25                  30

Trp Ile Gly Tyr Ile Phe His Thr Gly Glu Thr Asn Tyr Ser Pro Ser
        35                  40                  45

Leu Lys Gly Arg Val Ser Ile Ser Val Asp Thr Ser Glu Asp Gln Phe
50                  55                  60

Ser Leu Arg Leu Arg Ser Val Thr Ala Ala Asp Thr Ala Val Tyr Phe
65                  70                  75                  80

Cys Ala Ser Leu Pro Arg Gly Gln Leu Val Asn Ala Tyr Phe Arg Asn
                85                  90                  95

Trp Gly Arg Gly Ser Leu Val Ser Val Thr Ala
            100                 105

<210> SEQ ID NO 72
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Ser Tyr Glu Leu Thr Gln Pro Pro Ser Val Ser Val Ser Pro Gly Gln
1               5                   10                  15

Thr Ala Thr Ile Thr Cys Ser Gly Ala Ser Thr Asn Val Cys Trp Tyr
            20                  25                  30

Gln Val Lys Pro Gly Gln Ser Pro Glu Val Val Ile Phe Glu Asn Tyr
        35                  40                  45

Lys Arg Pro Ser Gly Ile Pro Asp Arg Phe Ser Gly Ser Lys Ser Gly
50                  55                  60

Ser Thr Ala Thr Leu Thr Ile Arg Gly Thr Gln Ala Ile Asp Glu Ala
65                  70                  75                  80

Asp Tyr Tyr Cys Gln Val Trp Asp Ser Phe Ser Thr Phe Val Phe Gly
                85                  90                  95

Ser Gly Thr Gln Val Thr Val Leu
            100

<210> SEQ ID NO 73
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Leu Val Glu Ser Gly Gly Gly Leu Val Lys Pro Gly Gly
1               5                   10                  15

Ser Leu Arg Leu Ser Cys Ser Ala Ser Gly Phe Asp Phe Asp Asn Ala
            20                  25                  30

-continued

```
Trp Met Thr Trp Val Arg Gln Pro Gly Lys Gly Leu Glu Trp Val
         35                  40                  45
Gly Arg Ile Thr Gly Pro Gly Glu Gly Trp Ser Val Asp Tyr Ala Ala
 50                  55                  60
Pro Val Glu Gly Arg Phe Thr Ile Ser Arg Leu Asn Ser Ile Asn Phe
 65                  70                  75                  80
Leu Tyr Leu Glu Met Asn Asn Leu Arg Met Glu Asp Ser Gly Leu Tyr
                 85                  90                  95
Phe Cys Ala Arg Thr Gly Lys Tyr Tyr Asp Phe Trp Ser Gly Tyr Pro
                100                 105                 110
Pro Gly Glu Glu Tyr Phe Gln Asp Trp Gly Arg Gly Thr Leu Val Thr
                115                 120                 125
Val Ser Ser
    130
```

<210> SEQ ID NO 74
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (110)..(110)
<223> OTHER INFORMATION: Any amino acid

<400> SEQUENCE: 74

```
Ser Tyr Glu Leu Thr Gln Glu Thr Gly Val Ser Val Ala Leu Gly Arg
 1               5                  10                  15
Thr Val Thr Ile Thr Cys Arg Gly Asp Ser Leu Arg Ser His Tyr Ala
                 20                  25                  30
Ser Trp Tyr Gln Lys Lys Pro Gly Gln Ala Pro Ile Leu Leu Phe Tyr
                 35                  40                  45
Gly Lys Asn Asn Arg Pro Ser Gly Val Pro Asp Arg Phe Ser Gly Ser
 50                  55                  60
Ala Ser Gly Asn Arg Ala Ser Leu Thr Ile Ser Gly Ala Gln Ala Glu
 65                  70                  75                  80
Asp Asp Ala Glu Tyr Tyr Cys Ser Ser Arg Asp Lys Ser Gly Ser Arg
                 85                  90                  95
Leu Ser Val Phe Gly Gly Gly Thr Lys Leu Thr Val Leu Xaa
                100                 105                 110
```

<210> SEQ ID NO 75
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 75

```
Gln Val Arg Leu Ser Gln Ser Gly Gly Gln Met Lys Lys Pro Gly Asp
 1               5                  10                  15
Ser Met Arg Ile Ser Cys Arg Ala Ser Gly Tyr Glu Phe Ile Asn Cys
                 20                  25                  30
Pro Ile Asn Trp Ile Arg Leu Ala Pro Gly Lys Arg Pro Glu Trp Met
                 35                  40                  45
Gly Trp Met Lys Pro Arg Gly Gly Ala Val Ser Tyr Ala Arg Gln Leu
 50                  55                  60
```

Gln Gly Arg Val Thr Met Thr Arg Asp Met Tyr Ser Glu Thr Ala Phe
65                  70                  75                  80

Leu Glu Leu Arg Ser Leu Thr Ser Asp Asp Thr Ala Val Tyr Phe Cys
            85                  90                  95

Thr Arg Gly Lys Tyr Cys Thr Ala Arg Asp Tyr Tyr Asn Trp Asp Phe
        100                 105                 110

Glu His Trp Gly Gln Gly Thr Pro Val Thr Val Ser Ser
        115                 120                 125

<210> SEQ ID NO 76
<211> LENGTH: 585
<212> TYPE: PRT
<213> ORGANISM: Homo sapiens

<400> SEQUENCE: 76

Lys Ser Pro Ile Phe Gly Pro Glu Val Asn Ser Val Glu Gly Asn
1               5                   10                  15

Ser Val Ser Ile Thr Cys Tyr Tyr Pro Pro Thr Ser Val Asn Arg His
            20                  25                  30

Thr Arg Lys Tyr Trp Cys Arg Gln Gly Ala Arg Gly Gly Cys Ile Thr
        35                  40                  45

Leu Ile Ser Ser Glu Gly Tyr Val Ser Ser Lys Tyr Ala Gly Arg Ala
50                  55                  60

Asn Leu Thr Asn Phe Pro Glu Asn Gly Thr Phe Val Val Asn Ile Ala
65                  70                  75                  80

Gln Leu Ser Gln Asp Asp Ser Gly Arg Tyr Lys Cys Gly Leu Gly Ile
            85                  90                  95

Asn Ser Arg Gly Leu Ser Phe Asp Val Ser Leu Glu Val Ser Gln Gly
        100                 105                 110

Pro Gly Leu Leu Asn Asp Thr Lys Val Tyr Thr Val Asp Leu Gly Arg
        115                 120                 125

Thr Val Thr Ile Asn Cys Pro Phe Lys Thr Glu Asn Ala Gln Lys Arg
        130                 135                 140

Lys Ser Leu Tyr Lys Gln Ile Gly Leu Tyr Pro Val Leu Val Ile Asp
145                 150                 155                 160

Ser Ser Gly Tyr Val Asn Pro Asn Tyr Thr Gly Arg Ile Arg Leu Asp
                165                 170                 175

Ile Gln Gly Thr Gly Gln Leu Leu Phe Ser Val Val Ile Asn Gln Leu
            180                 185                 190

Arg Leu Ser Asp Ala Gly Gln Tyr Leu Cys Gln Ala Gly Asp Asp Ser
        195                 200                 205

Asn Ser Asn Lys Lys Asn Ala Asp Leu Gln Val Leu Lys Pro Glu Pro
    210                 215                 220

Glu Leu Val Tyr Glu Asp Leu Arg Gly Ser Val Thr Phe His Cys Ala
225                 230                 235                 240

Leu Gly Pro Glu Val Ala Asn Val Ala Lys Phe Leu Cys Arg Gln Ser
                245                 250                 255

Ser Gly Glu Asn Cys Asp Val Val Val Asn Thr Leu Gly Lys Arg Ala
            260                 265                 270

Pro Ala Phe Glu Gly Arg Ile Leu Leu Asn Pro Gln Asp Lys Asp Gly
        275                 280                 285

Ser Phe Ser Val Val Ile Thr Gly Leu Arg Lys Glu Asp Ala Gly Arg
    290                 295                 300

Tyr Leu Cys Gly Ala His Ser Asp Gly Gln Leu Gln Glu Gly Ser Pro

-continued

```
                305                 310                 315                 320
        Ile Gln Ala Trp Gln Leu Phe Val Asn Glu Glu Ser Thr Ile Pro Arg
                        325                 330                 335

Ser Pro Thr Val Val Lys Gly Val Ala Gly Ser Val Ala Val Leu
                        340                 345                 350

Cys Pro Tyr Asn Arg Lys Glu Ser Lys Ser Ile Lys Tyr Trp Cys Leu
                        355                 360                 365

Trp Glu Gly Ala Gln Asn Gly Arg Cys Pro Leu Leu Val Asp Ser Glu
        370                 375                 380

Gly Trp Val Lys Ala Gln Tyr Glu Gly Arg Leu Ser Leu Leu Glu Glu
        385                 390                 395                 400

Pro Gly Asn Gly Thr Phe Thr Val Ile Leu Asn Gln Leu Thr Ser Arg
                        405                 410                 415

Asp Ala Gly Phe Tyr Trp Cys Leu Thr Asn Gly Asp Thr Leu Trp Arg
                        420                 425                 430

Thr Thr Val Glu Ile Lys Ile Ile Glu Gly Glu Pro Asn Leu Lys Val
                        435                 440                 445

Pro Gly Asn Val Thr Ala Val Leu Gly Glu Thr Leu Lys Val Pro Cys
        450                 455                 460

His Phe Pro Cys Lys Phe Ser Ser Tyr Glu Lys Tyr Trp Cys Lys Trp
        465                 470                 475                 480

Asn Asn Thr Gly Cys Gln Ala Leu Pro Ser Gln Asp Glu Gly Pro Ser
                        485                 490                 495

Lys Ala Phe Val Asn Cys Asp Glu Asn Ser Arg Leu Val Ser Leu Thr
                        500                 505                 510

Leu Asn Leu Val Thr Arg Ala Asp Glu Gly Trp Tyr Trp Cys Gly Val
                        515                 520                 525

Lys Gln Gly His Phe Tyr Gly Glu Thr Ala Ala Val Tyr Val Ala Val
                        530                 535                 540

Glu Glu Arg Lys Ala Ala Gly Ser Arg Asp Val Ser Leu Ala Lys Ala
        545                 550                 555                 560

Asp Ala Ala Pro Asp Glu Lys Val Leu Asp Ser Gly Phe Arg Glu Ile
                        565                 570                 575

Glu Asn Lys Ala Ile Gln Asp Pro Arg
                        580                 585

<210> SEQ ID NO 77
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Val Gln Leu Val Gln Pro Gly Thr Ala Met Lys Ser Leu Gly Ser
        1               5                   10                  15

Ser Leu Thr Ile Thr Cys Arg Val Ser Gly Asp Asp Leu Gly Ser Phe
                        20                  25                  30

His Phe Gly Thr Tyr Phe Met Ile Trp Val Arg Gln Ala Pro Gly Gln
                        35                  40                  45

Gly Leu Glu Tyr Met Gly Gly Ile Leu Pro Ser Thr Lys Thr Pro Thr
                        50                  55                  60

Tyr Ala His Lys Phe Arg Gly Arg Val Ser Ile Ser Ala Pro Gly Val
        65                  70                  75                  80
```

```
Pro Pro Val Leu Ser Leu Ala Leu Thr Asn Leu Thr Tyr Asp Asp Thr
                85                  90                  95

Ala Thr Tyr Phe Cys Ala Arg Glu Arg Gly Arg His Phe Glu Pro Lys
            100                 105                 110

Asn Arg Asp Asn Leu Glu Gly Lys Phe Phe Asp Leu Trp Gly Arg Gly
        115                 120                 125

Thr Phe Val Arg Val Ser Pro
130             135

<210> SEQ ID NO 78
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Ser Ala Leu Thr Gln Pro Ala Ser Val Ser Gly Ser Pro Gly Gln
1               5                   10                  15

Ser Ile Asn Ile Ser Cys Ala Gly Arg Ser Asp Arg Val Ser Trp Tyr
            20                  25                  30

Gln Gln Arg Pro Asn Gly Val Pro Lys Leu Leu Met Phe Asp Val Tyr
        35                  40                  45

Arg Arg Pro Ser Gly Val Ser Asp Arg Phe Ser Gly Ser His Ser Gly
50                  55                  60

Asp Thr Ala Phe Leu Thr Ile Ser Gly Leu Gln Thr Glu Asp Glu Ala
65                  70                  75                  80

Asp Tyr Tyr Cys Thr Ser His Pro Tyr Ala Phe Gly Ala Gly Thr Lys
                85                  90                  95

Val Asn Val Leu
            100

<210> SEQ ID NO 79
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid

<400> SEQUENCE: 79

Xaa Val Arg Leu Ser Gln Ser Gly Gly Gln Met Lys Lys Pro Gly Glu
1               5                   10                  15

Ser Met Arg Leu Ser Cys Arg Ala Ser Gly Tyr Glu Phe Leu Asn Cys
            20                  25                  30

Pro Ile Asn Trp Ile Arg Leu Ala Pro Gly Arg Arg Pro Glu Trp Met
        35                  40                  45

Gly Trp Leu Lys Pro Arg Trp Gly Ala Val Asn Tyr Ala Arg Lys Phe
50                  55                  60

Gln Gly Arg Val Thr Met Thr Arg Asp Val Tyr Ser Asp Thr Ala Phe
65                  70                  75                  80

Leu Glu Leu Arg Ser Leu Thr Ser Asp Asp Thr Ala Val Tyr Phe Cys
                85                  90                  95

Thr Arg Gly Lys Tyr Cys Thr Ala Arg Asp Tyr Tyr Asn Trp Asp Phe
            100                 105                 110
```

Glu His Trp Gly Arg Gly Ala Pro Val Thr Val Ser Ser
            115                 120                 125

<210> SEQ ID NO 80
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Ile Val Leu Thr Gln Ser Pro Ala Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Ala Asp Tyr Asn Leu Ser Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp Ile Lys Arg
            100

<210> SEQ ID NO 81
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Val Gln Leu Gln Glu Ser Gly Pro Gly Leu Val Lys Pro Ser Glu
1               5                   10                  15

Thr Leu Ser Val Thr Cys Ser Val Ser Gly Asp Ser Met Asn Asn Tyr
            20                  25                  30

Tyr Trp Thr Trp Ile Arg Gln Ser Pro Gly Lys Gly Leu Glu Trp Ile
        35                  40                  45

Gly Tyr Ile Ser Asp Arg Glu Ser Ala Thr Tyr Asn Pro Ser Leu Asn
    50                  55                  60

Ser Arg Val Val Ile Ser Arg Asp Thr Ser Lys Asn Gln Leu Ser Leu
65                  70                  75                  80

Lys Leu Asn Ser Val Thr Pro Ala Asp Thr Ala Val Tyr Tyr Cys Ala
                85                  90                  95

Thr Ala Arg Arg Gly Gln Arg Ile Tyr Gly Val Val Ser Phe Gly Glu
            100                 105                 110

Phe Phe Tyr Tyr Tyr Ser Met Asp Val Trp Gly Lys Gly Thr Thr Val
        115                 120                 125

Thr Val Ser Ser
    130

<210> SEQ ID NO 82
<211> LENGTH: 109
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 82

Ser Tyr Val Arg Pro Leu Ser Val Ala Leu Gly Glu Thr Ala Arg Ile
1               5                   10                  15

Ser Cys Gly Arg Gln Ala Leu Gly Ser Arg Ala Val Gln Trp Tyr Gln
            20                  25                  30

His Arg Pro Gly Gln Ala Pro Ile Leu Leu Ile Tyr Asn Asn Gln Asp
        35                  40                  45

Arg Pro Ser Gly Ile Pro Glu Arg Phe Ser Gly Thr Pro Asp Ile Asn
50                  55                  60

Phe Gly Thr Arg Ala Thr Leu Thr Ile Ser Gly Val Glu Ala Gly Asp
65                  70                  75                  80

Glu Ala Asp Tyr Tyr Cys His Met Trp Asp Ser Arg Ser Gly Phe Ser
                85                  90                  95

Trp Ser Phe Gly Gly Ala Thr Arg Leu Thr Val Leu Gly
            100                 105

<210> SEQ ID NO 83
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gln Gly Gln Leu Val Gln Ser Gly Ala Glu Leu Lys Lys Pro Gly Ala
1               5                   10                  15

Ser Val Lys Ile Ser Cys Lys Thr Ser Gly Tyr Arg Phe Asn Phe Tyr
            20                  25                  30

His Ile Asn Trp Ile Arg Gln Thr Ala Gly Arg Gly Pro Glu Trp Met
        35                  40                  45

Gly Trp Ile Ser Pro Tyr Ser Gly Asp Lys Asn Leu Ala Pro Ala Phe
    50                  55                  60

Gln Asp Arg Val Ile Met Thr Thr Asp Thr Glu Val Pro Val Thr Ser
65                  70                  75                  80

Phe Thr Ser Thr Gly Ala Ala Tyr Met Glu Ile Arg Asn Leu Lys Phe
                85                  90                  95

Asp Asp Thr Gly Thr Tyr Phe Cys Ala Lys Gly Leu Leu Arg Asp Gly
            100                 105                 110

Ser Ser Thr Trp Leu Pro Tyr Leu Trp Gly Gln Gly Thr Leu Leu Thr
        115                 120                 125

Val Ser Ser
    130

<210> SEQ ID NO 84
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Ser Val Leu Thr Gln Ser Ala Ser Val Ser Gly Ser Leu Gly Gln
1               5                   10                  15
```

```
Ser Val Thr Ile Ser Cys Thr Gly Pro Asn Ser Val Cys Cys Ser His
                20                  25                  30

Lys Ser Ile Ser Trp Tyr Gln Trp Pro Pro Gly Arg Ala Pro Thr Leu
            35                  40                  45

Ile Ile Tyr Glu Asp Asn Glu Arg Ala Pro Gly Ile Ser Pro Arg Phe
        50                  55                  60

Ser Gly Tyr Lys Ser Tyr Trp Ser Ala Tyr Leu Thr Ile Ser Asp Leu
65                  70                  75                  80

Arg Pro Glu Asp Glu Thr Thr Tyr Tyr Cys Cys Ser Tyr Thr His Asn
                85                  90                  95

Ser Gly Cys Val Phe Gly Thr Gly Thr Lys Val Ser Val Leu
            100                 105                 110
```

<210> SEQ ID NO 85
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

```
Glu Val Gln Leu Val Glu Ser Gly Ala Asn Val Val Arg Pro Gly Gly
1               5                   10                  15

Ser Leu Arg Leu Ser Cys Lys Ala Ser Gly Phe Ile Phe Glu Asn Phe
                20                  25                  30

Gly Phe Ser Trp Val Arg Gln Ala Pro Gly Lys Gly Leu Gln Trp Val
            35                  40                  45

Ala Gly Leu Asn Trp Asn Gly Gly Asp Thr Arg Tyr Ala Asp Ser Val
        50                  55                  60

Lys Gly Arg Phe Arg Met Ser Arg Asp Asn Ser Arg Asn Phe Val Tyr
65                  70                  75                  80

Leu Asp Met Asp Lys Val Gly Val Asp Thr Ala Phe Tyr Tyr Cys
                85                  90                  95

Ala Arg Gly Thr Asp Tyr Thr Ile Asp Asp Ala Gly Ile His Tyr Gln
            100                 105                 110

Gly Ser Gly Thr Phe Trp Tyr Phe Asp Leu Trp Gly Arg Gly Thr Leu
        115                 120                 125

Val Ser Val Ser Ser
        130
```

<210> SEQ ID NO 86
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

```
Glu Ile Val Leu Ala Gln Ser Pro Gly Thr Leu Ser Leu Ser Pro Gly
1               5                   10                  15

Glu Arg Ala Thr Leu Ser Cys Arg Ala Ser His Asn Val His Pro Lys
                20                  25                  30

Tyr Phe Ala Trp Tyr Gln Gln Lys Pro Gly Gln Ser Pro Arg Leu Leu
            35                  40                  45

Ile Tyr Gly Gly Ser Thr Arg Ala Ala Gly Ile Pro Gly Lys Phe Ser
        50                  55                  60
```

Gly Ser Gly Ser Gly Thr Asp Phe Thr Leu Thr Ile Ser Arg Val Asp
65                  70                  75                  80

Pro Glu Asp Phe Ala Val Tyr Tyr Cys Gln Gln Tyr Gly Gly Ser Pro
                85                  90                  95

Tyr Thr Phe Gly Gln Gly Thr Lys Val Glu Ile Lys
            100                 105

<210> SEQ ID NO 87
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Val Gln Leu Val Glu Ser Gly Gly Ser Val Val Arg Pro Gly Gly
1               5                   10                  15

Ser Leu Arg Leu Ser Cys Arg Ala Ser Gly Phe Ile Phe Glu Asn Tyr
                20                  25                  30

Gly Leu Thr Trp Val Arg Gln Val Pro Gly Lys Gly Leu His Trp Val
            35                  40                  45

Ser Gly Met Asn Trp Asn Gly Gly Asp Thr Arg Tyr Ala Asp Ser Val
        50                  55                  60

Arg Gly Arg Phe Ser Met Ser Arg Asp Asn Ser Asn Asn Ile Ala Tyr
65                  70                  75                  80

Leu Gln Met Asn Asn Leu Arg Val Glu Asp Thr Ala Leu Tyr Tyr Cys
                85                  90                  95

Ala Arg Gly Thr Asp Tyr Thr Ile Asp Asp Gln Gly Arg Phe Tyr Gln
            100                 105                 110

Gly Ser Gly Thr Phe Trp Tyr Phe Asp Phe Trp Gly Arg Gly Thr Leu
        115                 120                 125

Val Thr Val Ser Ser
            130

<210> SEQ ID NO 88
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Asn Val His Pro Arg
                20                  25                  30

Tyr Phe Ala Trp Tyr Gln Gln Lys Arg Gly Gln Ser Pro Arg Leu Leu
            35                  40                  45

Ile His Ser Gly Ser Thr Arg Ala Ala Gly Ile Ala Asp Arg Phe Ser
        50                  55                  60

Gly Gly Gly Ser Gly Met His Phe Thr Leu Thr Ile Thr Arg Val Glu
65                  70                  75                  80

Pro Glu Asp Phe Ala Val Tyr Phe Cys Gln Gln Tyr Gly Gly Ser Pro
                85                  90                  95

Tyr Thr Phe Gly Gln Gly Thr Arg Val Glu Leu Arg
            100                 105

<210> SEQ ID NO 89
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Glu Val Gln Leu Val Glu Ser Gly Gly Val Val Arg Pro Gly Gly
1               5                   10                  15

Ser Leu Arg Leu Ser Cys Ala Ala Ser Gly Phe Ile Phe Glu Asn Tyr
            20                  25                  30

Gly Leu Thr Trp Val Arg Gln Val Pro Gly Lys Gly Leu His Trp Val
        35                  40                  45

Ser Gly Met Asn Trp Asn Gly Asp Thr Arg Tyr Ala Asp Ser Val
    50                  55                  60

Arg Gly Arg Phe Ser Met Ser Arg Asp Asn Ser Asn Asn Ile Ala Tyr
65                  70                  75                  80

Leu Gln Met Lys Asn Leu Arg Val Asp Asp Thr Ala Leu Tyr Tyr Cys
                85                  90                  95

Ala Arg Gly Thr Asp Tyr Thr Ile Asp Asp Gln Gly Ile Phe Tyr Lys
            100                 105                 110

Gly Ser Gly Thr Phe Trp Tyr Phe Asp Leu Trp Gly Arg Gly Thr Leu
        115                 120                 125

Val Thr Val Ser Ser
    130

<210> SEQ ID NO 90
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val His Pro Lys
            20                  25                  30

Tyr Phe Ala Trp Tyr Gln Gln Lys Pro Gly Gln Ser Pro Arg Leu Leu
        35                  40                  45

Ile Tyr Ser Gly Ser Thr Arg Ala Ala Gly Ile Ala Asp Arg Phe Ser
    50                  55                  60

Gly Gly Gly Ser Gly Ile His Phe Thr Leu Thr Ile Thr Arg Val Glu
65                  70                  75                  80

Pro Glu Asp Phe Ala Val Tyr Phe Cys Gln Gln Tyr Gly Gly Ser Pro
                85                  90                  95

Tyr Thr Phe Gly Gln Gly Thr Lys Val Glu Leu Arg
            100                 105

<210> SEQ ID NO 91
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Glu Val Gln Leu Val Glu Ser Gly Gly Gly Leu Ile Arg Pro Gly Gly
1               5                   10                  15

Ser Leu Arg Leu Ser Cys Lys Gly Ser Gly Phe Ile Phe Glu Asn Phe
            20                  25                  30

Gly Phe Gly Trp Val Arg Gln Gly Pro Gly Lys Gly Leu Glu Trp Val
        35                  40                  45

Ser Gly Thr Asn Trp Asn Gly Gly Asp Ser Arg Tyr Gly Asp Ser Val
    50                  55                  60

Lys Gly Arg Phe Thr Ile Ser Arg Asp Asn Ser Asn Asn Phe Val Tyr
65                  70                  75                  80

Leu Gln Met Asn Ser Leu Arg Pro Glu Asp Thr Ala Ile Tyr Tyr Cys
                85                  90                  95

Ala Arg Gly Thr Asp Tyr Thr Ile Asp Asp Gln Gly Ile Arg Tyr Gln
            100                 105                 110

Gly Ser Gly Thr Phe Trp Tyr Phe Asp Val Trp Gly Arg Gly Thr Leu
        115                 120                 125

Val Thr Val Ser Ser
    130

<210> SEQ ID NO 92
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Glu Ile Val Leu Thr Gln Ser Pro Asp Thr Leu Ser Leu Ser Pro Gly
1               5                   10                  15

Glu Arg Ala Thr Leu Ser Cys Arg Ala Ser Gln Ser Val His Ser Arg
            20                  25                  30

Tyr Phe Ala Trp Tyr Gln His Lys Pro Gly Gln Pro Pro Arg Leu Leu
        35                  40                  45

Ile Tyr Gly Gly Ser Thr Arg Ala Thr Gly Ile Pro Asn Arg Phe Ser
    50                  55                  60

Ala Gly Gly Ser Gly Thr Gln Phe Thr Leu Thr Val Asn Arg Leu Glu
65                  70                  75                  80

Ala Glu Asp Phe Ala Val Tyr Tyr Cys Gln Gln Tyr Gly Arg Ser Pro
                85                  90                  95

Tyr Thr Phe Gly Gln Gly Thr Lys Val Glu Ile Arg
            100                 105

<210> SEQ ID NO 93
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gln Val His Leu Thr Gln Ser Gly Pro Glu Val Arg Lys Pro Gly Thr
1               5                   10                  15

Ser Val Lys Val Ser Cys Lys Ala Pro Gly Asn Thr Leu Lys Thr Tyr
            20                  25                  30

Asp Leu His Trp Val Arg Ser Val Pro Gly Gln Gly Leu Gln Trp Met

```
                    35                  40                  45
Gly Trp Ile Ser His Glu Gly Asp Lys Lys Val Ile Val Glu Arg Phe
 50                  55                  60

Lys Ala Lys Val Thr Ile Asp Trp Asp Arg Ser Thr Asn Thr Ala Tyr
 65                  70                  75                  80

Leu Gln Leu Ser Gly Leu Thr Ser Gly Asp Thr Ala Val Tyr Tyr Cys
                 85                  90                  95

Ala Lys Gly Ser Lys His Arg Leu Arg Asp Tyr Ala Leu Tyr Asp Asp
                100                 105                 110

Asp Gly Ala Leu Asn Trp Ala Val Asp Val Asp Tyr Leu Ser Asn Leu
                115                 120                 125

Glu Phe Trp Gly Gln Gly Thr Ala Val Thr Val Ser Ser
                130                 135                 140

<210> SEQ ID NO 94
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Asp Phe Val Leu Thr Gln Ser Pro His Ser Leu Ser Val Thr Pro Gly
 1               5                  10                  15

Glu Ser Ala Ser Ile Ser Cys Lys Ser Ser His Ser Leu Ile His Gly
                 20                  25                  30

Asp Arg Asn Asn Tyr Leu Ala Trp Tyr Val Gln Lys Pro Gly Arg Ser
                 35                  40                  45

Pro Gln Leu Leu Ile Tyr Leu Ala Ser Ser Arg Ala Ser Gly Val Pro
 50                  55                  60

Asp Arg Phe Ser Gly Ser Gly Ser Asp Lys Asp Phe Thr Leu Lys Ile
 65                  70                  75                  80

Ser Arg Val Glu Thr Glu Asp Val Gly Thr Tyr Tyr Cys Met Gln Gly
                 85                  90                  95

Arg Glu Ser Pro Trp Thr Phe Gly Gln Gly Thr Lys Val Asp Ile Lys
                100                 105                 110

<210> SEQ ID NO 95
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Val Gln Leu Val Glu Ser Gly Gly Gly Leu Val Lys Ala Gly Gly
 1               5                  10                  15

Ser Leu Ile Leu Ser Cys Gly Val Ser Asn Phe Arg Ile Ser Ala His
                 20                  25                  30

Thr Met Asn Trp Val Arg Arg Val Pro Gly Gly Gly Leu Glu Trp Val
                 35                  40                  45

Ala Ser Ile Ser Thr Ser Ser Thr Tyr Arg Asp Tyr Ala Asp Ala Val
                 50                  55                  60

Lys Gly Arg Phe Thr Val Ser Arg Asp Leu Glu Asp Phe Val Tyr
 65                  70                  75                  80

Leu Gln Met His Lys Met Arg Val Glu Asp Thr Ala Ile Tyr Tyr Cys
```

```
                            85                  90                  95

Ala Arg Lys Gly Ser Asp Arg Leu Ser Asp Asn Asp Pro Phe Asp Ala
                100                 105                 110

Trp Gly Pro Gly Thr Val Val Thr Val Ser Pro
            115                 120

<210> SEQ ID NO 96
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Asp Ile Gln Met Thr Gln Ser Pro Ser Thr Leu Ser Ala Ser Val Gly
1               5                   10                  15

Asp Thr Ile Thr Ile Thr Cys Arg Ala Ser Gln Ser Ile Glu Thr Trp
                20                  25                  30

Leu Ala Trp Tyr Gln Gln Lys Pro Gly Lys Ala Pro Lys Leu Leu Ile
            35                  40                  45

Tyr Lys Ala Ser Thr Leu Lys Thr Gly Val Pro Ser Arg Phe Ser Gly
50                  55                  60

Ser Gly Ser Gly Thr Glu Phe Thr Leu Thr Ile Ser Gly Leu Gln Phe
65                  70                  75                  80

Asp Asp Phe Ala Thr Tyr His Cys Gln His Tyr Ala Gly Tyr Ser Ala
                85                  90                  95

Thr Phe Gly Gln Gly Thr Arg Val Glu Ile Lys
                100                 105

<210> SEQ ID NO 97
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gln Val Gln Leu Val Gln Ser Gly Gly Gly Val Phe Lys Pro Gly Gly
1               5                   10                  15

Ser Leu Arg Leu Ser Cys Glu Ala Ser Gly Phe Thr Phe Thr Glu Tyr
                20                  25                  30

Tyr Met Thr Trp Val Arg Gln Ala Pro Gly Lys Gly Leu Glu Trp Leu
            35                  40                  45

Ala Tyr Ile Ser Lys Asn Gly Glu Tyr Ser Lys Tyr Ser Pro Ser Ser
50                  55                  60

Asn Gly Arg Phe Thr Ile Ser Arg Asp Asn Ala Lys Asn Ser Val Phe
65                  70                  75                  80

Leu Gln Leu Asp Arg Leu Ser Ala Asp Thr Ala Val Tyr Tyr Cys
                85                  90                  95

Ala Arg Ala Asp Gly Leu Thr Tyr Phe Ser Glu Leu Leu Gln Tyr Ile
                100                 105                 110

Phe Asp Leu Trp Gly Gln Gly Ala Arg Val Thr Val Ser Ser
            115                 120                 125

<210> SEQ ID NO 98
<211> LENGTH: 113
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 98

Asp Ile Val Met Thr Gln Ser Pro Asp Ser Leu Ala Val Ser Pro Gly
1               5                   10                  15

Glu Arg Ala Thr Ile His Cys Lys Ser Ser Gln Thr Leu Leu Tyr Ser
            20                  25                  30

Ser Asn Asn Arg His Ser Ile Ala Trp Tyr Gln Gln Arg Pro Gly Gln
        35                  40                  45

Pro Pro Lys Leu Leu Leu Tyr Trp Ala Ser Met Arg Leu Ser Gly Val
    50                  55                  60

Pro Asp Arg Phe Ser Gly Ser Gly Ser Gly Thr Asp Phe Thr Leu Thr
65                  70                  75                  80

Ile Asn Asn Leu Gln Ala Glu Asp Val Ala Ile Tyr Tyr Cys His Gln
                85                  90                  95

Tyr Ser Ser His Pro Pro Thr Phe Gly His Gly Thr Arg Val Glu Ile
            100                 105                 110

Lys

<210> SEQ ID NO 99
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Gln Val Gln Leu Gln Glu Ser Gly Pro Gly Leu Val Lys Pro Ser Gln
1               5                   10                  15

Thr Leu Ser Leu Ser Cys Thr Val Ser Gly Gly Ser Ser Ser Ser Gly
            20                  25                  30

Ala His Tyr Trp Ser Trp Ile Arg Gln Tyr Pro Gly Lys Gly Leu Glu
        35                  40                  45

Trp Ile Gly Tyr Ile His Tyr Ser Gly Asn Thr Tyr Tyr Asn Pro Ser
    50                  55                  60

Leu Lys Ser Arg Ile Thr Ile Ser Gln His Thr Ser Glu Asn Gln Phe
65                  70                  75                  80

Ser Leu Lys Leu Asn Ser Val Thr Val Ala Asp Thr Ala Val Tyr Tyr
                85                  90                  95

Cys Ala Arg Gly Thr Arg Leu Arg Thr Leu Arg Asn Ala Phe Asp Ile
            100                 105                 110

Trp Gly Gln Gly Thr Met Val Thr Val Ser Ser
            115                 120

<210> SEQ ID NO 100
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gln Ser Val Leu Thr Gln Pro Pro Ser Ala Ser Gly Ser Pro Gly Gln
1               5                   10                  15

```
Ser Val Thr Ile Ser Cys Thr Gly Thr Ser Ser Asp Val Gly Gly Tyr
            20                  25                  30

Asn Tyr Val Ser Trp Tyr Gln His His Pro Gly Lys Ala Pro Lys Leu
            35                  40                  45

Ile Ile Ser Glu Val Asn Asn Arg Pro Ser Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Glu Asp Glu Ala Glu Tyr Tyr Cys Ser Ser Tyr Thr Asp Ile
                85                  90                  95

His Asn Phe Val Phe Gly Gly Gly Thr Lys Leu Thr Val Leu Arg
            100                 105                 110

<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Gly Gly Gly Ser
1               5

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Gly Gly Gly Ser Gly Gly Gly Gly Ser
1               5                   10

<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Gly Gly Gly Ser Gly Gly Gly Gly Ser Gly Gly Gly Gly Ser
1               5                   10                  15

<210> SEQ ID NO 104
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Gly Gly Gly Ser Gly Gly Gly Gly Ser Gly Gly Gly Gly Ser Gly
1               5                   10                  15

Gly Gly Gly Ser
            20

<210> SEQ ID NO 105
```

```
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Leu Thr Val Ser Ser Gly Gly Gly Ser Gly Gly Gly Gly
        115                 120                 125

Ser Gly Gly Gly Gly Ser Gln Ile Val Leu Thr Gln Ser Pro Ala Ile
    130                 135                 140

Met Ser Ala Ser Pro Gly Glu Lys Val Thr Met Thr Cys Ser Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Leu Ala Ser Gly Val Pro
            180                 185                 190

Ala His Phe Arg Gly Ser Gly Ser Gly Thr Ser Tyr Ser Leu Thr Ile
        195                 200                 205

Ser Gly Met Glu Ala Glu Asp Ala Ala Thr Tyr Tyr Cys Gln Gln Trp
    210                 215                 220

Ser Ser Asn Pro Phe Thr Phe Gly Ser Gly Thr Lys Leu Glu Ile Lys
225                 230                 235                 240

<210> SEQ ID NO 106
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
                20                  25                  30

Thr Met His Trp Val Arg Gln Ala Pro Gly Gln Gly Leu Glu Trp Met
            35                  40                  45

Gly Tyr Ile Asn Pro Arg Ser Gly Tyr Thr His Tyr Asn Gln Lys Leu
    50                  55                  60

Lys Asp Lys Ala Thr Leu Thr Ala Asp Lys Ser Ala Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Ser Ala Tyr Tyr Asp Tyr Asp Gly Phe Ala Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Ser Asp Ile Gln Met Thr Gln Ser Pro Ser
130                 135                 140

Ser Leu Ser Ala Ser Val Gly Asp Arg Val Thr Ile Thr Cys Ser Ala
145                 150                 155                 160

Ser Ser Ser Val Ser Tyr Met Asn Trp Tyr Gln Gln Lys Pro Gly Lys
                165                 170                 175

Ala Pro Lys Arg Leu Ile Tyr Asp Thr Ser Lys Leu Ala Ser Gly Val
            180                 185                 190

Pro Ser Arg Phe Ser Gly Ser Gly Ser Gly Thr Asp Phe Thr Leu Thr
                195                 200                 205

Ile Ser Ser Leu Gln Pro Glu Asp Phe Ala Thr Tyr Tyr Cys Gln Gln
    210                 215                 220

Trp Ser Ser Asn Pro Pro Thr Phe Gly Gly Gly Thr Lys Leu Glu Ile
225                 230                 235                 240

Lys

<210> SEQ ID NO 107
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Thr Thr Tyr Ala Asp Ser Val
    50                  55                  60

Lys Gly Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser Gly Gly Gly Ser Gly
        115                 120                 125

Gly Gly Gly Ser Gly Gly Gly Ser Asp Ile Gln Met Thr Gln Ser
130                 135                 140

Pro Ser Ser Leu Ser Ala Ser Val Gly Asp Arg Val Thr Ile Thr Cys
145                 150                 155                 160

Arg Ala Ser Gln Asp Ile Arg Asn Tyr Leu Asn Trp Tyr Gln Gln Lys
                165                 170                 175

Pro Gly Lys Ala Pro Lys Leu Leu Ile Tyr Tyr Thr Ser Arg Leu Glu
            180                 185                 190
```

Ser Gly Val Pro Ser Arg Phe Ser Gly Ser Gly Ser Gly Thr Asp Tyr
            195                 200                 205

Thr Leu Thr Ile Ser Ser Leu Gln Pro Glu Asp Phe Ala Thr Tyr Tyr
            210                 215                 220

Cys Gln Gln Gly Asn Thr Leu Pro Trp Thr Phe Gly Gln Gly Thr Lys
225                 230                 235                 240

Val Glu Ile Lys

<210> SEQ ID NO 108
<211> LENGTH: 383
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
            20                  25                  30

Thr Met His Trp Val Arg Gln Ala Pro Gly Gln Gly Leu Glu Trp Met
        35                  40                  45

Gly Tyr Ile Asn Pro Arg Ser Gly Tyr Thr His Tyr Asn Gln Lys Leu
    50                  55                  60

Lys Asp Lys Ala Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala Tyr Tyr Asp Tyr Asp Gly Phe Ala Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Ser Ala
145                 150                 155                 160

Ser Ser Ser Val Ser Tyr Met Asn Trp Tyr Gln Gln Lys Pro Gly Lys
                165                 170                 175

Ala Pro Lys Arg Leu Ile Tyr Asp Thr Ser Lys Leu Ala Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Trp Ser Ser Asn Pro Pro Thr Phe Gly Gly Gly Thr Lys Leu Glu Ile
225                 230                 235                 240

Lys Gly Gly Gly Gly Ser Gln Glu Asp Glu Arg Ile Val Leu Val Asp
                245                 250                 255

Asn Lys Cys Lys Cys Ala Arg Ile Thr Ser Arg Ile Ile Arg Ser Ser
            260                 265                 270

Glu Asp Pro Asn Glu Asp Ile Val Glu Arg Asn Ile Arg Ile Ile Val
        275                 280                 285

Pro Leu Asn Asn Arg Glu Asn Ile Ser Asp Pro Thr Ser Pro Leu Arg
    290                 295                 300

```
Thr Arg Phe Val Tyr His Leu Ser Asp Leu Cys Lys Cys Asp Pro
305                 310                 315                 320

Thr Glu Val Glu Leu Asp Asn Gln Ile Val Thr Ala Thr Gln Ser Asn
                325                 330                 335

Ile Cys Asp Glu Asp Ser Ala Thr Glu Thr Cys Tyr Thr Tyr Asp Arg
            340                 345                 350

Asn Lys Cys Tyr Thr Ala Val Val Pro Leu Val Tyr Gly Gly Glu Thr
            355                 360                 365

Lys Met Val Glu Thr Ala Leu Thr Pro Asp Ala Cys Tyr Pro Asp
            370                 375                 380

<210> SEQ ID NO 109
<211> LENGTH: 388
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
                20                  25                  30

Thr Met His Trp Val Arg Gln Ala Pro Gly Gln Gly Leu Glu Trp Met
            35                  40                  45

Gly Tyr Ile Asn Pro Arg Ser Gly Tyr Thr His Tyr Asn Gln Lys Leu
50                  55                  60

Lys Asp Lys Ala Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala Tyr Tyr Asp Tyr Asp Gly Phe Ala Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
130                 135                 140

Ser Leu Ser Ala Ser Val Gly Asp Arg Val Thr Ile Thr Cys Ser Ala
145                 150                 155                 160

Ser Ser Ser Val Ser Tyr Met Asn Trp Tyr Gln Gln Lys Pro Gly Lys
                165                 170                 175

Ala Pro Lys Arg Leu Ile Tyr Asp Thr Ser Lys Leu Ala Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
210                 215                 220

Trp Ser Ser Asn Pro Pro Thr Phe Gly Gly Gly Thr Lys Leu Glu Ile
225                 230                 235                 240

Lys Gly Gly Gly Gly Ser Gly Gly Gly Ser Gln Glu Asp Glu Arg
                245                 250                 255

Ile Val Leu Val Asp Asn Lys Cys Lys Cys Ala Arg Ile Thr Ser Arg
            260                 265                 270

Ile Ile Arg Ser Ser Glu Asp Pro Asn Glu Asp Ile Val Glu Arg Asn
```

```
            275                 280                 285
Ile Arg Ile Ile Val Pro Leu Asn Asn Arg Glu Asn Ile Ser Asp Pro
            290                 295                 300

Thr Ser Pro Leu Arg Thr Arg Phe Val Tyr His Leu Ser Asp Leu Cys
305                 310                 315                 320

Lys Lys Cys Asp Pro Thr Glu Val Glu Leu Asp Asn Gln Ile Val Thr
                325                 330                 335

Ala Thr Gln Ser Asn Ile Cys Asp Glu Asp Ser Ala Thr Glu Thr Cys
                340                 345                 350

Tyr Thr Tyr Asp Arg Asn Lys Cys Tyr Thr Ala Val Val Pro Leu Val
                355                 360                 365

Tyr Gly Gly Glu Thr Lys Met Val Glu Thr Ala Leu Thr Pro Asp Ala
                370                 375                 380

Cys Tyr Pro Asp
385

<210> SEQ ID NO 110
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
                20                  25                  30

Thr Met His Trp Val Arg Gln Ala Pro Gly Gln Gly Leu Glu Trp Met
            35                  40                  45

Gly Tyr Ile Asn Pro Arg Ser Gly Tyr Thr His Tyr Asn Gln Lys Leu
    50                  55                  60

Lys Asp Lys Ala Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala Tyr Tyr Asp Tyr Asp Gly Phe Ala Tyr Trp Gly Gln
                100                 105                 110

Gly Thr Leu Val Thr Val Ser Ser Gly Gly Gly Gly Ser Gly Gly Gly
            115                 120                 125

Gly Ser Gly Gly Gly Ser Asp Ile Gln Met Thr Gln Ser Pro Ser
    130                 135                 140

Ser Leu Ser Ala Ser Val Gly Asp Arg Val Thr Ile Thr Cys Ser Ala
145                 150                 155                 160

Ser Ser Ser Val Ser Tyr Met Asn Trp Tyr Gln Gln Lys Pro Gly Lys
                165                 170                 175

Ala Pro Lys Arg Leu Ile Tyr Asp Thr Ser Lys Leu Ala Ser Gly Val
                180                 185                 190

Pro Ser Arg Phe Ser Gly Ser Gly Ser Gly Thr Asp Phe Thr Leu Thr
            195                 200                 205

Ile Ser Ser Leu Gln Pro Glu Asp Phe Ala Thr Tyr Tyr Cys Gln Gln
    210                 215                 220

Trp Ser Ser Asn Pro Pro Thr Phe Gly Gly Gly Thr Lys Leu Glu Ile
225                 230                 235                 240
```

```
Lys Gly Gly Gly Gly Ser Gly Gly Gly Ser Gly Gly Gly Ser
                245                 250                 255

Gln Glu Asp Glu Arg Ile Val Leu Val Asp Asn Lys Cys Lys Cys Ala
            260                 265                 270

Arg Ile Thr Ser Arg Ile Ile Arg Ser Ser Glu Asp Pro Asn Glu Asp
            275                 280                 285

Ile Val Glu Arg Asn Ile Arg Ile Ile Val Pro Leu Asn Asn Arg Glu
            290                 295                 300

Asn Ile Ser Asp Pro Thr Ser Pro Leu Arg Thr Arg Phe Val Tyr His
305                 310                 315                 320

Leu Ser Asp Leu Cys Lys Lys Cys Asp Pro Thr Glu Val Glu Leu Asp
                325                 330                 335

Asn Gln Ile Val Thr Ala Thr Gln Ser Asn Ile Cys Asp Glu Asp Ser
            340                 345                 350

Ala Thr Glu Thr Cys Tyr Thr Tyr Asp Arg Asn Lys Cys Tyr Thr Ala
            355                 360                 365

Val Val Pro Leu Val Tyr Gly Gly Glu Thr Lys Met Val Glu Thr Ala
            370                 375                 380

Leu Thr Pro Asp Ala Cys Tyr Pro Asp
385                 390

<210> SEQ ID NO 111
<211> LENGTH: 398
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
                20                  25                  30

Thr Met His Trp Val Arg Gln Ala Pro Gly Gln Gly Leu Glu Trp Met
            35                  40                  45

Gly Tyr Ile Asn Pro Arg Ser Gly Tyr Thr His Tyr Asn Gln Lys Leu
        50                  55                  60

Lys Asp Lys Ala Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala Tyr Tyr Asp Tyr Asp Gly Phe Ala Tyr Trp Gly Gln
            100                 105                 110

Gly Thr Leu Val Thr Val Ser Ser Gly Gly Gly Gly Ser Gly Gly Gly
            115                 120                 125

Gly Ser Gly Gly Gly Gly Ser Asp Ile Gln Met Thr Gln Ser Pro Ser
        130                 135                 140

Ser Leu Ser Ala Ser Val Gly Asp Arg Val Thr Ile Thr Cys Ser Ala
145                 150                 155                 160

Ser Ser Ser Val Ser Tyr Met Asn Trp Tyr Gln Gln Lys Pro Gly Lys
                165                 170                 175

Ala Pro Lys Arg Leu Ile Tyr Asp Thr Ser Lys Leu Ala Ser Gly Val
            180                 185                 190

Pro Ser Arg Phe Ser Gly Ser Gly Ser Gly Thr Asp Phe Thr Leu Thr
            195                 200                 205
```

Ile Ser Ser Leu Gln Pro Glu Asp Phe Ala Thr Tyr Tyr Cys Gln Gln
    210                 215                 220

Trp Ser Ser Asn Pro Pro Thr Phe Gly Gly Gly Thr Lys Leu Glu Ile
225                 230                 235                 240

Lys Gly Gly Gly Ser Gly Gly Gly Ser Gly Gly Gly Ser
            245                 250                 255

Gly Gly Gly Gly Ser Gln Glu Asp Glu Arg Ile Val Leu Val Asp Asn
            260                 265                 270

Lys Cys Lys Cys Ala Arg Ile Thr Ser Arg Ile Ile Arg Ser Ser Glu
        275                 280                 285

Asp Pro Asn Glu Asp Ile Val Glu Arg Asn Ile Arg Ile Val Pro
290                 295                 300

Leu Asn Asn Arg Glu Asn Ile Ser Asp Pro Thr Ser Pro Leu Arg Thr
305                 310                 315                 320

Arg Phe Val Tyr His Leu Ser Asp Leu Cys Lys Lys Cys Asp Pro Thr
                325                 330                 335

Glu Val Glu Leu Asp Asn Gln Ile Val Thr Ala Thr Gln Ser Asn Ile
            340                 345                 350

Cys Asp Glu Asp Ser Ala Thr Glu Thr Cys Tyr Thr Tyr Asp Arg Asn
        355                 360                 365

Lys Cys Tyr Thr Ala Val Val Pro Leu Val Tyr Gly Gly Glu Thr Lys
    370                 375                 380

Met Val Glu Thr Ala Leu Thr Pro Asp Ala Cys Tyr Pro Asp
385                 390                 395

<210> SEQ ID NO 112
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Glu Val Gln Leu Val Glu Ser Gly Gly Glu Leu Val Gln Ala Gly Gly
1               5                   10                  15

Ser Leu Arg Leu Ser Cys Ala Ala Ser Gly Leu Thr Phe Ser Ser Tyr
            20                  25                  30

Asn Met Gly Trp Phe Arg Arg Ala Pro Gly Lys Glu Arg Glu Phe Val
        35                  40                  45

Ala Ser Ile Thr Trp Ser Gly Arg Asp Thr Phe Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Lys Pro Glu Asp Thr Ala Val Tyr Tyr Cys
                85                  90                  95

Ala Ala Asn Pro Trp Pro Val Ala Ala Pro Arg Ser Gly Thr Tyr Trp
            100                 105                 110

Gly Gln Gly Thr Gln Val Thr Val Ser Ser
        115                 120

<210> SEQ ID NO 113
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 113

```
Gln Val Gln Leu Val Gln Ser Gly Gly Gln Met Lys Lys Pro Gly Glu
1               5                   10                  15

Ser Met Arg Ile Ser Cys Gln Ala Ser Gly Tyr Glu Phe Ile Asp Cys
            20                  25                  30

Thr Leu Asn Trp Val Arg Leu Ala Pro Gly Arg Arg Pro Glu Trp Met
        35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Ala Asp Asp Thr Ala Val Tyr Tyr Cys
                85                  90                  95

Thr Arg Gly Lys Asn Cys Asp Tyr Asn Trp Asp Phe Glu His Trp Gly
            100                 105                 110

Arg Gly Thr Pro Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 114
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Gln Val Gln Leu Val Gln Ser Gly Gly Gln Met Lys Lys Pro Gly Glu
1               5                   10                  15

Ser Met Arg Ile Ser Cys Gln Ala Ser Gly Tyr Glu Phe Ile Asp Cys
            20                  25                  30

Thr Leu Asn Trp Val Arg Leu Ala Pro Gly Arg Arg Pro Glu Trp Met
        35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Ala Asp Thr Ala Val Tyr Tyr Cys
                85                  90                  95

Thr Arg Gly Lys Asn Cys Asp Tyr Asn Trp Asp Phe Glu His Trp Gly
            100                 105                 110

Arg Gly Thr Pro Val Thr Val Ser Ser Gly Ser Ala Ser Ala Pro Thr
        115                 120                 125

Leu Phe Pro Leu Val Ser Cys Glu Asn Ser Pro Ser Asp Thr Ser Ser
130                 135                 140

Val Ala Val Gly Cys Leu Ala Gln Asp Phe Leu Pro Asp Ser Ile Thr
145                 150                 155                 160

Phe Ser Trp Lys Tyr Lys Asn Asn Ser Asp Ile Ser Ser Thr Arg Gly
                165                 170                 175

Phe Pro Ser Val Leu Arg Gly Gly Lys Tyr Ala Ala Thr Ser Gln Val
            180                 185                 190

Leu Leu Pro Ser Lys Asp Val Met Gln Gly Thr Asp Glu His Val Val
        195                 200                 205

Cys Lys Val Gln His Pro Asn Gly Asn Lys Glu Lys Asn Val Pro Leu
    210                 215                 220

Pro Val Ile Ala Glu Leu Pro Pro Lys Val Ser Val Phe Val Pro Pro
225                 230                 235                 240

Arg Asp Gly Phe Phe Gly Asn Pro Arg Lys Ser Lys Leu Ile Cys Gln
                245                 250                 255

Ala Thr Gly Phe Ser Pro Arg Gln Ile Gln Val Ser Trp Leu Arg Glu
            260                 265                 270

Gly Lys Gln Val Gly Ser Gly Val Thr Thr Asp Gln Val Gln Ala Glu
        275                 280                 285

Ala Lys Glu Ser Gly Pro Thr Thr Tyr Lys Val Thr Ser Thr Leu Thr
    290                 295                 300

Ile Lys Glu Ser Asp Trp Leu Ser Gln Ser Met Phe Thr Cys Arg Val
305                 310                 315                 320

Asp His Arg Gly Leu Thr Phe Gln Gln Asn Ala Ser Ser Met Cys Val
            325                 330                 335

Pro Asp Gln Asp Thr Ala Ile Arg Val Phe Ala Ile Pro Pro Ser Phe
        340                 345                 350

Ala Ser Ile Phe Leu Thr Lys Ser Thr Lys Leu Thr Cys Leu Val Thr
            355                 360                 365

Asp Leu Thr Thr Tyr Asp Ser Val Thr Ile Ser Trp Thr Arg Gln Asn
        370                 375                 380

Gly Glu Ala Val Lys Thr His Thr Asn Ile Ser Glu Ser His Pro Asn
385                 390                 395                 400

Ala Thr Phe Ser Ala Val Gly Glu Ala Ser Ile Cys Glu Asp Asp Trp
            405                 410                 415

Asn Ser Gly Glu Arg Phe Thr Cys Thr Val Thr His Thr Asp Leu Pro
            420                 425                 430

Ser Pro Leu Lys Gln Thr Ile Ser Arg Pro Lys Gly Val Ala Leu His
        435                 440                 445

Arg Pro Asp Val Tyr Leu Leu Pro Pro Ala Arg Glu Gln Leu Asn Leu
450                 455                 460

Arg Glu Ser Ala Thr Ile Thr Cys Leu Val Thr Gly Phe Ser Pro Ala
465                 470                 475                 480

Asp Val Phe Val Gln Trp Met Gln Arg Gly Gln Pro Leu Ser Pro Glu
            485                 490                 495

Lys Tyr Val Thr Ser Ala Pro Met Pro Glu Pro Gln Ala Pro Gly Arg
        500                 505                 510

Tyr Phe Ala His Ser Ile Leu Thr Val Ser Glu Glu Glu Trp Asn Thr
            515                 520                 525

Gly Glu Thr Tyr Thr Cys Val Val Ala His Glu Ala Leu Pro Asn Arg
530                 535                 540

Val Thr Glu Arg Thr Val Asp Lys Ser Thr Gly Lys Pro Thr Leu Tyr
545                 550                 555                 560

Asn Val Ser Leu Val Met Ser Asp Thr Ala Gly Thr Cys Tyr
            565                 570

<210> SEQ ID NO 115
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Arg Asn Leu Glu Ser Gly Asp
65                  70                  75                  80

Phe Gly Leu Tyr Tyr Cys Gln Gln Tyr Glu Phe Phe Gly Gln Gly Thr

```
                    85                  90                  95
Lys Val Gln Val Asp Ile Lys Arg Thr Val Ala Ala Pro Ser Val Phe
                100                 105                 110

Ile Phe Pro Pro Ser Asp Glu Gln Leu Lys Ser Gly Thr Ala Ser Val
                115                 120                 125

Val Cys Leu Leu Asn Asn Phe Tyr Pro Arg Glu Ala Lys Val Gln Trp
            130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
                165                 170                 175

Leu Ser Lys Ala Asp Tyr Glu Lys His Lys Val Tyr Ala Cys Glu Val
            180                 185                 190

Thr His Gln Gly Leu Ser Ser Pro Val Thr Lys Ser Phe Asn Arg Gly
                195                 200                 205

Glu Cys
    210

<210> SEQ ID NO 116
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Glu Val Gln Leu Val Glu Ser Gly Gly Gly Leu Val Lys Ala Gly Gly
1               5                   10                  15

Ser Leu Ile Leu Ser Cys Gly Val Ser Asn Phe Arg Ile Ser Ala His
                20                  25                  30

Thr Met Asn Trp Val Arg Arg Val Pro Gly Gly Gly Leu Glu Trp Val
            35                  40                  45

Ala Ser Ile Ser Thr Ser Ser Thr Tyr Arg Asp Tyr Ala Asp Ala Val
        50                  55                  60

Lys Gly Arg Phe Thr Val Ser Arg Asp Asp Leu Glu Asp Phe Val Tyr
65                  70                  75                  80

Leu Gln Met His Lys Met Arg Val Glu Asp Thr Ala Ile Tyr Tyr Cys
                85                  90                  95

Ala Arg Lys Gly Ser Asp Arg Leu Ser Asp Asn Asp Pro Phe Asp Ala
                100                 105                 110

Trp Gly Pro Gly Thr Val Val Thr Val Ser Pro Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
        210                 215                 220
```

```
Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
450

<210> SEQ ID NO 117
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Glu Val Gln Leu Val Glu Ser Gly Gly Gly Leu Val Lys Ala Gly Gly
1               5                   10                  15

Ser Leu Ile Leu Ser Cys Gly Val Ser Asn Phe Arg Ile Ser Ala His
            20                  25                  30

Thr Met Asn Trp Val Arg Arg Val Pro Gly Gly Gly Leu Glu Trp Val
        35                  40                  45

Ala Ser Ile Ser Thr Ser Ser Thr Tyr Arg Asp Tyr Ala Asp Ala Val
    50                  55                  60

Lys Gly Arg Phe Thr Val Ser Arg Asp Asp Leu Glu Asp Phe Val Tyr
65                  70                  75                  80

Leu Gln Met His Lys Met Arg Val Glu Asp Thr Ala Ile Tyr Tyr Cys
                85                  90                  95

Ala Arg Lys Gly Ser Asp Arg Leu Ser Asp Asn Asp Pro Phe Asp Ala
            100                 105                 110

Trp Gly Pro Gly Thr Val Val Thr Val Ser Pro Ala Ser Thr Lys Gly
        115                 120                 125
```

```
Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly
    450

<210> SEQ ID NO 118
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Asp Ile Gln Met Thr Gln Ser Pro Ser Thr Leu Ser Ala Ser Val Gly
1               5                   10                  15

Asp Thr Ile Thr Ile Thr Cys Arg Ala Ser Gln Ser Ile Glu Thr Trp
```

```
                20                  25                  30
Leu Ala Trp Tyr Gln Gln Lys Pro Gly Lys Ala Pro Lys Leu Leu Ile
            35                  40                  45

Tyr Lys Ala Ser Thr Leu Lys Thr Gly Val Pro Ser Arg Phe Ser Gly
 50                  55                  60

Ser Gly Ser Gly Thr Glu Phe Thr Leu Thr Ile Ser Gly Leu Gln Phe
 65                  70                  75                  80

Asp Asp Phe Ala Thr Tyr His Cys Gln His Tyr Ala Gly Tyr Ser Ala
                85                  90                  95

Thr Phe Gly Gln Gly Thr Arg Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 119
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Gln Val Gln Leu Gln Glu Ser Gly Pro Gly Leu Val Lys Pro Ser Gln
 1               5                  10                  15

Thr Leu Ser Leu Ser Cys Thr Val Ser Gly Gly Ser Ser Ser Ser Gly
            20                  25                  30

Ala His Tyr Trp Ser Trp Ile Arg Gln Tyr Pro Gly Lys Gly Leu Glu
            35                  40                  45

Trp Ile Gly Tyr Ile His Tyr Ser Gly Asn Thr Tyr Tyr Asn Pro Ser
 50                  55                  60

Leu Lys Ser Arg Ile Thr Ile Ser Gln His Thr Ser Glu Asn Gln Phe
 65                  70                  75                  80

Ser Leu Lys Leu Asn Ser Val Thr Val Ala Asp Thr Ala Val Tyr Tyr
                85                  90                  95

Cys Ala Arg Gly Thr Arg Leu Arg Thr Leu Arg Asn Ala Phe Asp Ile
            100                 105                 110

Trp Gly Gln Gly Thr Met Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160
```

```
Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
    195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 120
<211> LENGTH: 576
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Val Gln Leu Gln Glu Ser Gly Pro Gly Leu Val Lys Pro Ser Gln
1               5                   10                  15

Thr Leu Ser Leu Ser Cys Thr Val Ser Gly Gly Ser Ser Ser Gly
            20                  25                  30

Ala His Tyr Trp Ser Trp Ile Arg Gln Tyr Pro Gly Lys Gly Leu Glu
        35                  40                  45

Trp Ile Gly Tyr Ile His Tyr Ser Gly Asn Thr Tyr Tyr Asn Pro Ser
    50                  55                  60
```

```
Leu Lys Ser Arg Ile Thr Ile Ser Gln His Thr Ser Glu Asn Gln Phe
 65                  70                  75                  80

Ser Leu Lys Leu Asn Ser Val Thr Val Ala Asp Thr Ala Val Tyr Tyr
                 85                  90                  95

Cys Ala Arg Gly Thr Arg Leu Arg Thr Leu Arg Asn Ala Phe Asp Ile
            100                 105                 110

Trp Gly Gln Gly Thr Met Val Thr Val Ser Ser Gly Ser Ala Ser Ala
            115                 120                 125

Pro Thr Leu Phe Pro Leu Val Ser Cys Glu Asn Ser Pro Ser Asp Thr
        130                 135                 140

Ser Ser Val Ala Val Gly Cys Leu Ala Gln Asp Phe Leu Pro Asp Ser
145                 150                 155                 160

Ile Thr Phe Ser Trp Lys Tyr Lys Asn Asn Ser Asp Ile Ser Ser Thr
                165                 170                 175

Arg Gly Phe Pro Ser Val Leu Arg Gly Gly Lys Tyr Ala Ala Thr Ser
            180                 185                 190

Gln Val Leu Leu Pro Ser Lys Asp Val Met Gln Gly Thr Asp Glu His
        195                 200                 205

Val Val Cys Lys Val Gln His Pro Asn Gly Asn Lys Glu Lys Asn Val
210                 215                 220

Pro Leu Pro Val Ile Ala Glu Leu Pro Pro Lys Val Ser Val Phe Val
225                 230                 235                 240

Pro Pro Arg Asp Gly Phe Phe Gly Asn Pro Arg Lys Ser Lys Leu Ile
            245                 250                 255

Cys Gln Ala Thr Gly Phe Ser Pro Arg Gln Ile Gln Val Ser Trp Leu
            260                 265                 270

Arg Glu Gly Lys Gln Val Gly Ser Gly Val Thr Thr Asp Gln Val Gln
            275                 280                 285

Ala Glu Ala Lys Glu Ser Gly Pro Thr Thr Tyr Lys Val Thr Ser Thr
            290                 295                 300

Leu Thr Ile Lys Glu Ser Asp Trp Leu Ser Gln Ser Met Phe Thr Cys
305                 310                 315                 320

Arg Val Asp His Arg Gly Leu Thr Phe Gln Gln Asn Ala Ser Ser Met
                325                 330                 335

Cys Val Pro Asp Gln Asp Thr Ala Ile Arg Val Phe Ala Ile Pro Pro
            340                 345                 350

Ser Phe Ala Ser Ile Phe Leu Thr Lys Ser Thr Lys Leu Thr Cys Leu
        355                 360                 365

Val Thr Asp Leu Thr Thr Tyr Asp Ser Val Thr Ile Ser Trp Thr Arg
        370                 375                 380

Gln Asn Gly Glu Ala Val Lys Thr His Thr Asn Ile Ser Glu Ser His
385                 390                 395                 400

Pro Asn Ala Thr Phe Ser Ala Val Gly Glu Ala Ser Ile Cys Glu Asp
            405                 410                 415

Asp Trp Asn Ser Gly Glu Arg Phe Thr Cys Thr Val Thr His Thr Asp
            420                 425                 430

Leu Pro Ser Pro Leu Lys Gln Thr Ile Ser Arg Pro Lys Gly Val Ala
            435                 440                 445

Leu His Arg Pro Asp Val Tyr Leu Leu Pro Pro Ala Arg Glu Gln Leu
        450                 455                 460

Asn Leu Arg Glu Ser Ala Thr Ile Thr Cys Leu Val Thr Gly Phe Ser
465                 470                 475                 480
```

```
Pro Ala Asp Val Phe Val Gln Trp Met Gln Arg Gly Gln Pro Leu Ser
            485                 490                 495

Pro Glu Lys Tyr Val Thr Ser Ala Pro Met Pro Glu Pro Gln Ala Pro
        500                 505                 510

Gly Arg Tyr Phe Ala His Ser Ile Leu Thr Val Ser Glu Glu Trp
        515                 520                 525

Asn Thr Gly Glu Thr Tyr Thr Cys Val Val Ala His Glu Ala Leu Pro
        530                 535                 540

Asn Arg Val Thr Glu Arg Thr Val Asp Lys Ser Thr Gly Lys Pro Thr
545                 550                 555                 560

Leu Tyr Asn Val Ser Leu Val Met Ser Asp Thr Ala Gly Thr Cys Tyr
            565                 570                 575

<210> SEQ ID NO 121
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gln Ser Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln His Pro Gly Lys Ala Pro Lys Leu
        35                  40                  45

Ile Ile Ser Glu Val Asn Asn Arg Pro Ser Gly Val Pro Asp Arg Phe
 50                 55                  60

Ser Gly Ser Lys Ser Gly Asn Thr Ala Ser Leu Thr Val Ser Gly Leu
65                  70                  75                  80

Gln Ala Glu Asp Glu Ala Glu Tyr Tyr Cys Ser Ser Tyr Thr Asp Ile
                85                  90                  95

His Asn Phe Val Phe Gly Gly Gly Thr Lys Leu Thr Val Leu Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 122
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 122

```
Gln Val Gln Leu Val Gln Ser Gly Gly Val Phe Lys Pro Gly Gly
1               5                  10                  15
Ser Leu Arg Leu Ser Cys Glu Ala Ser Gly Phe Thr Phe Thr Glu Tyr
            20                  25                  30
Tyr Met Thr Trp Val Arg Gln Ala Pro Gly Lys Gly Leu Glu Trp Leu
        35                  40                  45
Ala Tyr Ile Ser Lys Asn Gly Glu Tyr Ser Lys Tyr Ser Pro Ser Ser
    50                  55                  60
Asn Gly Arg Phe Thr Ile Ser Arg Asp Asn Ala Lys Asn Ser Val Phe
65                  70                  75                  80
Leu Gln Leu Asp Arg Leu Ser Ala Asp Thr Ala Val Tyr Tyr Cys
                85                  90                  95
Ala Arg Ala Asp Gly Leu Thr Tyr Phe Ser Glu Leu Leu Gln Tyr Ile
            100                 105                 110
Phe Asp Leu Trp Gly Gln Gly Ala Arg Val Thr Val Ser Ser Ala Ser
        115                 120                 125
Thr Lys Gly Pro Ser Val Phe Pro Leu Ala Pro Ser Ser Lys Ser Thr
    130                 135                 140
Ser Gly Gly Thr Ala Ala Leu Gly Cys Leu Val Lys Asp Tyr Phe Pro
145                 150                 155                 160
Glu Pro Val Thr Val Ser Trp Asn Ser Gly Ala Leu Thr Ser Gly Val
                165                 170                 175
His Thr Phe Pro Ala Val Leu Gln Ser Ser Gly Leu Tyr Ser Leu Ser
            180                 185                 190
Ser Val Val Thr Val Pro Ser Ser Ser Leu Gly Thr Gln Thr Tyr Ile
        195                 200                 205
Cys Asn Val Asn His Lys Pro Ser Asn Thr Lys Val Asp Lys Lys Val
    210                 215                 220
Glu Pro Lys Ser Cys Asp Lys Thr His Thr Cys Pro Pro Cys Pro Ala
225                 230                 235                 240
Pro Glu Leu Leu Gly Gly Pro Ser Val Phe Leu Phe Pro Pro Lys Pro
                245                 250                 255
Lys Asp Thr Leu Met Ile Ser Arg Thr Pro Glu Val Thr Cys Val Val
            260                 265                 270
Val Asp Val Ser His Glu Asp Pro Glu Val Lys Phe Asn Trp Tyr Val
        275                 280                 285
Asp Gly Val Glu Val His Asn Ala Lys Thr Lys Pro Arg Glu Glu Gln
    290                 295                 300
Tyr Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Ala
                325                 330                 335
Leu Pro Ala Pro Ile Glu Lys Thr Ile Ser Lys Ala Lys Gly Gln Pro
            340                 345                 350
Arg Glu Pro Gln Val Tyr Thr Leu Pro Pro Ser Arg Asp Glu Leu Thr
        355                 360                 365
Lys Asn Gln Val Ser Leu Thr Cys Leu Val Lys Gly Phe Tyr Pro Ser
    370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Tyr
```

```
                     405                 410                 415
Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly
            450                 455
```

<210> SEQ ID NO 123
<211> LENGTH: 579
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

```
Gln Val Gln Leu Val Gln Ser Gly Gly Gly Val Phe Lys Pro Gly Gly
1               5                   10                  15

Ser Leu Arg Leu Ser Cys Glu Ala Ser Gly Phe Thr Phe Thr Glu Tyr
            20                  25                  30

Tyr Met Thr Trp Val Arg Gln Ala Pro Gly Lys Gly Leu Glu Trp Leu
            35                  40                  45

Ala Tyr Ile Ser Lys Asn Gly Glu Tyr Ser Lys Tyr Ser Pro Ser Ser
    50                  55                  60

Asn Gly Arg Phe Thr Ile Ser Arg Asp Asn Ala Lys Asn Ser Val Phe
65                  70                  75                  80

Leu Gln Leu Asp Arg Leu Ser Ala Asp Thr Ala Val Tyr Tyr Cys
                85                  90                  95

Ala Arg Ala Asp Gly Leu Thr Tyr Phe Ser Glu Leu Leu Gln Tyr Ile
            100                 105                 110

Phe Asp Leu Trp Gly Gln Gly Ala Arg Val Thr Val Ser Ser Gly Ser
            115                 120                 125

Ala Ser Ala Pro Thr Leu Phe Pro Leu Val Ser Cys Glu Asn Ser Pro
            130                 135                 140

Ser Asp Thr Ser Ser Val Ala Val Gly Cys Leu Ala Gln Asp Phe Leu
145                 150                 155                 160

Pro Asp Ser Ile Thr Phe Ser Trp Lys Tyr Lys Asn Asn Ser Asp Ile
                165                 170                 175

Ser Ser Thr Arg Gly Phe Pro Ser Val Leu Arg Gly Gly Lys Tyr Ala
            180                 185                 190

Ala Thr Ser Gln Val Leu Leu Pro Ser Lys Asp Val Met Gln Gly Thr
            195                 200                 205

Asp Glu His Val Val Cys Lys Val Gln His Pro Asn Gly Asn Lys Glu
            210                 215                 220

Lys Asn Val Pro Leu Pro Val Ile Ala Glu Leu Pro Pro Lys Val Ser
225                 230                 235                 240

Val Phe Val Pro Pro Arg Asp Gly Phe Phe Gly Asn Pro Arg Lys Ser
                245                 250                 255

Lys Leu Ile Cys Gln Ala Thr Gly Phe Ser Pro Arg Gln Ile Gln Val
            260                 265                 270

Ser Trp Leu Arg Glu Gly Lys Gln Val Gly Ser Gly Val Thr Thr Asp
            275                 280                 285

Gln Val Gln Ala Glu Ala Lys Glu Ser Gly Pro Thr Thr Tyr Lys Val
            290                 295                 300
```

Thr Ser Thr Leu Thr Ile Lys Glu Ser Asp Trp Leu Ser Gln Ser Met
305                 310                 315                 320

Phe Thr Cys Arg Val Asp His Arg Gly Leu Thr Phe Gln Gln Asn Ala
            325                 330                 335

Ser Ser Met Cys Val Pro Asp Gln Asp Thr Ala Ile Arg Val Phe Ala
            340                 345                 350

Ile Pro Pro Ser Phe Ala Ser Ile Phe Leu Thr Lys Ser Thr Lys Leu
        355                 360                 365

Thr Cys Leu Val Thr Asp Leu Thr Thr Tyr Asp Ser Val Thr Ile Ser
    370                 375                 380

Trp Thr Arg Gln Asn Gly Glu Ala Val Lys Thr His Thr Asn Ile Ser
385                 390                 395                 400

Glu Ser His Pro Asn Ala Thr Phe Ser Ala Val Gly Glu Ala Ser Ile
                405                 410                 415

Cys Glu Asp Asp Trp Asn Ser Gly Glu Arg Phe Thr Cys Thr Val Thr
            420                 425                 430

His Thr Asp Leu Pro Ser Pro Leu Lys Gln Thr Ile Ser Arg Pro Lys
        435                 440                 445

Gly Val Ala Leu His Arg Pro Asp Val Tyr Leu Leu Pro Pro Ala Arg
450                 455                 460

Glu Gln Leu Asn Leu Arg Glu Ser Ala Thr Ile Thr Cys Leu Val Thr
465                 470                 475                 480

Gly Phe Ser Pro Ala Asp Val Phe Val Gln Trp Met Gln Arg Gly Gln
                485                 490                 495

Pro Leu Ser Pro Glu Lys Tyr Val Thr Ser Ala Pro Met Pro Glu Pro
            500                 505                 510

Gln Ala Pro Gly Arg Tyr Phe Ala His Ser Ile Leu Thr Val Ser Glu
        515                 520                 525

Glu Glu Trp Asn Thr Gly Glu Thr Tyr Thr Cys Val Val Ala His Glu
    530                 535                 540

Ala Leu Pro Asn Arg Val Thr Glu Arg Thr Val Asp Lys Ser Thr Gly
545                 550                 555                 560

Lys Pro Thr Leu Tyr Asn Val Ser Leu Val Met Ser Asp Thr Ala Gly
                565                 570                 575

Thr Cys Tyr

<210> SEQ ID NO 124
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 124

Asp Ile Val Met Thr Gln Ser Pro Asp Ser Leu Ala Val Ser Pro Gly
1               5                   10                  15

Glu Arg Ala Thr Ile His Cys Lys Ser Ser Gln Thr Leu Leu Tyr Ser
            20                  25                  30

Ser Asn Asn Arg His Ser Ile Ala Trp Tyr Gln Gln Arg Pro Gly Gln
        35                  40                  45

Pro Pro Lys Leu Leu Leu Tyr Trp Ala Ser Met Arg Leu Ser Gly Val
    50                  55                  60

Pro Asp Arg Phe Ser Gly Ser Gly Ser Gly Thr Asp Phe Thr Leu Thr
65                  70                  75                  80

```
Ile Asn Asn Leu Gln Ala Glu Asp Val Ala Ile Tyr Tyr Cys His Gln
                85                  90                  95

Tyr Ser Ser His Pro Pro Thr Phe Gly His Gly Thr Arg Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130             135                 140

Phe Tyr Pro Arg Glu Ala Lys Val Gln Trp Lys Val Asp Asn Ala Leu
145             150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 125
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Glu Val Gln Leu Val Glu Ser Gly Gly Glu Leu Val Gln Ala Gly Gly
1               5                   10                  15

Ser Leu Arg Leu Ser Cys Ala Ala Ser Gly Leu Thr Phe Ser Ser Tyr
            20                  25                  30

Asn Met Gly Trp Phe Arg Arg Ala Pro Gly Lys Glu Arg Glu Phe Val
        35                  40                  45

Ala Ser Ile Thr Trp Ser Gly Arg Asp Thr Phe Tyr Ala Asp Ser Val
50              55                  60

Lys Gly Arg Phe Thr Ile Ser Arg Asp Asn Ala Lys Asn Thr Val Tyr
65              70                  75                  80

Leu Gln Met Ser Ser Leu Lys Pro Glu Asp Thr Ala Val Tyr Tyr Cys
                85                  90                  95

Ala Ala Asn Pro Trp Pro Val Ala Ala Pro Arg Ser Gly Thr Tyr Trp
            100                 105                 110

Gly Gln Gly Thr Gln Val Thr Val Ser Ser Gly Gly Gly Ser Gly
            115                 120                 125

Gly Gly Gly Ser Gly Gly Gly Ser Gln Glu Asp Glu Arg Ile Val
            130                 135                 140

Leu Val Asp Asn Lys Cys Lys Cys Ala Arg Ile Thr Ser Arg Ile Ile
145             150                 155                 160

Arg Ser Ser Glu Asp Pro Asn Glu Asp Ile Val Glu Arg Asn Ile Arg
                165                 170                 175

Ile Ile Val Pro Leu Asn Asn Arg Glu Asn Ile Ser Asp Pro Thr Ser
            180                 185                 190

Pro Leu Arg Thr Arg Phe Val Tyr His Leu Ser Asp Leu Cys Lys Lys
            195                 200                 205

Cys Asp Pro Thr Glu Val Glu Leu Asp Asn Gln Ile Val Thr Ala Thr
210             215                 220
```

```
Gln Ser Asn Ile Cys Asp Glu Asp Ser Ala Thr Glu Thr Cys Tyr Thr
225                 230                 235                 240

Tyr Asp Arg Asn Lys Cys Tyr Thr Ala Val Val Pro Leu Val Tyr Gly
                245                 250                 255

Gly Glu Thr Lys Met Val Glu Thr Ala Leu Thr Pro Asp Ala Cys Tyr
                260                 265                 270

Pro Asp
```

UNITED STATES PATENT AND TRADEMARK OFFICE
CERTIFICATE OF CORRECTION

PATENT NO. : 10,570,191 B2  
APPLICATION NO. : 15/566485  
DATED : February 25, 2020  
INVENTOR(S) : Bruce Alan Keyt, Dan T. Stinchcomb and Ole A. Olsen Page 1 of 1

It is certified that error appears in the above-identified patent and that said Letters Patent is hereby corrected as shown below:

In the Claims

Column 213, Line 29, Claim 1, replace "effector cell wherein the" with --effector cell, wherein the--

Column 217, Line 5, Claim 14, replace "A method of, controlling" with --A method of controlling--

Signed and Sealed this  
Fifth Day of January, 2021

Andrei Iancu  
*Director of the United States Patent and Trademark Office*